(12) United States Patent
Griffith et al.

(10) Patent No.: US 7,268,133 B2
(45) Date of Patent: Sep. 11, 2007

(54) CANNABINOID RECEPTOR LIGANDS AND USES THEREOF

(75) Inventors: David A. Griffith, Old Saybrook, CT (US); Marlys Hammond, Blue Bell, PA (US)

(73) Assignee: Pfizer, Inc. Patent Department, Groton, CT (US)

( * ) Notice: Subject to any disclaimer, the term of this patent is extended or adjusted under 35 U.S.C. 154(b) by 472 days.

(21) Appl. No.: 10/822,975

(22) Filed: Apr. 12, 2004

(65) Prior Publication Data

US 2004/0214837 A1 Oct. 28, 2004

Related U.S. Application Data

(60) Provisional application No. 60/540,048, filed on Jan. 29, 2004, provisional application No. 60/464,918, filed on Apr. 23, 2003.

(51) Int. Cl.
| | |
|---|---|
| C07D 413/04 | (2006.01) |
| C07D 487/04 | (2006.01) |
| A61K 31/5355 | (2006.01) |
| A61K 31/519 | (2006.01) |
| A61P 3/04 | (2006.01) |
| A61P 25/34 | (2006.01) |
| C07D 471/04 | (2006.01) |
| A61K 31/437 | (2006.01) |
| A61P 25/32 | (2006.01) |
| A61P 25/18 | (2006.01) |
| A61P 25/16 | (2006.01) |
| A61P 25/08 | (2006.01) |

(52) U.S. Cl. ............... 514/234.2; 514/262.1; 514/278; 514/303; 544/118; 544/230; 544/262; 546/15; 546/118

(58) Field of Classification Search ............... 544/262, 544/230, 106, 118; 514/262.1, 234.2
See application file for complete search history.

(56) References Cited

U.S. PATENT DOCUMENTS

| | | | |
|---|---|---|---|
| 4,925,846 A | 5/1990 | Deacon et al. | |
| 4,944,790 A | 7/1990 | Moser et al. | |
| 5,134,142 A | 7/1992 | Matsuo et al. | |
| 5,462,960 A | 10/1995 | Barth et al. | |
| 5,596,106 A | 1/1997 | Cullinan et al. | |
| 5,624,941 A | 4/1997 | Barth et al. | |
| 5,744,491 A | 4/1998 | Boigegrain et al. | |
| 5,744,493 A | 4/1998 | Boigegrain et al. | |
| 5,747,524 A | 5/1998 | Cullinan et al. | |
| 5,925,768 A | 7/1999 | Barth et al. | |
| 6,028,084 A | 2/2000 | Barth et al. | |
| 6,100,259 A | 8/2000 | Xiang et al. | |
| 6,211,187 B1 | 4/2001 | Yuan | 514/258 |
| 6,344,474 B1 | 2/2002 | Maruani et al. | |
| 6,355,631 B1 | 3/2002 | Bouchard et al. | |
| 6,432,984 B1 | 8/2002 | Barth et al. | |
| 6,476,060 B2 | 11/2002 | Lange et al. | |
| 6,479,479 B2 | 11/2002 | Achard et al. | |
| 6,509,367 B1 | 1/2003 | Martin et al. | |
| 6,518,264 B2 | 2/2003 | Achard et al. | |
| 6,566,356 B2 | 5/2003 | Achard et al. | |
| 2001/0027193 A1 | 10/2001 | Achard et al. | |
| 2001/0053788 A1 | 12/2001 | Lange et al. | |
| 2002/0019383 A1 | 2/2002 | Achard et al. | |
| 2002/0019421 A1 | 2/2002 | Biberman et al. | |
| 2002/0035102 A1 | 3/2002 | Achard et al. | |
| 2002/0091114 A1 | 7/2002 | Plot-Grosjean et al. | |
| 2002/0119972 A1 | 8/2002 | Leftheris et al. | |
| 2002/0128302 A1 | 9/2002 | Maruani et al. | |
| 2002/0188007 A1 | 12/2002 | Barth et al. | |
| 2003/0003145 A1 | 1/2003 | Abramovici et al. | |
| 2003/0055033 A1 | 3/2003 | Achard et al. | |
| 2003/0114495 A1 | 6/2003 | Finke et al. | |
| 2003/0139386 A1 | 7/2003 | Cote et al. | |
| 2003/0199536 A1 | 10/2003 | Thomas et al. | |
| 2004/0034061 A1 | 2/2004 | Nakazato et al. | 514/326 |
| 2004/0072833 A1 | 4/2004 | Nakai et al. | |

(Continued)

FOREIGN PATENT DOCUMENTS

EP  293220 B1  8/1994

(Continued)

OTHER PUBLICATIONS

Adams et. al., Expert Opin. Ther. Patents, 2002, 12(10), 1475-1489.*

(Continued)

*Primary Examiner*—Mark L. Berch
*Assistant Examiner*—Susanna Moore
(74) *Attorney, Agent, or Firm*—Julie M. Lappin

(57) ABSTRACT

Compounds of Formula (I) that act as cannabinoid receptor ligands and their uses in the treatment of diseases linked to the mediation of the cannabinoid receptors in animals are described herein

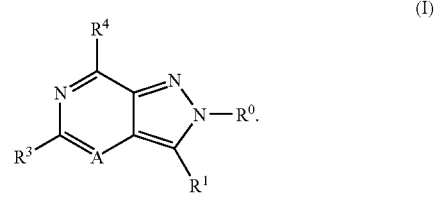

115 Claims, No Drawings

U.S. PATENT DOCUMENTS

| | | |
|---|---|---|
| 2004/0077650 A1 | 4/2004 | Dow |
| 2004/0092520 A1 | 5/2004 | Griffith |
| 2004/0122074 A1 | 6/2004 | Dow et al. .................. 514/397 |
| 2004/0157838 A1 | 8/2004 | Griffith .................... 514/227.8 |
| 2004/0157839 A1 | 8/2004 | Griffith .................... 514/227.8 |
| 2004/0214838 A1 | 10/2004 | Carpino et al. .......... 514/262.1 |
| 2004/0214855 A1 | 10/2004 | Carpino et al. ............. 514/303 |
| 2004/0214856 A1 | 10/2004 | Carpino et al. ............. 514/303 |

FOREIGN PATENT DOCUMENTS

| | | |
|---|---|---|
| EP | 1354884 | 10/2003 |
| WO | WO96/02248 A1 | 2/1996 |
| WO | WO0056734 | 3/2000 |
| WO | WO 00/15609 A1 | 5/2000 |
| WO | WO0158869 | 2/2001 |
| WO | WO 01/24798 A1 | 4/2001 |
| WO | WO 01/28557 A1 | 4/2001 |
| WO | WO 01/29007 A1 | 4/2001 |
| WO | WO 01/32629 A1 | 5/2001 |
| WO | WO 01/32663 A2 | 5/2001 |
| WO | WO 01/58450 A2 | 8/2001 |
| WO | WO 01/85092 A2 | 11/2001 |
| WO | WO02053565 | 7/2002 |
| WO | WO 02/076949 A1 | 10/2002 |
| WO | WO 03/006007 A1 | 1/2003 |
| WO | WO 03/007887 A2 | 1/2003 |
| WO | WO 03/018060 A1 | 3/2003 |
| WO | WO 03/020217 A2 | 3/2003 |
| WO | WO 03/020314 A1 | 3/2003 |
| WO | WO 03/026647 A1 | 4/2003 |
| WO | WO 03/026648 A1 | 4/2003 |
| WO | WO 03/027069 A1 | 4/2003 |
| WO | WO 03/027076 A2 | 4/2003 |
| WO | WO 03/027114 A1 | 4/2003 |
| WO | WO 03/040107 A1 | 5/2003 |
| WO | WO 03/051850 A1 | 6/2003 |
| WO | WO 03/051851 A1 | 6/2003 |
| WO | WO 03/075660 A1 | 9/2003 |
| WO | WO 03/077847 A2 | 9/2003 |
| WO | WO 03/078413 A1 | 9/2003 |
| WO | WO 03/082190 A2 | 10/2003 |
| WO | WO 03/082191 A2 | 10/2003 |
| WO | WO 03/082256 A2 | 10/2003 |
| WO | WO 03/082833 A1 | 10/2003 |
| WO | WO 03/084943 A2 | 10/2003 |
| WO | WO 03/086288 A2 | 10/2003 |
| WO | WO 03/087037 A1 | 10/2003 |
| WO | WO03095455 | 11/2003 |
| WO | WO 2004/012617 A2 | 2/2004 |

OTHER PUBLICATIONS

Mackie, Annu. Rev. Pharmacol. Toxicol., 2006, 46, 101-122.*
Pertwee et. al., Prostaglandins, Leukotrienes and Essential Fatty Acids, 2002, 66, 101-121.*
Tzavara, E.T., et al., "The CB1 Receptor Antagonist SR141716A selectively increases monoaminergic neurotransmission in the medial prefrontal cortex: Implications for Therapeutic Actions," *J Pharmacol*, 138, 544-553 (2003).
Racz, I., et al., "A Critical Role for the Cannabinoid CB1 Receptors in Alcohol Dependence and Stress-Stimulated Ethanol Drinking," *J Neurosci*, 23(6), 2453-2458 (2003).
Croci, T., et al., "Role of Cannabinoid CB1 Receptors and Tumor Necrosis Factor-α in the gut and systemic anti-inflammatory activity of SR 141716 (Rimonabant) in rodents," *Brit J Pharmacol*, 140, 115-122 (2003).
DaSilva, G.E., et al., "Potentiation of Penile Erection and Yawning Responses to Apomorphine by Cannabinoid Receptor Antagonists in Rats," *Neurosci Let*, 349, 49-52 (2003).

Wang, L., et al., "Endocannabinoid Signaling via Cannabinoid Receptor 1 is Involved in Ethanol Preference and its Age-Dependent Decline in Mice," *PNAS*, 100(3), 1393-1398 (2003).
Ruiu, S., et al., "Synthesis and Characterization of NESS 0327: A Novel Putative Antagonist of the CB1 Cannabinoid Receptor," *J Pharmacol Exp Therap*, 306, 363-370 (2003).
Howlett, A.C., et al., "International Union of Pharmacology. XXVII. Classification of Cannabinoid Receptors," *Pharmacol Rev*, 54, 161-202 (2002).
Gomez, R., et al., "A Peripheral Mechanism for CB1 Cannabinoid Receptor-Dependent Modulation of Feeding," *J. Neurosci*, 22(21), 9612-9617 (2002).
Wiley, J.L., et al., "Novel Pyrazole Cannabinoids: Insights into CB1 Receptor Recognition and Activation," *J Pharmacol Exp Therap*, 296(3), 1013-1022 (2001).
Lellemand, F., et al., "Effects of CB1 Cannabinoid Receptor Blockade on Ethanol Preference After Chronic Ethanol Administration," *Alcohol Clin Exp Res*, 25(9), 1317-1323 (2001).
Pertwee, R.G., "Cannabinoids and the Gastronintestinal Tract," *Gut*, 48, 859-867 (2001).
Pertwee, R.G., "Cannabinoid Receptor Ligands: Clinical and Neuropharmacological Considerations, Relevant to Future Drug Discovery and Development," *Exp. Opin. Invest. Drugs*, 9(7), 1573-1571 (2000).
Hungund, B.L. and B.S. Basavarajappa, "Are Anadamide and Cannabinoid Receptors involved in Ethanol Tolerance? A Review of the Evidence," *Alcohol & Alcoholism*. 35(2) 126-133, (2000).
Freedland, C.S., et al., "Effects of SR141716A, a Central Cannabinoid Receptor Antagonist, on Food-maintained Responding," *Pharmacol Biochem Behav*, 67, 265-270 (2000).
Lan, R., et al., "Structure-Activity Relationships of Pyrazole Derivatives as Cannabinoid Receptor Antagonists" *J. Med. Che.m*, 42, 769-776 (1999).
Pertwee, R.G., "Pharmacology of Cannabinoid Receptor Ligands" *Curr Med Chem*, 6, 635-664 (1999).
Basavarajappa, B.S., et al., "Chronic Ethanol Adminstration Down-regulates Cannabinoid Receptors in Mouse Brain Synaptic Plasma Membrane," *Brain Res*, 793, 212-218 (1998).
Thomas, B.F., et al., "Comparative Receptor Binding Analyses of Cannabinoid Agonists and Antagonists," *J Pharmacol Exp Therap*, 285, 285-292 (1998).
Colombo, G., et al., "Appetite Suppression and Weight Loss after the Cannabinoid Antagonist SR141716," *Life Sci.*, 63, PL113-PL117 (1998).
Simiand, J., et al., "SR141716, a CB1 Cannabinoid Receptor Antagonist, Selectively Reduces Sweet Food Intake in Marmose," *Behav. Pharmacol.*, 9, 179-181 (1998).
Chaperon, F., et al., "Involvement of Central Cannabinoid (CB1) Receptors in the Establishment of Place Conditioning in Rats," *Psychopharmacology*, 135, 324-332 (1998).
Arnone, M., et al., "Selective Inhibition of Sucrose and Ethanol Intake by SR141716, an Antagonist of Central Cannabinoid (CB1) Receptors," *Psychopharmacol*, 132, 104-106 (1997).
Savontaus, E., et al., "Anti-Obesity Effect of MPV-1743 A III, a Novel Imidazoline Derivative, in Genetic Obesity," *Eur J Pharmacol*, 328, 207-215 (1997).
Sanudo-Pena, M.C., et al., "Endogenous Cannabinoids as an Aversive or Counter-rewarding System in the Rat," *Neurosci Let*, 223, 125-128 (1997).
Gifford, A.N., et al., "Electrically Evoked Acetylcholine Relase from Hippocampal Silices is Inhibited by the Cannabinoid Receptor Agonist, WIN 55212-2 and is Potentiated by the Cannabinoid Antagonist, SR 141716A," *J Pharmacol Exp Ther*, 277, 1431-1436 (1996).
Compton, D.R., et al., "In Vivo Characterization of a Specific Cannabinoid Receptor Antagonist (SR141716A); Inhibition of Delta-9-Tetrahydrocannabinol-Induced Responses and Apparent Agonist Activity," *J Pharmacol Exp Ther*, 277, 586-594 (1996).
Mansbach, R.S., et al., "Effects of the Cannabinoid CB1 Receptor Antagonist SR141716A on the Behavior of Pigeons and Rats," *Psychopharmacology*, 124, 315-322 (1996).

Lichtman, A.H., et al., "Delta-9-Tetrahydrocannabinol Impairs Spatial Memory through a Cannabinoid Receptor Mechanism," *Psychopharmacology*, 126, 125-131 (1996).

Perio, A., et al., "Central Mediation of the Cannabinoid Cue: Activity of a Selective CB1 Antagonist, SR141716A," *Behavioral Pharamacology*, 7, 65-71 (1996).

Rinaldi-Carmona, M., et al., "Biochemical and Pharmacological Characteriszation of SR141716A, The First Potent and Selective Brain Cannabinoid Receptor Antagonist," *Life Sci*, 56, 1941-1947 (1995).

Pertwee, R., et al., "AM630, A Competitive Cannabinoid Receptor Antagonist," *Life Sci*, 56, 1949-1955 (1995).

Rinaldi-Carmona, M., et al., "SR141716A, a Patent and Selective Antagonist of the Brain Cannabinoid Receptor," *FEBS Letters*, 350, 240-244 (1994).

Dutta, A., et al., "The Synthesis and Pharmacological Evaluation of the Cannabinoid Antagonist SR 141716A", *Med. Chem. Rev.* 5, 54-62 (1994).

Drummond, J., et al., "Evaluation and Synthesis of Aminohydroxyisoxazoles and Pyrazoles as Potential Glycine Agonists," *J. Med. Chem*, 32, 2116-2128 (1989).

Murray, W., et al., "A Simple Regioselective Synthesis of Ethyl 1,5-Diarylpyrazole-3-carboxylates" *J. Heterocyclic Chem*, 26, 1389 (1989).

Dewey, W.L. "Cannabinoid Pharmacology," *Pharmacological Reviews*, 38(2)m 151-178 (1986).

Tewari, R.S., et al., "1,3-Dipolar Cycloaddition and Nucleophylic Substitution Reactions of C-Acetyl and C-Ethoxycarbonyl Derivative of Hydrazidoyl Bromides" *Tetrahedron*, 39(1) 129-136 (1983).

Birkofer, L. and K. Richtzenhain, "Silyl-Derivate von Pyrazol, Isoxazol und 1,2,3-Triazol" *Chem. Ber.* 112, 2829-2836 (1979).

Franke, H. et al., "Polare Cycloadditionen von elektronenreichen Mehrfach-bindungssystemen an 1,3,4-oxadiazolium-Salze: Synthese von 3aH-[1,3,4]Oxadiazolo[3,2-a]chinolinen" *Chem. Ber.* 112, 3623-3636 (1979).

Sucrow, W., et al., "Bimolekulare Cyclisierung von 2-(1-Methylhydrazino)maleinsaure-dimethylester" *Chem. Ber.* 112, 1712-1718 (1979).

Cusmano, et al., *Heterocycles*, "Synthesis of 2H-Pyrazolo[3,4-c]quinoline Derivatives by One Pot Rearrangement of Phenylhydrazones of 3-Acylindoles", vol. 24, pp. 3181-3186 (1986).

* cited by examiner

CANNABINOID RECEPTOR LIGANDS AND USES THEREOF

This application claims the benefit of U.S. Provisional Application Nos. 60/464,918, filed on Apr. 23, 2003 and 60/540,048, filed on Jan. 29, 2004, both of which are incorporated herein by reference in their entirety.

FIELD OF THE INVENTION

The present invention relates to pyrazolo[4,3-d]pyrimidine and pyrazolo[3,4-c]pyridine compounds as cannabinoid receptor ligands, in particular CB1 receptor antagonists, and uses thereof for treating diseases, conditions and/or disorders modulated by cannabinoid receptor antagonists.

BACKGROUND

Obesity is a major public health concern because of its increasing prevalence and associated health risks. Obesity and overweight are generally defined by body mass index (BMI), which is correlated with total body fat and estimates the relative risk of disease. BMI is calculated by weight in kilograms divided by height in meters squared ($kg/m^2$). Overweight is typically defined as a BMI of 25-29.9 $kg/m^2$, and obesity is typically defined as a BMI of 30 $kg/m^2$. See, e.g., National Heart, Lung, and Blood Institute, Clinical Guidelines on the Identification, Evaluation, and Treatment of Overweight and Obesity in Adults, The Evidence Report, Washington, D.C.: U.S. Department of Health and Human Services, NIH publication no. 98-4083 (1998).

The increase in obesity is of concern because of the excessive health risks associated with obesity, including coronary heart disease, strokes, hypertension, type 2 diabetes mellitus, dyslipidemia, sleep apnea, osteoarthritis, gall bladder disease, depression, and certain forms of cancer (e.g., endometrial, breast, prostate, and colon). The negative health consequences of obesity make it the second leading cause of preventable death in the United States and impart a significant economic and psychosocial effect on society. See, McGinnis M, Foege W H., "Actual Causes of Death in the United States," *JAMA*, 270, 2207-12 (1993).

Obesity is now recognized as a chronic disease that requires treatment to reduce its associated health risks. Although weight loss is an important treatment outcome, one of the main goals of obesity management is to improve cardiovascular and metabolic values to reduce obesity-related morbidity and mortality. It has been shown that 5-10% loss of body weight can substantially improve metabolic values, such as blood glucose, blood pressure, and lipid concentrations. Hence, it is believed that a 5-10% intentional reduction in body weight may reduce morbidity and mortality.

Currently available prescription drugs for managing obesity generally reduce weight by inducing satiety or decreasing dietary fat absorption. Satiety is achieved by increasing synaptic levels of norepinephrine, serotonin, or both. For example, stimulation of serotonin receptor subtypes 1B, 1D, and 2C and 1- and 2-adrenergic receptors decreases food intake by regulating satiety. See, Bray G A, "The New Era of Drug Treatment. Pharmacologic Treatment of Obesity: Symposium Overview," *Obes Res.*, 3(suppl 4), 415s-7s (1995). Adrenergic agents (e.g., diethylpropion, benzphetamine, phendimetrazine, mazindol, and phentermine) act by modulating central norepinephrine and dopamine receptors through the promotion of catecholamine release. Older adrenergic weight-loss drugs (e.g., amphetamine, methamphetamine, and phenmetrazine), which strongly engage in dopamine pathways, are no longer recommended because of the risk of their abuse. Fenfluramine and dexfenfluramine, both serotonergic agents used to regulate appetite, are no longer available for use.

More recently, CB1 cannabinoid receptor antagonists/inverse agonists have been suggested as potential appetite suppressants. See, e.g., Arnone, M., et al., "Selective Inhibition of Sucrose and Ethanol Intake by SR141716, an Antagonist of Central Cannabinoid (CB1) Receptors," *Psychopharmacol*, 132, 104-106 (1997); Colombo, G., et al., "Appetite Suppression and Weight Loss after the Cannabinoid Antagonist SR141716," *Life Sci.*, 63, PL113-PL117 (1998); Simiand, J., et al., "SR141716, a CB1 Cannabinoid Receptor Antagonist, Selectively Reduces Sweet Food Intake in Marmose," *Behav. Pharmacol.*, 9, 179-181 (1998); and Chaperon, F., et al., "Involvement of Central Cannabinoid (CB1) Receptors in the Establishment of Place Conditioning in Rats," *Psychopharmacology*, 135, 324-332 (1998). For a review of cannabinoid CB1 and CB2 receptor modulators, see Pertwee, R. G., "Cannabinoid Receptor Ligands: Clinical and Neuropharmacological Considerations, Relevant to Future Drug Discovery and Development," *Exp. Opin. Invest. Drugs*, 9(7), 1553-1571 (2000).

Although investigations are on-going, there still exists a need for a more effective and safe therapeutic treatment for reducing or preventing weight-gain.

In addition to obesity, there also exists an unmet need for treatment of alcohol abuse. Alcoholism affects approximately 10.9 million men and 4.4 million women in the United States. Approximately 100,000 deaths per year have been attributed to alcohol abuse or dependence. Health risks associated with alcoholism include impaired motor control and decision making, cancer, liver disease, birth defects, heart disease, drug/drug interactions, pancreatitis and interpersonal problems. Studies have suggested that endogenous cannabinoid tone plays a critical role in the control of ethanol intake. The endogenous CB1 receptor antagonist SR-141716A has been shown to block voluntary ethanol intake in rats and mice. See, Arnone, M., et al., "Selective Inhibition of Sucrose and Ethanol Intake by SR141716, an Antagonist of Central Cannabinoid (CB1) Receptors," *Psychopharmacol*, 132, 104-106 (1997). For a review, see Hungund, B. L and B. S. Basavarajappa, "Are Anandamide and Cannabinoid Receptors involved in Ethanol Tolerance? A Review of the Evidence," *Alcohol & Alcoholism.* 35(2) 126-133, 2000.

Current treatments for alcohol abuse or dependence generally suffer from non-compliance or potential hepatotoxicity; therefore, there is a high unmet need for more effective treatment of alcohol abuse/dependence.

SUMMARY

The present invention provides compounds of Formula (I) that act as cannabinoid receptor ligands (in particular, CB1 receptor antagonists)

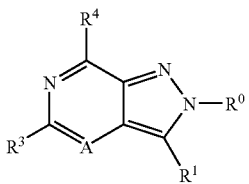

(I)

wherein

A is N or C(R$^2$), where R$^2$ is hydrogen, (C$_1$-C$_4$)alkyl, halo-substituted (C$_1$-C$_4$)alkyl, or (C$_1$-C$_4$)alkoxy;

R$^0$ is an optionally substituted heteroaryl or a substituted aryl (preferably, R$^0$ is a substituted phenyl, more preferably a phenyl substituted with one to three substituents independently selected from the group consisting of halo (preferably, chloro or fluoro), (C$_1$-C$_4$)alkoxy, (C$_1$-C$_4$)alkyl, halo-substituted (C$_1$-C$_4$)alkyl (preferably fluoro-substituted alkyl), and cyano, most preferably, R$^0$ is 2-chlorophenyl, 2-fluorophenyl, 2,4-dichlorophenyl, 2-fluoro-4-chlorophenyl, 2-chloro-4-fluorophenyl, or 2,4-difluorophenyl);

R$^1$ is an optionally substituted heteroaryl or a substituted aryl (preferably, R$^1$ is a substituted phenyl, more preferably a phenyl substituted with one to three substituents independently selected from the group consisting of halo (preferably, chloro or fluoro), (C$_1$-C$_4$)alkoxy, (C$_1$-C$_4$)alkyl, halo-substituted (C$_1$-C$_4$)alkyl (preferably fluoro-substituted alkyl), and cyano, most preferably, R$^1$ is 4-chlorophenyl or 4-fluorophenyl);

R$^3$ is hydrogen, (C$_1$-C$_4$)alkyl, halo-substituted (C$_1$-C$_4$) alkyl, or (C$_1$-C$_4$)alkoxy;

R$^4$ is (i) a group having Formula (IA) or Formula (IB)

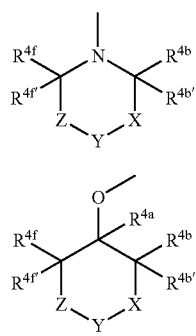

where R$^{4a}$ is hydrogen or (C$_1$-C$_3$)alkyl;

R$^{4b}$ and R$^{4b'}$ are each independently hydrogen, cyano, hydroxy, amino, H$_2$NC(O)—, or a chemical moiety selected from the group consisting of (C$_1$-C$_6$)alkyl, (C$_1$-C$_6$)alkoxy, acyloxy, acyl, (C$_1$-C$_3$)alkyl-O—C(O)—, (C$_1$-C$_4$)alkyl-NH—C(O)—, (C$_1$-C$_4$)alkyl)$_2$N—C(O)—, (C$_1$-C$_6$)alkylamino-, ((C$_1$-C$_4$)alkyl)$_2$amino-, (C$_3$-C$_6$)cycloalkylamino-, acylamino-, aryl(C$_1$-C$_4$)alkylamino-, heteroaryl(C$_1$-C$_4$)alkylamino-, aryl, heteroaryl, a 3-6 membered partially or fully saturated heterocycle, and a partially or fully saturated carbocyclic ring, where said moiety is optionally substituted with one or more substituents, or either R$^{4b}$ or R$^{4b'}$ taken together with R$^{4e}$, R$^{4e'}$, R$^{4f}$, or R$^{4f'}$ forms a bond, a methylene bridge, or an ethylene bridge;

X is a bond, —CH$_2$CH$_2$— or —C(R$^{4c}$)(R$^{4c'}$)—, where R$^{4c}$ and R$^{4c'}$ are each independently hydrogen, cyano, hydroxy, amino, H$_2$NC(O)—, or a chemical moiety selected from the group consisting of (C$_1$-C$_6$)alkyl, (C$_1$-C$_6$)alkoxy, acyloxy, acyl, (C$_1$-C$_3$)alkyl-O—C(O)—, (C$_1$-C$_4$)alkyl-NH—C(O)—, ((C$_1$-C$_4$)alkyl)$_2$N—C(O)—, (C$_1$-C$_6$)alkylamino-, di(C$_1$-C$_4$)alkylamino-, (C$_3$-C$_6$)cycloalkylamino-, acylamino-, aryl (C$_1$-C$_4$)alkylamino-, heteroaryl(C$_1$-C$_4$)alkylamino-, aryl, heteroaryl, a 3-6 membered partially or fully saturated heterocycle, and a 3-6 membered partially or fully saturated carbocyclic ring, where said moiety is optionally substituted with one or more substituents, or either R$^{4c}$ or R$^{4c'}$ taken together with R$^{4e}$, R$^{4e'}$, R$^{4f}$, or R$^{4f'}$ forms a bond, a methylene bridge or an ethylene bridge;

Y is oxygen, sulfur, —C(O)—, or —C(R$^{4d}$)(R$^{4d'}$)—, where R$^{4d}$ and R$^{4d'}$ are each independently hydrogen, cyano, hydroxy, amino, H$_2$NC(O)—, or a chemical moiety selected from the group consisting of (C$_1$-C$_6$) alkyl, (C$_1$-C$_6$)alkoxy, acyloxy, acyl, (C$_1$-C$_3$)alkyl-O—C(O)—, (C$_1$-C$_4$)alkyl-NH—C(O)—, ((C$_1$-C$_4$)alkyl)$_2$N—C(O)—, (C$_1$-C$_6$)alkylamino-, di(C$_1$-C$_4$)alkylamino-, (C$_3$-C$_6$)cycloalkylamino-, acylamino-, aryl (C$_1$-C$_4$)alkylamino-, heteroaryl(C$_1$-C$_4$)alkylamino-, aryl, heteroaryl, a 3-6 membered partially or fully saturated heterocycle, and a 3-6 membered partially or fully saturated carbocyclic ring, where said moiety is optionally substituted with one or more substituents, or R$^{4d}$ and R$^{4d'}$ taken together form a 3-6 membered partially or fully saturated carbocyclic ring, 3-6 membered partially or fully saturated heterocyclic ring, a 5-6 membered lactone ring, or a 4-6 membered lactam ring, where said carbocyclic ring, said heterocyclic ring, said lactone ring and said lactam ring are optionally substituted with one or more substituents and said lactone ring and said lactam ring optionally contain an additional heteroatom selected from oxygen, nitrogen or sulfur, or Y is —NR$^{4d''}$-, where R$^{4d''}$ is a hydrogen or a chemical moiety selected from the group consisting of (C$_1$-C$_6$) alkyl, (C$_3$-C$_6$)cycloalkyl, (C$_1$-C$_3$)alkylsulfonyl-, (C$_1$-C$_3$)alkylaminosulfonyl-, di(C$_1$-C$_3$)alkylaminosulfonyl-, acyl, (C$_1$-C$_6$)alkyl-O—C(O)—, aryl, and heteroaryl, where said moiety is optionally substituted with one or more substituents;

Z is a bond, —CH$_2$CH$_2$—, or —C(R$^{4e}$)(R$^{4e'}$)—, where R$^{4e}$ and R$^{4e'}$ are each independently hydrogen, cyano, hydroxy, amino, H$_2$NC(O)—, or a chemical moiety selected from the group consisting of (C$_1$-C$_6$)alkyl, (C$_1$-C$_6$)alkoxy, acyloxy, acyl, (C$_1$-C$_3$)alkyl-O—C(O)—, (C$_1$-C$_4$)alkyl-NH—C(O)—, ((C$_1$-C$_4$)alkyl)$_2$N—C(O)—, (C$_1$-C$_6$)alkylamino-, di(C$_1$-C$_4$)alkylamino-, (C$_3$-C$_6$)cycloalkylamino-, acylamino-, aryl (C$_1$-C$_4$)alkylamino-, heteroaryl(C$_1$-C$_4$)alkylamino-, aryl, heteroaryl, a 3-6 membered partially or fully saturated heterocycle, and a 3-6 membered partially or fully saturated carbocyclic ring, where said moiety is optionally substituted with one or more substituents, or either $R^{4e}$ or $R^{4e'}$ taken together with $R^{4b}$, $R^{4b'}$, $R^{4c}$, or $R^{4c'}$ forms a bond, a methylene bridge or an ethylene bridge; and $R^{4f}$ and $R^{4f'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl$)_2$N—C(O)—, $(C_1-C_6)$alkylamino-, di$(C_1-C_4)$alkylamino-, $(C_3-C_6)$cycloalkylamino-, acylamino-, aryl $(C_1-C_4)$alkylamino-, heteroaryl$(C_1-C_4)$alkylamino-, aryl, heteroaryl, a 3-6 membered partially or fully saturated heterocycle, and a 3-6 membered partially or fully saturated carbocyclic ring, where said moiety is optionally substituted with one or more substituents, or either $R^{4f}$ or $R^{4f'}$ taken together with $R^{4b}$, $R^{4b'}$, $R^{4c}$, or $R^{4c'}$ forms a bond, a methylene bridge or an ethylene bridge;

(ii) a group having Formula (IC)

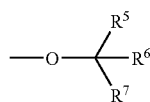

IC where $R^5$ and $R^6$ are each independently hydrogen, aryl, or $(C_1-C_4)$alkyl, and $R^7$ is an optionally substituted $(C_1-C_4)$alkyl-, or an optionally substituted 4-6 membered partially or fully saturated heterocylic ring containing 1 to 2 heteroatoms independently selected from oxygen, sulfur or nitrogen, or $R^5$ and $R^6$ or $R^5$ and $R^7$ taken together form a 5-6 membered lactone, 4-6 membered lactam, or a 4-6 membered partially or fully saturated heterocycle containing 1 to 2 heteroatoms independently selected from oxygen, sulfur or nitrogen, where said lactone, said lactam and said heterocycle are optionally substituted with one or more substituents;

(iii) an amino group having attached thereto at least one chemical moiety selected from the group consisting of $(C_1-C_8)$alkyl, aryl, aryl$(C_1-C_4)$alkyl, a 3-8 membered partially or fully saturated carbocyclic ring, hydroxy$(C_1-C_6)$alkyl, $(C_1-C_3)$alkoxy$(C_1-C_6)$alkyl, heteroaryl$(C_1-C_3)$alkyl, and a fully or partially saturated heterocycle, where said chemical moiety is optionally substituted with one or more substituents; or (iv) an $(C_1-C_6)$alkyl group having attached thereto at least one chemical moiety selected from the group consisting of hydroxy, $(C_1-C_6)$alkoxy, amino, $(C_1-C_6)$alkylamino, di$((C_1-C_6)$alkyl$)$amino $(C_1-C_3)$alkylsulfonyl, $(C_1-C_3)$alkylsulfamyl, di$((C_1-C_3)$alkyl$)$sulfamyl, acyloxy, a fully or partially saturated heterocycle, and a fully or partially saturated carbocyclic ring, where said chemical moiety is optionally substituted with one or more substituents;

a pharmaceutically acceptable salt thereof, a prodrug of the compound or the salt, or a solvate or hydrate of the compound, the salt or the prodrug.

In another embodiment of the present invention, a compound of Formula (II) is provided.

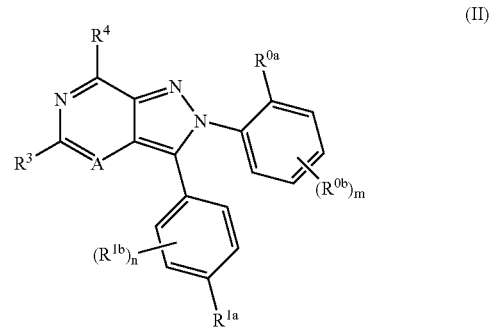

(II)

wherein

A is N or $C(R^2)$, where $R^2$ is hydrogen, $(C_1-C_4)$alkyl, halo-substituted $(C_1-C_4)$alkyl, or $(C_1-C_4)$alkoxy;

$R^{0a}$, $R^{0b}$, $R^{1a}$, and $R^{1b}$ are each independently halo, $(C_1-C_4)$alkoxy, $(C_1-C_4)$alkyl, halo-substituted $(C_1-C_4)$alkyl, or cyano;

n and m are each independently 0, 1 or 2;

$R^3$ is hydrogen, $(C_1-C_4)$alkyl, halo-substituted $(C_1-C_4)$alkyl, or $(C_1-C_4)$alkoxy;

$R^4$ is (i) a group having Formula (IA) or Formula (IB)

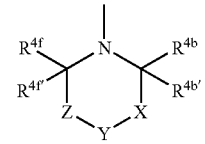

IA

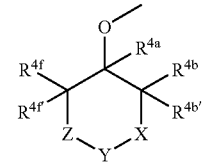

IB where $R^{4a}$ is hydrogen or $(C_1-C_3)$alkyl;

$R^{4b}$ and $R^{4b'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)$alkyl$)_2$N—C(O)—, $(C_1-C_6)$alkylamino-, $((C_1-C_4)$alkyl$)_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a 3-6 membered partially or fully saturated heterocycle, and a partially or fully saturated carbocyclic ring, where the moiety is optionally substituted with one or more substituents, or either $R^{4b}$ or $R^{4b'}$ taken together with $R^{4e}$, $R^{4e'}$, $R^{4f}$, or $R^{4f'}$ forms a bond, a methylene bridge, or an ethylene bridge;

X is a bond, —$CH_2CH_2$— or —$C(R^{4c})(R^{4c'})$—, where $R^{4c}$ and $R^{4c'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C (O)—, $(C_1$-$C_4)$alkyl-NH—C(O)—, $((C_1$-$C_4)$alkyl$)_2$N—C(O)—, $(C_1$-$C_6)$alkylamino-, di$(C_1$-$C_4)$alkylamino-, $(C_3$-$C_6)$cycloalkylamino-, acylamino-, aryl$(C_1$-$C_4)$alkylamino-, heteroaryl$(C_1$-$C_4)$alkylamino-, aryl, heteroaryl, a 3-6 membered partially or fully saturated heterocycle, and a 3-6 membered partially or fully saturated carbocyclic ring, where the moiety is optionally substituted with one or more substituents, or either $R^{4c}$ or $R^{4c'}$ taken together with $R^{4e}$, $R^{4e'}$, $R^{4f}$, or $R^{4f'}$ forms a bond, a methylene bridge or an ethylene bridge;

Y is oxygen, sulfur, —C(O)—, or —C($R^{4d}$)($R^{4d'}$)—, where $R^{4d}$ and $R^{4d'}$ are each independently hydrogen, cyano, hydroxy, amino, $H_2$NC(O)—, or a chemical moiety selected from the group consisting of $(C_1$-$C_6)$alkyl, $(C_1$-$C_6)$alkoxy, acyloxy, acyl, $(C_1$-$C_3)$alkyl-O—C(O)—, $(C_1$-$C_4)$alkyl-NH—C(O)—, $((C_1$-$C_4)$alkyl$)_2$N—C(O)—, $(C_1$-$C_6)$alkylamino-, di$(C_1$-$C_4)$alkylamino-, $(C_3$-$C_6)$cycloalkylamino-, acylamino-, aryl$(C_1$-$C_4)$alkylamino-, heteroaryl$(C_1$-$C_4)$alkylamino-, aryl, heteroaryl, a 3-6 membered partially or fully saturated heterocycle, and a 3-6 membered partially or fully saturated carbocyclic ring, where the moiety is optionally substituted with one or more substituents, or $R^{4d}$ and $R^{4d'}$ taken together form a 3-6 membered partially or fully saturated carbocyclic ring, a 3-6 membered partially or fully saturated heterocyclic ring, a 5-6 membered lactone ring, or a 4-6 membered lactam ring, where said carbocyclic ring, said heterocyclic ring, said lactone ring and said lactam ring are optionally substituted with one or more substituents and said lactone ring and said lactam ring optionally contain an additional heteroatom selected from oxygen, nitrogen or sulfur, or Y is —N$R^{4d''}$—, where $R^{4d''}$ is a hydrogen or a chemical moiety selected from the group consisting of $(C_1$-$C_6)$alkyl, $(C_3$-$C_6)$cycloalkyl, $(C_1$-$C_3)$alkylsulfonyl-, $(C_1$-$C_3)$alkylaminosulfonyl-, di$(C_1$-$C_3)$alkylaminosulfonyl-, acyl, $(C_1$-$C_6)$alkyl-O—C(O)—, aryl, and heteroaryl, where the moiety is optionally substituted with one or more substituents;

Z is a bond, —CH$_2$CH$_2$—, or —C($R^{4e}$)($R^{4e'}$)—, where $R^{4e}$ and $R^{4e'}$ are each independently hydrogen, cyano, hydroxy, amino, $H_2$NC(O)—, or a chemical moiety selected from the group consisting of $(C_1$-$C_6)$alkyl, $(C_1$-$C_6)$alkoxy, acyloxy, acyl, $(C_1$-$C_3)$alkyl-O—C(O)—, $(C_1$-$C_4)$alkyl-NH—C(O)—, $((C_1$-$C_4)$alkyl$)_2$N—C(O)—, $(C_1$-$C_6)$alkylamino-, di$(C_1$-$C_4)$alkylamino-, $(C_3$-$C_6)$cycloalkylamino-, acylamino-, aryl$(C_1$-$C_4)$alkylamino-, heteroaryl$(C_1$-$C_4)$alkylamino-, aryl, heteroaryl, a 3-6 membered partially or fully saturated heterocyclic ring, and a 3-6 membered partially or fully saturated carbocyclic ring, where the moiety is optionally substituted with one or more substituents, or either $R^{4e}$ or $R^{4e'}$ taken together with $R^{4b}$, $R^{4b'}$, $R^{4c}$, or $R^{4c'}$ forms a bond, a methylene bridge or an ethylene bridge; and $R^{4f}$ and $R^{4f'}$ are each independently hydrogen, cyano, hydroxy, amino, $H_2$NC(O)—, or a chemical moiety selected from the group consisting of $(C_1$-$C_6)$alkyl, $(C_1$-$C_6)$alkoxy, acyloxy, acyl, $(C_1$-$C_3)$alkyl-O—C(O)—, $(C_1$-$C_4)$alkyl-NH—C(O)—, $((C_1$-$C_4)$alkyl$)_2$N—C(O)—, $(C_1$-$C_6)$alkylamino-, di$(C_1$-$C_4)$alkylamino-, $(C_3$-$C_6)$cycloalkylamino-, acylamino-, aryl$(C_1$-$C_4)$alkylamino-, heteroaryl$(C_1$-$C_4)$alkylamino-, aryl, heteroaryl, a 3-6 membered partially or fully saturated heterocycle, and a 3-6 membered partially or fully saturated carbocyclic ring, where the moiety is optionally substituted with one or more substituents, or either $R^{4f}$ or $R^{4f'}$ taken together with $R^{4b}$, $R^{4b'}$, $R^{4c}$, or $R^{4c'}$ forms a bond, a methylene bridge or an ethylene bridge;

(ii) a group having Formula (IC)

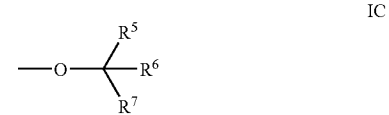

IC where $R^5$ and $R^6$ are each independently hydrogen, aryl, or $(C_1$-$C_4)$alkyl, and $R^7$ is an optionally substituted $(C_1$-$C_4)$alkyl-, or an optionally substituted 4-6 membered partially or fully saturated heterocylic ring containing 1 to 2 heteroatoms independently selected from oxygen, sulfur or nitrogen, or $R^5$ and $R^6$ or $R^5$ and $R^7$ taken together form a 5-6 membered lactone, 4-6 membered lactam, or a 4-6 membered partially or fully saturated heterocycle containing 1 to 2 heteroatoms independently selected from oxygen, sulfur or nitrogen, where said lactone, said lactam and said heterocycle are optionally substituted with one or more substituents;

(iii) an amino group having attached thereto at least one chemical moiety selected from the group consisting of $(C_1$-$C_8)$alkyl, aryl, aryl$(C_1$-$C_4)$alkyl, a 3-8 membered partially or fully saturated carbocyclic ring, hydroxy$(C_1$-$C_6)$alkyl, $(C_1$-$C_3)$alkoxy$(C_1$-$C_6)$alkyl, heteroaryl$(C_1$-$C_3)$alkyl, and a fully or partially saturated heterocycle, where said chemical moiety is optionally substituted with one or more substituents; or (iv) an $(C_1$-$C_6)$alkyl group having attached thereto at least one chemical moiety selected from the group consisting of hydroxy, $(C_1$-$C_6)$alkoxy, amino, $(C_1$-$C_6)$alkylamino, di$((C_1$-$C_6)$alkyl)amino$(C_1$-$C_3)$alkylsulfonyl, $(C_1$-$C_3)$alkylsulfamyl, di$((C_1$-$C_3)$alkyl)sulfamyl, acyloxy, a fully or partially saturated heterocycle, and a fully or partially saturated carbocyclic ring, where said chemical moiety is optionally substituted with one or more substituents;

a pharmaceutically acceptable salt thereof, a prodrug of the compound or the salt, or a solvate or hydrate of the compound, the salt or the prodrug.

A preferred compound of the present invention is a compound of Formula (I) or (II) where $R^4$ is a group of Formula (IA). Preferably, $R^{4b}$ and $R^{4b'}$ are each independently hydrogen, $H_2$NC(O)—, or a chemical moiety selected from the group consisting of $(C_1$-$C_6)$alkyl, acyl, $(C_1$-$C_3)$alkyl-O—C(O)—, $(C_1$-$C_4)$alkyl-NH—C(O)—, $(C_1$-$C_4)$alkyl$)_2$N—C(O)—, aryl, heteroaryl, a partially or fully saturated 3-6 membered heterocycle, and a partially or fully saturated carbocyclic ring, where the moiety is optionally substituted, or $R^{4b}$ or $R^{4b'}$ taken together with $R^{4e}$, $R^{4e'}$, $R^{4f}$, or $R^{4f'}$ forms a bond, a methylene bridge, or an ethylene bridge;

X is a bond, —CH$_2$CH$_2$— or —C($R^{4c}$)($R^{4c'}$)—, where $R^{4c}$ is hydrogen, cyano, hydroxy, amino, $H_2$NC(O)—, or a chemical moiety selected from the group consisting of $(C_1$-$C_6)$alkyl, $(C_1$-$C_6)$alkoxy, acyloxy, acyl, $(C_1$-$C_3)$alkyl-O—C(O)—, $(C_1$-$C_4)$alkyl-NH—C(O)—, $((C_1$-$C_4)$alkyl$)_2$N—C(O)—, $(C_1$-$C_6)$alkylamino-, $((C_1$-$C_4)$alkyl$)_2$amino-, $(C_3$-$C_6)$cycloalkylamino-, acylamino-, aryl$(C_1$-$C_4)$alkylamino-, heteroaryl$(C_1$-$C_4)$alkylamino-, aryl, heteroaryl, a partially or fully saturated 3-6 membered heterocycle, and a partially or fully saturated carbocyclic ring, where the moiety is optionally substituted, or $R^{4c}$ taken together with $R^{4e}$, $R^{4e'}$, $R^{4f}$, or $R^{4'}$ forms a bond, a methylene bridge, or an ethylene bridge, and $R^{4c'}$ is hydrogen, $H_2NC(O)$—, or a chemical moiety selected from the group consisting of $(C_1-C_6)$alkyl acyl, $(C_1-C_3)$alkyl-O—C(O)—, $(C_1-C_4)$alkyl-NH—C(O)—, $(C_1-C_4)$alkyl)$_2$N—C(O)—, aryl, heteroaryl, a partially or fully saturated 3-6 membered heterocycle, and a partially or fully saturated carbocyclic ring, where the moiety is optionally substituted, or $R^{4c'}$ taken together with $R^{4e}$, $R^{4e'}$, $R^{4f}$, or $R^{4o}$ forms a bond, a methylene bridge, or an ethylene bridge;

Y is oxygen, sulfur, —C(O)—, or —C($R^{4d}$)($R^{4d'}$)—, where $R^{4d}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)$alkyl)$_2$N—C(O)—, $(C_1-C_6)$alkylamino-, $((C_1-C_4)$alkyl)$_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a partially or fully saturated 3-6 membered heterocycle, and a partially or fully saturated carbocyclic ring, where the moiety is optionally substituted, and $R^{4d'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)$alkyl)$_2$N—C(O)—, aryl, heteroaryl, a partially or fully saturated 3-6 membered heterocycle, and a partially or fully saturated carbocyclic ring, where the moiety is optionally substituted, or $R^{4d}$ and $R^{4d'}$ taken together form a partially or fully saturated, 3-6 membered heterocyclic ring, a 5-6 membered lactone ring, or a 4-6 membered lactam ring, where the heterocyclic ring, the lactone ring and the lactam ring are optionally substituted and the lactone ring and the lactam ring optionally contain an additional heteroatom selected from oxygen, nitrogen or sulfur, or Y is —$NR^{4d}$—, where $R^{4d}$ is a hydrogen or a chemical moiety selected from the group consisting of $(C_1-C_6)$alkyl, $(C_3-C_6)$cycloalkyl, $(C_1-C_3)$alkylsulfonyl-, $(C_1-C_3)$alkylaminosulfonyl-, di$(C_1-C_3)$alkylaminosulfonyl-, acyl, $(C_1-C_6)$alkyl-O—C(O)—, aryl, and heteroaryl, where the moiety is optionally substituted;

Z is a bond, —$CH_2CH_2$—, or —C($R^{4e}$)($R^{4e'}$)—, where $R^{4e}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)$alkyl)$_2$N—C(O)—, $(C_1-C_6)$alkylamino-, $((C_1-C_4)$alkyl)$_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a partially or fully saturated 3-6 membered heterocycle, and a partially or fully saturated carbocyclic ring, where the moiety is optionally substituted, or $R^{4e}$ taken together with $R^{4b}$, $R^{4b'}$, $R^{4c}$, or $R^{4c'}$ forms a bond, a methylene bridge, or an ethylene bridge, and $R^{4e'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)$alkyl)$_2$N—C(O)—, aryl, heteroaryl, a partially or fully saturated 3-6 membered heterocycle, and a partially or fully saturated carbocyclic ring, where the moiety is optionally substituted, or $R^{4e'}$ taken together with $R^{4b}$, $R^{4b'}$, $R^{4c}$, or $R^{4c'}$ forms a bond, a methylene bridge, or an ethylene bridge; and $R^{4f}$ and $R^{4f'}$ are each independently hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)$alkyl)$_2$N—C(O)—, aryl, heteroaryl, a partially or fully saturated 3-6 membered heterocycle, and a partially or fully saturated carbocyclic ring, where the moiety is optionally substituted, or $R^{4f}$ or $R^{4f'}$ taken together with $R^{4b}$, $R^{4b'}$, $R^{4c}$, or $R^{4c'}$ forms a bond, a methylene bridge, or an ethylene bridge;

a pharmaceutically acceptable salt thereof, a prodrug of the compound or the salt, or a solvate or hydrate of the compound, the salt or the prodrug.

Preferably, $R^{4b}$ is hydrogen, an optionally substituted $(C_1-C_3)$alkyl, or taken together with $R^{4e}$, $R^{4e'}$, $R^{4f}$, or $R^{4f'}$ forms a bond, a methylene bridge, or an ethylene bridge; $R^{4b'}$ is hydrogen, an optionally substituted $(C_1-C_3)$alkyl, or taken together with $R^{4e}$, $R^{4e'}$, $R^{4f}$, or $R^{4f'}$ forms a bond, a methylene bridge, or an ethylene bridge; $R^{4f}$ is hydrogen, an optionally substituted $(C_1-C_3)$alkyl, or taken together with $R^{4b}$, $R^{4b'}$, $R^{4c}$, or $R^{4c'}$ forms a bond, a methylene bridge, or an ethylene bridge; and $R^{4f'}$ is hydrogen, an optionally substituted $(C_1-C_3)$alkyl, or taken together with $R^{4b}$, $R^{4b'}$, $R^{4c}$, or $R^{4c'}$ forms a bond, a methylene bridge, or an ethylene bridge, and even more preferably, $R^{4b}$, $R^{4b'}$, $R^{4f}$, and $R^{4f'}$ are all hydrogen.

When Y is —$NR^{4d''}$—, then $R^{4d''}$ is preferably a hydrogen or a chemical moiety selected from the group consisting of $(C_1-C_6)$alkyl, $(C_3-C_6)$cycloalkyl, $(C_1-C_3)$alkylsulfonyl, $(C_1-C_3)$alkylaminosulfonyl, di$(C_1-C_3)$alkylaminosulfonyl, acyl, $(C_1-C_6)$alkyl-O—C(O)—, aryl, and heteroaryl, where the moiety is optionally substituted (more preferably, $R^{4d''}$ is a hydrogen or a chemical moiety selected from the group consisting of $(C_1-C_3)$alkylsulfonyl, $(C_1-C_3)$alkylaminosulfonyl, di$(C_1-C_3)$alkylaminosulfonyl, acyl, $(C_1-C_6)$alkyl-O—C(O)—, and heteroaryl, where the moiety is optionally substituted (preferably the $(C_1-C_3)$alkylsulfonyl, $(C_1-C_3)$alkylaminosulfonyl, di$(C_1-C_3)$alkylaminosulfonyl, acyl, and $(C_1-C_6)$alkyl-O—C(O)— are optionally substituted with 1-3 fluorines, and the heteroaryl is optionally substituted with 1 to 2 substituents independently selected from the group consisting of chloro, fluoro, $(C_1-C_3)$alkoxy, $(C_1-C_3)$alkyl, and fluoro-substituted $(C_1-C_3)$alkyl);

X is —C($R^{4c}$)($R^{4c'}$)—, where $R^{4c}$ and $R^{4c'}$ are each independently hydrogen, $H_2NC(O)$—, an optionally substituted $(C_1-C_6)$alkyl, $(C_1-C_4)$alkyl-NH—C(O)—, or $((C_1-C_4)$alkyl)$_2$N—C(O)—, or either $R^{4c}$ or $R^{4c'}$ taken together with $R^{4e}$, $R^{4e'}$, $R^{4f}$, or $R^{4f'}$ forms a bond, a methylene bridge or an ethylene bridge; and Z is —C($R^{4e}$)($R^{4e'}$)—, where $R^{4e}$ and $R^{4e'}$ are each independently hydrogen, $H_2NC(O)$—, an optionally substituted $(C_1-C_6)$alkyl, $(C_1-C_4)$alkyl-NH—C(O)—, or $((C_1-C_4)$alkyl)$_2$N—C(O)—, or either $R^{4e}$ or $R^{4e'}$ taken together with $R^{4b}$, $R^{4b'}$, $R^{4c}$, or $R^{4c'}$ forms a bond, a methylene bridge or an ethylene bridge.

When Y is —C($R^{4d}$)($R^{4d'}$)—, then $R^{4d}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)$alkyl)$_2$N—C(O)—, $(C_1-C_6)$alkylamino-, $((C_1-C_4)$alkyl)$_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a partially or fully saturated 3-6 membered heterocycle, and a partially or fully saturated carbocyclic ring, where the moiety is optionally substituted (preferably, $R^{4d}$ is amino, $(C_1-C_6)$alkylamino, di$(C_1-C_4)$alkylamino, $(C_3-C_6)$cycloalkylamino, acylamino, aryl$(C_1-C_4)$alkylamino-, or heteroaryl$(C_1-C_4)$alkylamino, more preferably, $R^{4d}$ is amino, $(C_1-C_6)$alkylamino, di$(C_1-C_4)$alkylamino, $(C_3-C_6)$cycloalkylamino), and $R^{4d'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $((C_1-C_4)$alkyl$)_2$N—C(O)—, aryl, heteroaryl, a partially or fully saturated 3-6 membered heterocycle, and a partially or fully saturated carbocyclic ring, where the moiety is optionally substituted (preferably, $R^{4d'}$ is $(C_1-C_6)$alkyl, $H_2NC(O)$—, $(C_1-C_4)$alkyl-NH—C(O)—, or $((C_1-C_4)$alkyl$)_2$N—C(O)—, or aryl, more preferably, $R^{4d'}$ is $H_2NC(O)$—, $(C_1-C_4)$alkyl-NH—C(O)—, or $((C_1-C_4)$alkyl$)_2$N—C(O)—), or $R^{4d}$ and $R^{4d'}$ taken together form a partially or fully saturated, 3-6 membered heterocyclic ring, a 5-6 membered lactone ring, or a 4-6 membered lactam ring, where the heterocyclic ring, the lactone ring and the lactam ring are optionally substituted and the lactone ring and the lactam ring optionally contain an additional heteroatom selected from oxygen, nitrogen or sulfur;

X is a bond or —C($R^{4c}$)($R^{4c'}$)—, where $R^{4c}$ and $R^{4c'}$ are each hydrogen; and Z is a bond or —C($R^{4e}$)($R^{4e'}$)—, where $R^{4e}$ and $R^{4e'}$ are each hydrogen.

Preferred compounds include: 3-(4-chlorophenyl)-2-(2,4-dichlorophenyl)-7-(4-methylpiperazin-1-yl)-2H-pyrazolo[4,3-d]pyrimidine; 3-(4-chlorophenyl)-2-(2-chlorophenyl)-7-(5-cyclopentyl-2,5-diaza-bicyclo[2.2.1]hept-2-yl)-2H-pyrazolo[4,3-d]pyrimidine; 5-[3-(4-chlorophenyl)-2-(2-chlorophenyl)-2H-pyrazolo[4,3-d]pyrimidin-7-yl]-2,5-diazabicyclo[2.2.1]heptane-2-carboxylic acid tert-butyl ester; 5-[3-(4-chlorophenyl)-2-(2,4-dichlorophenyl)-2H-pyrazolo[4,3-d]pyrimidin-7-yl]-2,5-diazabicyclo[2.2.1]heptane-2-carboxylic acid tert-butyl ester; 3-(4-chlorophenyl)-2-(2-chlorophenyl)-7-(5-methanesulfonyl-2,5-diazabicyclo[2.2.1]hept-2-yl)-2H-pyrazolo[4,3-d]pyrimidine; 3-(4-chlorophenyl)-2-(2-chlorophenyl)-7-[5-(propane-2-sulfonyl)-2,5-diazabicyclo[2.2.1]hept-2-yl]-2H-pyrazolo[4,3-d]pyrimidine; 3-(4-chlorophenyl)-2-(2-chlorophenyl)-7[5-(2,2,2-trifluoroethanesulfonyl)-2,5-diazabicyclo[2.2.1]hept-2-yl]-2H-pyrazolo[4,3-d]pyrimidine; 5-[3-(4-chlorophenyl)-2-2-sulfonic acid dimethylamide; 4-[3-(4-chlorophenyl)-2-(2-chlorophenyl)-2H-pyrazolo[4,3-d]pyrimidin-7-yl]-piperazine-1-sulfonic acid dimethylamide; 3-(4-chlorophenyl)-2-(2-chlorophenyl)-7-(4-ethanesulfonylpiperazin-1-yl)-2H-pyrazolo[4,3-d]pyrimidine; 3-(4-chlorophenyl)-2-(2-chlorophenyl)-7-(4-(2,2,2-trifluoroethane)sulfonylpiperazin-1-yl)-2H-pyrazolo[4,3-d]pyrimidine; 3-(4-chlorophenyl)-2-(2-chlorophenyl)-7-(4-methanesulfonylpiperazin-1-yl)-2H-pyrazolo[4,3-d]pyrimidine; 3-(4-chlorophenyl)-2-(2-chlorophenyl)-7-(4-(propane-2-sulfonyl)piperazin-1-yl)-2H-pyrazolo[4,3-d]pyrimidine; and 3-(4-chlorophenyl)-2-(2,4-dichlorophenyl)-7-(4-methylpiperazin-1-yl)-2H-pyrazolo[3,4-c]pyridine; a pharmaceutically acceptable salt thereof, or a solvate or hydrate of said compound or said salt.

In another preferred embodiment, a compound of Formula (I) or (II) is provided where Y is —C($R^{4d}$)($R^{4d'}$)—, $R^{4b}$, $R^{4b'}$, $R^{4f}$, and $R^{4f'}$ are all hydrogen; $R^{4d}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)$alkyl$)_2$N—C(O)—, $(C_1-C_6)$alkylamino-, $((C_1-C_4)$alkyl$)_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a 3-6 membered partially or fully saturated heterocycle, and a partially or fully saturated carbocyclic ring, where said moiety is optionally substituted with one or more substituents; and $R^{4d'}$ is hydrogen, $H_2NC(O)$—, or a chemical moiety selected from the group consisting of $(C_1-C_6)$alkyl, acyl, $(C_1-C_3)$ alkyl-O—C(O)—, $(C_1-C_4)$alkyl-NH—C(O)—, $(C_1-C_4)$alkyl$)_2$N—C(O)—, aryl, heteroaryl, a 3-6 membered partially or fully saturated heterocycle, and a partially or fully saturated carbocyclic ring, where said moiety is optionally substituted with one or more substituents.

In this embodiment, X is preferably —C($R^{4c}$)($R^{4c'}$)—, where $R^{4c}$ and $R^{4c'}$ are each independently hydrogen or an optionally substituted $(C_1-C_6)$alkyl, or either $R^{4c}$ or $R^{4c'}$ taken together with $R^{4e}$ or $R^{4e'}$, forms a bond, a methylene bridge or an ethylene bridge (preferably, $R^4$ and $R^{4c'}$ are each hydrogen or either $R^{4c}$ or $R^{4c'}$ taken together with $R^{4e}$ or $R^{43'}$ forms a bond); and Z is preferably —C($R^{4e}$)($R^{4e'}$)—, where $R^{4e}$, and $R^{4e'}$ are each independently hydrogen or an optionally substituted $(C_1-C_6)$alkyl, or either $R^{4e}$ or $R^{4e'}$ taken together with $R^{4c}$ or $R^{4c'}$ forms a bond, a methylene bridge or an ethylene bridge (preferably, $R^{4e}$ and $R^{4e'}$ are each hydrogen or either $R^{4e}$ or $R^{4e'}$ taken together with $R^4C$ or $R^{4c'}$ forms a bond). Preferably, $R^{4d}$ is amino, $(C_1-C_6)$alkylamino, di$(C_1-C_4)$alkylamino, azetidinyl, piperidinyl, pyrrolidinyl, morpholinyl, $(C_3-C_6)$cycloalkylamino, acylamino, aryl$(C_1-C_4)$alkylamino-, or heteroaryl$(C_1-C_4)$alkylamino-; and $R^{4d'}$ is $(C_1-C_6)$alkyl, $H_2NC(O)$—, $(C_1-C_4)$alkyl-NH—C(O)—, $((C_1-C_4)$alkyl$)_2$N—C(O)—, or aryl. More preferably, $R^{4d}$ is amino, $(C_1-C_6)$alkylamino, di$(C_1-C_4)$alkylamino, $(C_3-C_6)$cycloalkylamino, piperidinyl, pyrrolidinyl, or morpholinyl; and $R^{4d'}$ is $H_2NC(O)$—, $(C_1-C_4)$alkyl-NH—C(O)—, or $((C_1-C_4)$alkyl$)_2$N—C(O)—.

In yet another preferred embodiment, a compound of Formula (I) or (II) is provided where Y is C($R^{4d}$)($R^{4d'}$), $R^{4b}$, $R^{4b'}$, $R^{4f}$, and $R^{4f'}$ are all hydrogen; and $R^{4d}$ and $R^{4d'}$ taken together form a partially or fully saturated 3-6 membered heterocyclic ring, a 5-6 membered lactone ring, or a 4-6 membered lactam ring, where the heterocyclic ring, the lactone ring and the lactam ring are optionally substituted with one or more substituents and the lactone ring or the lactam ring optionally contains an additional heteroatom selected from oxygen, nitrogen or sulfur (preferably, $R^{4d}$ and $R^{4d'}$ taken together form a 5-6 membered lactam ring, where the lactam ring is optionally substituted and optionally contains an additional heteroatom selected from nitrogen or oxygen). In this embodiment, X is preferably a bond, —CH$_2$CH$_2$— or —C($R^{4c}$)($R^{4c'}$)—, where $R^{4c}$ and $R^{4c'}$ are each independently hydrogen or an optionally substituted $(C_1-C_6)$alkyl, or either $R^{4c}$ or $R^{4c'}$ taken together with $R^{4e}$ or $R^{4e'}$ forms a bond, a methylene bridge or an ethylene bridge (more preferably, X is a bond or —C($R^{4c}$)($R^{4c'}$)—, where $R^{4c}$ and $R^{4c'}$ are each hydrogen); and Z is preferably a bond, —CH$_2$CH$_2$— or —C($R^{4e}$)($R^{4e'}$)—, where $R^{4e}$ and $R^{4e'}$ are each independently hydrogen or an optionally substituted $(C_1-C_6)$alkyl, or either $R^{4e}$ or $R^{4e'}$ taken together with $R^{4c}$ or $R^{4c'}$ forms a bond, a methylene bridge or an ethylene bridge (more preferably, Z is a bond or —C($R^{4e}$)($R^{4e'}$)—, where $R^{4e}$ and $R^{4e'}$ are each hydrogen).

Preferred compounds include: 1-[3-(4-chlorophenyl)-2-(2-chlorophenyl)-2H-pyrazolo[4,3-d]pyrimidin-7-yl]-3-ethylaminoazetidine-3-carboxylic acid amide; 1-[3-(4-chlorophenyl)-2-(2-chlorophenyl)-2H-pyrazolo[4,3-d]pyrimidin-7-yl]-3-methylaminoazetidine-3-carboxylic acid amide; 1-[3-(4-chlorophenyl)-2-(2-chlorophenyl)-2H-pyrazolo[4,3-d]pyrimidin-7-yl]-3-(2-propylamino)azetidine-3-carboxylic acid amide; 1-[3-(4-chlorophenyl)-2-(2-chlorophenyl)-2H-pyrazolo[4,3-d]pyrimidin-7-yl]-4-isopropylaminopiperidine-4-carboxylic acid amide; 1-[3-(4-chlorophenyl)-2-(2-chlorophenyl)-2H-pyrazolo[4,3-d]pyrimidin-7-yl]-4-ethylaminopiperidine-4-carboxylic acid amide; 1'-[3-(4-chlorophenyl)-2-(2-chlorophenyl)-2H-pyrazolo[4,3-d]pyrimidin-7-yl]-[1,4']bipiperidinyl-4'-carboxylic acid amide; 8-[3-(4-chlorophenyl)-2-(2-chlorophenyl)-2H-pyrazolo[4,3-d]pyrimidin-7-yl]-3-pyrrolidin-1-yl-8-aza-bicyclo[3.2.1]octane-3-carboxylic acid amide; 1'-[3-(4-chlorophenyl)-2-(2-chlorophenyl)-2H-pyrazolo[4,3-d]pyrimidin-7-yl]-[1,3']bipyrrolidinyl-3'-carboxylic acid amide; 1-[3-(4-chlorophenyl)-2-(2-chlorophenyl)-2H-pyrazolo[4,3-d]pyrimidin-7-yl]-3-morpholin-4-yl-pyrrolidine-3-carboxylic acid amide; 1-[3-(4-chlorophenyl)-2-(2-chlorophenyl)-2H-pyrazolo[4,3-d]pyrimidin-7-yl]-3-isopropylaminopyrrolidine-3-carboxylic acid amide; 1-[3-(4-chlorophenyl)-2-(2,4-dichlorophenyl)-2H-pyrazolo[3,4-c]pyridin-7-yl]-4-isopropylaminopiperidine-4-carboxylic acid amide; 1-[3-(4-chlorophenyl)-2-(2,4-dichlorophenyl)-2H-pyrazolo[3,4-c]pyridin-7-yl]4-ethylaminopiperidine-4-carboxylic acid amide; and 1'-[3-(4-chlorophenyl)-2-(2,4-dichlorophenyl)-2H-pyrazolo[3,4-c]pyridin-7-yl]-[1,4']bipiperidinyl-4'-carboxylic acid amide a pharmaceutically acceptable salt thereof or a solvate or hydrate of said compound or said salt.

More preferred compounds include: 1-[3-(4-chlorophenyl)-2-(2-chlorophenyl)-2H-pyrazolo[4,3-d]pyrimidin-7-yl] 4-isopropylaminopiperidine-4-carboxylic acid amide; 1-[3-(4-chlorophenyl)-2-(2-chlorophenyl)-2H-pyrazolo[4,3-d]pyrimidin-7-yl]4-ethylaminopiperidine-4-carboxylic acid amide; 1-[3-(4-chlorophenyl)-2-(2-chlorophenyl)-2H-pyrazolo[4,3-d]pyrimidin-7-yl]-3-isopropylaminopyrrolidine-3-carboxylic acid amide; and 1'-[3-(4-chlorophenyl)-2-(2-chlorophenyl)-2H-pyrazolo[4,3-d]pyrimidin-7-yl]-[1,4']bipiperidinyl-4'-carboxylic acid amide; a pharmaceutically acceptable salt thereof or a solvate or hydrate of said compound or said salt.

Another set of preferred compounds include: 1-[3-(4-chlorophenyl)-2-(2-chlorophenyl)-2H-pyrazolo[4,3-d]pyrimidin-7-yl]-4-phenylpiperidin-4-ol; 1-[3-(4-chlorophenyl)-2-(2-chlorophenyl)-2H-pyrazolo[4,3-d]pyrimidin-7-yl]4-ethylpiperidin-4-ol; 1-[3-(4-chlorophenyl)-2-(2-chlorophenyl)-2H-pyrazolo[4,3-d]pyrimidin-7-yl]-4-isopropylpiperidin-4-ol; 1-[3-(4-chlorophenyl)-2-(2-chlorophenyl)-2H-pyrazolo[4,3-d]pyrimidin-7-yl]-4-sec-butylpiperidin-4-ol; 1-[3-(4-chlorophenyl)-2-(2-chlorophenyl)-2H-pyrazolo[4,3-d]pyrimidin-7-yl]-4-methylpiperidin-4-ol; 8-[3-(4-chlorophenyl)-2-(2-chlorophenyl)-2H-pyrazolo[4,3-d]pyrimidin-7-yl]-3-ethyl-8-azabicyclo[3.2.1]octan-3-ol; 8-[3-(4-chlorophenyl)-2-(2-chlorophenyl)-2H-pyrazolo[4,3-d]pyrimidin-7-yl]-3-sec-butyl-8-azabicyclo[3.2.1]octan-3-ol; 8-[3-(4-chlorophenyl)-2-(2-chlorophenyl)-2H-pyrazolo[4,3-d]pyrimidin-7-yl]-3-isopropyl-8-azabicyclo[3.2.1]octan-3-ol; 1-[3-(4-chlorophenyl)-2-(2-chlorophenyl)-2H-pyrazolo[4,3-d]pyrimidin-7-yl]-3-isobutyl-pyrrolidin-3-ol; 1-[3-(4-chlorophenyl)-2-(2-chlorophenyl)-2H-pyrazolo[4,3-d]pyrimidin-7-yl]-3-isopropyl-pyrrolidin-3-ol; {8-[3-(4-chlorophenyl)-2-(2-chlorophenyl)-2H-pyrazolo[4,3-d]pyrimidin-7-yl]-8-aza-bicyclo[3.2.1]oct-3-yl -ethyl-amine; 3-(4-chlorophenyl)-2-(2-chlorophenyl)-7-(3-pyrrolidin-1-yl-8-aza-bicyclo[3.2.1]oct-8-yl)-2H-pyrazolo[4,3-d]pyrimidine; 7-(3-bromo-8-azabicyclo[3.2.1]oct-8-yl)-3-(4-chlorophenyl)-2-(2-chlorophenyl)-2H-pyrazolo[4,3-d]pyrimidine; 7-(3-bromo-8-azabicyclo[3.2.1]oct-8-yl)-3-(4-chlorophenyl)-2-(2,4-dichlorophenyl)-2H-pyrazolo[4,3-d]pyrimidine; 3-(4-chlorophenyl)-2-(2-chlorophenyl)-7-(4-methylpiperidin-1-yl)-2H-pyrazolo[4,3-d]pyrimidine; 3-(4-chlorophenyl)-2-(2-chlorophenyl)-7-(3-hydroxypiperidin-1-yl)-2H-pyrazolo[4,3-d]pyrimidine; 1-[3-(4-chlorophenyl)-2-(2-chlorophenyl)-2H-pyrazolo[4,3-d]pyrimidin-7-yl]-4-(3-methoxyphenyl)-piperidine-4-carbonitrile; 1-[3-(4-chlorophenyl)-2-(2-chlorophenyl)-2H-pyrazolo[4,3-d]pyrimidin-7-yl]-4-phenylpiperidine-4-carbonitrile; 1-{1-[3-(4-chlorophenyl)-2-(2-chlorophenyl)-2H-pyrazolo[4,3-d]pyrimidin-7-yl]-4-phenylpiperidin-4-yl -propan-1-one; 1'-[3-(4-chlorophenyl)-2-(2-chlorophenyl)-2H-pyrazolo[4,3-d]pyrimidin-7-yl]-2',3',5',6'-tetrahydro-1'H-[3,4']bipyridinyl-4'-carbonitrile; 1-[3-(4-chlorophenyl)-2-(2-chlorophenyl)-2H-pyrazolo[4,3-d]pyrimidin-7-yl]-2,3,5,6-tetrahydro-1H-[4,4']bipyridinyl-4-carbonitrile; 1-[3-(4-chlorophenyl)-2-(2-chlorophenyl)-2H-pyrazolo[4,3-d]pyrimidin-7-yl]-2,3,5,6-tetrahydro-1H-[2,4']bipyridinyl-4-carbonitrile; {1-[3-(4-chlorophenyl)-2-(2-chlorophenyl)-2H-pyrazolo[4,3-d]pyrimidin-7-yl]4-phenylpiperidin-4-yl -morpholin-4-yl-methanone; benzyl-{8-[3-(4-chlorophenyl)-2-(2-chlorophenyl)-2H-pyrazolo[4,3-d]pyrimidin-7-yl]-8-aza-bicyclo[3.2.1]oct-3-yl -amine; {1-[3-(4-chlorophenyl)-2-(2-chlorophenyl)-2H-pyrazolo[4,3-d]pyrimidin-7-yl]-pyrrolidin-3-yl -methylcarbamic acid tert-butyl ester; {1-[3-(4-chlorophenyl)-2-(2-chlorophenyl)-2H-pyrazolo[4,3-d]pyrimidin-7-yl]-pyrrolidin-3-yl -carbamic acid tert-butyl ester; N-{1-[3-(4-chlorophenyl)-2-(2-chlorophenyl)-2H-pyrazolo[4,3-d]pyrimidin-7-yl]-pyrrolidin-3-yl}-N-methylacetamide; and {1-[3-(4-chlorophenyl)-2-(2-chlorophenyl)-2H-pyrazolo[4,3-d]pyrimidin-7-yl]-pyrrolidin-3-yl -dimethylamine; a pharmaceutically acceptable salt thereof, or a solvate or hydrate of said compound or said salt.

Yet another set of preferred compounds include: 2-[3-(4-chlorophenyl)-2-(2-chlorophenyl)-2H-pyrazolo[4,3-d]pyrimidin-7-yl]-5-methyl-2,5,7-triaza-spiro[3.4]octan-8-one; 8-[3-(4-chloro-phenyl)-2-(2-chlorophenyl)-2H-pyrazolo[4,3-d]pyrimidin-7-yl]-1-isopropyl-1,3,8-triaza-spiro[4.5]decan-4-one; 3-(4-chlorophenyl)-2-(2-chlorophenyl)-7-(1,4-dioxa-8-aza-spiro[4.5]dec-8-yl)-2H-pyrazolo[4,3-d]pyrimidine; 3-[3-(4-chlorophenyl)-2-(2-chlorophenyl)-2H-pyrazolo[4,3-d]pyrimidin-7-yl]-1-spiro[(5-methoxy)tetrahydronaphthalene-1,4'-piperidine]; 3-[3-(4-chlorophenyl)-2-(2-chlorophenyl)-2H-pyrazolo[4,3-d]pyrimidin-7-yl]-1-spiro[(6-methoxy)tetrahydronaphthalene-1,4'-piperidine]; and 3-[3-(4-chlorophenyl)-2-(2-chlorophenyl)-2H-pyrazolo[4,3-d]pyrimidin-7-yl]-1-spiro[indane-1,4'-piperidine]; a pharmaceutically acceptable salt thereof or a solvate or hydrate of said compound or said salt.

Another preferred compound of the present invention is a compound of Formula (I) or (II) where $R^4$ is a group of Formula (IB) where where $R^{4a}$ is as defined above, $R^{4b}$ is hydrogen, cyano, hydroxy, amino, $H_2NC(O)$—, or a chemical moiety selected from the group consisting of $(C_1-C_6)$ alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)$alkyl)$_2$N—C(O)—, $(C_1-C_6)$alkylamino-, $((C_1-C_4)$alkyl)$_2$amino-, $(C_3-C_6)$ cycloalkylamino-, acylamino-, aryl$(C_1-C_4)$alkylamino-, heteroaryl$(C_1-C_4)$alkylamino-, aryl, heteroaryl, a partially or fully saturated 3-6 membered heterocycle, and a partially or fully saturated carbocyclic ring, where the moiety is optionally substituted with one or more substituents, $R^{4b'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)$alkyl)$_2$N—C(O)—, aryl, heteroaryl, a partially or fully saturated 3-6 membered heterocycle, and a partially or fully saturated carbocyclic ring, where the moiety is optionally substituted with one or more substituents, or $R^{4b}$ or $R^{4b'}$ taken together with $R^{4e}$, $R^{4e'}$, $R^{4f}$, or $R^{4fo}$ forms a bond, a methylene bridge, or an ethylene bridge;

X is a bond, —$CH_2CH_2$— or —$C(R^{4c})(R^{4c'})$—, where $R^{4c}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)$alkyl)$_2$N—C(O)—, $(C_1-C_6)$alkylamino-, $((C_1-C_4)$alkyl)$_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a partially or fully saturated 3-6 membered heterocycle, and a partially or fully saturated carbocyclic ring, where the moiety is optionally substituted with one or more substituents, or $R^{4c}$ taken together with $R^{4e}$, $R^{4e'}$, $R^{4f}$, or $R^{4f'}$ forms a bond, a methylene bridge, or an ethylene bridge, and $R^{4c'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)$alkyl)$_2$N—C(O)—, aryl, heteroaryl, a partially or fully saturated 3-6 membered heterocycle, and a partially or fully saturated carbocyclic ring, where the moiety is optionally substituted with one or more substituents, or $R^{4c'}$ taken together with $R^{4e}$, $R^{4e'}$, $R^{4f}$, or $R^{4f'}$ forms a bond, a methylene bridge, or an ethylene bridge (preferably, X is a bond, —CH$_2$CH$_2$— or —C(R$^{4c}$)(R$^{4c'}$)—, where $R^{4c}$ and $R^{4c'}$ are each independently hydrogen or $(C_1-C_6)$alkyl);

Y is oxygen, sulfur, —C(O)—, or —C(R$^{4d}$)(R$^{4d'}$)—, where $R^{4d}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)$alkyl)$_2$N—C(O)—, $(C_1-C_6)$alkylamino-, $((C_1-C_4)$alkyl)$_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a partially or fully saturated 3-6 membered heterocycle, and a partially or fully saturated carbocyclic ring, where the moiety is optionally substituted with one or more substituents, and $R^{4d'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)$alkyl)$_2$N—C(O)—, aryl, heteroaryl, a partially or fully saturated 3-6 membered heterocycle, and a partially or fully saturated carbocyclic ring, where the moiety is optionally substituted with one or more substituents, or $R^{4d}$ and $R^{4d'}$ taken together form a partially or fully saturated, 3-6 membered heterocyclic ring, a 5-6 membered lactone ring, or a 4-6 membered lactam ring, where the heterocyclic ring, the lactone ring and the lactam ring are optionally substituted with one or more substituents and the lactone ring and the lactam ring optionally contain an additional heteroatom selected from oxygen, nitrogen or sulfur, or Y is —NR$^{4d''}$—, where $R^{4d''}$ is a hydrogen or a chemical moiety selected from the group consisting of $(C_1-C_6)$alkyl, $(C_3-C_6)$cycloalkyl, $(C_1-C_3)$alkylsulfonyl-, $(C_1-C_3)$alkylaminosulfonyl-, di$(C_1-C_3)$alkylaminosulfonyl-, acyl, $(C_1-C_6)$alkyl-O—C(O)—, aryl, and heteroaryl, where the moiety is optionally substituted with one or more substituents (preferably, Y is —NR$^{4d''}$—, where $R^{4d''}$ is a hydrogen or a chemical moiety selected from the group consisting of $(C_1-C_6)$alkyl, $(C_3-C_6)$cycloalkyl, $(C_1-C_3)$alkylsulfonyl-, $(C_1-C_3)$alkylaminosulfonyl-, di$(C_1-C_3)$alkylaminosulfonyl-, acyl, $(C_1-C_6)$alkyl-O—C(O)—, aryl, and heteroaryl, where the moiety is optionally substituted with one or more substituents);

Z is a bond, —CH$_2$CH$_2$—, or —C(R$^{4e}$)(R$^{4e'}$)—, where $R^{4e}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)$alkyl)$_2$N—C(O)—, $(C_1-C_6)$alkylamino-, $((C_1-C_4)$alkyl)$_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a partially or fully saturated 3-6 membered heterocycle, and a partially or fully saturated carbocyclic ring, where the moiety is optionally substituted with one or more substituents, or $R^{4e}$ taken together with $R^{4b}$, $R^{4b'}$, $R^{4c}$, or $R^{4c'}$ forms a bond, a methylene bridge, or an ethylene bridge, and $R^{4e'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)$alkyl)$_2$N—C(O)—, aryl, heteroaryl, a partially or fully saturated 3-6 membered heterocycle, and a partially or fully saturated carbocyclic ring, where the moiety is optionally substituted with one or more substituents, or $R^{4e'}$ taken together with $R^{4b}$, $R^{4b'}$, $R^{4c}$, or $R^{4c'}$ forms a bond, a methylene bridge, or an ethylene bridge (preferably, Z is a bond, —CH$_2$CH$_2$— or —C(R$^{4c}$)(R$^{4c'}$)—, where $R^{4c}$ and $R^{4c'}$ are each independently hydrogen or $(C_1-C_6)$alkyl);

$R^{4f}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)$alkyl)$_2$N—C(O)—, $(C_1-C_6)$alkylamino-, $((C_1-C_4)$alkyl)$_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a partially or fully saturated 3-6 membered heterocycle, and a partially or fully saturated carbocyclic ring, where the moiety is optionally substituted with one or more substituents; and $R^{4f'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)$alkyl)$_2$N—C(O)—, aryl, heteroaryl, a partially or fully saturated 3-6 membered heterocycle, and a partially or fully saturated carbocyclic ring, where the moiety is optionally substituted with one or more substituents, or $R^{4f}$ or $R^{4f'}$ taken together with $R^{4b}$, $R^{4b'}$, $R^{4c}$, or $R^{4c'}$ forms a bond, a methylene bridge, or an ethylene bridge;

a pharmaceutically acceptable salt thereof, a prodrug of the compound or the salt, or a solvate or hydrate of the compound, the salt or the prodrug.

Preferred compounds include: 7-(1-benzhydrylazetidin-3-yloxy)-3-(4-chlorophenyl)-2-(2-chlorophenyl)-2H-pyrazolo[4,3-d]pyrimidine; and 7-(1-benzylpyrrolidin-3-yloxy)-3-(4-chlorophenyl)-2-(2-chlorophenyl)-2H-pyrazolo[4,3-d]pyrimidine; a pharmaceutically acceptable salt thereof or a solvate or hydrate of said compound or said salt.

Yet another preferred compound of the present invention is a compound of Formula (I) or (II) where $R^4$ is a group of Formula (IC), where where $R^5$ and $R^6$ are each independently hydrogen, aryl, or $(C_1-C_4)$alkyl, and $R^7$ is an optionally substituted $(C_1-C_4)$alkyl-, or an optionally substituted 4-6 membered partially or fully saturated heterocylic ring containing 1 to 2 heteroatoms independently selected from oxygen, sulfur or nitrogen, or $R^5$ and $R^6$ or $R^5$ and $R^7$ taken together form a 5-6 membered lactone, 4-6 membered lactam, or a 4-6 membered partially or fully saturated heterocycle containing 1 to 2 heteroatoms independently selected from oxygen, sulfur or nitrogen, where said lactone, said lactam and said heterocycle are optionally substituted with one or more substituents; a pharmaceutically acceptable salt thereof, or a solvate or hydrate of said compound or said salt.

Preferred compounds include: 2-(2-chlorophenyl)-7-isopropoxy-3-(4-trifluoromethylphenyl)-2H-pyrazolo[4,3-d]

pyrimidine; 2-(2-chloro-4-methylphenyl)-5-methyl-7-(2,2,2-trifluoroethoxy)-3-(4-trifluoromethylphenyl)-2H-pyrazolo[4,3-d]pyrimidine; 2-(2-chlorophenyl)-3-(4-methoxyphenyl)-5-methyl-7-(2,2,2-trifluoroethoxy)-2H-pyrazolo[4,3-d]pyrimidine; 2-(2-bromophenyl)-3-(4-chlorophenyl)-7-(2,2-difluoropropoxy)-5-methyl-2H-pyrazolo[4,3-d]pyrimidine; 2-(2-bromophenyl)-3-(4-methoxyphenyl)-5-methyl-7-(2,2,2-trifluoroethoxy)-2H-pyrazolo[4,3-d]pyrimidine; 2-[3-(4-chlorophenyl)-7-(2,2-difluoropropoxy)-5-methylpyrazolo[4,3-d]pyrimidin-2-yl]-benzonitrile; 2-(2-bromophenyl)-7-(2,2-difluoropropoxy)-3-(4-methoxyphenyl)-5-methyl-2H-pyrazolo[4,3-d]pyrimidine; 3-(4-bromophenyl)-2-(2-chlorophenyl)-7-(2,2-difluoropropoxy)-5-methyl-2H-pyrazolo[4,3-d]pyrimidine; 2-(2-chlorophenyl)-7-(2,2-difluoropropoxy)-3-(4-methoxyphenyl)-5-methyl-2H-pyrazolo[4,3-d]pyrimidine; 3-(4-chlorophenyl)-2-(2-chlorophenyl)-7-isopropoxy-2H-pyrazolo[4,3-d]pyrimidine; 3-(4-chlorophenyl)-2-(2-chlorophenyl)-7-(2,2,2-trifluoroethoxy)-2H-pyrazolo[4,3-d]pyrimidine; 3-(4-chlorophenyl)-2-(2-chlorophenyl)-7-methoxy-2H-pyrazolo[4,3-d]pyrimidine; 3-(4-chlorophenyl)-2-(2-chlorophenyl)-7-ethoxy-2H-pyrazolo[4,3-d]pyrimidine; 3-(4-chlorophenyl)-2-(2-chlorophenyl)-7-propoxy-2H-pyrazolo[4,3-d]pyrimidine; 7-butoxy-3-(4-chlorophenyl)-2-(2-chlorophenyl)-2H-pyrazolo[4,3-d]pyrimidine; 3-(4-chlorophenyl)-2-(2-chlorophenyl)-5-ethyl-7-(2,2,2-trifluoroethoxy)-2H-pyrazolo[4,3-d]pyrimidine; 3-(4-chlorophenyl)-2-(2-chlorophenyl)-5-isopropyl-7-(2,2,2-trifluoroethoxy)-2H-pyrazolo[4,3-d]pyrimidine; 3-(4-chlorophenyl)-2-(2-chlorophenyl)-7-ethoxy-5-trifluoromethyl-2H-pyrazolo[4,3-d]pyrimidine; 3-(4-chlorophenyl)-2-(2-chlorophenyl)-7-(2,2,2-trifluoroethoxy)-5-trifluoromethyl-2H-pyrazolo[4,3-d]pyrimidine; and 3-(4-chlorophenyl)-2-(2-chlorophenyl)-7-(2,2-difluorobutoxy)-5-methyl-2H-pyrazolo[4,3-d]pyrimidine;

a pharmaceutically acceptable salt thereof or a solvate or hydrate of said compound or said salt.

Yet another preferred compound of the present invention is a compound of Formula (I) or (II) wherein $R^4$ is an amino group having attached thereto at least one chemical moiety selected from the group consisting of $(C_1-C_8)$alkyl, aryl, aryl$(C_1-C_4)$alkyl, a 3-8 membered partially or fully saturated carbocyclic ring, hydroxy$(C_1-C_6)$alkyl, $(C_1-C_3)$alkoxy$(C_1-C_6)$alkyl, heteroaryl$(C_1-C_3)$alkyl, and a fully or partially saturated heterocycle, where said chemical moiety is optionally substituted with one or more substituents.

Preferred compounds include: N-4-[3-(4-chlorophenyl)-2-(2-chlorophenyl)-2H-pyrazolo[4,3-d]pyrimidin-7-yl]-N,N-diethylpentane-1,4-diamine; [3-(4-chlorophenyl)-2-(2-chlorophenyl)-2H-pyrazolo[4,3-d]pyrimidin-7-yl]-(1-methyl-2-morpholin-4-yl-ethyl)-amine; [3-(4-chlorophenyl)-2-(2-chlorophenyl)-2H-pyrazolo[4,3-d]pyrimidin-7-yl]-pyridin-2-yl-amine; [3-(4-chlorophenyl)-2-(2-chlorophenyl)-2H-pyrazolo[4,3-d]pyrimidin-7-yl]-(5-methylpyridin-2-yl)-amine; [3-(4-chlorophenyl)-2-(2-chlorophenyl)-2H-pyrazolo[4,3-d]pyrimidin-7-yl]-(5-methoxypyridin-2-yl)-amine; [3-(4-chlorophenyl)-2-(2-chlorophenyl)-2H-pyrazolo[4,3-d]pyrimidin-7-yl]-(3,4,5,6-tetrahydro-2H-[1,2']bipyridinyl-5'-yl)-amine; (6-azetidin-1-yl-pyridin-3-yl)-[3-(4-chlorophenyl)-2-(2-chlorophenyl)-2H-pyrazolo[4,3-d]pyrimidin-7-yl]-amine; [3-(4-chlorophenyl)-2-(2-chlorophenyl)-2H-pyrazolo[4,3-d]pyrimidin-7-yl]-pyridin-2-ylmethylamine; [3-(4-chlorophenyl)-2-(2-chlorophenyl)-2H-pyrazolo[4,3-d]pyrimidin-7-yl]-(5-methyl-pyridin-2-ylmethyl)-amine; [3-(4-chlorophenyl)-2-(2-chlorophenyl)-2H-pyrazolo[4,3-d]pyrimidin-7-yl]-pyridin-3-ylmethylamine; [3-(4-chlorophenyl)-2-(2,4-dichlorophenyl)-2H-pyrazolo[4,3-d]pyrimidin-7-yl]-diethylamine; bicyclo[2.2.1]hept-2-yl-[3-(4-chlorophenyl)-2-(2,4-dichlorophenyl)-2H-pyrazolo[4,3-d]pyrimidin-7-yl]-amine; [3-(4-chlorophenyl)-2-(2-chlorophenyl)-2H-pyrazolo[4,3-d]pyrimidin-7-yl]-cyclohexylamine; [3-(4-chlorophenyl)-2-(2-chlorophenyl)-2H-pyrazolo[4,3-d]pyrimidin-7-yl]-diethylamine; bicyclo[2.2.1]hept-2-yl-[3-(4-chlorophenyl)-2-(2-chlorophenyl)-2H-pyrazolo[4,3-d]pyrimidin-7-yl]-amine; [3-(4-chlorophenyl)-2-(2-chlorophenyl)-2H-pyrazolo[4,3-d]pyrimidin-7-yl]-(4-methyl-cyclohexyl)amine; adamantan-2-yl-[3-(4-chlorophenyl)-2-(2-chlorophenyl)-2H-pyrazolo[4,3-d]pyrimidin-7-yl]-amine; [3-(4-chlorophenyl)-2-(2-chlorophenyl)-2H-pyrazolo[4,3-d]pyrimidin-7-yl]-(1,7,7-trimethylbicyclo[2.2.1]hept-2-yl)-amine; [3-(4-chlorophenyl)-2-(2-chlorophenyl)-2H-pyrazolo[4,3-d]pyrimidin-7-yl]-(3-methylcyclohexyl)amine; 2-[3-(4-chlorophenyl)-2-(2-chlorophenyl)-2H-pyrazolo[4,3-d]pyrimidin-7-ylamino]cyclopentanecarboxylic acid ethyl ester; 2-[3-(4-chlorophenyl)-2-(2-chlorophenyl)-2H-pyrazolo[4,3-d]pyrimidin-7-ylamino]cyclopentanol; 2-[3-(4-chlorophenyl)-2-(2-chlorophenyl)-2H-pyrazolo[4,3-d]pyrimidin-7-ylamino]cyclohexanol; [3-(4-chlorophenyl)-2-(2-chlorophenyl)-2H-pyrazolo[4,3-d]pyrimidin-7-yl]-(2,6-dimethylcyclohexyl)amine; [3-(4-chlorophenyl)-2-(2-chlorophenyl)-2H-pyrazolo[4,3-d]pyrimidin-7-yl]cycloheptylamine; [3-(4-chlorophenyl)-2-(2-chlorophenyl)-2H-pyrazolo[4,3-d]pyrimidin-7-yl]cyclobutylamine; 2-[3-(4-chlorophenyl)-2-(2-chlorophenyl)-2H-pyrazolo[4,3-d]pyrimidin-7-ylamino]-2-methylpropane-1,3-diol; [3-(4-chlorophenyl)-2-(2-chlorophenyl)-2H-pyrazolo[4,3-d]pyrimidin-7-yl]-(1-methyl-1-phenylethyl)amine; {1-[3-(4-chlorophenyl)-2-(2-chlorophenyl)-2H-pyrazolo[4,3-d]pyrimidin-7-ylamino]cyclopentyl methanol; 2-[3-(4-chlorophenyl)-2-(2-chlorophenyl)-2H-pyrazolo[4,3-d]pyrimidin-7-ylamino]-2-methylpropan-1-ol; [3-(4-chlorophenyl)-2-(2-chlorophenyl)-2H-pyrazolo[4,3-d]pyrimidin-7-yl]-(1,1-dimethylpropyl)amine; 2-[3-(4-chlorophenyl)-2-(2-chlorophenyl)-2H-pyrazolo[4,3-d]pyrimidin-7-ylamino]-3-phenylpropan-1-ol; [3-(4-chlorophenyl)-2-(2-chlorophenyl)-2H-pyrazolo[4,3-d]pyrimidin-7-yl]-indan-2-ylamine; [3-(4-chlorophenyl)-2-(2-chlorophenyl)-2H-pyrazolo[4,3-d]pyrimidin-7-yl]-(1,2,3,4-tetrahydronaphthalen-1-yl)amine; 2-[3-(4-chlorophenyl)-2-(2-chlorophenyl)-2H-pyrazolo[4,3-d]pyrimidin-7-ylamino]-1-pyrrolidin-1-ylpropan-1-one; 4-{2-[3-(4-chlorophenyl)-2-(2-chlorophenyl)-2H-pyrazolo[4,3-d]pyrimidin-7-ylamino]propyl phenol; [3-(4-chlorophenyl)-2-(2-chlorophenyl)-2H-pyrazolo[4,3-d]pyrimidin-7-yl]-(1-cyclohexylethyl)amine; [3-(4-chlorophenyl)-2-(2-chlorophenyl)-2H-pyrazolo[4,3-d]pyrimidin-7-yl]-(1-p-tolylethyl)amine; (3-(4-chlorophenyl)-2-(2-chlorophenyl)-2H-pyrazolo[4,3-d]pyrimidin-7-yl]-(2-phenylcyclopropyl)amine; 2-[3-(4-chlorophenyl)-2-(2-chlorophenyl)-2H-pyrazolo[4,3-d]pyrimidin-7-ylamino]indan-1-ol; [3-(4-chlorophenyl)-2-(2-chlorophenyl)-2H-pyrazolo[4,3-d]pyrimidin-7-yl]-(2-morpholin-4-yl-ethyl)amine; (1H-Benzoimidazol-2-ylmethyl)-[3-(4-chlorophenyl)-2-(2-chlorophenyl)-2H-pyrazolo[4,3-d]pyrimidin-7-yl]-amine; 1-[3-(4-chlorophenyl)-2-(2-chlorophenyl)-2H-pyrazolo[4,3-d]pyrimidin-7-ylamino]propan-2-ol; [3-(4-chlorophenyl)-2-(2-chlorophenyl)-2H-pyrazolo[4,3-d]pyrimidin-7-yl]-(2,2,2-trifluoroethyl)amine; [3-(4-chlorophenyl)-2-(2-chlorophenyl)-2H-pyrazolo[4,3-d]pyrimidin-7-yl]-cyclopropylmethylamine; [3-(4-chlorophenyl)-2-(2-chlorophenyl)-2H-pyrazolo[4,3-d]pyrimidin-7-yl]-(1-cyclohexylethyl)amine; and 3-(4-chlorophenyl)-2-(2,4-dichlorophenyl)-7-pyrrolidin-1-yl- 2H-pyrazolo[3,4-c]pyridine; a pharmaceutically acceptable salt thereof or a solvate or hydrate of said compound or said salt.

More preferred compounds include: [3-(4-chlorophenyl)-2-(2,4-dichlorophenyl)-2H-pyrazolo[4,3-d]pyrimidin-7-yl]-diethylamine; bicyclo[2.2.1]hept-2-yl-[3-(4-chlorophenyl)-2-(2,4-dichlorophenyl)-2H-pyrazolo[4,3-d]pyrimidin-7-yl]-amine; [3-(4-chlorophenyl)-2-(2-chlorophenyl)-2H-pyrazolo[4,3-d]pyrimidin-7-yl]-diethylamine; bicyclo[2.2.1]hept-2-yl-[3-(4-chlorophenyl)-2-(2-chlorophenyl)-2H-pyrazolo[4,3-d]pyrimidin-7-yl]-amine; [3-(4-chlorophenyl)-2-(2-chlorophenyl)-2H-pyrazolo[4,3-d]pyrimidin-7-yl]-cyclohexylamine; adamantan-2-yl-[3-(4-chlorophenyl)-2-(2-chlorophenyl)-2H-pyrazolo[4,3-d]pyrimidin-7-yl]-amine; 2-[3-(4-chlorophenyl)-2-(2-chlorophenyl)-2H-pyrazolo[4,3-d]pyrimidin-7-ylamino]cyclohexanol; [3-(4-chlorophenyl)-2-(2-chlorophenyl)-2H-pyrazolo[4,3-d]pyrimidin-7-yl]cyclobutylamine; [3-(4-chlorophenyl)-2-(2-chlorophenyl)-2H-pyrazolo[4,3-d]pyrimidin-7-yl]-(1-methyl-1-phenylethyl)amine; {1-[3-(4-chlorophenyl)-2-(2-chlorophenyl)-2H-pyrazolo[4,3-d]pyrimidin-7-ylamino]cyclopentyl} methanol; 2-[3-(4-chlorophenyl)-2-(2-chlorophenyl)-2H-pyrazolo[4,3-d]pyrimidin-7-ylamino]-3-phenylpropan-1-ol; [3-(4-chlorophenyl)-2-(2-chlorophenyl)-2H-pyrazolo[4,3-d]pyrimidin-7-yl]-indan-2-ylamine; [3-(4-chlorophenyl)-2-(2-chlorophenyl)-2H-pyrazolo[4,3-d]pyrimidin-7-yl]-(1-cyclohexylethyl)amine; and 2-[3-(4-chlorophenyl)-2-(2-chlorophenyl)-2H-pyrazolo[4,3-d]pyrimidin-7-ylamino]indan-1-ol; a pharmaceutically acceptable salt thereof or a solvate or hydrate of said compound or said salt.

Another aspect of the present invention comprises the following intermediates which may be used in the preparation of the compounds of Formula (I) and (II).

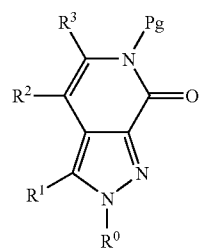

(1c)

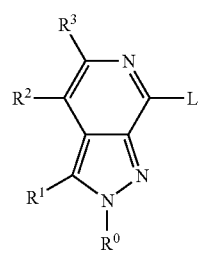

(1d)

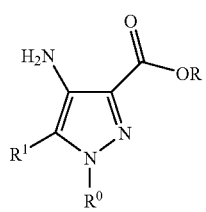

(2e)

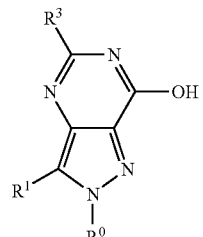

(2f)

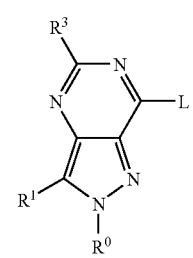

(2g)

wherein $R^0$, $R^1$, $R^2$, $R^3$ are as defined above; R is an alkyl group (preferably, a ($C_1$-$C_4$)alkyl, more preferably, an ethyl); Pg is an amino-protecting group; and L is a leaving group.

Some of the compounds described herein contain at least one chiral center; consequently, those skilled in the art will appreciate that all stereoisomers (e.g., enantiomers and diastereoisomers) of the compounds illustrated and discussed herein are within the scope of the present invention. In addition, tautomeric forms of the compounds are also within the scope of the present invention. Those skilled in the art will recognize that chemical moieties such as an alpha-amino ether or an alpha-chloro amine may be too unstable to isolate; therefore, such moieties do not form a part of this invention.

Compounds of the present invention have been shown to be useful cannabinoid receptor ligands (in particular, CB1 receptor antagonists). Accordingly, another aspect of the present invention is a pharmaceutical composition that comprises (1) a compound of the present invention, and (2) a pharmaceutically acceptable excipient, diluent, or carrier. Preferably, the composition comprises a therapeutically effective amount of a compound of the present invention. The composition may also contain at least one additional pharmaceutical agent (described herein). Preferred agents include nicotine receptor partial agonists, opioid antagonists (e.g., naltrexone and nalmefene), dopaminergic agents (e.g., apomorphine), attention deficit disorder (ADD including attention deficit hyperactivity disorder (ADHD)) agents (e.g., Ritalin™, Strattera™, Concerta™ and Adderall™), and anti-obesity agents (described herein below).

In yet another embodiment of the present invention, a method for treating a disease, condition or disorder modulated by a cannabinoid receptor (preferably, a CB1 receptor) antagonists in animals that includes the step of administering to an animal in need of such treatment a therapeutically effective amount of a compound of the present invention (or a pharmaceutical composition thereof).

Diseases, conditions, and/or disorders modulated by cannabinoid receptor antagonists include eating disorders (e.g., binge eating disorder, anorexia, and bulimia), weight loss or control (e.g., reduction in calorie or food intake, and/or appetite suppression), obesity, depression, atypical depression, bipolar disorders, psychoses, schizophrenia, behavioral addictions, suppression of reward-related behaviors (e.g., conditioned place avoidance, such as suppression of cocaine- and morphine-induced conditioned place preference), substance abuse, addictive disorders, impulsivity, alcoholism (e.g., alcohol abuse, addiction and/or dependence including treatment for abstinence, craving reduction and relapse prevention of alcohol intake), tobacco abuse (e.g., smoking addiction, cessation and/or dependence including treatment for craving reduction and relapse prevention of tobacco smoking), dementia (including memory loss, Alzheimer's disease, dementia of aging, vascular dementia, mild cognitive impairment, age-related cognitive decline, and mild neurocognitive disorder), sexual dysfunction in males (e.g., erectile difficulty), seizure disorders, epilepsy, inflammation, gastrointestinal disorders (e.g., dysfunction of gastrointestinal motility or intestinal propulsion), attention deficit disorder (ADD/ADHD), Parkinson's disease, and type II diabetes. In a preferred embodiment, the method is used in the treatment of weight loss, obesity, bulimia, ADD/ADHD, Parkinson's disease, dementia, alcoholism, and/or tobacco abuse.

Compounds of the present invention may be administered in combination with other pharmaceutical agents. Preferred pharmaceutical agents include nicotine receptor partial agonists, opioid antagonists (e.g., naltrexone (including naltrexone depot), antabuse, and nalmefene), dopaminergic agents (e.g., apomorphine), ADD/ADHD agents (e.g., methylphenidate hydrochloride (e.g., Ritalin™ and Concerta™), atomoxetine (e.g., Strattera™), and amphetamines (e.g., Adderall™)) and anti-obesity agents, such as apo-B/MTP inhibitors, 11β-hydroxy steroid dehydrogenase-1 (11β-HSD type 1) inhibitors, peptide $YY_{3-36}$ or analogs thereof, MCR-4 agonists, CCK-A agonists, monoamine reuptake inhibitors, sympathomimetic agents, $β_3$ adrenergic receptor agonists, dopamine receptor agonists, melanocyte-stimulating hormone receptor analogs, 5-HT2c receptor agonists, melanin concentrating hormone receptor antagonists, leptin, leptin analogs, leptin receptor agonists, galanin receptor antagonists, lipase inhibitors, bombesin receptor agonists, neuropeptide-Y receptor antagonists (e.g., NPY-5 receptor antagonists such as those described herein below), thyromimetic agents, dehydroepiandrosterone or analogs thereof, glucocorticoid receptor antagonists, orexin receptor antagonists, glucagon-like peptide-1 receptor agonists, ciliary neurotrophic factors, human agouti-related protein antagonists, ghrelin receptor antagonists, histamine 3 receptor antagonists or inverse agonists, and neuromedin U receptor agonists, and the like.

The combination therapy may be administered as (a) a single pharmaceutical composition which comprises a compound of the present invention, at least one additional pharmaceutical agent described herein and a pharmaceutically acceptable excipient, diluent, or carrier; or (b) two separate pharmaceutical compositions comprising (i) a first composition comprising a compound of the present invention and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions may be administered simultaneously or sequentially and in any order.

In yet another aspect of the present invention, a pharmaceutical kit is provided for use by a consumer to treat diseases, conditions or disorders modulated by cannabinoid receptor antagonists in an animal. The kit comprises a) a suitable dosage form comprising a compound of the present invention; and b) instructions describing a method of using the dosage form to treat diseases, conditions or disorders that are modulated by cannabinoid receptor (in particular, the CB1 receptor) antagonists.

In yet another embodiment of the present invention is a pharmaceutical kit comprising: a) a first dosage form comprising (i) a compound of the present invention and (ii) a pharmaceutically acceptable carrier, excipient or diluent; b) a second dosage form comprising (i) an additional pharmaceutical agent described herein, and (ii) a pharmaceutically acceptable carrier, excipient or diluent; and c) a container.

Definitions

As used herein, the term "alkyl" refers to a hydrocarbon radical of the general formula $C_nH_{2n+1}$. The alkane radical may be straight or branched. For example, the term "($C_1$-$C_6$)alkyl" refers to a monovalent, straight, or branched aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, and the like). Similarly, the alkyl portion (i.e., alkyl moiety) of an alkoxy, acyl (e.g., alkanoyl), alkylamino, dialkylamino, and alkylthio group have the same definition as above. When indicated as being "optionally substituted", the alkane radical or alkyl moiety may be unsubstituted or substituted with one or more substituents (generally, one to three substituents except in the case of halogen substituents such as perchloro or perfluoroalkyls) independently selected from the group of substituents listed below in the definition for "substituted." "Halo-substituted alkyl" refers to an alkyl group substituted with one or more halogen atoms (e.g., fluoromethyl, difluoromethyl, trifluoromethyl, perfluoroethyl, and the like). When substituted, the alkane radicals or alkyl moieties are preferably substituted with 1 to 3 fluoro substituents, or 1 or 2 substituents independently selected from ($C_1$-$C_3$)alkyl, ($C_3$-$C_6$)cycloalkyl, ($C_2$-$C_3$)alkenyl, aryl, heteroaryl, 3- to 6-membered heterocycle, chloro, cyano, hydroxy, ($C_1$-$C_3$) alkoxy, aryloxy, amino, ($C_1$-$C_6$)alkyl amino, di-($C_1$-$C_4$)alkyl amino, aminocarboxylate (i.e., ($C_1$-$C_3$)alkyl-O—C(O)—NH—), hydroxy($C_2$-$C_3$)alkylamino, or keto (oxo), and more preferably, 1 to 3 fluoro groups, or 1 substituent selected from ($C_1$-$C_3$)alkyl, ($C_3$-$C_6$)cycloalkyl, ($C_6$)aryl, 6-membered-heteroaryl, 3- to 6-membered heterocycle, ($C_1$-$C_3$) alkoxy, ($C_1$-$C_4$)alkyl amino or di-($C_1$-$C_2$)alkyl amino. When a carbon atom has attached thereto geminal alkyl groups, then the alkyls may be taken together to form a carbocyclic ring. For example, a carbon having two geminal methyl groups would be equivalent to a cyclopropyl group.

The terms "partially or fully saturated carbocyclic ring" (also referred to as "partially or fully saturated cycloalkyl") refers to nonaromatic rings that are either partially or fully hydrogenated and may exist as a single ring, bicyclic ring or a spiral ring. Unless specified otherwise, the carbocyclic ring is generally a 3- to 8-membered ring. For example, partially or fully saturated carbocyclic rings (or cycloalkyl) include groups such as cyclopropyl, cyclopropenyl, cyclobutyl, cyclobutenyl, cyclopentyl, cyclpentenyl, cyclopentadienyl, cyclohexyl, cyclohexenyl, cyclohexadienyl, norbornyl (bicyclo[2.2.1]heptyl), norbornenyl, bicyclo[2.2.2]octyl, and the like. When designated as being "optionally substituted", the partially saturated or fully saturated cycloalkyl group may be unsubstituted or substituted with one or more substituents (typically, one to three substituents) independently selected from the group of substituents listed below in the definition for "substituted." A substituted carbocyclic ring also includes groups wherein the carbocyclic ring is fused to a phenyl ring (e.g., indanyl). The carbocyclic group may be attached to the chemical entity or moiety by any one of the carbon atoms within the carbocyclic ring system. When substituted, the carbocyclic group is preferably substituted with 1 or 2 substituents independently selected from ($C_1$-$C_3$)alkyl, ($C_2$-$C_3$)alkenyl, ($C_1$-$C_6$)alkylidenyl, aryl, heteroaryl, 3- to 6-membered heterocycle, chloro, fluoro, cyano, hydroxy, ($C_1$-$C_3$)alkoxy, aryloxy, amino, ($C_1$-$C_6$)alkyl amino, di-($C_1$-$C_4$)alkyl amino, aminocarboxylate (i.e., ($C_1$-$C_3$)alkyl-O—C(O)—NH—), hydroxy($C_2$-$C_3$)alkylamino, or keto (oxo), and more preferably 1 or 2 from substituents independently selected from ($C_1$-$C_2$)alkyl, 3- to 6-membered heterocycle, fluoro, ($C_1$-$C_3$)alkoxy, ($C_1$-$C_4$)alkyl amino or di-($C_1$-$C_2$)alkyl amino. Similarly, any cycloalkyl portion of a group (e.g., cycloalkylalkyl, cycloalkylamino, etc.) has the same definition as above.

The term "partially saturated or fully saturated heterocyclic ring" (also referred to as "partially saturated or fully saturated heterocycle") refers to nonaromatic rings that are either partially or fully hydrogenated and may exist as a single ring, bicyclic ring or a spiral ring. Unless specified otherwise, the heterocyclic ring is generally a 3- to 6-membered ring containing 1 to 3 heteroatoms (preferably 1 or 2 heteroatoms) independently selected from sulfur, oxygen and/or nitrogen. Partially saturated or fully saturated heterocyclic rings include groups such as epoxy, aziridinyl, tetrahydrofuranyl, dihydrofuranyl, dihydropyridinyl, pyrrolidinyl, N-methylpyrrolidinyl, imidazolidinyl, imidazolinyl, piperidinyl, piperazinyl, pyrazolidinyl, 2H-pyranyl, 4H-pyranyl, 2H-chromenyl, oxazinyl, morpholino, thiomorpholino, tetrahydrothienyl, tetrahydrothienyl 1,1-dioxide, and the like. When indicated as being "optionally substituted", the partially saturated or fully saturated heterocycle group may be unsubsituted or substituted with one or more substituents (typically, one to three substituents) independently selected from the group of substituents listed below in the definition for "substituted." A substituted heterocyclic ring includes groups wherein the heterocyclic ring is fused to an aryl or heteroaryl ring (e.g., 2,3-dihydrobenzofuranyl, 2,3-dihydroindolyl, 2,3-dihydrobenzothiophenyl, 2,3-dihydrobenzothiazolyl, etc.). When substituted, the heterocycle group is preferably substituted with 1 or 2 substituents independently selected from ($C_1$-$C_3$)alkyl, ($C_3$-$C_6$)cycloalkyl, ($C_2$-$C_4$)alkenyl, aryl, heteroaryl, 3- to 6-membered heterocycle, chloro, fluoro, cyano, hydroxy, ($C_1$-$C_3$)alkoxy, aryloxy, amino, ($C_1$-$C_6$)alkyl amino, di-($C_1$-$C_3$)alkyl amino, aminocarboxylate (i.e., ($C_1$-$C_3$)alkyl-O—C(O)—NH—), or keto (oxo), and more preferably with 1 or 2 substituents independently selected from ($C_1$-$C_3$)alkyl, ($C_3$-$C_6$)cycloalkyl, ($C_6$)aryl, 6-membered-heteroaryl, 3- to 6-membered heterocycle, or fluoro. The heterocyclic group may be attached to the chemical entity or moiety by any one of the ring atoms within the heterocyclic ring system. Similarly, any heterocycle portion of a group (e.g., heterocycle-substituted alkyl, heterocycle carbonyl, etc.) has the same definition as above.

The term "aryl" or "aromatic carbocyclic ring" refers to aromatic moieties having a single (e.g., phenyl) or a fused ring system (e.g., naphthalene, anthracene, phenanthrene, etc.). A typical aryl group is a 6- to 10-membered aromatic carbocyclic ring(s). When indicated as being "optionally substituted", the aryl groups may be unsubstituted or substituted with one or more substituents (preferably no more than three substituents) independently selected from the group of substituents listed below in the definition for "substituted." Substituted aryl groups include a chain of aromatic moieties (e.g., biphenyl, terphenyl, phenylnaphthalyl, etc.). When substituted, the aromatic moieties are preferably substituted with 1 or 2 substituents independently selected from ($C_1$-$C_4$)alkyl, ($C_2$-$C_3$)alkenyl, aryl, heteroaryl, 3- to 6-membered heterocycle, bromo, chloro, fluoro, iodo, cyano, hydroxy, ($C_1$-$C_4$)alkoxy, aryloxy, amino, ($C_1$-$C_6$)alkyl amino, di-($C_1$-$C_3$)alkyl amino, or aminocarboxylate (i.e., ($C_1$-$C_3$)alkyl-O—C(O)—NH—), and more preferably, 1 or 2 substituents independently selected from ($C_1$-$C_4$)alkyl, chloro, fluoro, cyano, hydroxy, or ($C_1$-$C_4$)alkoxy. The aryl group may be attached to the chemical entity or moiety by any one of the carbon atoms within the aromatic ring system. Similarly, the aryl portion (i.e., aromatic moiety) of an aroyl or aroyloxy (i.e., (aryl)-C(O)—O—) has the same definition as above.

The term "heteroaryl" or "heteroaromatic ring" refers to aromatic moieties containing at least one heteroatom (e.g., oxygen, sulfur, nitrogen or combinations thereof) within a 5- to 10-membered aromatic ring system (e.g., pyrrolyl, pyridyl, pyrazolyl, indolyl, indazolyl, thienyl, furanyl, benzofuranyl, oxazolyl, imidazolyl, tetrazolyl, triazinyl, pyrimidyl, pyrazinyl, thiazolyl, purinyl, benzimidazolyl, quinolinyl, isoquinolinyl, benzothiophenyl, benzoxazolyl, etc.). The heteroaromatic moiety may consist of a single or fused ring system. A typical single heteroaryl ring is a 5- to 6-membered ring containing one to three heteroatoms independently selected from oxygen, sulfur and nitrogen and a typical fused heteroaryl ring system is a 9- to 10-membered ring system containing one to four heteroatoms independently selected from oxygen, sulfur and nitrogen. When indicated as being "optionally substituted", the heteroaryl groups may be unsubstituted or substituted with one or more substituents (preferably no more than three substituents) independently selected from the group of substituents listed below in the definition for "substituted." When substituted, the heteroaromatic moieties are preferably substituted with 1 or 2 substituents independently selected from ($C_1$-$C_4$)alkyl, ($C_2$-$C_3$)alkenyl, aryl, heteroaryl, 3- to 6-membered heterocycle, bromo, chloro, fluoro, iodo, cyano, hydroxy, ($C_1$-$C_4$)alkoxy, aryloxy, amino, ($C_1$-$C_6$)alkyl amino, di-($C_1$-$C_3$)alkyl amino, or aminocarboxylate (i.e., ($C_1$-$C_3$)alkyl-O—C(O)—NH—), and more preferably, 1 or 2 substituents independently selected from ($C_1$-$C_4$)alkyl, chloro, fluoro, cyano, hydroxy, ($C_1$-$C_4$)alkoxy, ($C_1$-$C_4$)alkyl amino or di-($C_1$-$C_2$)alkyl amino. The heteroaryl group may be attached to the chemical entity or moiety by any one of the atoms within the aromatic ring system (e.g., imidazol-1-yl, imidazol-2-yl, imidazol-4-yl, imidazol-5-yl, pyrid-2-yl, pyrid-3-yl, pyrid-4-yl, pyrid-5-yl, or pyrid-6-yl). Similarly, the heteroaryl portion (i.e., heteroaromatic moiety) of a heteroaroyl or heteroaroyloxy (i.e., (heteroaryl)-C(O)—O—) has the same definition as above.

The term "acyl" refers to hydrogen, alkyl, partially saturated or fully saturated cycloalkyl, partially saturated or fully saturated heterocycle, aryl, and heteroaryl substituted carbonyl groups. For example, acyl includes groups such as ($C_1$-$C_6$)alkanoyl (e.g., formyl, acetyl., propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-car bonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions above. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "substituted" specifically envisions and allows for one or more substitutions that are common in the art. However, it is generally understood by those skilled in the art that the substituents should be selected so as to not adversely affect the pharmacological characteristics of the compound or adversely interfere with the use of the medicament. Suitable substituents for any of the groups defined above include $(C_1-C_6)$alkyl, $(C_3-C_7)$cycloalkyl, $(C_2-C_6)$alkenyl, $(C_1-C_6)$alkylidenyl, aryl, heteroaryl, 3- to 6-membered heterocycle, halo (e.g., chloro, bromo, iodo and fluoro), cyano, hydroxy, $(C_1-C_6)$alkoxy, aryloxy, sulfhydryl (mercapto), $(C_1-C_6)$alkylthio, arylthio, amino, mono- or di-$(C_1-C_6)$alkyl amino, quaternary ammonium salts, amino$(C_1-C_6)$alkoxy, aminocarboxylate (i.e., $(C_1-C_6)$alkyl-O—C(O)—NH—), hydroxy$(C_2-C_6)$alkylamino, amino$(C_1-C_6)$alkylthio, cyanoamino, nitro, $(C_1-C_6)$carbamyl, keto (oxo), acyl, $(C_1-C_6)$alkyl-$CO_2$—, glycolyl, glycyl, hydrazino, guanyl, sulfamyl, sulfonyl, sulfinyl, thio$(C_1-C_6)$alkyl-C(O)—, thio$(C_1-C_6)$alkyl-$CO_2$—, and combinations thereof. In the case of substituted combinations, such as "substituted aryl $(C_1-C_6)$alkyl", either the aryl or the alkyl group may be substituted, or both the aryl and the alkyl groups may be substituted with one or more substituents (typically, one to three substituents except in the case of perhalo substitutions). An aryl or heteroaryl substituted carbocyclic or heterocyclic group may be a fused ring (e.g., indanyl, dihydrobenzofuranyl, dihydroindolyl, etc.).

The term "solvate" refers to a molecular complex of a compound represented by Formula (I) or (II) (including prodrugs and pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The term "protecting group" or "Pg" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —$CH_2CH_2SO_2$Ph, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, *Protective Groups in Organic Synthesis*, John Wiley & Sons, New York, 1991.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "animal" refers to humans (male or female), companion animals (e.g., dogs, cats and horses), food-source animals, zoo animals, marine animals, birds and other similar animal species. "Edible animals" refers to food-source animals such as cows, pigs, sheep and poultry.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment.

The terms "modulated by a cannabinoid receptor" or "modulation of a cannabinoid receptor" refers to the activation or deactivation of a cannabinoid receptor. For example, a ligand may act as an agonist, partial agonist, inverse agonist, antagonist, or partial antagonist.

As used herein, the term "antagonist" includes both full antagonists and partial antagonists, as well as inverse agonists.

The term "compounds of the present invention" (unless specifically identified otherwise) refer to compounds of Formula (I) and Formula (II), prodrugs thereof, pharmaceutically acceptable salts of the compounds, and/or prodrugs, and hydrates or solvates of the compounds, salts, and/or prodrugs, as well as, all stereoisomers (including diastereoisomers and enantiomers), tautomers and isotopically labeled compounds.

DETAILED DESCRIPTION

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v.1-19, Wiley, New York (1967-1999 ed.), or *Beilsteins Handbuch der organischen Chemie*, 4, Aufl. ed. Springer-Verlag, Berlin, including supplements (also available via the *Beilstein* online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, *Protective Groups in Organic Synthesis*, John Wiley & Sons, New York, 1991.

Scheme I outlines the general procedures one could use to provide compounds of the present invention where A is $C(R^2)$ and $R^2$ and $R^3$ are hydrogen, alkyl or halo substituted alkyl.

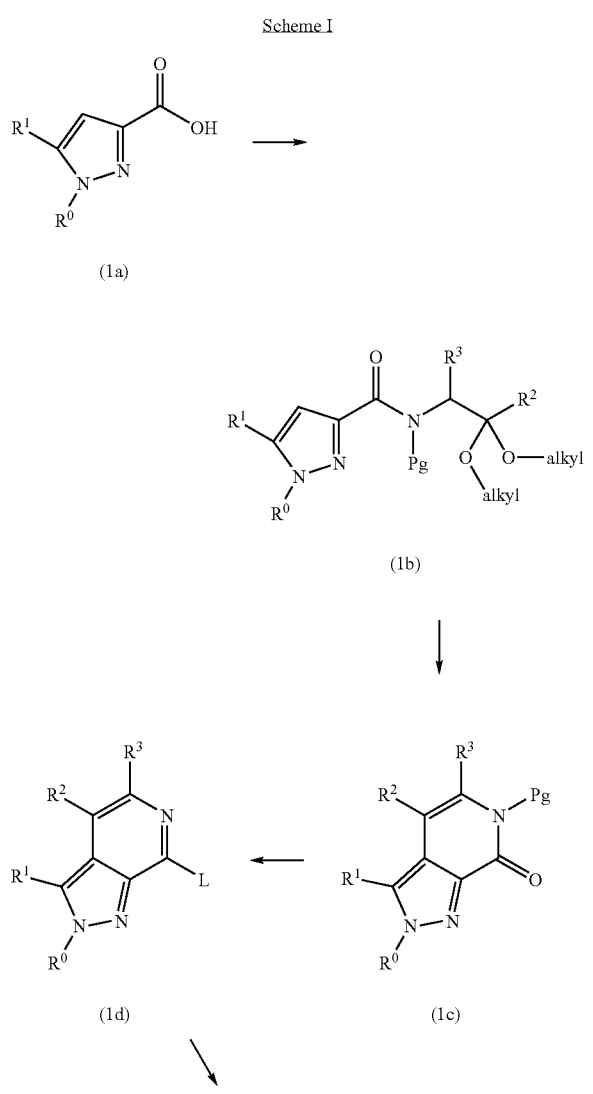

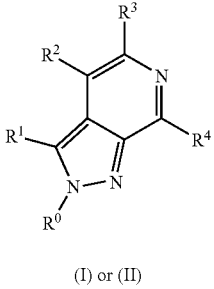

(I) or (II)

The pyrazole carboxylic acid (1a) may be prepared using the methods described in U.S. Pat. No. 5,624,941, incorporated herein by reference. Intermediate (1b) may be prepared by condensing the pyrazole carboxylic acid (a) with a protected α-aminoacetal or protected α-aminoketal (e.g., N-benzylaminoacetaldehyde dimethyl acetal or N-benzyl-N-(2,2-diethoxyethyl)amine) using conditions well known to those skilled in the art. For example intermediate (1b) may be formed by coupling (1a) and the amine in an aprotic solvent (e.g., methylene chloride) at about room temperature using 1-(3-dimethylaminopropyl)-3-ethylcarbodiimide hydrochloride and a base (e.g., diisopropylethylamine). Cyclization to the pyridinone (1c) may be accomplished using procedures described by Dumas, D. J., in *J. Org. Chem.*, 53, 4650-1853 (1988) or by Brimble, M. A., et al., *Aust. J. Chem.*, 41, 1583-1590 (1988). For example, pyridinone (1c) may be formed by treating (1b) with toluenesulfonic acid in refluxing toluene. Introduction of a leaving group (L) and aromatization of the pyridinone (c) to form the aromatic intermediate (1d) may be accomplished using conventional procedures well-known to those skilled in the art. For example, debenzylation/halogenation may be accomplished using phosphorus oxychloride under refluxing conditions. Alternatively, the protecting group could be cleaved as a first step, followed by halogenation (e.g., $POCl_3$ or $SOCl_2$ in the presence or absence of a base like triethylamine or pyridine at reflux) or mesylation (e.g., methansulfonic anhydride and tertiary amine base).

When $R^4$ is an amine functionality (e.g., $R^4$=an amino group of Formula (IA) or an amino group substituted with one or more substituents described above), the amine may be introduced via a coupling reaction between intermediate (1d) and the corresponding amino compound ($R^4$—H) to give a compound of the present invention where $R^4$ is an amino group. For example, intermediate (1d) is generally stirred with the desired amine ($R^4$—H). The amine may act as the solvent (e.g., butylamine, morpholine, pyrrolidine) or a solvent (e.g., methylene chloride, N,N-dimethylformamide, ethanol) may be added to assist in solubilization of the reactants and/or provide a media having the appropriate refluxing temperature to complete the substitution. The reaction may be heated to accelerate the process. Suitable reaction temperatures range from about −40° C. to 100° C., and are preferably conducted at around 60° C. In addition, a suitable base (e.g., triethylamine, diisopropylethylamine) may be employed to quench the acid produced in the process. Suitable amino compounds can be either purchased commercially or easily prepared using standard procedures well-known to those skilled in the art. Preferred amino compounds ($R^4$—H) include 4-alkylaminopiperidine-4-carboxamides (Scheme III) and 3-alkylaminoazetidine-3-carboxamides that are described below. For a detailed description of representative compounds prepared using the procedures generally described in Scheme I above where in $R^4$ is an amine functionality, see Example 1A-1 in the Examples section below.

Scheme II below outlines the general procedures that may be used to produce compounds of the present invention where A is N.

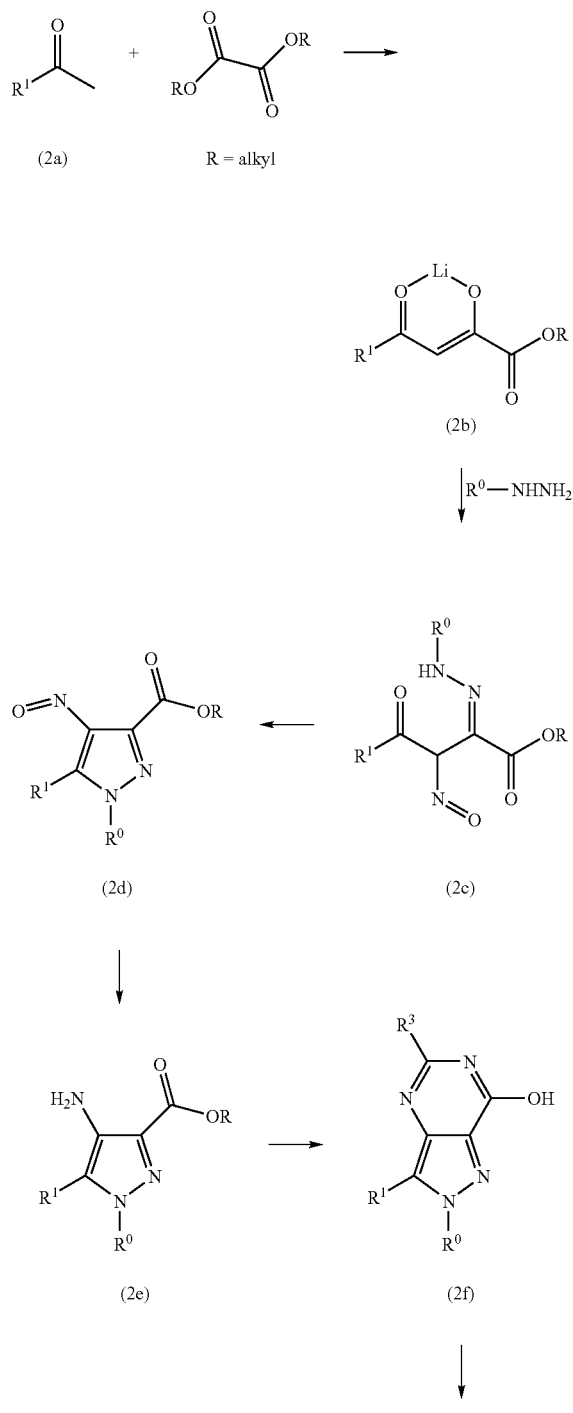

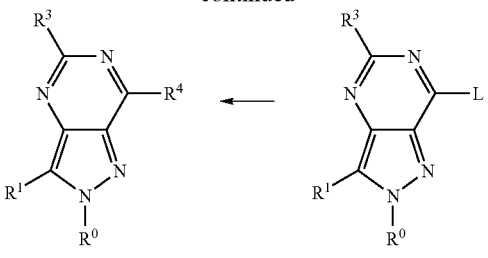

Lithium salt (2b) can be prepared by treatment of methyl ketone (2a) with lithium hexamethyldisilazide at a temperature of about −78° C. in an aprotic solvent such as THF, followed by condensation with diethyl oxalate, as described in WO 00/46209. The isolated lithium salt (2b) is then dissolved in an acid such as acetic acid and nitrosated by dropwise addition of aqueous sodium nitrite at a temperature of about 0-10° C. (*Tetrahedron*, 3, 209 (1958); *Bull. Chem. Soc. Jpn.* 52, 208 (1979)). A substituted hydrazine may then be added directly to the reaction mixture to afford intermediate (2c). Cyclization of (2c) is accomplished by heating intermediate (2c) and a catalytic amount of an acid such as concentrated sulfuric acid in a solvent such isopropanol at a temperature of about 60° C. to provide nitrosopyrazole (2d). The nitroso group of intermediate (2d) can be reduced by treatment of (2d) with sodium dithionite in a mixture of solvents such as ethyl acetate and water, affording aminopyrazole (2e), which is reacted with an appropriate amidine (such as formamidine when $R^3$=H) in an aprotic solvent such as 2-ethoxyethanol at an elevated temperature, such as reflux (202° C. for 2-ethoxyethanol) to provide pyrazolopyrimidine (2f). A leaving group (L) is then introduced in preparation for the introduction of the $R^4$ group. For example, chloropyrazolopyrimidine intermediate (2g, where L is Cl) may be prepared by treatment of a suspension of (2f) in an aprotic solvent such as 1,2-dichloroethane with phosphorous oxychloride and heating the resultant suspension to reflux (83° C. for 1,2-dichloroethane). Compounds of formula I or II (A=N) are then obtained by displacement of the leaving group (e.g., Cl) of (2g) with a nucleophile such as an amine in a solvent such as ethanol at a temperature of about 20-60° C. (see above). For a detailed description of representative compounds prepared using the procedures generally described in Scheme II above wherein $R^4$ is an amine functionality, see Examples 2A-1 and 3A-1 in the Examples section below.

Numerous amine compounds of Formula (IA) are available from commercial sources or prepared by known methods readily available to those skilled in the art. Representative preparations of amine compounds of Formula (IA) are illustrated in the Examples below. The 4-aminopiperidine-4-carboxamide groups of Formula (IA) and 4-amino-4-cyano piperidine groups of Formula (IA) and their benzyl protected precursors may be prepared using the procedures described by P. A. J. Janssen in U.S. Pat. No. 3,161,644, C. van de Westeringh et al. in *J. Med. Chem.*, 7, 619-623 (1964), and K. A. Metwally et al. in *J. Med. Chem.*, 41, 5084-5093 (1998) where the above 4-amino groups are unsubstituted, monosubstituted, disubstituted, or part of a heterocyclic ring. Related bicyclic derivatives are described by K. Frohlich et al. in *Tetrahedron*, 54, 13115-13128 (1998) and references contained therein. Spiro-substituted piperidines of formula (IA) are described by P. A. J. Janssen in U.S. Pat. No. 3,155,670, K. A. Metwally et al. in *J. Med Chem.*, 41, 5084-5093 (1998), T. Toda et al. in *Bull. Chem. Soc. Japan*, 44, 3445-3450 (1971), and W. Brandau and S. Samnick in WO 9522544. The preparation of 3-aminoazetidine-3-carboxamide is described by A. P. Kozikowski and A. H. Fauq in *Synlett*, 783-784 (1991). The preparation of preferred 4-alkylaminopiperidine-4-carboxamide groups of Formula (IA) are depicted in Scheme III below. The corresponding 3-alkylaminoazetidine-3-carboxamides and 3-alkylaminopyrolidine-3-carboxamides may be prepared in an analogous fashion. Spiro-substituted derivatives are available by procedures analogous to those contained in the above references. A detailed description of some representative spiro-substituted amines may be found in the "Preparation of Key Intermediates" section of the Examples below (see, e.g., I-2A-69d and I-3A-50d).

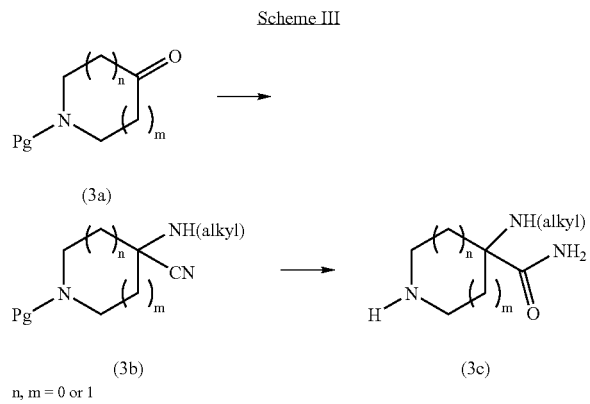

Scheme III (3a)

(3b)

(3c)

n, m = 0 or 1

The amino group of 4-piperidinone is first protected to provide intermediate (3a). A useful protection group is benzyl. 4-Piperidinone and derivatives thereof may be purchased commercially from a variety of sources (e.g., Interchem Corporation, Paramus, N.J. and Sigma-Aldrich Co., St. Louis, Mo.). Piperidinone (3a) may then be reacted with the desired alkylamine and potassium cyanide in an aqueous HCl/ethanol solvent mixture at about 0° C. to about 30° C. The cyano group is converted to the corresponding amide with acid and water, or with alkaline hydrogen peroxide in the presence of DMSO (see Y. Sawaki and Y. Ogata in Bull. *Chem. Soc. Jpn.* 54, 793-799 (1981)). The protecting group is then removed using conventional methods for the particular protecting group employed. For example, a benzyl protecting group may be removed by hydrogenation in the presence of Pd/C. A detailed description of some representative amines having Formula (3c) above may be found in the "Preparation of Key Intermediates" section of the Examples below (see, e.g., I-1A-1f, I-2A-90a, and I-1A-6c).

Compounds of the present invention where $R^4$ is an alkoxy group (i.e., $R^4$=a group of Formula (1B) or (1C), may be prepared by treating intermediate (1d) or (2g) with the desired alcohol in the presence of a base (e.g., potassium t-butoxide, NaH, 1,4-diazabicyclo[2.2.2]octane, diisopropylethylamine, NaHCO$_3$). The alcohol may act as solvent, or an aprotic solvent may be added to assist in solubilization of the reactants and/or provide a media having the appropriate refluxing temperature to complete the substitution (e.g., THF, methylene chloride, DMF). Suitable alcohols can be either purchased commercially or easily prepared using standard procedures well known to those skilled in the art. For a detailed description of representative compounds prepared using this procedure, see Examples 7A-1, 8A-1, 9A-1 and 12A-1 in the Examples section below.

An alternative route to compounds where $R^4$ is an alkoxy group involves O-alkylation of the pyrazolopyrimidinol (2f) or pyrazolopyrimidinol. The latter intermediate can be prepared by deprotecting (1c) using standard procedures. Alternatively, the pyrazolopyrimidinol can be prepared by hydrolyzing intermediate (1d), such as by heating with aqueous acid (e.g., HCl) in an appropriate solvent (e.g., THF). For a detailed description of representative compounds prepared using this procedure, see Example 10A-1 in the Examples section below.

For compounds of Formula (I) and (II) where $R^4$ is an aminoalkyl, alkylaminoalkyl, or dialkylaminoalkyl group, the leaving group (e.g., L=Cl) in intermediate (1d) or (2g) may first be displaced with a cyano group (e.g., treating with tetrabutylammonium cyanide in the presence of 1,4-diazabicyclo[2.2.2]octane (DABCO) in an aprotic solvent (e.g., acetonitrile) at room temperature). See, e.g., Hocek, et al. *Collect. Czech. Chem. Commun.* 60, 1386 (1995). The cyano group may then be reduced to the alkyl amine using standard reduction methods well-known to those skilled in the art (e.g., treating with DIBAL or hydrogen in the presence of Pd/C). The amino group can then be alkylated using standard reductive alkylation procedures. Generally, a Schiff base is formed by reacting the amine with the desired ketone or aldehyde in a polar solvent at a temperature from about 10° C. to about 140° C. for about 2 to about 24 hours in the presence of 3 Å molecular sieves. Typically, an equivalent or a slight excess of the amino compound is added to the ketone or aldehyde. Suitable polar solvents include methylene chloride, 1,2-dichloroethane, dimethyl sulfoxide, dimethylformamide, alcohols (e.g., methanol or ethanol), or mixtures thereof. A preferred solvent is methanol. In the same reaction vessel, the imine may then be reduced to the secondary amine in the presence of a reducing agent at a temperature from about 0° C. to about 10° C. and then warmed to a temperature from about 20° C. to about 40° C. for about 30 minutes to about 2 hours. Suitable reducing agents include pyridine-borane complex and metal borohydrides, such as sodium borohydride, sodium triacetoxy borohydride and sodium cyanoborohydride. Suitable aldehydes or ketones include paraformaldehyde, acetaldehyde, acetone, benzaldehyde, and the like.

Alternatively, the amino alkyl group may be introduced using the methods described by Hocek, et al. in *Tetrahedron*, 53(6), 2291-2302 (1997). Intermediate (1d), where L=Cl, Br or OTf, or intermediate (2g) may be converted to the acetyl-derivative compound by reacting intermediate (1 d) or (2q) with 1-ethoxyvinyl)tri-n-butyltin under Pd(PPh$_3$)$_4$ catalysis followed by hydrolysis using a mixture of acetone and aqueous HCl (or DMF/aq. HCl mixture) at reflux temperatures. The acetyl group may then be converted to an amine or substituted amine by reductive amination, a process well-known to those skilled in the art. An exemplary procedure employs the desired amine salt (e.g., ammonium chloride, methylammonium chloride, allylammonium chloride, cyclopropylammonium chloride, cyclohexylammonium chloride, dimethylammonium chloride, benzylammonium chloride, etc.) and a reducing agent (e.g., NaBH$_4$, NaBH$_3$CN, or triacetoxyborohydride) in polar solvent at room temperature. See Abdel-Magid, et al., *J. Org. Chem.*, 61, 3849-3862 (1996) for a wide variety of aldehydes, ketones and amines that may be used in either the reductive alkylation or the reductive amination.

Compounds of Formula (I) above where $R^4$ contains a primary or secondary amine can be alkylated, sulfonated and/or acylated to provide additional derivatives (e.g., alkylamines, dialkylamines, sulfonamides, amides, carbamates, ureas, etc.) using standard procedures well known to those skilled in the art. In some cases the amine is protected, and must be unmasked before further functionalization. For a more detailed description of representative compounds prepared using these procedures, see Examples 4A-1, 5A-1 and 6A-1 in the Examples section below.

Alternatively, compounds of Formula (I) or (II) where $R^4$ is a hydroxy or alkoxy substituted alkyl group may be produced by replacing the chlorine group of intermediate (1d), L=Cl, or (2g) with the desired electrophile using procedures described by Sugimoto, et al., in Tetrahedron Letters, 40, 2139-2140 (1999). The intermediate (1d), L=Cl, or (2a) may be reacted with lithium n-butanetellurolate (tellurium reacted with n-butyllithium) in an aprotic solvent (e.g., THF) at −78° C. followed by the addition of the desired electrophile (e.g., acetaldehyde, benzaldehyde, acetone, methylethyl ketone, etc.) and then warmed to room temperature to form the desired hydroxyalkyl derivative. Alternately, the hydroxy derivative may be formed using the procedures described by Leonard, et al., in *J. Org. Chem.*, 44(25), 4612-4616 (1979). Intermediate (1d), L=Cl, or (2g) is treated with n-butyl lithium to form the carbanion at −78° C., followed by reaction with the desired electrophile (e.g., ketone or aldehyde) to form the hydroxyalkyl derivative.

In yet another approach, an aroyl derivative of formula (I) or (II), where $R^4$=aroyl, can be prepared by the procedures described by Miyashita, et al., in *Chem. Pharm. Bull*, 46(30), 390-399 (1998). The aroyl group can then be reduced to the corresponding secondary alcohol by treating with a reducing agent such as lithium aluminum hydride. The tertiary alcohol can be obtained upon treatment with an alkyl metal reagent, such as an alkyl Grignard reagent, in a suitable solvent (e.g., tetrahydrofuran, diethyl ether). Finally, an amine could be introduced by reductive amination (see above).

In the above examples, the resultant hydroxyalkyl group can then be alkylated or acylated to form the desired alkoxy or acylate (e.g., (alkyl)-C(O)—O—, (aryl)-C(O)—O—, (heteroaryl)-C(O)—O—, etc.) using standard procedures well-known to those skilled in the art. Alternatively, the hydroxy group may be condensed with other moieties to provide a variety of substituents (e.g., sulfamyl, sulfonyl, etc.). The aminoalkyl group could be modified in a similar fashion to give amides, sulfonamides, etc.

An alternate route for the synthesis of intermediate (2e) is shown in Scheme IV below.

Scheme IV

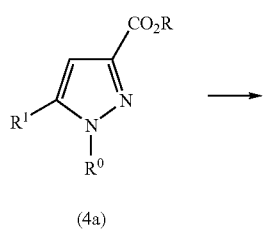

(4a)

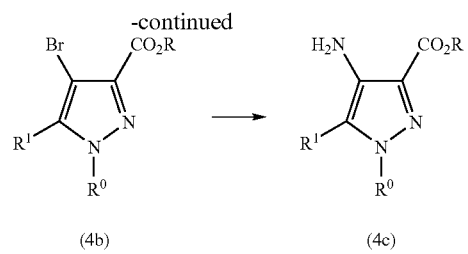

(4b)     (4c)

The starting pyrazolo ester (R=alkyl group) may be prepared by procedures described in U.S. Pat. No. 5,624,941 and is incorporated herein by reference. The bromo intermediate (4b) may be prepared from (4a) using conventional bromination procedures well-known to those skilled in the art. For example, the pyrazolo ester may be treated with bromine in a protic solvent (e.g., acetic acid) at a temperature from about 10° C. to about −10° C. Amine deriviative (4c), which is equivalent to (2e) when R=Et, may then be prepared by palladium-catalyzed methods described by X. Huang and S. L. Buchwald in *Org. Lett.*, 3, 3417-3419 (2001), and with references contained therein.

Conventional methods and/or techniques of separation and purification known to one of ordinary skill in the art can be used to isolate the compounds of the present invention, as well as the various intermediates related thereto. Such techniques will be well known to one of ordinary skill in the art and may include, for example, all types of chromatography (high pressure liquid chromatography (HPLC), column chromatography using common adsorbents such as silica gel, and thin-layer chromatography), recrystallization, and differential (i.e., liquid-liquid) extraction techniques.

The compounds of the present invention may be isolated and used per se or in the form of its pharmaceutically acceptable salt, solvate and/or hydrate. The term "salts" refers to inorganic and organic salts of a compound of the present invention. These salts can be prepared in situ during the final isolation and purification of a compound, or by separately reacting the compound, N-oxide, or prodrug with a suitable organic or inorganic acid or base and isolating the salt thus formed. Representative salts include the hydrobromide, hydrochloride, hydroiodide, sulfate, bisulfate, nitrate, acetate, trifluoroacetate, oxalate, besylate, palmitiate, pamoate, malonate, stearate, laurate, malate, borate, benzoate, lactate, phosphate, hexafluorophosphate, benzene sulfonate, tosylate, formate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, e.g., Berge, et al., *J. Pharm. Sci.*, 66, 1-19 (1977).

The term "prodrug" means a compound that is transformed in vivo to yield a compound of Formula (I) or a pharmaceutically acceptable salt, hydrate or solvate of the compound. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A. C. S. Symposium Series, and in Bioreversible Carriers in Drug Design, ed. Edward B. Roche, American Pharmaceutical Association and Pergamon Press, 1987.

For example, if a compound of the present invention contains a carboxylic acid functional group, a prodrug can comprise an ester formed by the replacement of the hydrogen atom of the acid group with a group such as ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl.

Similarly, if a compound of the present invention contains an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkanoyl, arylacyl and α-aminoacyl, or α-aminoacyl-α-aminoacyl, where each α-aminoacyl group is independently selected from the naturally occurring L-amino acids, P(O)(OH)$_2$, P(O)(O($C_1$-$C_6$)alkyl)$_2$ or glycosyl (the radical resulting from the removal of a hydroxyl group of the hemiacetal form of a carbohydrate).

If a compound of the present invention incorporates an amine functional group, a prodrug can be formed by the replacement of a hydrogen atom in the amine group with a group such as R-carbonyl, RO-carbonyl, NRR'-carbonyl where R and R' are each independently ($C_1$-$C_{10}$)alkyl, ($C_3$-$C_7$)cycloalkyl, benzyl, or R-carbonyl is a natural α-aminoacyl or natural α-aminoacyl-natural α-aminoacyl, —C(OH)C(O)OY' wherein Y' is H, ($C_1$-$C_6$)alkyl or benzyl, —C(OY$_0$)Y$_1$ wherein Y$_0$ is ($C_1$-$C_4$)alkyl and Y$_1$ is ($C_1$-$C_6$)alkyl, carboxy($C_1$-$C_6$)alkyl, amino($C_1$-$C_4$)alkyl or mono-N— or di-N,N-($C_1$-$C_6$)alkylaminoalkyl, —C(Y$_2$)Y$_3$ wherein Y$_2$ is H or methyl and Y$_3$ is mono-N— or di-N,N-($C_1$-$C_6$)alkylamino, morpholino, piperidin-1-yl or pyrrolidin-1-yl.

The compounds of the present invention may contain asymmetric or chiral centers, and, therefore, exist in different stereoisomeric forms. It is intended that all stereoisomeric forms of the compounds of the present invention as well as mixtures thereof, including racemic mixtures, form part of the present invention. In addition, the present invention embraces all geometric and positional isomers. For example, if a compound of the present invention incorporates a double bond or a fused ring, both the cis- and trans- forms, as well as mixtures, are embraced within the scope of the invention. Both the single positional isomers and mixture of positional isomers resulting from the N-oxidation of the pyrimidine and pyrazine rings are also within the scope of the present invention.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

The compounds of the present invention may exist in unsolvated as well as solvated forms with pharmaceutically acceptable solvents such as water, ethanol, and the like, and it is intended that the invention embrace both solvated and unsolvated forms.

It is also possible that the compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The present invention also embraces isotopically-labeled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine, iodine, and chlorine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{123}$I, $^{125}$I and $^{36}$Cl, respectively.

Certain isotopically-labeled compounds of the present invention (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C, and $^{18}$F are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Compounds of the present invention are useful for treating diseases, conditions and/or disorders modulated by cannabinoid receptor antagonists; therefore, another embodiment of the present invention is a pharmaceutical composition comprising a therapeutically effective amount of a compound of the present invention and a pharmaceutically acceptable excipient, diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable dosage of the drug and to give the patient an elegant and easily handleable product.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present invention further provides a method of treating diseases, conditions and/or disorders modulated by cannabinoid receptor antagonists in an animal that includes administering to an animal in need of such treatment a therapeutically effective amount of a compound of the present invention or a pharmaceutical composition comprising an effective amount of a compound of the present invention and a pharmaceutically acceptable excipient, diluent, or carrier. The method is particularly useful for treating diseases, conditions and/or disorders modulated by cannabinoid receptor (in particular, CB1 receptor) antagonists.

Preliminary investigations have indicated that the following diseases, conditions, and/or disorders are modulated by cannabinoid receptor antagonists: eating disorders (e.g., binge eating disorder, anorexia, and bulimia), weight loss or control (e.g., reduction in calorie or food intake, and/or appetite suppression), obesity, depression, atypical depression, bipolar disorders, psychoses, schizophrenia, behavioral addictions, suppression of reward-related behaviors (e.g., conditioned place avoidance, such as suppression of cocaine- and morphine-induced conditioned place preference), substance abuse, addictive disorders, impulsivity, alcoholism (e.g., alcohol abuse, addiction and/or dependence including treatment for abstinence, craving reduction and relapse prevention of alcohol intake), tobacco abuse (e.g., smoking addiction, cessation and/or dependence including treatment for craving reduction and relapse prevention of tobacco smoking), dementia (including memory loss, Alzheimer's disease, dementia of aging, vascular dementia, mild cognitive impairment, age-related cognitive decline, and mild neurocognitive disorder), sexual dysfunction in males (e.g., erectile difficulty), seizure disorders, epilepsy, inflammation, gastrointestinal disorders (e.g., dysfunction of gastrointestinal motility or intestinal propulsion), attention deficit disorder (ADD including attention deficit hyperactivity disorder (ADHD)), Parkinson's disease, and type II diabetes. Accordingly, the compounds of the present invention described herein are useful in treating diseases, conditions, or disorders that are modulated by cannabinoid receptor antagonists. Consequently, the compounds of the present invention (including the compositions and processes used therein) may be used in the manufacture of a medicament for the therapeutic applications described herein.

Other diseases, conditions and/or disorders for which cannabinoid receptor antagonists may be effective include: premenstrual syndrome or late luteal phase syndrome, migraines, panic disorder, anxiety, post-traumatic syndrome, social phobia, cognitive impairment in non-demented individuals, non-amnestic mild cognitive impairment, post operative cognitive decline, disorders associated with impulsive behaviours (such as, disruptive behaviour disorders (e.g., anxiety/depression, executive function improvement, tic disorders, conduct disorder and/or oppositional defiant disorder), adult personality disorders (e.g., borderline personality disorder and antisocial personality disorder), diseases associated with impulsive behaviours (e.g., substance abuse, paraphilias and self-mutilation), and impulse control disorders (e.g., intermittene explosive disorder, kleptomania, pyromania, pathological gambling, and trichotillomania)), obsessive compulsive disorder, chronic fatigue syndrome, sexual dysfunction in males (e.g., premature ejaculation), sexual dysfunction in females, disorders of sleep (e.g., sleep apnea), autism, mutism, neurodengenerative movement disorders, spinal cord injury, damage of the central nervous system (e.g., trauma), stroke, neurodegenerative diseases or toxic or infective CNS diseases (e.g., encephalitis or meningitis), cardiovascular disorders (e.g., thrombosis), and diabetes.

The compounds of the present invention can be administered to a patient at dosage levels in the range of from about 0.7 mg to about 7,000 mg per day. For a normal adult human having a body weight of about 70 kg, a dosage in the range of from about 0.01 mg to about 100 mg per kilogram body weight is typically sufficient. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

The compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include anti-obesity agents such as apolipoprotein-B secretion/microsomal triglyceride transfer protein (apo-B/MTP) inhibitors, 11β-hydroxy steroid dehydrogenase-1 (11β-HSD type 1) inhibitors, peptide $YY_{3-36}$ or analogs thereof, MCR-4 agonists, cholecystokinin-A (CCK-A) agonists, monoamine reuptake inhibitors (such as sibutramine), sympathomimetic agents, $β_3$ adrenergic receptor agonists, dopamine agonists (such as bromocriptine), melanocyte-stimulating hormone receptor analogs, 5HT2c agonists, melanin concentrating hormone antagonists, leptin (the OB protein), leptin analogs, leptin receptor agonists, galanin antagonists, lipase inhibitors (such as tetrahydrolipstatin, i.e. orlistat), anorectic agents (such as a bombesin agonist), Neuropeptide-Y receptor antagonists (e.g., NPY Y5 receptor antagonists, such as the spiro compounds described in U.S. Pat. Nos. 6,566,367; 6,649,624; 6,638,942; 6,605,720; 6,495,559; 6,462,053; 6,388,077; 6,335,345; and 6,326,375; US Publication Nos. 2002/0151456 and 2003/036652; and PCT Publication Nos. WO 03/010175. WO 03/082190 and WO 02/048152), thyromimetic agents, dehydroepiandrosterone or an analog thereof, glucocorticoid receptor agonists or antagonists, orexin receptor antagonists, glucagon-like peptide-1 receptor agonists, ciliary neurotrophic factors (such as Axokine™ available from Regeneron Pharmaceuticals, Inc., Tarrytown, N.Y. and Procter & Gamble Company, Cincinnati, Ohio), human agouti-related proteins (AGRP), ghrelin receptor antagonists, histamine 3 receptor antagonists or inverse agonists, neuromedin U receptor agonists and the like. Other anti-obesity agents, including the preferred agents set forth hereinbelow, are well known, or will be readily apparent in light of the instant disclosure, to one of ordinary skill in the art.

Especially preferred are anti-obesity agents selected from the group consisting of orlistat, sibutramine, bromocriptine, ephedrine, leptin, pseudoephedrine; peptide $YY_{336}$ or an analog thereof; and 2-oxo-N-(5-phenylpyrazinyl)spiro-[isobenzofuran-1(3H),4'-piperidine]-1'-carboxamide. Preferably, compounds of the present invention and combination therapies are administered in conjunction with exercise and a sensible diet.

Representative anti-obesity agents for use in the combinations, pharmaceutical compositions, and methods of the invention can be prepared using methods known to one of ordinary skill in the art, for example, sibutramine can be prepared as described in U.S. Pat. No. 4,929,629; bromocriptine can be prepared as described in U.S. Pat. Nos. 3,752,814 and 3,752,888; orlistat can be prepared as described in U.S. Pat. Nos. 5,274,143; 5,420,305; 5,540,917; and 5,643,874; $PYY_{3-36}$ (including analogs) can be prepared as described in US Publication No. 2002/0141985 and WO 03/027637; and the NPY Y5 receptor antagonist 2-oxo-N-(5-phenylpyrazinyl)spiro[isobenzofuran-1(3H),4'-piperidine]-1'-carboxamide can be prepared as described in US Publication No. 2002/0151456. Other useful NPY Y5 receptor antagonists include those described in PCT Publication No. 03/082190, such as 3-oxo-N-(5-phenyl-2-pyrazinyl)-spiro[isobenzofuran-1(3H), 4'-piperidine]-1'-carboxamide; 3-oxo-N-(7-trifluoromethylpyrido[3,2-b]pyridin-2-yl)-spiro-[isobenzofuran-1(3H), 4'-piperidine]-1'-carboxamide; N-[5-(3-fluorophenyl)-2-pyrimidinyl]-3-oxospiro-[isobenzofuran-1(3H), [4'-piperidine]-1'-carboxamide; trans-3'-oxo-N-(5-phenyl-2-pyrimidinyl)]spiro[cyclohexane-1,1'(3'H)-isobenzofuran]-4-carboxamide; trans-3'-oxo-N-[1-(3-quinolyl)-4-imidazolyl]spiro[cyclohexane-1,1'(3'H)-isobenzofuran]-4-carboxamide; trans-3-oxo-N-(5-phenyl-2-pyrazinyl)spiro[4-azaiso-benzofuran-1(3H),1'-cyclohexane]-4'-carboxamide; trans-N-[5-(3-fluorophenyl)-2-pyrimidinyl]-3-oxospiro[5-azaisobenzofuran-[(3H), 1'-cyclohexane]-4'-carboxamide; trans-N-[5-(2-fluorophenyl)-2-pyrimidinyl]-3-oxospiro[5-azaisobenzofuran-1(3H), 1'-cyclohexane]-4'-carboxamide; trans-N-[1-(3,5-difluorophenyl)-4-imidazolyl]-3-oxospiro [7-azaisobenzofuran-1(3H),1'-cyclohexane]-4'-carboxamide; trans-3-oxo-N-(1-phenyl-4-pyrazolyl)spiro[4-azaisobenzofuran-1(3H),1'-cyclohexane]-4'-carboxamide; trans-N-[1-(2-fluorophenyl)-3-pyrazolyl]-3-oxospiro[6-azaisobenzofuran-1(3H),1'-cyclohexane]-4'-carboxamide; trans-3-oxo-N-(1-phenyl-3-pyrazolyl)spiro[6-azaisobenzofuran-1(3H),1'-cyclohexane]-4'-carboxamide; trans-3-oxo-N-(2-phenyl-1,2,3-triazol-4-yl)spiro[6-azaisobenzofuran-1 (3H),1'-cyclohexane]-4'-carboxamide; and pharmaceutically acceptable salts and esters thereof. All of the above recited U.S. patents and publications are incorporated herein by reference.

Other suitable pharmaceutical agents that may be administered in combination with the compounds of the present invention include agents designed to treat tobacco abuse (e.g., nicotine receptor partial agonists, bupropion hypochloride (also known under the tradename Zyban™) and nicotine replacement therapies), agents to treat erectile dysfunction (e.g., dopaminergic agents, such as apomorphine), ADD/ADHD agents (e.g., Ritalin™, Strattera™, Concerta™ and Adderall™), and agents to treat alcoholism, such as opioid antagonists (e.g., naltrexone (also known under the tradename ReVia™) and nalmefene), disulfiram (also known under the tradename Antabuse™), and acamprosate (also known under the tradename Campral™)). In addition, agents for reducing alcohol withdrawal symptoms may also be co-administered, such as benzodiazepines, beta-blockers, clonidine, carbamazepine, pregabalin, and gabapentin (Neurontin™). Treatment for alcoholism is preferably administered in combination with behavioral therapy including such components as motivational enhancement therapy, cognitive behavioral therapy, and referral to self-help groups, including Alcohol Anonymous (AA).

Other pharmaceutical agents that may be useful include antihypertensive agents; anti-inflammatory agents (e.g., COX-2 inhibitors); antidepressants (e.g., fluoxetine hydrochloride (Prozac™)); cognitive improvement agents (e.g., donepezil hydrochloride (Aircept™) and other acetylcholinesterase inhibitors); neuroprotective agents (e.g., memantine); antipsychotic medications (e.g., ziprasidone (Geodon™), risperidone (Risperdal™), and olanzapine (Zyprexa™)); insulin and insulin analogs (e.g., LysPro insulin); GLP-1 (7-37) (insulinotropin) and GLP-1 (7-36)—$NH_2$; sulfonylureas and analogs thereof: chlorpropamide, glibenclamide, tolbutamide, tolazamide, acetohexamide, Glypizide®, glimepiride, repaglinide, meglitinide; biguanides: metformin, phenformin, buformin; α2-antagonists and imidazolines: midaglizole, isaglidole, deriglidole, idazoxan, efaroxan, fluparoxan; other insulin secretagogues: linogliride, A-4166; glitazones: ciglitazone, Actos® (pioglitazone), englitazone, troglitazone, darglitazone, Avandia® (BRL49653); fatty acid oxidation inhibitors: clomoxir, etomoxir; α-glucosidase inhibitors: acarbose, miglitol, emiglitate, voglibose, MDL-25,637, camiglibose, MDL-73,945; β-agonists: BRL 35135, BRL 37344, RO 16-8714, ICI D7114, CL 316,243; phosphodiesterase inhibitors: L-386, 398; lipid-lowering agents: benfluorex: fenfluramine; vanadate and vanadium complexes (e.g., Naglivan®) and peroxovanadium complexes; amylin antagonists; glucagon antagonists; gluconeogenesis inhibitors; somatostatin analogs; antilipolytic agents: nicotinic acid, acipimox, WAG 994, pramlintide (Symlin™), AC 2993, nateglinide, aldose reductase inhibitors (e.g., zopolrestat), glycogen phosphorylase inhibitors, sorbitol dehydrogenase inhibitors, sodium-hydrogen exchanger type 1 (NHE-1) inhibitors and/or cholesterol biosynthesis inhibitors or cholesterol absorption inhibitors, especially a HMG-CoA reductase inhibitor (e.g., atorvastatin or the hemicalcium salt thereof), or a HMG-CoA synthase inhibitor, or a HMG-CoA reductase or synthase gene expression inhibitor, a CETP inhibitor, a bile acid sequesterant, a fibrate, an ACAT inhibitor, a squalene synthetase inhibitor, an anti-oxidant or niacin. The compounds of the present invention may also be administered in combination with a naturally occurring compound that acts to lower plasma cholesterol levels. Such naturally occurring compounds are commonly called nutraceuticals and include, for example, garlic extract, Hoodia plant extracts, and niacin.

The dosage of the additional pharmaceutical agent is generally dependent upon a number of factors including the health of the subject being treated, the extent of treatment desired, the nature and kind of concurrent therapy, if any, and the frequency of treatment and the nature of the effect desired. In general, the dosage range of the additional pharmaceutical agent is in the range of from about 0.001 mg to about 100 mg per kilogram body weight of the individual per day, preferably from about 0.1 mg to about 10 mg per kilogram body weight of the individual per day. However, some variability in the general dosage range may also be required depending upon the age and weight of the subject being treated, the intended route of administration, the particular anti-obesity agent being administered and the like. The determination of dosage ranges and optimal dosages for a particular patient is also well within the ability of one of ordinary skill in the art having the benefit of the instant disclosure.

According to the methods of the invention, a compound of the present invention or a combination of a compound of the present invention and at least one additional pharmaceutical agent is administered to a subject in need of such treatment, preferably in the form of a pharmaceutical composition. In the combination aspect of the invention, the compound of the present invention and at least one other pharmaceutical agent (e.g., anti-obesity agent, nicotine receptor partial agonist, dopaminergic agent, or opioid antagonist) may be administered either separately or in the pharmaceutical composition comprising both. It is generally preferred that such administration be oral. However, if the subject being treated is unable to swallow, or oral administration is otherwise impaired or undesirable, parenteral or transdermal administration may be appropriate.

According to the methods of the invention, when a combination of a compound of the present invention and at least one other pharmaceutical agent are administered together, such administration can be sequential in time or simultaneous with the simultaneous method being generally preferred. For sequential administration, a compound of the present invention and the additional pharmaceutical agent can be administered in any order. It is generally preferred that such administration be oral. It is especially preferred that such administration be oral and simultaneous. When a compound of the present invention and the additional pharmaceutical agent are administered sequentially, the administration of each can be by the same or by different methods.

According to the methods of the invention, a compound of the present invention or a combination of a compound of the present invention and at least one additional pharmaceutical agent (referred to herein as a "combination") is preferably administered in the form of a pharmaceutical composition. Accordingly, a compound of the present invention or a combination can be administered to a patient separately or together in any conventional oral, rectal, transdermal, parenteral, (for example, intravenous, intramuscular, or subcutaneous) intracisternal, intravaginal, intraperitoneal, intravesical, local (for example, powder, ointment or drop), or buccal, or nasal, dosage form.

Compositions suitable for parenteral injection generally include pharmaceutically acceptable sterile aqueous or non-aqueous solutions, dispersions, suspensions, or emulsions, and sterile powders for reconstitution into sterile injectable solutions or dispersions. Suitable aqueous and nonaqueous carriers or diluents (including solvents and vehicles) include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain excipients such as preserving, welting, emulsifying, and dispersing agents. Prevention of microorganism contamination of the compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and gelatin.

Solid dosage forms for oral administration include capsules, tablets, powders, and granules. In such solid dosage forms, a compound of the present invention or a combination is admixed with at least one inert excipient, diluent or carrier. Suitable excipients, diluents or carriers include materials such as sodium citrate or dicalcium phosphate or (a) fillers or extenders (e.g., starches, lactose, sucrose, mannitol, silicic acid and the like); (b) binders (e.g., carboxymethylcellulose, alginates, gelatin, polyvinylpyrrolidone, sucrose, acacia and the like); (c) humectants (e.g., glycerol and the like); (d) disintegrating agents (e.g., agar-agar, calcium carbonate, potato or tapioca starch, alginic acid, certain complex silicates, sodium carbonate and the like); (e) solution retarders (e.g., paraffin and the like); (f) absorption accelerators (e.g., quaternary ammonium compounds and the like); (g) wetting agents (e.g., cetyl alcohol, glycerol monostearate and the like); (h) adsorbents (e.g., kaolin, bentonite and the like); and/or (i) lubricants (e.g., talc, calcium stearate, magnesium stearate, solid polyethylene glycols, sodium lauryl sulfate and the like). In the case of capsules and tablets, the dosage forms may also comprise buffering agents. Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings and shells, such as enteric coatings and others well known in the art. They may also contain opacifying agents, and can also be of such composition that they release the compound of the present invention and/or the additional pharmaceutical agent in a delayed manner. Examples of embedding compositions that can be used are polymeric substances and waxes. The drug can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the compound of the present invention or the combination, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed oil, groundnut oil, corn germ oil, olive oil, castor oil, sesame seed oil and the like), glycerol, tetrahydrofurfuryl alcohol, polyethylene glycols and fatty acid esters of sorbitan, or mixtures of these substances, and the like.

Besides such inert diluents, the composition can also include excipients, such as wetting agents, emulsifying and suspending agents, sweetening, flavoring, and perfuming agents.

Suspensions, in addition to the compound of the present invention or the combination, may further comprise carriers such as suspending agents, e.g., ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration preferably comprise suppositories, which can be prepared by mixing a compound of the present invention or a combination with suitable non-irritating excipients or carriers, such as cocoa butter, polyethylene glycol or a suppository wax which are solid at ordinary room temperature but liquid at body temperature and therefore melt in the rectum or vaginal cavity thereby releasing the active component(s).

Dosage forms for topical administration of the compounds of the present invention and combinations of the compounds of the present invention with anti-obesity agents may comprise ointments, powders, sprays and inhalants. The drugs are admixed under sterile conditions with a pharmaceutically acceptable excipient, diluent or carrier, and any preservatives, buffers, or propellants that may be required. Ophthalmic formulations, eye ointments, powders, and solutions are also intended to be included within the scope of the present invention.

The following paragraphs describe exemplary formulations, dosages, etc. useful for non-human animals. The administration of the compounds of the present invention and combinations of the compounds of the present invention with anti-obesity agents can be effected orally or non-orally (e.g., by injection).

An amount of a compound of the present invention or combination of a compound of the present invention with an anti-obesity agent is administered such that an effective dose is received. Generally, a daily dose that is administered orally to an animal is between about 0.01 and about 1,000 mg/kg of body weight, preferably between about 0.01 and about 300 mg/kg of body weight.

Conveniently, a compound of the present invention (or combination) can be carried in the drinking water so that a therapeutic dosage of the compound is ingested with the daily water supply. The compound can be directly metered into drinking water, preferably in the form of a liquid, water-soluble concentrate (such as an aqueous solution of a water-soluble salt).

Conveniently, a compound of the present invention (or combination) can also be added directly to the feed, as such, or in the form of an animal feed supplement, also referred to as a premix or concentrate. A premix or concentrate of the compound in an excipient, diluent or carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the compound in the finished feed with which the premix is blended. Preferably, the compound is thoroughly blended into the premix and, subsequently, the feed. In this respect, the compound may be dispersed or dissolved in a suitable oily vehicle such as soybean oil, corn oil, cottonseed oil, and the like, or in a volatile organic solvent and then blended with the carrier. It will be appreciated that the proportions of compound in the concentrate are capable of wide variation since the amount of the compound in the finished feed may be adjusted by blending the appropriate proportion of premix with the feed to obtain a desired level of compound.

High potency concentrates may be blended by the feed manufacturer with proteinaceous carrier such as soybean oil meal and other meals, as described above, to produce concentrated supplements, which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound of the present invention. The mixtures are thoroughly blended by standard procedures, such as in a twin shell blender, to ensure homogeneity.

If the supplement is used as a top dressing for the feed, it likewise helps to ensure uniformity of distribution of the compound across the top of the dressed feed.

Drinking water and feed effective for increasing lean meat deposition and for improving lean meat to fat ratio are generally prepared by mixing a compound of the present invention with a sufficient amount of animal feed to provide from about $10^{-3}$ to about 500 ppm of the compound in the feed or water.

The preferred medicated swine, cattle, sheep and goat feed generally contain from about 1 to about 400 grams of a compound of the present invention (or combination) per ton of feed, the optimum amount for these animals usually being about 50 to about 300 grams per ton of feed.

The preferred poultry and domestic pet feeds usually contain about 1 to about 400 grams and preferably about 10 to about 400 grams of a compound of the present invention (or combination) per ton of feed.

For parenteral administration in animals, the compounds of the present invention (or combination) may be prepared in the form of a paste or a pellet and administered as an implant, usually under the skin of the head or ear of the animal in which increase in lean meat deposition and improvement in lean meat to fat ratio is sought.

In general, parenteral administration involves injection of a sufficient amount of a compound of the present invention (or combination) to provide the animal with about 0.01 to about 20 mg/kg/day of body weight of the drug. The preferred dosage for poultry, swine, cattle, sheep, goats and domestic pets is in the range of from about 0.05 to about 10 mg/kg/day of body weight of drug.

Paste formulations can be prepared by dispersing the drug in a pharmaceutically acceptable oil such as peanut oil, sesame oil, corn oil or the like.

Pellets containing an effective amount of a compound of the present invention, pharmaceutical composition, or combination can be prepared by admixing a compound of the present invention or combination with a diluent such as carbowax, carnuba wax, and the like, and a lubricant, such as magnesium or calcium stearate, can be added to improve the pelleting process.

It is, of course, recognized that more than one pellet may be administered to an animal to achieve the desired dose level which will provide the increase in lean meat deposition and improvement in lean meat to fat ratio desired. Moreover, implants may also be made periodically during the animal treatment period in order to maintain the proper drug level in the animal's body.

The present invention has several advantageous veterinary features. For the pet owner or veterinarian who wishes to increase leanness and/or trim unwanted fat from pet animals, the instant invention provides the means by which this may be accomplished. For poultry, beef and swine breeders, utilization of the method of the present invention yields leaner animals that command higher sale prices from the meat industry.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

Unless specified otherwise, starting materials are generally available from commercial sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), and AstraZeneca Pharmaceuticals (London, England).

The acronyms listed below have the following corresponding meanings:
LiN(TMS)$_2$—lithium hexamethyldisilazide
PS-DIEA—polystyrene-bound diisopropylethylamine (available from Argonaut Technologies, Foster City, Calif.)

General Experimental Procedures

NMR spectra were recorded on a Varian Unity™ 400 or 500 (available from Varian Inc., Palo Alto, Calif.) at room temperature at 400 and 500 MHz $^1$H, respectively. Chemical shifts are expressed in parts per million (δ) relative to residual solvent as an internal reference. The peak shapes are denoted as follows: s, singlet; d, doublet; t, triplet; q, quartet; m, multiplet; br s, broad singlet; v br s, very broad singlet; br m, broad multiplet; 2s, two singlets. In some cases only representative $^1$H NMR peaks are given.

Mass spectra were recorded by direct flow analysis using positive and negative atmospheric pressure chemical ionization (APcI) scan modes. A Waters APcI/MS model ZMD mass spectrometer equipped with Gilson 215 liquid handling system was used to carry out the experiments Mass spectrometry analysis was also obtained by RP-HPLC gradient method for chromatographic separation. Molecular weight identification was recorded by positive and negative electrospray ionization (ESI) scan modes. A Waters/Micromass ESI/MS model ZMD or LCZ mass spectrometer equipped with Gilson 215 liquid handling system and HP 1100 DAD was used to carry out the experiments.

Where the intensity of chlorine or bromine-containing ions are described, the expected intensity ratio was observed (approximately 3:1 for $^{35}$Cl/$^{37}$Cl-containing ions and 1:1 for $^{79}$Br/$^{81}$Br-containing ions) and only the lower mass ion is given. MS peaks are reported for all examples.

Optical rotations were determined on a PerkinElmer™ 241 polarimeter (available from PerkinElmer Inc., Wellesley, Mass.) using the sodium D line (λ=589 nm) at the indicated temperature and are reported as follows $[\alpha]_D^{temp}$, concentration (c=g/100 ml), and solvent.

Column chromatography was performed with either Baker™ silica gel (40 μm; J. T. Baker, Phillipsburg, N.J.) or Silica Gel 50 (EM Sciences™, Gibbstown, N.J.) in glass columns or in Biotage™ columns (ISC, Inc., Shelton, Conn.) under low nitrogen pressure. Radial chromatography was performed using a Chromatotron™ (Harrison Research).

Preparation of Key Intermediates

Preparation of Intermediate 5-(4-Chlorophenyl)-1-(2,4-dichlorophenyl)-1H-pyrazole-3-carboxylic acid (2,2-diethoxyethyl)-amide (I-1A-1a):

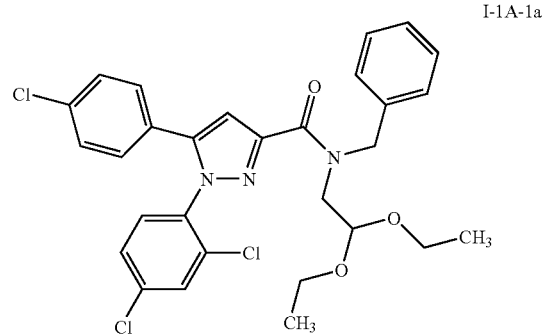

I-1A-1a

To a stirred solution of 5-(4-chlorophenyl)-1-(2,4-dichlorophenyl)-1H-pyrazole-3-carboxylic acid (prepared according to the methods described by Barth, et al. in U.S. Pat. No. 5,624,941); 740 mg, 2.01 mmol) and N-benzyl-N-(2,2-diethoxyethyl)amine (450 mg, 2.01 mmol) in methylene chloride (6.5 ml) at room temperature was added 1-(3-dimethylaminopropyl)-3-ethylcarbodiimide hydrochloride (464 mg, 2.42 mmol) and then diisopropylethylamine (0.42 ml, 2.2 mmol), dropwise. After stirring for 23 hours, the reaction mixture was concentrated, in vacuo, and then extracted from saturated aqueous sodium bicarbonate with ethyl acetate. The combined organic layers were washed with brine, dried (MgSO$_4$), and concentrated, in vacuo. The crude material (1.05 g) was purified on a Biotage™ Flash 40S column using 0-20% ethyl acetate in hexanes as eluant to afford I-1A-1a as a foam (534 mg, 46%): +ESI MS (M+1) 572.1; $^1$H NMR (500 MHz, CD$_2$Cl$_2$) 1:1 mixture of rotamers, δ 7.51 (br s, 0.5H), 7.47 (d, J=2.1 Hz, 0.5H), 7.38-7.34 (m, 2H), 7.38-7.23 (m, 9H), 7.18-7.11 (m, 2H), 7.03 (s, 0.5H), 6.95 (s, 0.5H), 5.22 (s, 1H), 4.91 (s, 1H), 4.83-4.79 (m, 1H), 3.56-3.07 (m, 6H), 1.20 (t, J=7.0 Hz, 3H), 1.07 (t, J=7.0 Hz, 3H).

Preparation of Intermediate 6-Benzyl-3-(4-chlorophenyl)-2-(2,4-dichlorophenyl)-2,6-dihydropyrazolo[3,4-c]pyridin-7-one (I-1A-1b):

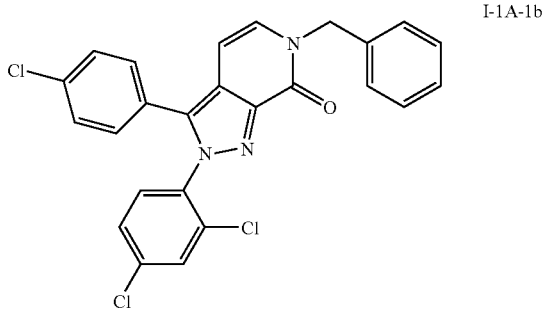

I-1A-1b

A mixture of 5-(4-chlorophenyl)-1-(2,4-dichlorophenyl)-1H-pyrazole-3-carboxylic acid (2,2-diethoxyethyl)-amide (I-1A-1a; 528 mg, 0.92 mmol) and p-toluenesulfonic acid monohydrate (175 mg, 0.92 mmol) in toluene (5 ml) was heated to reflux in round bottom flask fitted with a Dean-Stark condenser. After 1 hour, the reaction mixture was cooled to room temperature, and then extracted from saturated aqueous sodium bicarbonate with ethyl acetate. The combined organic layers were washed with brine, dried (MgSO$_4$), and concentrated in vacuo. The crude material (0.49 g) was purified on a Biotage™ Flash 40S column using 10-20-40% ethyl acetate in hexanes as eluant to afford I-1A-1b as a solid (69 mg, 16%): +ESI MS (M+1) 480.1; $^1$H NMR (500 MHz, CD$_2$Cl$_2$) δ 7.50 (d, J=1.5 Hz, 1H), 7.48 (d, J=8.3 Hz, 1H), 7.42 (dd, J=8.3, 2.1 Hz, 1H), 7.38-7.27 (m, 7H), 7.18 (d, J=8.7 Hz, 2H), 6.95 (d, J=7.5 Hz, 1H), 6.42 (d, J=7.5 Hz, 1H), 5.21 (s, 2H).

Preparation of Intermediate 7-Chloro-3-(4-chlorophenyl)-2-(2,4-dichlorophenyl)-2H-pyrazolo[3,4-c]pyridine (I-1A-1c):

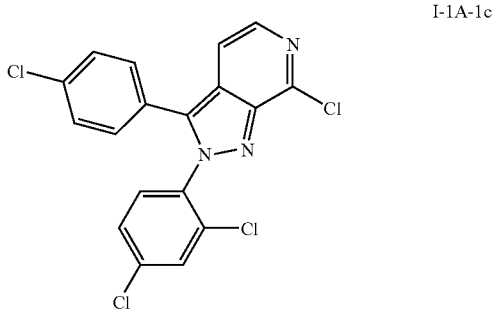

I-1A-1c

A stirred suspension of 6-benzyl-3-(4-chlorophenyl)-2-(2,4-dichlorophenyl)-2,6-dihydropyrazolo[3,4-c]pyridin-7-one (I-1A-1b; 153 mg, 0.32 mmol) in POCl$_3$ (3.5 ml) was heated to reflux for 48 hr. After the reaction was cooled and concentrated, in vacuo, an ethyl acetate solution of the residue was washed with saturated aqueous NaHCO$_3$ and then brine. The solution was dried (Na$_2$SO$_4$), concentrated, in vacuo, and then purified on a Biotage™ Flash 12M column using 0-15-30% ethyl acetate in hexanes to afford I-1A-1c as an off-white solid (75 mg, 58%): +ESI MS (M+1) 408.0; $^1$H NMR (400 MHz, CD$_2$Cl$_2$) δ 8.01 (d, J=5.8 Hz, 1H), 7.57-7.53 (m, 3H), 7.47 (dd, J=8.7, 2.1 Hz, 1H), 7.41 (d, J=8.7 Hz, 2H), 7.27 (d, J=8.7 Hz, 2H).

Preparation of Intermediate 1-Benzyl-4-ethylaminopiperidine-4-carbonitrile (I-1A-1d):

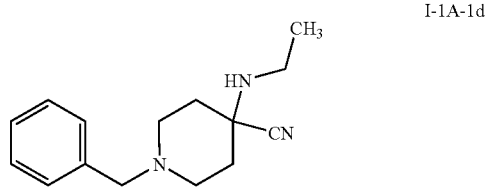

I-1A-1d

To a solution of 4-N-benzylpiperidone (5.69 g, 29.5 mmol) in ethanol (4.2 ml) cooled in an ice bath was added ethylamine hydrochloride (2.69 g, 32.3 mmol) in water (3 ml), keeping the internal temperature of the reaction below 10° C. A solution of KCN (2.04 g, 31.3 mmol) in water (7 ml) was added to the reaction solution over 10 minutes while keeping the internal temperature below 10° C. The reaction mixture was then warmed to room temperature and stirred 18 hours. Isopropanol (10 ml) was added to the reaction mixture to give two distinct layers: lower colorless aqueous layer and orange organic upper layer. The organic layer was separated and stirred with water (30 ml) for 30 minutes. The organic layer was separated (orange organic layer now the bottom layer), the solvent was removed in vacuo, and the resultant oil diluted in methylene chloride (30 ml). The organic layer was washed with brine, dried (Na$_2$SO$_4$), filtered and concentrated, in vacuo, to give I-1A-1d as an orange oil (6.05 g, 84%): +APcI MS (M+1) 244.2; $^1$H NMR (400 MHz, CD$_2$Cl$_2$) δ 7.32 (d, J=4.1 Hz, 4H), 7.29-7.23 (m, 1H), 3.54 (s, 2H), 2.81-2.76 (m, 2H), 2.75 (q, J=7.1 Hz, 2H), 2.35-2.29 (m, 2H), 2.01-1.98 (m, 2H), 1.74-1.68 (m, 2H), 1.14 (t, J=7.1 Hz, 3H).

Preparation of Intermediate 1-Benzyl-4-ethylaminopiperidine-4-carboxylic Acid Amide (I-1A-1e):

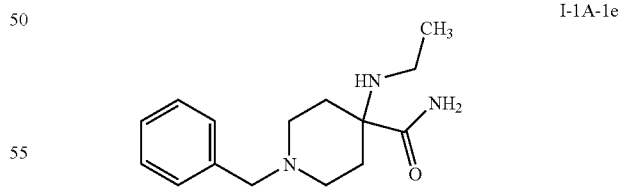

I-1A-1e

A solution of 1-benzyl-4-ethylaminopiperidine-4-carbonitrile I-1A-1d (0.58 g, 2.38 mmol) in methylene chloride (2 ml) cooled in an ice bath was treated with H$_2$SO$_4$ (1.8 ml, 33 mmol), dropwise, while keeping the internal temperature below 20° C. The reaction mixture was then warmed to room temperature and stirred for 19 hours. After stirring was discontinued, the thick pale orange H$_2$SO$_4$ bottom layer was separated, cooled in an ice bath, and then carefully quenched with concentrated NH$_4$OH keeping the internal temperature below 55° C. The aqueous layer was extracted with methylene chloride (2×10 ml), the combined organic layers were washed with brine (20 ml), dried (Na$_2$SO$_4$), and then concentrated, in vacuo, to afford I-1A-1e as a pale orange oil that solidified to a peach colored solid upon standing (0.54 g, 87%): +APcl MS (M+1) 262.2; $^1$H NMR (400 MHz, CD$_2$Cl$_2$) δ 7.34-7.30 (m, 4H), 7.29-7.21 (m, 1H), 7.16 (br s, 1H), 3.48 (s, 2H), 2.71-2.68 (m, 2H), 2.47 (q, J=7.0 Hz, 2H), 2.17-2.02 (m, 4H), 1.62-1.58 (m, 2H), 1.41 (br s, 1H), 1.09 (t, J=7.0 Hz, 3H).

Preparation of Intermediate
4-Ethylaminopiperidine-4-carboxylic Acid Amide
(I-1A-1f):

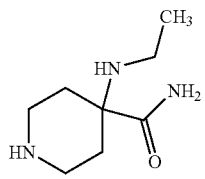

I-1A-1f

To a solution of 1-benzyl-4-ethylaminopiperidine-4-carboxylic acid amide (I-1A-1e; 7.39 g, 28.3 mmol) in methanol (100 ml) was added 20% Pd(OH)$_2$ on carbon (50% water; 1.48 g). The mixture was placed on a Parr® shaker and was reduced (50 psi H$_2$) at room temperature overnight. The mixture was filtered through a pad of Celite®, and then concentrated to give a colorless solid I-1A-if (4.84 g, quantitative): +APcl MS (M+1) 172.2; $^1$H NMR (400 MHz, CD$_2$Cl$_2$) δ 2.89 (ddd, J=12.9, 8.7, 3.3 Hz, 2H), 2.75 (ddd, J=12.9, 6.6, 3.7 Hz, 2H), 2.45 (q, J=7.2 Hz, 2H), 1.95 (ddd, J=13.7, 8.3, 3.7 Hz, 2H), 1.55 (ddd, J=13.7, 6.6, 3.3 Hz, 2 h), 1.08 (t, J=7.1 Hz, 3H).

Preparation of Intermediate 7-Chloro-3-(4-chlorophenyl)-2-(2-chlorophenyl)-2H-pyrazolo[3,4-c]pyridine (I-1A-6a):

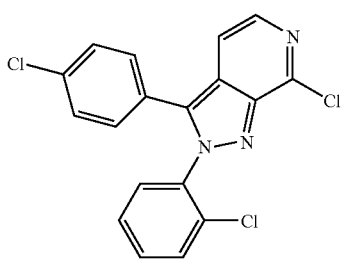

I-1A-6a

Intermediate I-1A-6a was prepared by procedures analogous to those described above for the preparation of 7-chloro-3-(4-chlorophenyl)-2-(2,4-dichlorophenyl)-2H-pyrazolo[3,4-c]pyridine (I-1A-1c) using appropriate starting materials: +ESI MS (M+1) 374.3; $^1$H NMR (400 MHz, CD$_2$Cl$_2$) δ 8.00 (d, J=6.2 Hz, 1H), 7.60-7.45 (m, 5H), 7.38 (d, J=8.7 Hz, 2H), 7.27 (d, J=8.7 Hz, 2H).

Preparation of Intermediate
1-Benzhydryl-3-ethylaminoazetidine-3-carboxylic
Acid Amide (I-1A-6b):

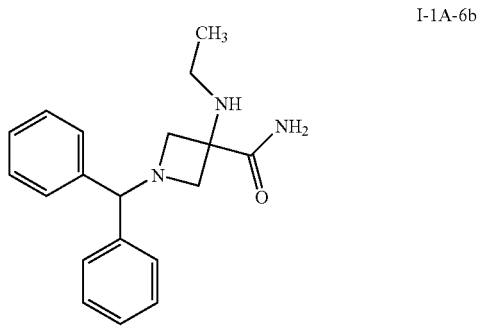

I-1A-6b

Oxalyl chloride (145.2 g, 1.121 mol) was added to dichloromethane (3.75 liters) and the resulting solution was cooled to −78° C. Dimethyl sulfoxide (179.1 g, 2.269 mol) was then added over a duration of 20 minutes while maintaining internal temperature of the reaction below −70° C. during addition. 1-Benzhydrylazetidin-3-ol (250.0 g, 1.045 mol) was then added as a solution in dichloromethane (1.25 liter) to the −78° C. solution of DMSO/oxalyl chloride over a duration of 40 minutes (note—internal temperature maintained below −70° C. during addition). The solution was stirred for 1 hour at −78° C. followed by the addition of triethylamine (427.1 g, 4.179 mol) over 30 minutes (maintained internal temperature below −70° C. during addition). The reaction mixture was then allowed to come to room temperature slowly and stir for 20 hours. 1.0 M hydrochloric acid (3.2 liters, 3.2 mol) was added to the crude reaction solution over 30 minutes, followed by stirring for 10 minutes at room temperature. The heavy dichloromethane layer (clear yellow in color) was then separated and discarded. The remaining acidic aqueous phase (clear, colorless) was treated with 50% sodium hydroxide (150 ml, 2.1 mol) with stirring over a 30-minute period. The final aqueous solution had a pH=9. At this pH, the desired product precipitated from solution as a colorless solid. The pH=9 solution was stirred for 30 minutes and then the precipitated product was collected by filtration. The collected solid was washed with 1.0 liter of water and then air dried for 36 hr to give 1-benzhydrylazetidin-3-one (184.1 g, 74%) as an off-white solid: +ESI MS (M+1 of hydrated ketone) 256.3; $^1$H NMR (400 MHz, CD$_2$Cl$_2$) δ 7.47-7.49 (m, 4H), 7.27-7.30 (m, 4H), 7.18-7.22 (m, 2H), 4.60 (s, 1H), 3.97 (s, 4H).

To a solution of 1-benzhydrylazetidin-3-one (53.4 g, 225 mmol) in methanol (750 ml) was added ethylamine hydrochloride (20.2 g, 243 mmol), KCN (15.4 g, 229 mmol) and then acetic acid (14.3 ml, 247 mmol) at room temperature. After stirring for 2.5 hours at room temperature, at which point the starting ketone had been consumed, the mixture was heated at 55° C. for 15 hours. The reaction mixture was cooled to 50° C. and treated with dimethyl sulfoxide (19.2 ml, 270 mmol) and then 2N aqueous NaOH (251 ml) over a 10-minute period. A solution of 11% aqueous peroxide (80 ml, 247 mmol) was added over 5 minutes (exothermic reaction), during which time a precipitate formed. Additional water (270 ml) was added to aid stirring. After the solution was cooled to room temperature and stirred for an additional hour, a solid precipitated out of solution and was collected on a sintered funnel, washed with water, and then dried, in vacuo, to give crude I-1A-6b (55.3 g, 79%) as a solid.

For purification purposes, crude 1-benzhydryl-3-ethylaminoazetidine-3-carboxylic acid amide (I-2A-1f; 83.0 g, 268 mmol) was added to 1 M HCl (1.3 l), portionwise. After washing the solution with methylene chloride (1 liter, then 0.8 liter), the mixture was treated with 50% aqueous NaOH (130 ml) to bring the pH=10. The precipitate that formed on basification was collected on a sintered funnel, washed with water, and then dried, in vacuo, to give I-1A-6b (72.9 g, 88%) as a colorless solid: +ESI MS (M+1) 310.5; $^1$H NMR (400 MHz, CD$_3$OD) δ 7.41 (d, J=7.1 Hz, 4H), 7.25 (t, J=7.5 Hz, 4H), 7.16 (t, J=7.5 Hz, 2H), 4.49 (s, 1H), 3.44 (d, J=8.3 Hz, 2H), 3.11 (d, J=8.3 Hz, 2H), 2.47 (q, J=7.1 Hz, 2H), 1.10 (t, J=7.3 Hz, 3H).

Preparation of Intermediate
3-Ethylaminoazetidine-3-carboxylic Acid Amide,
Hydrochloride Salt (I-1A-6c):

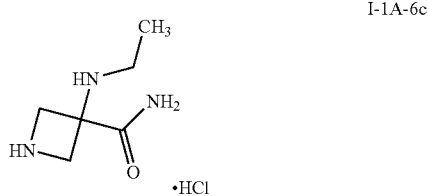

I-1A-6c

To a suspension of 1-benzhydryl-3-ethylaminoazetidine-3-carboxylic acid amide (I-1A-6b; 36.1 g, 117 mmol) in methanol (560 ml) at room temperature was added concentrated aqueous HCl (19.5 ml, 234 mmol), resulting in a clear solution. To 20% Pd(OH)$_2$ on carbon (3.75 g) was added methanol (85 ml), followed by the methanolic solution of I-1A-6b. The mixture was placed on a Parr® shaker and then reduced (50 psi H$_2$) at room temperature for 20 hours. The reaction was then filtered through Celite® and concentrated to a fraction of the original volume under reduced pressure, at which point a precipitate formed. The suspension was diluted with t-butylmethyl ether (MTBE; 500 ml), stirred for an additional hour, and the precipitate collected by vacuum filtration. The solid was washed with MTBE and then dried, in vacuo, to afford I-1A-6c (24.8 g, 98%) as a colorless solid: +APcI MS (M+1) 144.1; $^1$H NMR (400 MHz, CD$_2$Cl$_2$) δ 4.56 (br s, 4H), 3.00 (q, J=7.2 Hz, 2H), 1.36 (t, J=7.1 Hz, 3H).

Preparation of Intermediate 4-amino-1-(2-chlorophenyl)-5-(4-chlorophenyl)-1H-pyrazole-3-carboxylic acid ethyl ester (I-2A-1a):

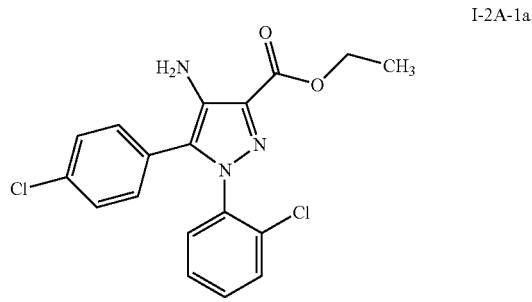

I-2A-1a

To a solution of LiN(TMS)$_2$ (1.0 M in THF, 100 ml, 100 mmol) in 400 ml diethyl ether at −78° C. under nitrogen, 1-(4-chlorophenyl)ethanone (14.3 ml, 110 mmol) in ether (80 ml) was added, dropwise, via addition funnel. After the addition was complete, the reaction mixture was stirred at −78° C. for 40 minutes. Oxalic acid diethyl ester (14.3 ml, 105 mmol) was added in one portion via syringe. The reaction mixture was warmed to room temperature and stirred overnight. The pale white precipitate that formed was collected by filtration. The solid was dried in vacuo to give 4-(4-chlorophenyl)-2-hydroxy-4-oxobut-2-enoic acid ethyl ester lithium salt (24.0 g, 92%).

4-(4-Chlorophenyl)-2-hydroxy-4-oxobut-2-enoic acid ethyl ester lithium salt (10 g, 38.37 mmol) was dissolved in acetic acid (400 ml). After the solution was cooled to 10° C. with an ice-water bath, a concentrated aqueous solution of sodium nitrite (2.86 g, 40.29 mmol) was added dropwise, keeping the temperature between 10 and 15° C. The reaction mixture was stirred for another 45 minutes, and 2-chlorophenylhydrazine HCl salt (8.5 g, 46.04 mmol) was added in portions. Stirring was continued for 3 hours. Upon completion of the reaction, the reaction mixture was poured into 600 ml ice-cold water. A yellow solid precipitated and after 2 hours, it was collected, washed with water, and dried to give crude 4-(4-chlorophenyl)-2-[(2-chlorophenyl)hydrazono]-3-nitroso-4-oxobutyric acid ethyl ester which was used in the next step without further purification.

The yellow solid obtained from last step was redissolved into isopropanol and concentrated H$_2$SO$_4$ (1 ml) was added. The reaction mixture was heated to 60° C. for 3 hours. After cooling to room temperature, the reaction mixture was poured into ice/saturated aqueous NaHCO$_3$. The precipitate was formed and collected by filtration and dried to give 1-(2-chlorophenyl)-5-(4-chlorophenyl)-4-nitroso-1H-pyrazole-3-carboxylic acid ethyl ester. It was used in the next step without further purification.

1-(2-Chlorophenyl)-5-(4-chlorophenyl)4-nitroso-1H-pyrazole-3-carboxylic acid ethyl ester obtained from the last step was dissolved in ethyl acetate (200 ml) and water (200 ml). Sodium dithionite was added until the disappearance of 1-(2-chlorophenyl)-5-(4-chlorophenyl)-4-nitroso-1H-pyrazole-3-carboxylic acid ethyl ester was confirmed by TLC (ethyl acetate/hexane, 50/50). The organic layer was separated and the aqueous layer was extracted with ethyl acetate. The combined organic layers were dried over magnesium sulfate and the solvent was removed, in vacuo. The red solid obtained was further purified by plug filtration (silica, ethyl acetate/hexane, 50/50) to give 4-amino-1-(2-chlorophenyl)-5-(4-chlorophenyl)-1H-pyrazole-3-carboxylic acid ethyl ester I-2A-1a (21.86 g, 76%). MS: 376.1 (M+1)$^+$.

Preparation of Intermediate 3-(4-chlorophenyl)-2-(2-chlorophenyl)-2H-pyrazolo[4,3-d]pyrimidin-7-ol (I-2A-1b):

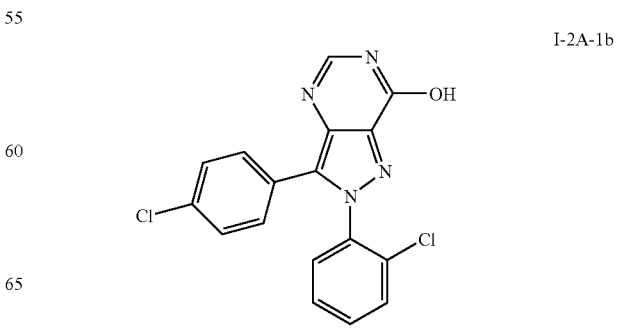

I-2A-1b

A mixture of 4-amino-1-(2-chlorophenyl)-5-(4-chlorophenyl)-1H-pyrazole-3-carboxylic acid ethyl ester I-2A-1a (19.27 g, 51.2 mmol) and formamidine acetate (15.99g, 153.6 mmol) in 2-ethoxyethanol (100 ml) was refluxed for 3.5 h under nitrogen. The reaction mixture was then cooled to room temperature and poured into ice-cold water. The yellow precipitate that formed was collected by filtration and washed with water. The solid was stirred in 45 ml methyl tert-butyl ether for 30 minutes. Cyclohexane (90 ml) was added, and the stirring was continued for another 45 minutes. The pale yellow solid was collected by filtration and dried to give 3-(4-chlorophenyl)-2-(2-chlorophenyl)-2H-pyrazolo[4,3-d]pyrimidin-7-ol 1-2A-1 b (17.55 g, 87%): MS: 357.1 (M+1)$^+$.

Preparation of Intermediate 7-Chloro-3-(4-chlorophenyl)-2-(2-chlorophenyl)-2H-pyrazolo[4,3-d]pyrimidine (I-2A-1c):

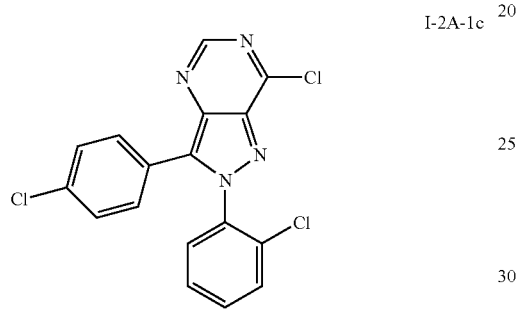

I-2A-1c

To a suspension of 3-(4-chlorophenyl)-2-(2-chlorophenyl)-2H-pyrazolo[4,3-d]pyrimidin-7-ol I-2A-1 b (17.55 g, 49.1 mmol) in 1,2-dichloroethane (109 ml) was added N,N-diethylaniline (32.8 ml, 206.22 mmol) followed by POCl$_3$ (70 ml, 0.7 M). The reaction mixture was heated to reflux under nitrogen for 3 hours, and cooled to room temperature. The solvent was removed under reduced pressure. Excess POCl$_3$ was removed by co-evaporation with toluene three times. The residue was dissolved in methylene chloride and slowly poured into vigorously stirred 1:1 CH$_2$Cl$_2$/saturated aqueous NaHCO$_3$ (500 ml). Additional saturated aqueous NaHCO$_3$ was added until the pH of the mixture was adjusted to neutral. The organic layer was separated and the aqueous layer was extracted with 200 ml methylene chloride three times. The organic layers were combined, dried (MgSO$_4$), and concentrated. The residue was purified by SiO2-gel chromatography using 100% CH$_2$Cl$_2$ as the eluant to give 7-chloro-3-(4-chlorophenyl)-2-(2-chlorophenyl)-2H-pyrazolo[4,3-d]pyrimidine I-2A-1c (18.4 g, 76%): MS: 375.0 (M+1)$^+$.

Preparation of Intermediate 1-Benzhydryl-3-methylaminoazetidine-3-carbonitrile (I-2A-69a):

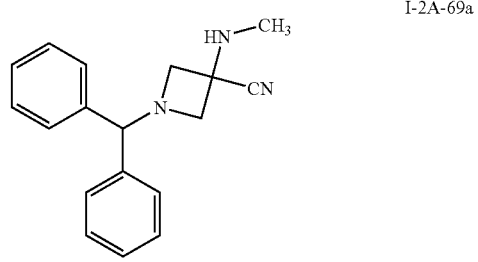

I-2A-69a

To a solution of 1-benzhydrylazetidin-3-one (2.13 g, 8.98 mmol) in methanol (17 ml) was added methylamine hydrochloride (1.21 g, 18.0 mmol) and then acetic acid (1.03 ml, 18.0 mmol) at room temperature. After stirring for 5 minutes, solid KCN (1.17 g, 18.0 mmol) was added and the mixture was heated to 60° C. for 19 hours. The reaction was cooled; the solid product was collected by vacuum filtration, rinsed with methanol, and then dried, in vacuo, to afford I-2A-69a as a colorless solid (2.50 g, quantitative): +ESI MS (M+1) 278.3; $^1$H NMR (400 MHz, CD$_2$Cl$_2$) δ 7.43 (d, J=7.5 Hz, 4H), 7.29 (t, J=7.5 Hz, 4H), 7.23 (t, J=7.3 Hz, 2H), 4.45 (s, 1H), 3.55 (d, J=7.5 Hz, 2H), 3.15 (d, J=7.1 Hz, 2H), 2.40 (s, 3H).

Preparation of Intermediate 1-Benzhydryl-3-methylaminoazetidine-3-carboxylic Acid Amide (I-2A-69b):

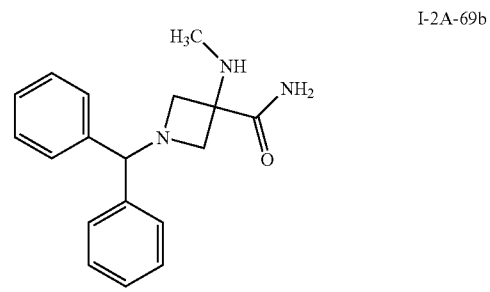

I-2A-69b

A vigorously stirred solution of 1-benzhydryl-3-methylaminoazetidine-3-carbonitrile (I-2A-69a; 2.10 g, 7.57 mmol) in methylene chloride (25 ml) cooled in an ice bath was treated with H$_2$SO$_4$ (4.0 ml, 76 mmol), dropwise. After the reaction mixture was allowed to warm to room temperature and stir overnight, it was cooled in an ice bath and then carefully quenched with concentrated NH$_4$OH to pH 11. The mixture was extracted with methylene chloride, the combined organic layers were dried (Na$_2$SO$_4$) and then concentrated, in vacuo, to afford I-2A-69b (1.2 g, 54%) as an off-white solid: +ESI MS (M+1) 296.3; $^1$H NMR (400 MHz, CD$_3$OD) δ 7.41 (d, J=7.5 Hz, 4H), 7.25 (t, J=7.5 Hz, 4H), 7.16 (t, J=7.1 Hz, 2H), 4.48 (s, 1H), 3.41 (d, J=8.7 Hz, 2H), 3.09 (d, J=8.7 Hz, 2H), 2.24 (s, 3H).

Preparation of Intermediate 2-Benzhydryl-5-methyl-2,5,7-triazaspiro[3,4]oct-6-en-8-one (I-2A-69c):

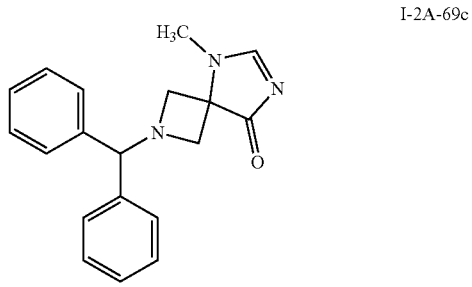

I-2A-69c

N,N-Dimethylformamide dimethyl acetal (1.1 ml, 8.3 mmol) was combined with 1-benzhydryl-3-methylaminoazetidine-3-carboxylic acid amide (I-2A-69b; 153 mg, 0.52 mmol) and heated to reflux. After 3 hours, the suspension was cooled and extracted from saturated aqueous NaHCO₃ with ethyl acetate. The combined extracts were dried (Na₂SO₄), and concentrated, in vacuo, to afford I-2A-69c as a solid (152 mg, 96%): +ESI MS (M+1) 306.3; ¹H NMR (400 MHz, CD₃OD) δ 8.42 (s, 1H), 7.47 (d, J=7.5 Hz, 4H), 7.27 (t, J=7.5 Hz, 4H), 7.17 (t, J=7.5 Hz, 2H), 4.57 (s, 1H), 3.58 (s, 3H), 3.55 (d, J=10.0 Hz, 2H), 3.34 (d, J=10.0 Hz, 2H).

Preparation of Intermediate
5-Methyl-2,5,7-triazaspiro[3.4]octan-8-one, Hydrochloride Salt (I-2A-69d):

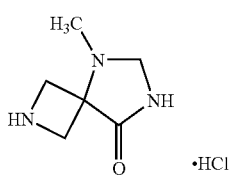

To a solution of 2-benzhydryl-5-methyl-2,5,7-triazaspiro[3.4]oct-6-en-8-one (I-2A-69c; 189 mg, 0.619 mmol) in methanol (30 ml) was added 1 M HCl in diethyl ether (1.3 ml). After the addition of 20% Pd(OH)₂ on carbon (50% water; 95 mg), the mixture was placed on a Parr® shaker and then reduced (50 psi H₂) at room temperature for 5 hours. The reaction mixture was filtered through a 0.45 PM disk, and then concentrated, in vacuo, to give a solid. Trituration from diethyl ether afforded I-2A-69d (124 mg, 94%) as an off-white solid: +APcI MS (M+1) 142.0; ¹H NMR (400 MHz, CD₃OD) δ 4.38 (d, J=12.0 Hz, 2H), 4.17 (s, 2H), 4.13 (d, J=12.5 Hz, 2H), 2.71 (s, 3H).

Preparation of Intermediate
3-Methylaminoazetidine-3-carboxylic Acid Amide, Hydrochloride Salt (I-2A-90a):

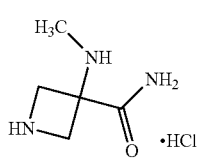

To a suspension of 1-benzhydryl-3-methylaminoazetidine-3-carboxylic acid amide (I-2A-69b; 13.5 g, 45.8 mmol) in methanol (90 ml) was added concentrated aqueous HCl (8.0 ml, 96 mol), dropwise, to give a homogeneous solution. After the addition of 20% Pd(OH)₂ on carbon (50% water; 4.1 g), the mixture was placed on a Parr® shaker and then reduced (50 psi H₂) at room temperature for 7 hours. The mixture was filtered through a pad of Celite®, washing with a copious amount of 9:1 methanol/water, and then 9:1 tetrahydrofuran/water until no product eluted (determined with ninhydrin stain). The filtrate was then concentrated, in vacuo, and the residue was then triturated from diethyl ether to give I-2A-90a (9.3 g, quantitative) as a brown solid:

+APcI MS (M+1) 129.9; ¹H NMR (400 MHz, CD₃OD) δ 4.50 (d, J=12.0 Hz, 2H), 4.43 (d, J=12.9 Hz, 2H), 2.64 (s, 3H).

Preparation of Intermediate
1-Benzhydryl-3-benzylaminoazetidine-3-carbonitrile (I-3A-50a):

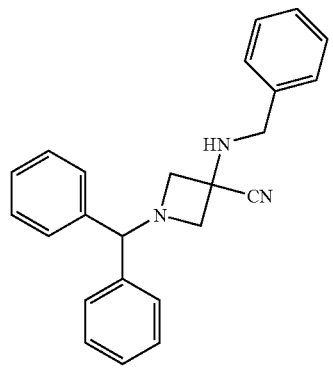

To a solution of 1-benzhydrylazetidin-3-one (3.3 g, 14 mmol) in methanol (35 ml) was added benzylamine (1.6 ml, 15 mmol) and then acetic acid (0.88 ml, 15 mmol) at room temperature. After stirring for 45 minutes, solid NaCN (0.76 g, 15 mmol) was added in portions over 2 minutes and the mixture was heated to reflux overnight. The reaction, which now contained a precipitate, was cooled and then stirred at room temperature. The solids were collected by vacuum filtration, rinsed with a small volume of cold methanol, and then dried, in vacuo, to give I-3A-50a as a solid (3.56 g, 72%): +APcI MS (M+1) 354.4; ¹H NMR (400 MHz, CD₃OD) δ 7.40 (d, J=7.5 Hz, 4H), 7.35 (d, J=7.5 Hz, 2H), 7.31-7.20 (m, 7H), 7.16 (t, J=7.3 Hz, 2H), 4.44 (s, 1H), 3.76 (s, 2H), 3.48 (d, J=8.3 Hz, 2H), 3.05 (d, J=8.3 Hz, 2H).

Preparation of Intermediate
1-Benzhydryl-3-benzylaminoazetidine-3-carboxylic Acid Amide (I-3A-50b):

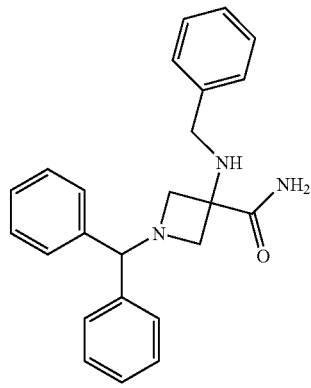

A solution of 1-benzhydryl-3-benzylaminoazetidine-3-carbonitrile I-3A-50a (3.45 g, 9.76 mmol) in methylene chloride (55 ml) cooled in an ice bath was treated with H₂SO₄ (8.1 ml, 0.15 mol), dropwise. After the reaction mixture was allowed to warm to room temperature and stir overnight, it was cooled in an ice bath and then carefully quenched with concentrated NH₄OH to pH 10. The mixture was extracted with methylene chloride; the combined organic layers were washed with brine, dried (Na₂SO₄), and then concentrated, in vacuo, to afford a brown solid. Trituration of this material from hexanes/diethyl ether afforded a light tan solid which was collected by vacuum filtration, washed with additional hexanes and dried, in vacuo, to give I-3A-50b (3.34 g, 92%): +ESI MS (M+1) 372.4; ¹H NMR (400 MHz, CD₃OD) δ 7.41 (d, J=7.5 Hz, 4H), 7.35 (d, J=7.5 Hz, 2H), 7.31-7.22 (m, 7H), 7.16 (t, J=7.7 Hz, 2H), 4.50 (s, 1H), 3.60 (s, 2H), 3.48 (d, J=8.3 Hz, 2H), 3.16 (d, J=8.3 Hz, 2H).

Preparation of Intermediate 2-Benzhydryl-5-benzyl-2,5,7-triazaspiro[3.4]oct-6-en-8-one (I-3A-50c):

I-3A-50c

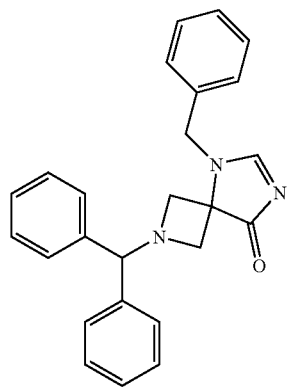

N,N-Dimethylformamide dimethyl acetal (16 ml, 121 mmol) was combined with 1-benzhydryl-3-benzylaminoazetidine-3-carboxylic acid amide (I-3A-50b; 3.03 g, 8.16 mmol) and heated to reflux. After 4 hours, the suspension was cooled and extracted from saturated aqueous NaHCO₃ with ethyl acetate. The combined extracts were dried (Na₂SO₄) and concentrated, in vacuo, to give a crude solid (3.50 g). Purification of the residue on a Biotage™ Flash 40M column using 0-3% methanol in methylene chloride as eluant afforded I-3A-50c as a yellowish solid (1.92 g, 62%): +ESI MS (M+1) 382.3; ¹H NMR (400 MHz, CD₃OD) δ 8.66 (s, 1H), 7.59 (d, J=7.1 Hz, 2H), 7.49-7.11 (m, 13H), 5.12 (s, 2H), 4.44 (s, 1H), 3.31 (d, J=9.6 Hz, 2H), 3.20 (d, J=9.6 Hz, 2H).

Preparation of Intermediate 2,5,7-Triazaspiro[3.4]octan-8-one, Hydrochloride Salt (I-3A-50d):

I-3A-50d

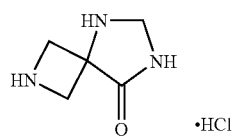
·HCl

To a solution of 2-benzhydryl-5-benzyl-2,5,7-triazaspiro[3.4]oct-6-en-8-one (I-3A-50c; 1.83 g, 4.80 mmol) in methanol/methylene chloride was added excess 1 M HCl in diethyl ether (10 ml). After stirring for 10 minutes, the solvent was removed, in vacuo, and the resultant hydrochloride salt was dissolved in methanol (50 ml). After the addition of 20% Pd(OH)₂ on carbon (50% water; 1.1 g), the mixture was placed on a Parr® shaker and then reduced (50 psi H₂) at room temperature for 22 hours. The reaction was filtered through a 0.45 μM disk, and then concentrated, in vacuo, to give a gummy solid. This material was triturated from methanol to afford I-3A-50d (450 mg, 47%) as a tan solid: +APcI MS (M+1) 127.9; ¹H NMR (400 MHz, CD₃OD) δ 4.51 (s, 2H), 4.41-4.33 (m, 4H).

Preparation of Intermediate 3-(4-Chlorophenyl)-2-(2-chlorophenyl)-5-ethyl-2H-pyrazolo[4,3-d]pyrimidin-7-ol (I-10A-1a):

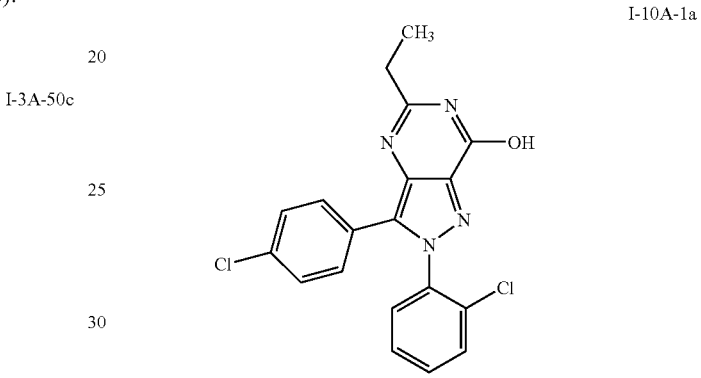

Potassium t-butoxide (3.0 ml, 1 M in THF; 3.0 mmol) was added to a suspension of propionamidine hydrochloride (326 mg; 3.0 mmol) in ethoxyethanol (3 ml). The reaction mixture was immediately concentrated under vacuum. The residue was re-suspended in ethoxyethanol (3 ml), and 4-amino-1-(2-chlorophenyl)-5-(4-chlorophenyl)-1H-pyrazole-3-carboxylic acid ethyl ester I-2A-1a (376 mg, 1 mmol) and glacial acetic acid (250 μl; 4.4 mmol) were added. The resulting mixture was heated at 125° C. for 43 hours, cooled to room temperature, quenched with saturated aqueous NaCl, and extracted with ethyl acetate (2×). The combined organic extracts were washed with 0.5 M citric acid, 1 M aqueous K₂CO₃, and saturated aqueous NaCl, dried, and concentrated in vacuo. The residue was purified by radial chromatography (4 mm silica gel plate; elution with CH₂Cl₂, followed by 50% hexane/ethyl acetate) to give the desired product I-10A-1a (7 mg). A solid also precipitated out of the combined aqueous layers and was collected by filtration to give, after drying overnight, additional product (15 mg): MS (M+1)⁺ 385.4; ¹H NMR (400 MHz, d₆-DMSO) δ 12.05 (s, 1H), 7.78-7.40 (dd, J=7.5, 1.4 Hz, 1H), 7.67-7.53 (m, 3H), 7.47-7.42 (m, 2H), 7.39-7.34 (m, 2H), 2.59 (q, J=7.5 Hz, 2H), 1.20 (t, J=7.5 Hz, 3H).

Preparation of Intermediate Benzoic Acid 2,2-Difluorobutyl ester (I-10A-6a):

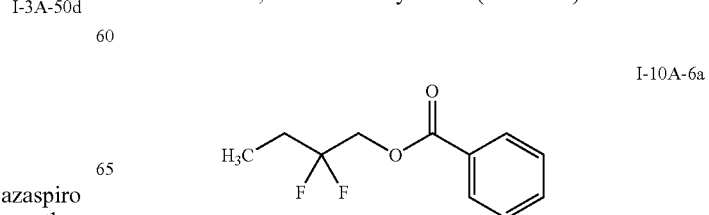

To a solution of benzoic acid 2-oxobutyl ester (20 g, 104 mmol) in CH$_2$Cl$_2$ (40 ml) at room temperature was added (diethylamino)sulfur trifluoride (DAST, 36.9 g, 30 ml, 228.9 mmol) and ethanol (0.4 ml). The reaction mixture was stirred for 17 hours. Additional DAST (4.5 ml) was added dropwise, and the resulting mixture was stirred for 72 hours. The reaction mixture was quenched first with cold water (250 ml) and then with cold saturated aqueous NaHCO$_3$ (100 ml). The organic layer was separated, and the aqueous phase was extracted with CH$_2$Cl$_2$ (2×). The combined extracts were dried and concentrated under vacuum. The crude residue was purified via silica gel chromatography using a solvent gradient of 0-2% ethyl acetate/hexanes to give the desired product, benzoic acid 2,2-difluorobutyl ester (I-10A-6a), as a colorless oil: $^1$H NMR (400 MHz, CDCl$_3$) δ 8.05 (d, J=1.2 Hz, 2H), 7.58 (m, 1H), 7.45 (m, 2H), 4.48 (t, J=12.0 Hz, 2H), 2.04 (m, 2H), 1.08 (t, J=7.5 Hz, 3H).

Preparation of Intermediate 2,2-Difluorobutan-1-ol (I-10A-6b):

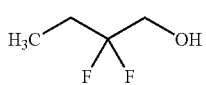

A solution of benzoic acid 2,2-difluorobutyl ester (I-10A-6a; 16 g, 75 mmol) in 1:1.6 6N aqueous NaOH/methanol (65 ml) was stirred at ambient temperature for 2 hours. The reaction mixture was concentrated under vacuum to remove the methanolic solvent. The aqueous residue was extracted with diethyl ether (2×) and the combined ether extracts were dried and concentrated to give the desired product, 2,2-difluorobutan-1-ol (I-10A-6b), as a yellow oil contaminated with some diethyl ether and methanol (6.5 g, 79%): $^1$H NMR (400 MHz, CDCl$_3$) δ 3.72 (t, 2H), 1.9 (m, 2H), 1.02 (t, 3H).

Preparation of Intermediate Trifluoromethanesulfonic Acid 2,2-Difluorobutyl Ester (I-10A-6c):

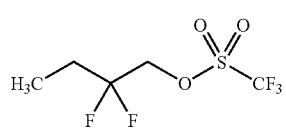

A solution of 2,2-difluorobutan-1-ol (I-10A-6b; 1.00 g, 9.1 mmol), N-phenyltrifluoromethanesulfonimide (4.87 g, 13.6 mmol), and triethylamine (3 ml) in CH$_2$Cl$_2$ (15 ml) was stirred at ambient temperature for 2 hours. The reaction mixture was quenched with 1 N aqueous NaOH and extracted with CH$_2$Cl$_2$ (3×). The combined organic extracts were washed with saturated aqueous NaCl, dried, and concentrated under vacuum. The crude residue was purified via silica gel chromatography using a solvent gradient of 10-50% ethyl acetate/hexanes to give the product, trifluoromethanesulfonic acid 2,2-difluoro-butyl ester (I-10A-6c), as a colorless oil (0.70 g, 32%): $^1$H NMR (400 MHz, CDCl$_3$) δ 4.5 (t, J=11.0 Hz, 2H), 1.95 (m, 2H), 1.08 (t, J=7.5 Hz, 3H).

Preparation of Intermediate Benzoic Acid 2,2-Difluoropropyl Ester (I-10A-7a):

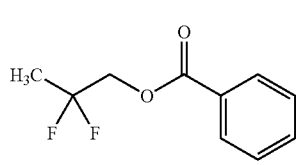

The title compound I-10A-7a (47.8 g, 94%) was prepared from benzoic acid 2-oxopropyl ester (41.4 g, 232 mmol) using the procedure described above for the preparation of I-10A-6a. The crude product was used without further purification: $^1$H NMR (400 MHz, CDCl$_3$) δ 8.05 (d, 2H), 7.58 (m, 1H), 7.45 (m, 2H), 4.47 (t, J=12.0 Hz, 2H), 1.73 (t, J=18.7 Hz, 3H).

Preparation of Intermediate 2,2-Difluoropropan-1-ol (I-10A-7b):

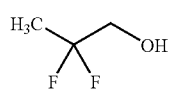

A two-phase mixture of benzoic acid 2,2-difluoropropyl ester (I-10A-7a; 20 g, 100 mmol) in 1:1.5:2 6N NaOH/H$_2$O/diethyl ether (183 ml) was stirred at 50° C. for 17 hours. After cooling to ambient temperature, the reaction mixture was extracted with diethyl ether (3×), and the combined extracts were dried and concentrated under reduced pressure. The orange-colored crude residue was distilled to give the desired product, 2,2-difluoropropan-1-ol (I-10A-7b), as a colorless oil (2.8 g, 29%): boiling point—100° C. (1 atm); $^1$H NMR (400 MHz, CDCl$_3$) δ 3.71 (t, J=12.5 Hz, 2H), 1.64 (t, J=18.7 Hz, 3H).

Preparation of Intermediate Trifluoromethanesulfonic Acid 2,2-Difluoropropyl Ester (I-10A-7c):

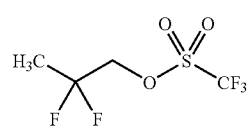

To a solution of 2,2-difluoropropan-1-ol (I-10A-7b; 1.76 g, 18.3 mmol), dimethylaminopropylamine (DMAP: 157 mg, 1.3 mmol), and triethylamine (2.20 g, 3.1 ml, 22 mmol) in CH$_2$Cl$_2$ (15 ml) at 0° C. was added triflic anhydride (Tf$_2$O; 6.2 g, 3.7 ml, 22 mmol). The reaction mixture initially turned a pink color, then a yellow color following the complete addition of Tf$_2$O. The reaction mixture was stirred at 0° C. for 2 hours and diluted with CH$_2$Cl$_2$. The organic solution was washed with water, 1 M aqueous citric acid, and saturated aqueous NaHCO$_3$, dried, and concentrated under reduced pressure (225 mm/Hg; bath temperature −30° C.) to give the desired product, trifluoromethanesulfonic acid 2,2-difluoropropyl ester (I-10A-7c), as a pink oil (3 g, 72%): ¹H NMR (400 MHz, CDCl₃) δ 4.49 (t, J=10.8 Hz, 2H), 1.74 (t, 3H).

Preparation of Intermediate 3-(4-Chlorophenyl)-2-(2-chlorophenyl)-2H-pyrazolo[3,4-c]pyridin-7-ol (I-10A-14a):

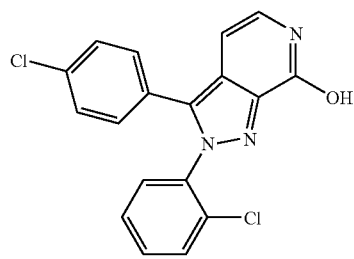

I-10A-14a

A stirred mixture of 7-chloro-3-(4-chlorophenyl)-2-(2-chlorophenyl)-2H-pyrazolo[3,4-c]pyridine (I-1A-6a; 420 mg, 1.12 mmol) in 3M aqueous HCl (7.5 ml) and tetrahydrofuran (12 ml) was heated overnight at 45° C. The reaction mixture was cooled and the pH adjusted to 8 with 5M aqueous NaOH. The aqueous layer was dried (Na₂SO₄), concentrated, in vacuo, and the resulting solid repulped from 40% ethyl acetate/isopropyl ether (20 ml) to afford I-10A-14a as an off-white solid (320 mg, 80%): +ESI MS (M+1) 356.3; ¹H NMR (400 MHz, CD₂Cl₂) δ 9.64 (br s, 1H), 7.55-7.41 (m, 4H), 7.34 (d, J=8.7 Hz, 2H), 7.21 (d, J=8.7 Hz, 2H), 6.96 (dd, J=7.5, 5.8 Hz, 1H), 6.50 (d, J=7.5 Hz, 1H).

Example 1

Preparation of 1-[3-(4-Chlorophenyl)-2-(2,4-dichlorophenyl)-2H-pyrazolo[3,4-c]pyridin-7-yl]-4-ethylaminopiperidine-4-carboxylic Acid Amide (1A-1):

1A-1

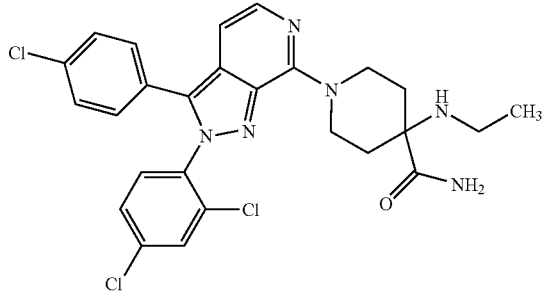

7-Chloro-3-(4-chlorophenyl)-2-(2,4-dichlorophenyl)-2H-pyrazolo[3,4-c]pyridine (I-1A-1c; 71 mg, 0.17 mmol), 4-ethylaminopiperidine-4-carboxylic acid amide (I-1A-1f; 62 mg, 0.36 mmol) and triethylamine (52 microliters, 0.52 mmol) were combined in ethanol (1.2 ml) and the heterogeneous mixture was stirred and heated to 60° C. After 3 days, the reaction was cooled to room temperature and purified on a Biotage™ Flash 12M column using a solvent gradient of 0-2-4-6% methanol in methylene chloride as eluant to afford title compound I-1A-1 (73 mg, 78%) as a glass: +ESI MS (M+1) 543.1; ¹H NMR (500 MHz, CD₃OD) δ 7.63 (d, J=2.1 Hz, 1H), 7.60 (d, J=8.7 Hz, 1H), 7.57 (d, J=6.2 Hz, 1H), 7.49 (dd, J=8.3, 2.1 Hz, 1H), 7.38 (d, J=8.3 Hz, 2H), 7.26 (d, J=8.3 Hz, 2H), 6.84 (d, J=6.2 Hz, 1H), 4.35-4.28 (m, 2H), 4.10 (ddd, J=13.3, 9.1, 3.3 Hz, 2H), 2.51 (q, J=7.1 Hz, 2H), 2.12 (ddd, J=13.7, 9.1, 3.7 Hz, 2H), 1.73 (dq, J=13.3, 3.3 Hz, 2H), 1.10 (t, J=7.1 Hz, 3H).

The hydrochloride salt of compound 1A-1 may be prepared using the following procedure:

To a solution of 1-[3-(4-chlorophenyl)-2-(2,4-dichlorophenyl)-2H-pyrazolo[3,4-c]pyridin-7-yl]-4-ethylaminopiperidine-4-carboxylic acid amide (I-1A-1; 69 mg, 0.13 mmol) in methylene chloride (3 ml) was added 1 M HCl in diethyl ether (0.32 ml), dropwise. A precipitate formed after 3 minutes. After stirring for 10 minutes, the ether was removed, in vacuo, the solids were washed with diethyl ether and then dried, in vacuo, to afford the hydrochloride salt of 1A-1 as an off-white solid (69 mg, 88%): ¹H NMR (500 MHz, CD₃OD) δ 7.74-7.70 (m, 2H), 7.59 (dd, J=8.7, 2.0 Hz, 1H), 7.48 (d, J=8.3 Hz, 2H), 7.40 (d, J=7.1 Hz, 1H), 7.35 (d, J=8.7 Hz, 2H), 7.18 (d, J=7.1 Hz, 1H), 3.08 (q, J=7.2 Hz, 2H), 2.76-2.66 (br m, 2H), 2.32 (ddd, J=14.1, 9.6, 4.1 Hz, 2H), 1.37 (t, J=7.3 Hz, 3H).

The compounds listed in Table 1 below were prepared using procedures analogous to those described above for the synthesis of Compound 1A-1 using the appropriate starting materials which are available commercially, prepared using preparations well-known to those skilled in the art, or prepared in a manner analogous to routes described above for other intermediates. The compounds listed below were generally isolated as their free base and then converted to their corresponding hydrochloride salts prior to in vivo testing.

TABLE 1

| Example No. | —R⁰ᵇ | —NRR' | MS (M + H)⁺ |
|---|---|---|---|
| 1A-2 | —Cl | pyrrolidinyl | 443.1 |
| 1A-3 | —Cl | 4-methylpiperazinyl | 472.2 |

TABLE 1-continued

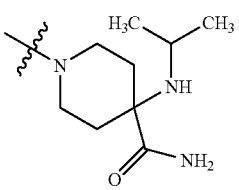

| Example No. | —R^{0b} | —NRR' | MS (M + H)^+ |
|---|---|---|---|
| 1A-4 | —Cl |  | 557.2 |
| 1A-5 | —Cl | 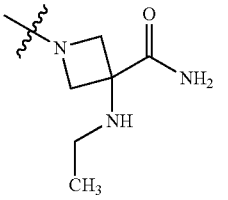 | 583.2 |
| 1A-6 | —H | 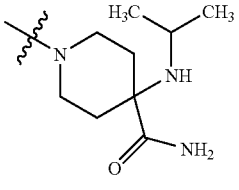 | 481.4 |
| 1A-7 | —H | 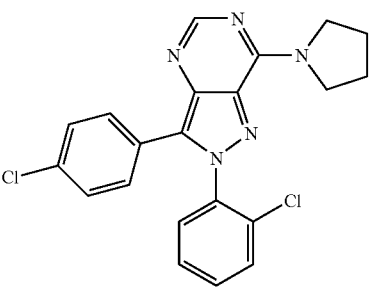 | 523.5 |

Example 2

Preparation of 3-(4-Chlorophenyl)-2-(2-chlorophenyl)-7-pyrrolidin-1-yl-2H-pyrazolo[4,3-d]pyrimidine (2A-1):

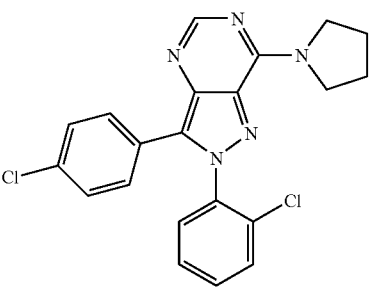

To a suspension of 7-chloro-3-(4-chlorophenyl)-2-(2-chlorophenyl)-2H-pyrazolo[4,3-d]pyrimidine I-2A-1c (40 mg, 0.1 mmol) in 5 ml ethanol was added pyrrolidine (711 mg, 10 mmol). The reaction mixture was stirred at room temperature for 1 hour and became homogeneous. After the reaction was complete (as monitored by TLC, ethyl acetate/hexane, 50/50), ethanol was removed under reduced pressure. The residue was redissolved in ethyl acetate, washed with water, dried over magnesium sulfate, and concentrated. The crude product was purified by HPLC to give 3-(4-chlorophenyl)-2-(2-chlorophenyl)-7-pyrrolidin-1-yl-2H-pyrazolo[4,3-d]pyrimidine 2A-1 (17 mg, 38.2%). MS: 410.2 (M+1)^+; $^1$H NMR (400 MHz, CD$_2$Cl$_2$) δ 8.3 (s, 1H), 7.5 (m, 6H), 7.3 (d, J=8.7 Hz, 2H), 4.2 (t, J=6.3 Hz, 2H), 3.8 (t, J=7.1 Hz, 2H), 2.1 (m, 4H).

The compounds listed in Table 2 below were prepared using procedures analogous to those described above for the synthesis of Compound 2A-1 using the appropriate starting materials which are available commercially, prepared using preparations well-known to those skilled in the art, or prepared in a manner analogous to routes described above for other intermediates. The compounds listed below were generally isolated as their free base and then converted to their corresponding hydrochloride salts prior to in vivo testing.

TABLE 2

| Example No. | R^{0a} | R^{0b} | —NRR' | MS (M + H)^+ |
|---|---|---|---|---|
| 2A-2 | Cl | Cl | —N(CH$_2$CH$_3$)$_2$ | 448.2 |
| 2A-3 | Cl | Cl | (piperidine) | 458.1 |

TABLE 2-continued
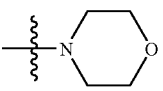
| Example No. | R⁰ᵃ | R⁰ᵇ | —NRR' | MS (M+H)⁺ |
|---|---|---|---|---|
| 2A-4 | Cl | Cl |  | 460.1 |
| 2A-5 | Cl | Cl | 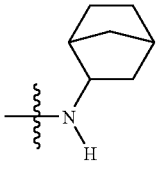 | 473.2 |
| 2A-6 | Cl | Cl | 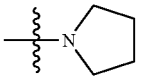 | 484.2 |
| 2A-7 | Cl | Cl | 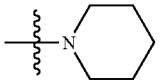 | 446.1 |
| 2A-8 | Cl | H | 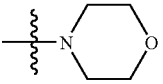 | 424.2 |
| 2A-9 | Cl | H |  | 426.2 |
| 2A-10 | Cl | H | 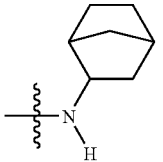 | 439.2 |
| 2A-11 | Cl | H | —N(CH₂CH₃)₂ | 412.2 |
| 2A-12 | Cl | H | 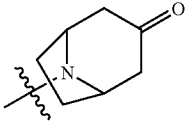 | 450.2 |
| 2A-13 | Cl | H | 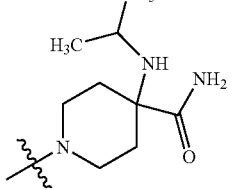 | 464.1 |
| 2A-14 | Cl | H | 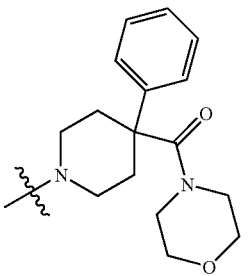 | 524.2 |
| 2A-15 | Cl | H | 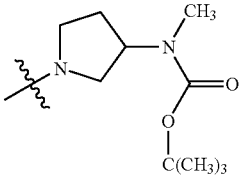 | 613.2 |
| 2A-16 | Cl | H | 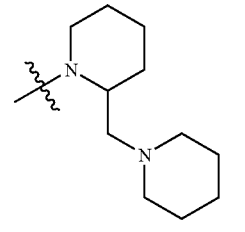 | 539.2 |
| 2A-17 | Cl | H | 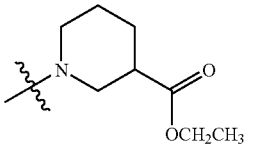 | 521.2 |
| 2A-18 | Cl | H |  | 496.1 |

TABLE 2-continued

| Example No. | R⁰ᵃ | R⁰ᵇ | —NRR' | MS (M+H)⁺ |
|---|---|---|---|---|
| 2A-19 | Cl | Cl | (difluoro bridged bicyclic amine) | 568.1 |
| 2A-20 | Cl | H | pyrrolidin-3-yl NH-C(O)OC(CH₃)₃ | 525.2 |
| 2A-21 | Cl | H | 2-((dimethylamino)methyl)piperidin-1-yl | 481.2 |
| 2A-22 | Cl | H | 4-(ethoxycarbonyl)piperidin-1-yl | 496.1 |
| 2A-23 | Cl | Cl | 2-(2-(pyrrolidin-1-yl)ethyl)piperidin-1-yl | 555.2 |
| 2A-24 | Cl | H | 3-(benzylamino)-8-azabicyclo[3.2.1]octan-8-yl | 555.2 |
| 2A-25 | Cl | H | 3-(N-methylacetamido)pyrrolidin-1-yl | 481.1 |
| 2A-26 | Cl | H | 4-hydroxy-4-phenylpiperidin-1-yl | 516.2 |
| 2A-27 | Cl | H | 5-methoxy-spiro[piperidine-tetrahydronaphthalene] | 570.2 |
| 2A-28 | Cl | Cl | 3-(hydroxymethyl)piperidin-1-yl | 488.1 |
| 2A-29 | Cl | H | 3-(dimethylamino)pyrrolidin-1-yl | 453.1 |
| 2A-30 | Cl | H | 1,4-dioxa-8-azaspiro[4.5]decan-8-yl | 482.1 |
| 2A-31 | Cl | H | methoxy-spiro[piperidine-tetrahydronaphthalene] | 570.2 |

TABLE 2-continued

| Example No. | R⁰ᵃ | R⁰ᵇ | —NRR' | MS (M + H)⁺ |
|---|---|---|---|---|
| 2A-32 | Cl | Cl | 4-benzylpiperidinyl | 548.2 |
| 2A-33 | Cl | H | 5-methyl-2,5-diazabicyclic | 451.1 |
| 2A-34 | Cl | H | dimethyl-dioxolane-fused pyrrolidinyl | 482.1 |
| 2A-35 | Cl | H | 3,5-dimethylpiperidinyl | 452.2 |
| 2A-36 | Cl | H | 3-(3-methoxyphenyl)piperidinyl | 530.2 |
| 2A-37 | Cl | Cl | 3,3-dimethylpiperidinyl | 486.1 |
| 2A-38 | Cl | H | methyl-oxa-bridged bicyclic pyrrolidinyl | 492.1 |
| 2A-39 | Cl | H | 2-(2-(azepan-1-yl)ethyl)piperidinyl | 549.3 |
| 2A-40 | Cl | Cl | decahydroquinolinyl | 512.1 |
| 2A-41 | Cl | H | 3,4-dihydroxypyrrolidinyl | 442.1 |
| 2A-42 | Cl | H | 2,5-dimethylpyrrolidinyl | 438.1 |
| 2A-43 | Cl | H | 2,3-dimethylpiperidinyl | 452.2 |
| 2A-44 | Cl | H | spiro[indene-piperidine]yl | 524.2 |

TABLE 2-continued

[Structure: 3-(4-chlorophenyl)-2-(2,4-disubstituted phenyl)-2H-pyrazolo[3,4-d]pyrimidin-7-amine with R^0a, R^0b substituents and NRR' group]

| Example No. | R^0a | R^0b | —NRR' | MS (M + H)^+ |
|---|---|---|---|---|
| 2A-45 | Cl | Cl | [2-((dimethylamino)methyl)piperidin-1-yl] | 517.1 |
| 2A-46 | Cl | H | [(3R)-3-hydroxypyrrolidin-1-yl] | 426.1 |
| 2A-47 | Cl | H | [tert-butyl 2,5-diazabicyclo carboxylate] | 537.2 |
| 2A-48 | Cl | H | [4-(piperidin-1-yl)piperidin-1-yl] | 507.2 |
| 2A-49 | Cl | H | [3-cyclohexylpiperidin-1-yl] | 506.2 |
| 2A-50 | Cl | H | [(2S)-2-(hydroxymethyl)pyrrolidin-1-yl] | 440.1 |
| 2A-51 | Cl | H | [3-hydroxy-4-isopropoxypyrrolidin-1-yl] | 484.1 |
| 2A-52 | Cl | H | [6,7-dimethoxy-spiro-isochroman-piperidine] | 602.2 |
| 2A-53 | Cl | H | [4-cyano-4-(3-methoxyphenyl)piperidin-1-yl] | 555.2 |
| 2A-54 | Cl | H | [2-(hydroxymethyl)pyrrolidin-1-yl] | 440.1 |
| 2A-55 | Cl | H | [(3R)-3-((4-methoxy-2,3-dihydro-1H-inden-5-yl)oxy)pyrrolidin-1-yl] | 572.2 |
| 2A-56 | Cl | H | [3-(2-ethoxy-2-oxoethyl)piperidin-1-yl] | 510.2 |

TABLE 2-continued

| Example No. | R⁰ᵃ | R⁰ᵇ | —NRR' | MS (M+H)⁺ |
|---|---|---|---|---|
| 2A-57 | Cl | H | 2-methylpiperidinyl | 438.2 |
| 2A-58 | Cl | H | 2-(pyrrolidin-1-ylmethyl)pyrrolidinyl | 493.2 |
| 2A-59 | Cl | H | 4-(cyano(phenyl)methyl)piperidinyl | 539.2 |
| 2A-60 | Cl | H | 3-(pyridin-2-yloxy)piperidinyl | 517.2 |
| 2A-61 | Cl | H | 3-methylpiperidinyl | 438.1 |
| 2A-62 | Cl | H | spiro[indane-1,4'-piperidine] | 526.2 |

TABLE 2-continued

| Example No. | R⁰ᵃ | R⁰ᵇ | —NRR' | MS (M+H)⁺ |
|---|---|---|---|---|
| 2A-63 | Cl | H | trimethyl azabicyclic | 492.2 |
| 2A-64 | Cl | Cl | N-Boc-diazabicyclic | 571.1 |
| 2A-65 | Cl | Cl | 3-(benzylamino)quinuclidinyl | 591.1 |
| 2A-66 | Cl | H | 3-bromo-8-azabicyclo[3.2.1]octanyl | 564.0 |
| 2A-67 | Cl | H | 4-piperidin-1-yl-piperidine-4-carboxamide | 550.1 |
| 2A-68 | Cl | H | 4-(ethylamino)piperidine-4-carboxamide | 510.1 |
| 2A-69 | Cl | H | 1-thia-4,8-diazaspiro[4.5]decanyl | 497.0 |
| 2A-70 | Cl | H | 1-methyl-2,7-diazaspiro[3.4]octan-6-one | 480.1 |

TABLE 2-continued
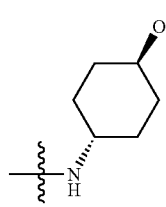
| Example No. | R⁰ᵃ | R⁰ᵇ | —NRR' | MS (M + H)⁺ |
|---|---|---|---|---|
| 2A-71 | Cl | Cl | —N(CH₂CH₃)₂ | 448.2 |
| 2A-72 | Cl | H |  | 454.1 |
| 2A-73 | Cl | Cl | 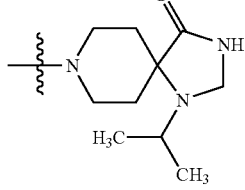 | 564.0 |
| 2A-74 | Cl | H | 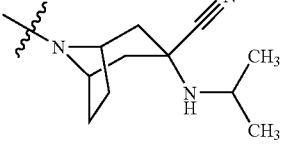 | 536.2 |
| 2A-75 | Cl | H |  | 532.5 |
| 2A-76 | Cl | H |  | 468.2 |
| 2A-77 | Cl | H | 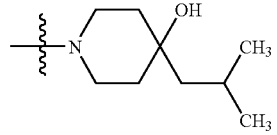 | 482.2 |
| 2A-78 | Cl | H | 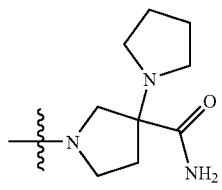 | 496.3 |
TABLE 2-continued
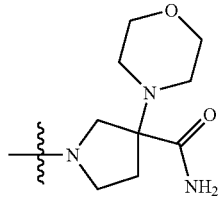
| Example No. | R⁰ᵃ | R⁰ᵇ | —NRR' | MS (M + H)⁺ |
|---|---|---|---|---|
| 2A-79 | Cl | H | 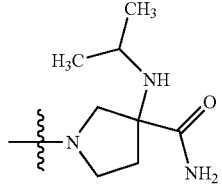 | 522.3 |
| 2A-80 | Cl | H | 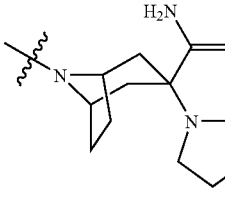 | 538.2 |
| 2A-81 | Cl | H | 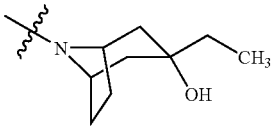 | 510.2 |
| 2A-82 | Cl | H | 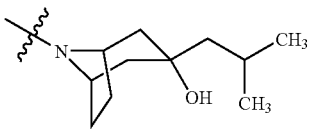 | 562.2 |
| 2A-83 | Cl | H | | 494.0 |
| 2A-84 | Cl | H | | 522.1 |

TABLE 2-continued

[Structure: pyrazolo[4,3-d]pyrimidine core with 4-Cl-phenyl, NRR', and phenyl bearing R⁰ᵃ and R⁰ᵇ substituents]

| Example No. | R⁰ᵃ | R⁰ᵇ | —NRR' | MS (M + H)⁺ |
|---|---|---|---|---|
| 2A-85 | Cl | H | [bicyclic N with isopropyl and OH] | 508 |
| 2A-86 | Cl | H | [N-piperidinyl with OH and CH₃] | 454.3 |
| 2A-87 | Cl | H | [N-pyrrolidinyl with OH and CH₂CH₃] | 454.2 |
| 2A-88 | Cl | H | [N-pyrrolidinyl with OH and isobutyl] | 482.4 |
| 2A-89 | Cl | H | [N-pyrrolidinyl with OH, CH₃, and isopropyl] | 468.3 |
| 2A-90 | Cl | H | [N-pyrrolidinyl with OH and CH₃] | 440.3 |
| 2A-91 | Cl | H | [N-azetidinyl with C(O)NH₂ and NHCH₃] | 468.1 |

Example 3

Preparation of 3-(4-Chlorophenyl)-2-(2-chlorophenyl)-7-piperidinyl-1-yl-2H-pyrazolo[4,3-d]pyrimidine (3A-1):

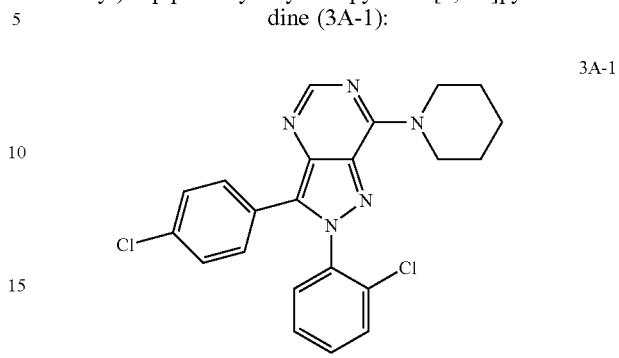

3A-1

To the mixture of piperidine (102 mg, 1.20 mmol), PS-DIEA (polystyrene-diisopropylethylamine; 130 mg, 3.72 mmol/g) in 1.0 ml ethanol was added 7-chloro-3-(4-chlorophenyl)-2-(2-chlorophenyl)-2H-pyrazolo[4,3-d]pyrimidine I-2A-1c (100 mg, 0.26 mmol). The reaction mixture was shaken for 24 hours at 50° C. The PS-DIEA was then filtered off, and the filtrate was concentrated in vacuo. The residue was purified by chromatography (silica, 20% ethyl acetate in hexanes grading to 50% ethyl acetate in hexanes). The purified product was dissolved in ethyl acetate (1 ml). HCl in ether (0.2 ml of a 1.0 M solution in diethyl ether) was added, and the precipitate that formed was collected by filtration and dried to provide 3-(4-chlorophenyl)-2-(2-chlorophenyl)-7-piperidinyl-1-yl-2H-pyrazolo[4,3-d]pyrimidine 3A-1 (94.4 mg): MS: 423.1 (M+1)⁺; ¹H NMR (400 MHz, CD₂Cl₂) δ 8.5 (s, 1H), 7.5 (m, 4H), 7.4 (s, 4H), 4.7 (m, 2H), 4.3 (m, 2H), 1.8 (m, 6H).

The compounds listed in Table 3 below were prepared using procedures analogous to those described above for the synthesis of Compound 3A-1 using the appropriate starting materials which are available commercially, prepared using preparations well-known to those skilled in the art, or prepared in a manner analogous to routes described above for other intermediates. The compounds listed below were generally isolated as their free base and then converted to their corresponding hydrochloride salts prior to in vivo testing.

TABLE 3

[Structure: pyrazolo[4,3-d]pyrimidine core with 4-Cl-phenyl, NRR', and 2-Cl-phenyl]

| Example No. | —NRR' | MS (M + H)⁺ |
|---|---|---|
| 3A-2 | [NH-cyclohexyl with CH₃] | 452.1 |

TABLE 3-continued
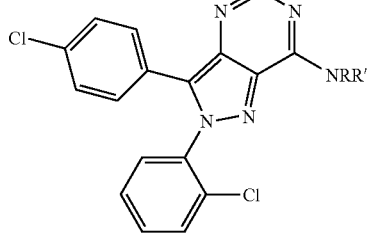
| Example No. | —NRR' | MS (M + H)+ |
|---|---|---|
| 3A-3 | 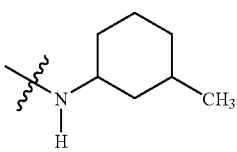 | 490.2 |
| 3A-4 | 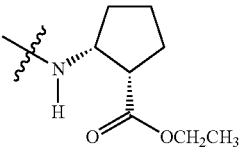 | 452.2 |
| 3A-5 | 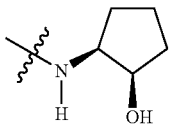 | 496.1 |
| 3A-6 | 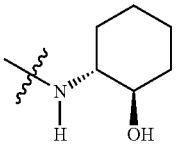 | 440.1 |
| 3A-7 | 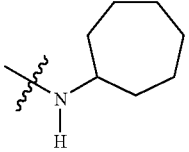 | 454.1 |
| 3A-8 | 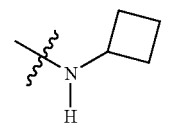 | 452.1 |
| 3A-9 | 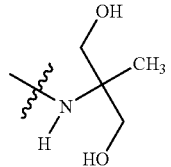 | 410.1 |
| 3A-10 | 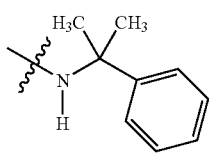 | 444.1 |
TABLE 3-continued
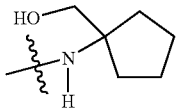
| Example No. | —NRR' | MS (M + H)+ |
|---|---|---|
| 3A-11 | 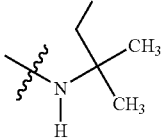 | 474.1 |
| 3A-12 | 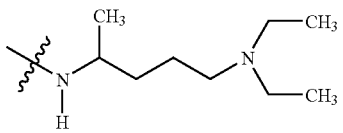 | 454.1 |
| 3A-13 | 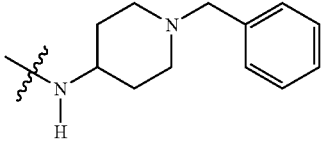 | 426.1 |
| 3A-14 | 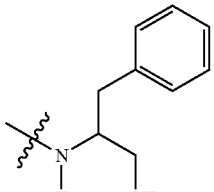 | 497.2 |
| 3A-15 | 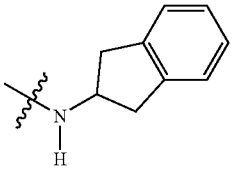 | 529.2 |
| 3A-16 | | 490.1 |
| 3A-17 | | 472.1 |

TABLE 3-continued

| Example No. | —NRR' | MS (M + H)+ |
|---|---|---|
| 3A-18 | 1,2,3,4-tetrahydronaphthalen-1-yl-amino | 486.1 |
| 3A-19 | 1-phenylethylamino | 460.1 |
| 3A-20 | 3-benzyl-3-azabicyclo[3.1.0]hexan-6-yl-amino | 527.2 |
| 3A-21 | 1-(pyrrolidin-1-yl)-1-oxopropan-2-yl-amino | 481.1 |
| 3A-22 | 1-(4-hydroxyphenyl)propan-2-yl-amino | 490.1 |
| 3A-23 | 1-cyclohexylethylamino | 466.2 |

TABLE 3-continued

| Example No. | —NRR' | MS (M + H)+ |
|---|---|---|
| 3A-24 | 1-(p-tolyl)ethylamino | 474.1 |
| 3A-25 | 1-(p-tolyl)ethylamino | 474.1 |
| 3A-26 | 2-phenylcyclopropylamino | 472.1 |
| 3A-27 | 3-hydroxy-2,3-dihydro-1H-inden-1-yl-amino | 488.1 |
| 3A-28 | 1-morpholinopropan-2-yl-amino | 483.2 |
| 3A-29 | pyridin-2-yl-amino | 433.1 |

TABLE 3-continued

| Example No. | —NRR' | MS (M + H)+ |
|---|---|---|
| 3A-30 | 5-methylpyridin-2-ylamino | 447.1 |
| 3A-31 | 6-methoxypyridin-3-ylamino | 463.1 |
| 3A-32 | 6-(piperidin-1-yl)pyridin-3-ylamino | 516.2 |
| 3A-33 | 6-(azetidin-1-yl)pyridin-3-ylamino | 488.1 |
| 3A-34 | (pyridin-2-ylmethyl)amino | 447.1 |
| 3A-35 | ((6-methylpyridin-2-yl)methyl)amino | 461.1 |
| 3A-36 | (pyridin-3-ylmethyl)amino | 447.1 |

TABLE 3-continued

| Example No. | —NRR' | MS (M + H)+ |
|---|---|---|
| 3A-37 | (2-morpholinoethyl)amino | 469.1 |
| 3A-38 | (1H-benzimidazol-2-ylmethyl)amino | 486.1 |
| 3A-39 | (2-hydroxypropyl)amino | 414.1 |
| 3A-40 | (2,2,2-trifluoroethyl)amino | 438.1 |
| 3A-41 | (cyclopropylmethyl)amino | 410.1 |
| 3A-42 | 4-cyano-4-phenylpiperidin-1-yl | 525.2 |
| 3A-43 | (3R)-3-hydroxypiperidin-1-yl | 440.1 |

TABLE 3-continued

[Structure: 3-(4-chlorophenyl)-2-(2-chlorophenyl)-2H-pyrazolo[3,4-d]pyrimidine with NRR' substituent]

| Example No. | —NRR' | MS (M + H)⁺ |
|---|---|---|
| 3A-44 | 3-(diethylamino)pyrrolidin-1-yl | 481.2 |
| 3A-45 | 4-phenyl-4-propanoylpiperidin-1-yl | 556.2 |
| 3A-46 | (2-hydroxycyclohexyl)amino | 454.1 |
| 3A-47 | cyclohexylamino | 438.1 |
| 3A-48 | 3-(ethylamino)-3-carbamoylazetidin-1-yl | 482.0 |
| 3A-49 | 3-(isopropylamino)-3-carbamoylazetidin-1-yl | 496.1 |
| 3A-50 | 2,6-diazaspiro[3.4]octan-7-one-2-yl | 466.0 |
| 3A-51 | (1-benzylpyrrolidin-3-yl)amino | 425.1 |
| 3A-52 | 4-methylpiperidin-1-yl | 438.2 |
| 3A-53 | 4-(dimethylamino)piperidin-1-yl | 546.1 |

Example 4

Preparation of Rac-(S,S)-3-(4-Chlorophenyl)-2-(2-chlorophenyl)-7-(2,5-diazabicyclo[2.2.1]hept-2-yl)-2H-pyrazolo[4,3-d]pyrimidine, Hydrochloride Salt (4A-1):

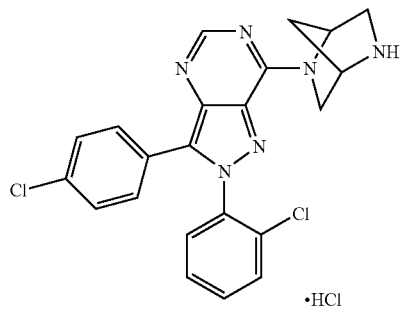

4A-1

·HCl

To the solution of 5-[3-(4-chlorophenyl)-2-(2-chlorophenyl)-2H-pyrazolo[4,3-d]pyrimidin-7-yl]-2,5-diazabicyclo[2.2.1]heptane-2-carboxylic acid tert-butyl ester 2A-46 (595 mg, 1.11 mmol) in dioxane (8 ml) was added HCl (2.22 ml, 4 N in dioxane, 8.88 mmol). The reaction mixture was stirred for 3 hours under nitrogen at room temperature. Then, the reaction mixture was concentrated and co-evaporated with diethyl ether (25 ml). The residue was further dried in a drying pistol under vacuum at 65° C. to give Rac-(S,S)-3-(4-chlorophenyl)-2-(2-chlorophenyl)-7-(2,5-diazabicyclo[2.2.1]hept-2-yl)-2H-pyrazolo[4,3-d]pyrimidine HCl salt 4A-1 (522 mg, 92%): MS: 437.1 (M+1)$^+$; $^1$H NMR (400 MHz, CD$_3$OD) δ 8.6 (d, J=6.2 Hz, 1H), 7.7 (dd, J=15.8, 7.1 Hz, 1H), 7.6 (m, 2H), 7.5 (m, 1H), 7.4 (dd, J=8.3, 3.3 Hz, 2H), 7.3 (t, J=7.5 Hz, 2H), 6.3 (s, 0.5H), 5.8 (s, 0.5H), 4.7 (m, 1H), 4.6 (d, J=13.7 Hz, 0.5H), 4.5 (dd, J=13.7, 2.5 Hz, 0.5H), 4.2 (ddd, J=29.5, 14.1, 1.7 Hz, 1H), 3.6 (m, 2H), 2.5 (dd, J=24.0, 12.0 Hz, 1H), 2.3 (t, J=11.2 Hz, 1H).

The compounds listed in Table 4 below were prepared using procedures analogous to those described above for the synthesis of Compound 4A-1 using the appropriate starting materials which are available commercially, prepared using preparations well-known to those skilled in the art, or prepared in a manner analogous to routes described above for other intermediates.

TABLE 4

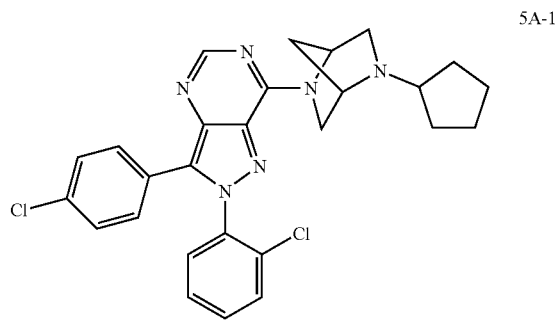

| Example No. | —NRR' | MS (M + H)$^+$ |
|---|---|---|
| 4A-2 | NH$_2$ pyrrolidinyl | 425.1 |
| 4A-3 | N-methylamino pyrrolidinyl | 439.1 |
| 4A-4 | piperazinyl | 425.1 |

Example 5

Preparation of Rac-(S,S)-3-(4-Chlorophenyl)-2-(2-chlorophenyl)-7-(5-cyclopentyl-2,5-diazabicyclo[2.2.1]hept-2-yl)-2H-pyrazolo[4,3-d]pyrimidine (5A-1):

5A-1

To the mixture of Rac-(S,S)-3-(4-chlorophenyl)-2-(2-chlorophenyl)-7-(2,5-diazabicyclo[2.2.1]hept-2-yl)-2H-pyrazolo[4,3-d]pyrimidine HCl salt 4A-1 (50.5 mg, 0.1 mmol), triethylammonium chloride (27 mg, 0.2 mmol), and triethylamine (0.028 ml, 0.2 mmol) in absolute ethanol (1 ml) was added cyclopentanone (8.8 ml, 0.1 mmol), followed by borohydride resin (40 mg, 2.5 mmol/g). The mixture was stirred overnight at room temperature. After removal of solvent and resin, the residue was further purified by HPLC to give Rac-(S,S)-3-(4-chlorophenyl)-2-(2-chlorophenyl)-7-(5-cyclopentyl-2,5-diazabicyclo[2.2.1]hept-2-yl)-2H-pyrazolo[4,3-d]pyrimidine 5A-1 (23 mg, 46%): MS: 504.8 (M+1)$^+$; $^1$H NMR (400 MHz, CD$_3$OD) δ 8.3 (s, 1H), 8.2 (s, 1H), 7.6 (m, 4H), 7.4 (m, 3H), 6.1 (s, 0.5H), 5.4 (s, 0.5H), 4.6 (m, 1.5H), 4.3 (m, 0.5H), 4.1 (m, 1H), 3.7 (m, 3H), 2.4 (m, 2H), 2.3 (m, 1H), 2.2 (m, 1H), 1.8 (m, 2H), 1.6 (m, 4H).

The compounds listed in Table 5 below were prepared using procedures analogous to those described above for the synthesis of Compound 5A-1 using the appropriate starting materials which are available commercially, prepared using preparations well-known to those skilled in the art, or prepared in a manner analogous to routes described above for other intermediates. The compounds listed below were generally isolated as their free base and then converted to their corresponding hydrochloride salts prior to in vivo testing.

TABLE 5

| Example No. | —NRR' | MS (M + H)+ |
|---|---|---|
| 5A-2 | | 493.0 |
| 5A-3 | | 493.1 |
| 5A-4 | | 479.1 |
| 5A-5 | | 466.8 |
| 5A-6 | | 519.1 |
| 5A-7 | | 465.1 |
| 5A-8 | | 493.1 |

TABLE 5-continued

| Example No. | —NRR' | MS (M + H)+ |
|---|---|---|
| 5A-9 | | 507.1 |
| 5A-10 | | 481.1 |

Example 6

Preparation of Rac-(S,S)-3-(4-Chlorophenyl)-2-(2-chlorophenyl)-7-(5-methanesulfonyl-2,5-diaza-bicyclo[2.2.1]hept-2-yl)-2H-pyrazolo[4,3-d]pyrimidine (6A-1):

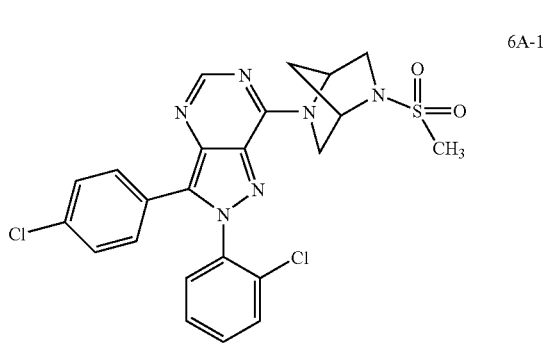

A solution of Rac-(S,S)-3-(4-chlorophenyl)-2-(2-chlorophenyl)-7-(2,5-diazabicyclo[2.2.1]hept-2-yl)-2H-pyrazolo[4,3-d]pyrimidine 4A-1 (63 mg, 0.12 mmol) in dichloromethane (2 ml) was charged with triethylamine (0.1 ml). Methanesulfonyl chloride (0.01 ml, 0.14 mmol) was added via syringe, and the resultant mixture was stirred at 23° C. for 3 days. The reaction mixture was then washed with water (2 ml) and the layers were separated. The organic solution was dried over anhydrous magnesium sulfate and concentrated. Purification of the residue by reverse-phase HPLC afforded Rac-(S, S)-3-(4-chlorophenyl)-2-(2-chlorophenyl)-7-(5-methanesulfonyl-2,5-diaza-bicyclo[2.2.1]hept-2-yl)-2H-pyrazolo[4,3-d]pyrimidine 6A-1 (63 mg, quantitative): MS: 515.0 (M+1)+; $^1$H NMR (400 MHz, CD$_3$OD) δ 8.3 (s, 0,5H), 8.1 (s, 0.5H), 7.6 (m, 4H), 7.4 (m, 4H), 6.1 (s, 0.5H), 5.2 (s, 0.5H), 4.7 (m, 1H), 4.4 (m, 0.5H), 4.2 (m, 0.5H), 4.0 (m, 1H), 3.8 (m, 1H), 3.5 (m, 3H), 3.0 (s, 3H).

The compounds listed in Table 6 below were prepared using procedures analogous to those described above for the synthesis of Compound 6A-1 using the appropriate starting materials which are available commercially, prepared using preparations well-known to those skilled in the art, or prepared in a manner analogous to routes described above for other intermediates. The compounds listed below were generally isolated as their free base and then converted to their corresponding hydrochloride salts prior to in vivo testing.

TABLE 6

| Example No. | —NRR' | MS (M + H)+ |
|---|---|---|
| 6A-2 | | 515.0 |
| 6A-3 | | 544.2 |
| 6A-4 | | 532.2 |
| 6A-5 | | 582.9 |
| 6A-6 | | 503.2 |
| 6A-7 | | 531.2 |
| 6A-8 | | 517.2 |
| 6A-9 | | 571.1 |

Example 7

Preparation of 7-(1-Benzylpyrrolidin-3-yloxy)-3-(4-chlorophenyl)-2-(2-chlorophenyl)-2H-pyrazolo[4,3-d]pyrimidine (7A-1):

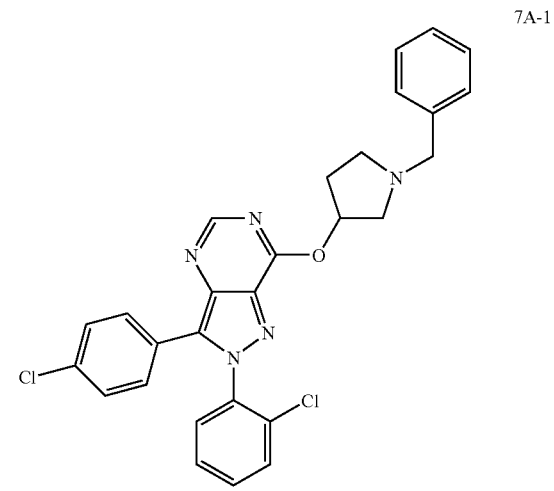

7A-1

Sodium hydride (24 mg of a 60% dispersion in mineral oil, 0.6 mmol) was added to a solution of 1-benzylpyrrolidin-3-ol (0.1 ml, 0.6 mmol) in dimethylformamide (1 ml), and the resultant mixture was stirred at room temperature for 5 min. Next, 7-chloro-3-(4-chlorophenyl)-2-(2-chlorophenyl)-2H-pyrazolo[4,3-d]pyrimidine 1-2A-1c (50 mg, 0.13 mmol) was added in one portion, and the mixture was stirred for 2 hours. The reaction mixture was diluted with methyl tert-butyl ether and washed with water (3×). The organic phase was dried over anhydrous magnesium sulfate and concentrated. Purification of the residue by flash column chromatography (50% ethyl acetate in hexanes) provided the title compound 7-(1-benzylpyrrolidin-3-yloxy)-3-(4-chlorophenyl)-2-(2-chlorophenyl)-2H-pyrazolo[4,3-d]pyrimidine 7A-1 (21 mg): MS: 516.1 (M+1)+; $^1$H NMR (400 MHz, CDCl$_3$) δ 8.6 (s, 1H), 7.5 (m, 6H), 7.3 (m, 7H), 5.8 (m, 1H), 3.7 (s, 2H), 3.2 (m, 1H), 2.9 (m, 1H), 2.8 (m, 1H), 2.7 (m, 1H), 2.5 (m, 1H), 2.2 (m, 1H).

Example 8

Preparation of 3-(4-Chlorophenyl)-2-(2-chlorophenyl)-7-isopropoxy-2H-pyrazolo[4,3-d]pyrimidine (8A-1):

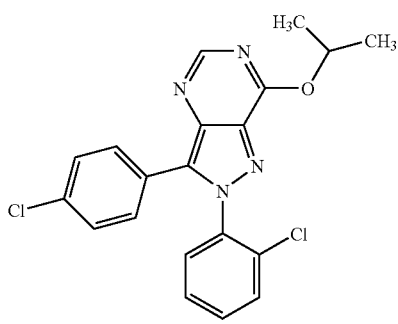

8A-1

Sodium (21 mg, 0.9 mmol) was added to 2-propanol (2 ml), and the resultant mixture was stirred at 65° C. for 16 hours. Next, 7-chloro-3-(4-chlorophenyl)-2-(2-chlorophenyl)-2H-pyrazolo[4,3-d]pyrimidine I-2A-1c (75 mg, 0.2 mmol) was added in one portion, and the mixture was stirred at 65° C. for 2 hours. The reaction mixture was partitioned between ethyl acetate and water. The organic layer was dried over anhydrous magnesium sulfate and concentrated. Purification of the residue by flash column chromatography (50% ethyl acetate in hexanes) provided the title compound 3-(4-chlorophenyl)-2-(2-chlorophenyl)-7-isopropoxy-2H-pyrazolo[4,3-d]pyrimidine 8A-1 (41 mg): MS: 399.1 (M+1)$^+$; $^1$H NMR (400 MHz, CDCl$_3$) δ 8.6 (s, 1H), 7.6 (d, J=6.6 Hz, 1H), 7.5 (m, 5H), 7.3 (d, J=8.7 Hz, 2H), 5.8 (pentuplet, J=6.2 Hz, 1H), 1.5 (d, J=6.2 Hz, 6H).

Example 9

Preparation of 7-(1-Benzhydrylazetidin-3-yloxy)-3-(4-chlorophenyl)-2-(2-chlorophenyl)-2H-pyrazolo[4,3-d]pyrimidine (9A-1):

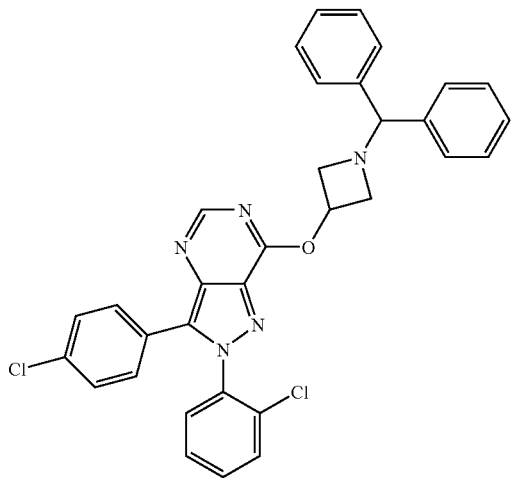

9A-1

A solution of 7-chloro-3-(4-chlorophenyl)-2-(2-chlorophenyl)-2H-pyrazolo[4,3-d]pyrimidine (I-2A-1c; 50 mg, 0.13 mmol), 1,4-diazabicyclo[2.2.2]octane (DABCO, 15 mg, 0.13 mmol), and triethylamine (0.054 ml, 0.39 mmol) in 1,2-dichloroethane (1 ml) was stirred for 16 hours. The reaction mixture was diluted with dichloromethane and washed with water. The organics were dried over anhydrous magnesium sulfate and were concentrated. Purification of the residue by flash column chromatography (20% ethyl acetate in hexanes) provided the title compound 7-(1-benzhydrylazetidin-3-yloxy)-3-(4-chlorophenyl)-2-(2-chlorophenyl)-2H-pyrazolo[4,3-d]pyrimidine 9A-1 (32 mg): $^1$H NMR (400 MHz, CDCl$_3$) δ 8.6 (s, 1H), 7.4 (complex, 18H), 5.6 (m, 1H), 4.5 (br s, 1H), 3.8 (br s, 2H), 3.3 (br s, 2H).

Example 10

Preparation of 3-(4-Chlorophenyl)-2-(2-chlorophenyl)-5-ethyl-6-(2,2,2-trifluoroethyl)-2,6-dihydropyrazolo[4,3-d]pyrimidin-7-one (10A-1):

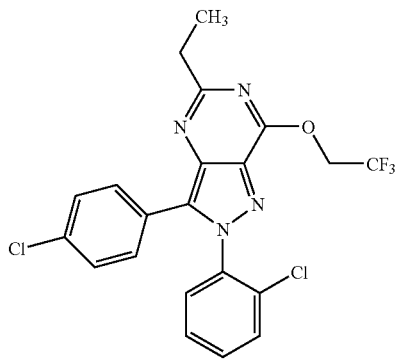

10A-1

A mixture of 3-(4-chlorophenyl)-2-(2-chlorophenyl)-5-ethyl-2H-pyrazolo[4,3-d]pyrimidin-7-ol (I-10A-1a; 15 mg, 0.039 mmol), Cs$_2$CO$_3$ (52 mg, 0.16 mmol) and CF$_3$CH$_2$I (39 microliters, 0.4 mmol) in dimethylformamide (1 ml) was stirred at 100° C. for 18 hours. The reaction mixture was cooled to room temperature, quenched with saturated aqueous sodium chloride, and extracted with ethyl acetate (2×). The combined extracts were washed with saturated aqueous NaCl, dried over Na$_2$SO$_4$, filtered, and concentrated in vacuo. The residue was purified by radial chromatography (1 mm silica gel plate; solvent gradient of 25-50% ethyl acetate/hexane) to provide the desired product, 3-(4-chlorophenyl)-2-(2-chlorophenyl)-5-ethyl-6-(2,2,2-trifluoroethyl)-2,6-dihydropyrazolo[4,3-d]pyrimidin-7-one 10A-1 (4 mg): MS (M+1)$_+$467.4; $^1$H NMR (400 MHz, CD$_2$Cl$_2$) δ 7.59-7.46 (m, 6H), 7.37-7.33 (m, 2H), 4.35 (br m, 2H), 3.04 (q, J=7.4 Hz, 2H), 1.40 (t, J=7.4 Hz, 3H).

The compounds listed in Table 7 below were prepared using procedures analogous to those described above for the synthesis of Compound 10A-1 using the appropriate starting materials which are available commercially, prepared using preparations well-known to those skilled in the art, or prepared in a manner analogous to routes described above for other intermediates. Examples 10A-12, 10A-13 and 10A-14 were alkylated at room temperature.

TABLE 7

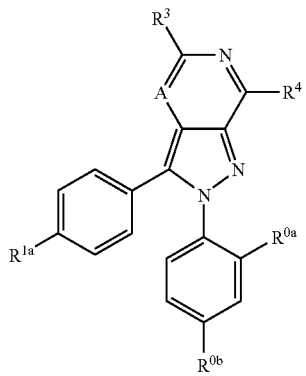

| Example No. | A | —R⁰ᵃ | —R⁰ᵇ | —R¹ᵃ | —R³ | —R⁴ | MS (M + 1)⁺ |
|---|---|---|---|---|---|---|---|
| 10A-2 | N | —Cl | —H | —Cl | i-Pr | —OCH₂CF₃ | 481.4 |
| 10A-3 | N | —Cl | —H | —OMe | —Me | —OCH₂CF₃ | 449.4 |
| 10A-4 | N | —Cl | —H | —Cl | —CF₃ | —OCH₂CH₃ | 453.3 |
| 10A-5 | N | —Cl | —H | —Cl | —CF₃ | —OCH₂CF₃ | 507.1 |
| 10A-6 | N | —Cl | —H | —Cl | —Me | —OCH₂CF₂CH₂CH₃ | 463.4 |
| 10A-7 | N | —Br | —H | —Cl | —Me | —OCH₂CF₂CH₃ | 492.9 |
| 10A-8 | N | —Br | —H | —OMe | —Me | —OCH₂CF₃ | 493.0 |
| 10A-9 | N | —Br | —H | —OMe | —Me | —OCH₂CF₂CH₃ | 489.0 |
| 10A-10 | N | —Cl | —H | —Br | —Me | —OCH₂CF₂CH₃ | 492.8 |
| 10A-11 | N | —Cl | —H | —OMe | —Me | —OCH₂CF₂CH₃ | 445.1 |
| 10A-12 | N | —Cl | —H | —CF₃ | —H | —OCH(CH₃)₂ | 433.4 |
| 10A-13 | N | —Cl | —Me | —CF₃ | —Me | —OCH₂CF₃ | 501.5 |
| 10A-14 | CH | —Cl | —H | —Cl | —H | —OCH₂CF₃ | 438.3 |

Me = —CH₃; i-Pr = CH(CH₃)₂

Example 11

Preparation of 2-[3-(4-Chlorophenyl)-7-(2,2-difluoropropoxy)-5-methyl-pyrazolo[4,3-d]pyrimidin-2-yl]-benzonitrile (11A-1):

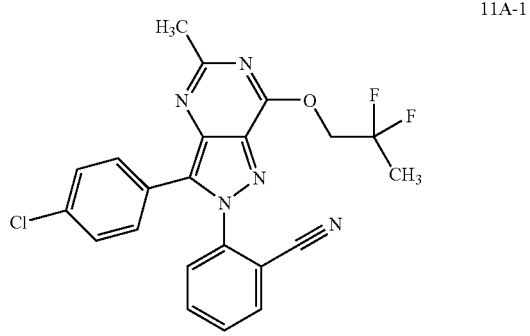

11A-1

A mixture of 2-(2-bromophenyl)-3-(4-chlorophenyl)-7-(2,2-difluoropropoxy)-5-methyl-2H-pyrazolo[4,3-d]pyrimidine (10A-7, 50 mg, 0.1 mmol), Zn(CN)₂ (20 mg, 0.17 mmol), Pd(PPh₃)₄ (15 mg, 0.01 mmol) in DMF (1 ml) was heated in a microwave apparatus (Emrys Optimizer, Personal Chemistry) at 200° C. for 3 minutes. The reaction mixture was quenched with saturated aqueous NaCl and extracted with ethyl acetate (2×). The combined organic extracts were dried and concentrated under vacuum. The crude residue was purified via HPLC (Shimadzu) using a solvent gradient of 30% CH₃CN/hexanes to 100% CH₃CN to give the desired product, 2-[3-(4-chlorophenyl)-7-(2,2-difluoropropoxy)-5-methylpyrazolo[4,3-d]pyrimidin-2-yl]-benzonitrile (11A-1), as a colorless solid (25 mg): MS (M+1)₊440.0; ¹H NMR (400 MHz, CDCl₃) δ 7.80-7.64 (m, 4H), 7.40-7.26 (m, 4H), 4.8 (t, J=11.6 Hz, 2H), 2.7 (s, 3H), 1.79 (t, J=18.67 Hz, 3H).

Example 12

Preparation of 3-(4-Chlorophenyl)-2-(2-chlorophenyl)-7-ethoxy-2H-pyrazolo[4,3-d]pyrimidine (12A-1):

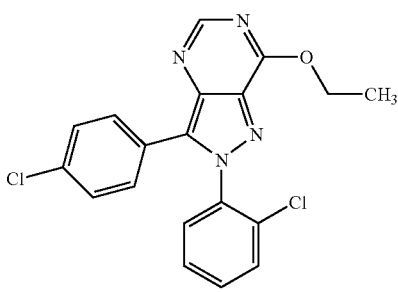

12A-1

To a solution of 7-chloro-3-(4-chlorophenyl)-2-(2-chlorophenyl)-2H-pyrazolo[4,3-d]pyrimidine (I-2A-1c; 50 mg, 0.133 mmol) and ethanol (0.016 ml, 0.27 mmol) in tetrahydrofuran (1.5 ml) was added NaH (60% dispersion in oil, 14 mg, 0.33 mmol). After stirring for 1 hour, the reaction was extracted from saturated aqueous NaHCO₃ with ethyl acetate, the combined organic layers were dried (MgSO₄), concentrated and purified on a Biotage® Flash 12M column using a solvent gradient of 0-20% ethyl acetate in hexanes as eluant to afford 12A-1 (46 mg, 92%) as a colorless solid: +ESI MS (M+1) 385.4; ¹H NMR (400 MHz, CD₂Cl₂) δ 8.56 (s, 1H), 7.58-7.46 (m, 6H), 7.34 (d, J=8.7 Hz, 2H), 4.70 (q, J=7.1 Hz, 2H), 1.53 (t, J=7.1 Hz, 3H).

The compounds listed in Table 8 below were prepared using procedures analogous to those described above for the synthesis of Compound 12A-1 using the appropriate starting materials which are available commercially, prepared using preparations well-known to those skilled in the art, or prepared in a manner analogous to routes described above for other intermediates.

TABLE 8

| Example No. | A | —R[4] | MS (M + H)[+] |
|---|---|---|---|
| 12A-2 | N | —OCH$_2$CH$_2$CH$_3$ | 399.4 |
| 12A-3 | N | —OCH$_2$CH$_2$CH$_2$CH$_3$ | 413.4 |
| 12A-4 | CH | —OCH(CH$_3$)$_2$ | 398.4 |

Pharmacological Testing

The utility of the compounds of the present invention in the practice of the instant invention can be evidenced by activity in at least one of the protocols described hereinbelow. The following acronyms are used in the protocols described below.

BSA—bovine serum albumin
DMSO—dimethylsulfoxide
EDTA—ethylenediamine tetracetic acid
PBS—phosphate-buffered saline
EGTA—ethylene glycol-bis(β-aminoethyl ether) N,N,N',N'-tetraacetic acid
GDP—guanosine diphosphate
sc—subcutaneous
po—orally
ip—intraperitoneal
icv—intra cerebro ventricular
iv—intravenous
[$^3$H]SR141716A-radiolabeled N-(piperidin-1-yl)-5-(4-chlorophenyl)-1-(2,4-dichlorophenyl)-4-methyl-1H-pyrazole-3-carboxamide hydrochloride available from Amersham Biosciences, Piscataway, N.J.
[$^3$H]CP-55940-radiolabled 5-(1,1-dimethylheptyl)-2-[5-hydroxy-2-(3-hydroxypropyl)-cyclohexyl]-phenol available from NEN Life Science Products, Boston, Mass.
AM251-N-(piperidin-1-yl)-1-(2,4-dichlorophenyl)-5-(4-iodophenyl)-4-methyl-1H-pyrazole-3-carboxamide available from Tocris™, Ellisville, Mo.

All of the compounds listed in the Example section above were tested in the CB-1 receptor binding assay below. The compounds provided a range of binding activities from 0.2 nM to 1.6 μM. The compounds having an activity <20 nM were then tested in the CB-1 GTPγ[$^{35}$S] Binding Assay and the CB-2 binding assay described below in the Biological Binding Assays section. Selected compounds were then tested in vivo using one or more of the functional assays described in the Biological Functional Assays section below.

In Vitro Biological Assays

Bioassay systems for determining the CB-1 and CB-2 receptor binding properties and pharmacological activity of cannabinoid receptor ligands are described by Roger G. Pertwee in "Pharmacology of Cannabinoid Receptor Ligands" *Current Medicinal Chemistry*, 6, 635-664 (1999) and in WO 92/02640 (U.S. application Ser. No. 07/564,075 filed Aug. 8, 1990, incorporated herein by reference).

The following assays were designed to detect compounds that inhibit the binding of [$^3$H]-SR141716A (selective radiolabeled CB-1 receptor ligand) and [$^3$H]-5-(1,1-dimethylheptyl)-2-[5-hydroxy-2-(3-hydroxypropyl)-cyclohexyl]-phenol; radiolabeled CB-1/CB-2 receptor ligand) to their respective receptors.

Rat CB-1 Receptor Binding Protocol

PelFreeze brains (available from Pel Freeze Biologicals, Rogers, Ark.) were cut up and placed in tissue preparation buffer (5 mM Tris HCl, pH=7.4 and 2 mM EDTA), polytroned at high speed and kept on ice for 15 minutes. The homogenate was then spun at 1,000×g for 5 minutes at 4° C. The supernatant was recovered and centrifuged at 100,000×G for 1 hour at 4° C. The pellet was then re-suspended in 25 ml of TME (25 nM Tris, pH=7.4, 5 mM MgCl$_2$, and 1 mM EDTA) per brain used. A protein assay was performed and 200 μl of tissue totaling 20 μg was added to the assay.

The test compounds were diluted in drug buffer (0.5% BSA, 10% DMSO and TME) and then 25 μl were added to a deep well polypropylene plate. [$^3$H]-SR141716A was diluted in a ligand buffer (0.5% BSA plus TME) and 25 μl were added to the plate. A BCA protein assay was used to determine the appropriate tissue concentration and then 200 μl of rat brain tissue at the appropriate concentration was added to the plate. The plates were covered and placed in an incubator at 20° C. for 60 minutes. At the end of the incubation period 250 μl of stop buffer (5% BSA plus TME) was added to the reaction plate. The plates were then harvested by Skatron onto GF/B filtermats presoaked in BSA (5 mg/ml) plus TME. Each filter was washed twice. The filters were dried overnight. In the morning the filters were counted on a Wallac Betaplate™ counter (available from PerkinElmer Life Sciences™, Boston, Mass.).

Human CB-1 Receptor Binding Protocol

Human embryonic kidney 293 (HEK 293) cells transfected with the CB-1 receptor cDNA (obtained from Dr. Debra Kendall, University of Connecticut) were harvested in homogenization buffer (10 mM EDTA, 10 mM EGTA, 10 mM Na Bicarbonate, protease inhibitors; pH=7.4), and homogenized with a Dounce Homogenizer. The homogenate was then spun at 1,000×G for 5 minutes at 4° C. The supernatant was recovered and centrifuged at 25,000×G for 20 minutes at 4° C. The pellet was then re-suspended in 10 ml of homogenization buffer and re-spun at 25,000×G for 20 minutes at 4° C. The final pellet was re-suspended in 1 ml of TME (25 mM Tris buffer (pH=7.4) containing 5 mM MgCl$_2$ and 1 mM EDTA). A protein assay was performed and 200 μl of tissue totaling 20 μg was added to the assay.

The test compounds were diluted in drug buffer (0.5% BSA, 10% DMSO and TME) and then 25 μl were added to a deep well polypropylene plate. [$^3$H]-SR141716A was diluted in a ligand buffer (0.5% BSA plus TME) and 25 μl were added to the plate. The plates were covered and placed in an incubator at 30° C. for 60 minutes. At the end of the incubation period 250 µl of stop buffer (5% BSA plus TME) was added to the reaction plate. The plates were then harvested by Skatron onto GF/B filtermats presoaked in BSA (5 mg/ml) plus TME. Each filter was washed twice. The filters were dried overnight. In the morning, the filters were counted on a Wallac Betaplate™ counter (available from PerkinElmer Life Sciences™, Boston, Mass.).

CB-2 Receptor Binding Protocol

Chinese hamster ovary-K1 (CHO-K1) cells transfected with CB-2 receptor cDNA (obtained from Dr. Debra Kendall, University of Connecticut) were harvested in tissue preparation buffer (5 mM Tris-HCl buffer (pH=7.4) containing 2 mM EDTA), polytroned at high speed and kept on ice for 15 minutes. The homogenate was then spun at 1,000×G for 5 minutes at 4° C. The supernatant was recovered and centrifuged at 100,000×G for 1 hour at 4° C. The pellet was then re-suspended in 25 ml of TME (25 mM Tris buffer (pH=7.4) containing 5 mM $MgCl_2$ and 1 mM EDTA) per brain used. A protein assay was performed and 200 µl of tissue totaling 10 µg was added to the assay.

The test compounds were diluted in drug buffer (0.5% BSA, 10% DMSO, and 80.5% TME) and then 25 µl were added to the deep well polypropylene plate. [$^3$H]-5-(1,1-Dimethyl-heptyl)-2-[5-hydroxy-2-(3-hydroxy-propyl)-cyclohexyl]-phenol was diluted a ligand buffer (0.5% BSA and 99.5% TME) and then 25 µl were added to each well at a concentration of 1 nM. A BCA protein assay was used to determine the appropriate tissue concentration and 200 µl of the tissue at the appropriate concentration was added to the plate. The plates were covered and placed in an incubator at 30° C. for 60 minutes. At the end of the incubation period 250 µl of stop buffer (5% BSA plus TME) was added to the reaction plate. The plates were then harvested by Skatron format onto GF/B filtermats presoaked in BSA (5 mg/ml) plus TME. Each filter was washed twice. The filters were dried overnight. The filters were then counted on the Wallac Betaplate™ counter.

CB-1 Receptor GTPγ[$^{35}$S] Binding Assay

Membranes were prepared from CHO-K1 cells stably transfected with the human CB-1 receptor cDNA. Membranes were prepared from cells as described by Bass et al., in "Identification and characterization of novel somatostatin antagonists," *Molecular Pharmacology*, 50, 709-715 (1996). GTPγ[$^{35}$S] binding assays were performed in a 96 well FlashPlate™ format in duplicate using 100 µM GTPγ[$^{35}$S] and 10 µg membrane per well in assay buffer composed of 50 mM Tris HCl, pH 7.4, 3 mM $MgCl_2$, pH 7.4, 10 mM $MgCl_2$, 20 mM EGTA, 100 mM NaCl, 30 µM GDP, 0.1% bovine serum albumin and the following protease inhibitors: 100 µg/ml bacitracin, 100 µg/ml benzamidine, 5 µg/ml aprotinin, 5 µg/ml leupeptin. The assay mix was then incubated with increasing concentrations of antagonist ($10^{-10}$ M to $10^{-5}$ M) for 10 minutes and challenged with the cannabinoid agonist 5-(1,1-dimethyl-heptyl)-2-[5-hydroxy-2-(3-hydroxy-propyl)-cyclohexyl]-phenol (10 µM). Assays were performed at 30° C. for one hour. The FlashPlates™ were then centrifuged at 2000×G for 10 minutes. Stimulation of GTPγ[$^{35}$S] binding was then quantified using a Wallac Microbeta. $EC_{50}$ calculations done using Prism™ by Graphpad.

Inverse agonism was measured in the absense of agonist.

CB-1 Receptor FLIPR-based Functional Assay Protocol

CHO-K1 cells co-transfected with the human CB-1 receptor cDNA (obtained from Dr. Debra Kendall, University of Connecticut) and the promiscuous G-protein G16 were used for this assay. Cells were plated 48 hours in advance at 12500 cells per well on collagen coated 384 well black clear assay plates. Cells were incubated for one hour with 4 µM Fluo-4 µM (Molecular Probes) in DMEM (Gibco) containing 2.5 mM probenicid and pluronic acid (0.04%). The plates were then washed 3 times with HEPES-buffered saline (containing probenicid; 2.5 mM) to remove excess dye. After 20 min the plates were added to the FLIPR individually and fluorescence levels was continuously monitored over an 80 second period. Compound additions were made simultaneously to all 384 wells after 20 seconds of baseline. Assays were performed in triplicate and 6 point concentration-response curves generated. Antagonist compounds were subsequently challenged with 3 µM WIN 55,212-2 (agonist). Data were analyzed using Graph Pad Prism.

Detection of Inverse Agonists

The following cyclic-AMP assay protocol using intact cells was used to determine inverse agonist activity.

Cells were plated into a 96-well plate at a plating density of 10,000-14,000 cells per well at a concentration of 100 µl per well. The plates were incubated for 24 hours in a 37° C. incubator. The media was removed and media lacking serum (100 µl) was added. The plates were then incubated for 18 hours at 37° C.

Serum free medium containing 1 mM IBMX was added to each well followed by 10 µl of test compound (1:10 stock solution (25 mM compound in DMSO) into 50% DMSO/PBS) diluted 10× in PBS with 0.1% BSA. After incubating for 20 minutes at 37° C., 2 µM of forskolin was added and then incubated for an additional 20 minutes at 37° C. The media was removed, 100 µl of 0.01 N HCl was added and then incubated for 20 minutes at room temperature. Cell lysate (75 µl) along with 25 µl of assay buffer (supplied in FlashPlate™ cAMP assay kit available from NEN Life Science Products Boston, Mass.) into a Flashplate. cAMP standards and cAMP tracer were added following the kit's protocol. The flashplate was then incubated for 18 hours at 4° C. The content of the wells were aspirated and counted in a Scintillation counter.

In Vivo Biological Assays

Cannabinoid agonists such as $\Delta^9$-tetrahydrocannabinol ($\Delta^9$-THC) and 5-(1,1-dimethyl-heptyl)-2-[5-hydroxy-2-(3-hydroxy-propyl)-cyclohexyl]-phenol have been shown to affect four characteristic behaviors in mice, collectively known as the Tetrad. For a description of these behaviors see: Smith, P. B., et al. in "The pharmacological activity of anandamide, a putative endogenous cannabinoid, in mice." J. Pharmacol. Exp. Ther., 270(1), 219-227 (1994) and Wiley, J., et al. in "Discriminative stimulus effects of anandamide in rats," Eur. J. Pharmacol., 276(1-2), 49-54 (1995). Reversal of these activities in the locomotor activity, catalepsy, hypothermia, and hot plate assays described below provides a screen for in vivo activity of CB-1 receptor antagonists.

All data is presented as % reversal from agonist alone using the following formula: (5-(1,1-dimethyl-heptyl)-2-[5-hydroxy-2-(3-hydroxy-propyl)-cyclohexyl]-phenol/agonist-vehicle/agonist)/(vehicle/vehicle-vehicle/agonist). Negative numbers indicate a potentiation of the agonist activity or non-antagonist activity. Positive numbers indicate a reversal of activity for that particular test.

Locomotor Activity

Male ICR mice (n=6; 17-19 g, Charles River Laboratories, Inc., Wilmington, Mass.) were pre-treated with test compound (sc, po, ip, or icv). Fifteen minutes later, the mice were challenged with 5-(1,1-dimethyl-heptyl)-2-[5-hydroxy-2-(3-hydroxy-propyl)-cyclohexyl]-phenol (sc). Twenty-five minutes after the agonist injection, the mice were placed in clear acrylic cages (431.8 cm×20.9 cm×20.3 cm) containing clean wood shavings. The subjects were allowed to explore surroundings for a total of about 5 minutes and the activity was recorded by infrared motion detectors (available from Coulbourn Instruments™, Allentown, Pa.) that were placed on top of the cages. The data was computer collected and expressed as "movement units."

Catalepsy

Male ICR mice (n=6; 17-19 g upon arrival) were pre-treated with test compound (sc, po, ip or icv). Fifteen minutes later, the mice were challenged with 5-(1,1-dimethyl-heptyl)-2-[5-hydroxy-2-(3-hydroxy-propyl)-cyclohexyl]-phenol (sc). Ninety minutes post injection, the mice were placed on a 6.5 cm steel ring attached to a ring stand at a height of about 12 inches. The ring was mounted in a horizontal orientation and the mouse was suspended in the gap of the ring with fore- and hind-paws gripping the perimeter. The duration that the mouse remained completely motionless (except for respiratory movements) was recorded over a 3-minute period.

The data were presented as a percent immobility rating. The rating was calculated by dividing the number of seconds the mouse remains motionless by the total time of the observation period and multiplying the result by 100. A percent reversal from the agonist was then calculated.

Hypothermia

Male ICR mice (n=5; 17-19 g upon arrival) were pre-treated with test compounds (sc, po, ip or icv). Fifteen minutes later, mice were challenged with the cannabinoid agonist 5-(1,1-dimethyl-heptyl)-2-[5-hydroxy-2-(3-hydroxy-propyl)-cyclohexyl]-phenol (sc). Sixty-five minutes post agonist injection, rectal body temperatures were taken. This was done by inserting a small thermostat probe approximately 2-2.5 cm into the rectum. Temperatures were recorded to the nearest tenth of a degree Hot Plate Male ICR mice (n=7; 17-19 g upon arrival) are pre-treated with test compounds (sc, po, ip or iv). Fifteen minutes later, mice were challenged with a cannabinoid agonist 5-(1,1-dimethyl-heptyl)-2-[5-hydroxy-2-(3-hydroxy-propyl)-cyclohexyl]-phenol (sc). Forty-five minutes later, each mouse was tested for reversal of analgesia using a standard hot plate meter (Columbus Instruments). The hot plate was 10"×10"×0.75" with a surrounding clear acrylic wall. Latency to kick, lick or flick hindpaw or jump from the platform was recorded to the nearest tenth of a second. The timer was experimenter activated and each test had a 40 second cut off. Data were presented as a percent reversal of the agonist induced analgesia.

Food Intake

The following screen was used to evaluate the efficacy of test compounds for inhibiting food intake in Sprague-Dawley rats after an overnight fast.

Male Sprague-Dawley rats were obtained from Charles River Laboratories, Inc. (Wilmington, Mass.). The rats were individually housed and fed powdered chow They were maintained on a 12-hour light/dark cycle and received food and water ad libitum. The animals were acclimated to the vivarium for a period of one week before testing was conducted. Testing was completed during the light portion of the cycle.

To conduct the food intake efficacy screen, rats were transferred to individual test cages without food the afternoon prior to testing, and the rats were fasted overnight. After the overnight fast, rats were dosed the following morning with vehicle or test compounds. A known antagonist was dosed (3 mg/kg) as a positive control, and a control group received vehicle alone (no compound). The test compounds were dosed at ranges between 0.1 and 100 mg/kg depending upon the compound. The standard vehicle was 0.5% (w/v) methylcellulose in water and the standard route of administration was oral. However, different vehicles and routes of administration were used to accommodate various compounds when required. Food was provided to the rats 30 minutes after dosing and the Oxymax automated food intake system (Columbus Instruments, Columbus, Ohio) was started. Individual rat food intake was recorded continuously at 10-minute intervals for a period of two hours. When required, food intake was recorded manually using an electronic scale; food was weighed every 30 minutes after food was provided up to four hours after food was provided. Compound efficacy was determined by comparing the food intake pattern of compound-treated rats to vehicle and the standard positive control.

Alcohol Intake

The following protocol evaluates the effects of alcohol intake in alcohol preferring (P) female rats (bred at Indiana University) with an extensive drinking history. The following references provide detailed descriptions of P rats: Li, T.-K., et al., "Indiana selection studies on alcohol related behaviors" in *Development of Animal Models as Pharmacogenetic Tools* (eds McClearn C. E., Deitrich R. A. and Erwin V. G.), Research Monograph 6, 171-192 (1981) NIAAA, ADAMHA, Rockville, Md.; Lumeng, L, et al., "New strains of rats with alcohol preference and nonpreference" *Alcohol And Aldehyde Metabolizing Systems*, 3, Academic Press, New York, 537-544 (1977); and Lumeng, L, et al., "Different sensitivities to ethanol in alcohol-preferring and -nonpreferring rats," *Pharmacol, Biochem Behav.*, 16, 125-130 (1982).

Female rats were given 2 hours of access to alcohol (10% v/v and water, 2-bottle choice) daily at the onset of the dark cycle. The rats were maintained on a reverse cycle to facilitate experimenter interactions. The animals were initially assigned to four groups equated for alcohol intakes: Group 1—vehicle (n=8); Group 2—positive control (e.g. 5.6 mg/kg AM251; n=8); Group 3—low dose test compound (n=8); and Group 4—high dose of test compound (n=8). Test compounds were generally mixed into a vehicle of 30% (w/v) β-cyclodextrin in distilled water at a volume of 1-2 ml/kg. Vehicle injections were given to all groups for the first two days of the experiment. This was followed by 2 days of drug injections (to the appropriate groups) and a final day of vehicle injections. On the drug injection days, drugs were given sc 30 minutes prior to a 2-hour alcohol access period. Alcohol intake for all animals was measured during the test period and a comparison was made between drug and vehicle-treated animals to determine effects of the compounds on alcohol drinking behavior.

Additional drinking studies were done utilizing female C57Bl/6 mice (Charles River). Several studies have shown that this strain of mice will readily consume alcohol with little to no manipulation required (Middaugh et al., "Ethanol Consumption by C57BL/6 Mice: Influence of Gender and Procedural Variables" *Alcohol*, 17 (3), 175-183,1999; Le et al., "Alcohol Consumption by C57BL/6, BALA/c, and DBA/2 Mice in a Limited Access Paradigm" *Pharmacology Biochemistry and Behavior*, 47, 375-378, 1994).

For our purposes, upon arrival (17-19 g) mice were individually housed and given unlimited access to powdered rat chow, water and a 10% (w/v) alcohol solution. After 2-3 weeks of unlimited access, water was restricted for 20 hours and alcohol was restricted to only 2 hours access daily. This was done in a manner that the access period was the last 2 hours of the dark part of the light cycle.

Once drinking behavior stabilized, testing commenced. Mice were considered stable when the average alcohol consumption for 3 days was ±20% of the average for all 3 days. Day 1 of test consisted of all mice receiving vehicle injection (sc or ip). Thirty to 120 minutes post injection access was given to alcohol and water. Alcohol consumption for that day was calculated (g/kg) and groups were assigned (n=7-10) so that all groups had equivocal alcohol intake. On day 2 and 3, mice were injected with vehicle or drug and the same protocol as the previous day was followed. Day 4 was wash out and no injections were given. Data was analyzed using repeated measures ANOVA. Change in water or alcohol consumption was compared back to vehicle for each day of the test. Positive results would be interpreted as a compound that was able to significantly reduce alcohol consumption while having no effect on water Oxygen Consumption Methods:

Whole body oxygen consumption was measured using an indirect calorimeter (Oxymax from Columbus Instruments, Columbus, Ohio) in male Sprague Dawley rats (if another rat strain or female rats are used, it will be specified). Rats (300-380 g body weight) were placed in the calorimeter chambers and the chambers were placed in activity monitors. These studies were done during the light cycle. Prior to the measurement of oxygen consumption, the rats were fed standard chow ad libitum. During the measurement of oxygen consumption, food was not available. Basal pre-dose oxygen consumption and ambulatory activity were measured every 10 minutes for 2.5 to 3 hours. At the end of the basal pre-dosing period, the chambers were opened and the animals were administered a single dose of compound (the usual dose range is 0.001 to 10 mg/kg) by oral gavage (or other route of administration as specified, i.e., sc, ip, iv). Drugs were prepared in methylcellulose, water or other specified vehicle (examples include PEG400, 30% beta-cyclo dextran and propylene glycol). Oxygen consumption and ambulatory activity were measured every 10 minutes for an additional 1-6 hours post-dosing.

The Oxymax calorimeter software calculated the oxygen consumption (ml/kg/h) based on the flow rate of air through the chambers and difference in oxygen content at inlet and output ports. The activity monitors have 15 infrared light beams spaced one inch apart on each axis, ambulatory activity was recorded when two consecutive beams are broken and the results are recorded as counts.

Resting oxygen consumption, during pre- and post-dosing, was calculated by averaging the 10-minute $O_2$ consumption values, excluding periods of high ambulatory activity (ambulatory activity count>100) and excluding the first 5 values of the pre-dose period and the first value from the post-dose period. Change in oxygen consumption was reported as percent and was calculated by dividing the post-dosing resting oxygen consumption by the pre-dose oxygen consumption *100. Experiments would typically be done with n=4-6 rats and results reported are mean +/−SEM.

Interpretation:

An increase in oxygen consumption of >10% was considered a positive result. Historically, vehicle-treated rats have no change in oxygen consumption from pre-dose basal.

What is claimed is:

1. A compound of Formula (I)

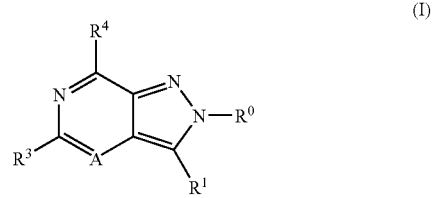

wherein
A is N;
$R^0$ is an optionally substituted aryl or an optionally substituted heteroaryl;
$R^1$ is an optionally substituted aryl or an optionally substituted heteroaryl;
$R^3$ is hydrogen, $(C_1-C_4)$alkyl, halo-substituted $(C_1-C_4)$alkyl, or $(C_1-C_4)$alkoxy;
$R^4$ is
(i) a group having Formula (IA) or Formula (IB)

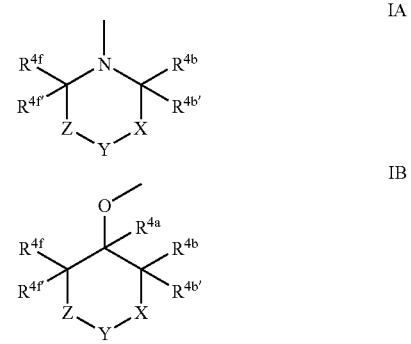

where $R^{4a}$ is hydrogen or $(C_1-C_3)$alkyl;
$R^{4b}$ and $R^{4b'}$ are each independently hydrogen, cyano, hydroxy, amino, $H_2NC(O)$—, or a chemical moiety selected from the group consisting of $(C_1-C_6)$alkyl, ($C_1$-$C_6$)alkoxy, acyloxy, acyl, ($C_1$-$C_3$)alkyl-O—C(O)—, ($C_1$-$C_4$)alkyl-NH—C(O)—, (($C_1$-$C_4$)alkyl)$_2$N—C(O)—, ($C_1$-$C_6$)alkylamino-, (($C_1$-$C_4$)alkyl)$_2$amino-, ($C_3$-$C_6$)cycloalkylamino-, acylamino-, aryl($C_1$-$C_4$)alkylamino-, heteroaryl($C_1$-$C_4$)alkylamino-, aryl, heteroaryl, a 3-6 membered partially or fully saturated heterocycle, and a partially or fully saturated carbocyclic ring, where said moiety is optionally substituted with one or more substituents, or either $R^{4b}$ or $R^{4b'}$ taken together with $R^{4e}$, $R^{4e'}$, $R^{4f}$, or $R^{4f'}$ forms a bond, a methylene bridge, or an ethylene bridge;

X is a bond, —CH$_2$CH$_2$— or —C($R^{4c}$)($R^{4c'}$)—, where $R^{4c}$ and $R^{4c'}$ are each independently hydrogen, cyano, hydroxy, amino, H$_2$NC(O)—, or a chemical moiety selected from the group consisting of ($C_1$-$C_6$)alkyl, ($C_1$-$C_6$)alkoxy, acyloxy, acyl, ($C_1$-$C_3$)alkyl-O—C(O)—, ($C_1$-$C_4$)alkyl-NH—C(O)—, (($C_1$-$C_4$)alkyl)$_2$N—C(O)—, ($C_1$-$C_6$)alkylamino-, di($C_1$-$C_4$)alkylamino-, ($C_3$-$C_6$)cycloalkylamino-, acylamino-, aryl($C_1$-$C_4$)alkylamino-, heteroaryl($C_1$-$C_4$)alkylamino-, aryl, heteroaryl, a 3-6 membered partially or fully saturated heterocycle, and a 3-6 membered partially or fully saturated carbocyclic ring, where said moiety is optionally substituted with one or more substituents, or either $R^{4c}$ or $R^{4c'}$ taken together with $R^{4e}$, $R^{4e'}$, $R^{4f}$, or $R^{4f'}$ forms a bond, a methylene bridge, or an ethylene bridge;

Y is oxygen, sulfur, —C(O)—, or —C($R^{4d}$)($R^{4d'}$)—, where $R^{4d}$ and $R^{4d'}$ are each independently hydrogen, cyano, hydroxy, amino, H$_2$NC(O)—, or a chemical moiety selected from the group consisting of ($C_1$-$C_6$)alkyl, ($C_1$-$C_6$)alkoxy, acyloxy, acyl, ($C_1$-$C_3$)alkyl-O—C(O)—, ($C_1$-$C_4$)alkyl-NH—C(O)—, (($C_1$-$C_4$)alkyl)$_2$N—C(O)—, ($C_1$-$C_6$)alkylamino-, di($C_1$-$C_4$)alkylamino-, ($C_3$-$C_6$)cycloalkylamino-, acylamino-, aryl($C_1$-$C_4$)alkylamino-, heteroaryl($C_1$-$C_4$)alkylamino-, aryl, heteroaryl, a 3-6 membered partially or fully saturated heterocycle, and a 3-6 membered partially or fully saturated carbocyclic ring, where said moiety is optionally substituted with one or more substituents, or $R^{4d}$ and $R^{4d'}$ taken together form a 3-6 membered partially or fully saturated carbocyclic ring, 3-6 membered partially or fully saturated heterocyclic ring, a 5-6 membered lactone ring, or a 4-6 membered lactam ring, where said carbocyclic ring, said heterocyclic ring, said lactone ring and said lactam ring are optionally substituted with one or more substituents and said lactone ring and said lactam ring optionally contain an additional heteroatom selected from oxygen, nitrogen or sulfur, or Y is —NR$^{4d''}$—, where $R^{4d''}$ is a hydrogen or a chemical moiety selected from the group consisting of ($C_1$-$C_6$)alkyl, ($C_3$-$C_6$)cycloalkyl, ($C_1$-$C_3$)alkylsulfonyl-, ($C_1$-$C_3$)alkylaminosulfonyl-, di($C_1$-$C_3$)alkylaminosulfonyl-, acyl, ($C_1$-$C_6$)alkyl-O—C(O)—, aryl, and heteroaryl, where said moiety is optionally substituted with one or more substituents;

Z is a bond, —CH$_2$CH$_2$—, or —C($R^{4e}$)($R^{4e'}$)—, where $R^{4e}$ and $R^{4e'}$ are each independently hydrogen, cyano, hydroxy, amino, H$_2$NC(O)—, or a chemical moiety selected from the group consisting of ($C_1$-$C_6$)alkyl, ($C_1$-$C_6$)alkoxy, acyloxy, acyl, ($C_1$-$C_3$)alkyl-O—C(O)—, ($C_1$-$C_4$)alkyl-NH—C(O)—, (($C_1$-$C_4$)alkyl)$_2$N—C(O)—, ($C_1$-$C_6$)alkylamino-, di($C_1$-$C_4$)alkylamino-, ($C_3$-$C_6$)cycloalkylamino-, acylamino-, aryl($C_1$-$C_4$)alkylamino-, heteroaryl($C_1$-$C_4$)alkylamino-, aryl, heteroaryl, a 3-6 membered partially or fully saturated heterocycle, and a 3-6 membered partially or fully saturated carbocyclic ring, where said moiety is optionally substituted with one or more substituents, or either $R^{4e}$ or $R^{4e'}$ taken together with $R^{4b}$, $R^{4b'}$, $R^{4c}$, or $R^{4c'}$ forms a bond, a methylene bridge or an ethylene bridge; and $R^{4f}$ and $R^{4f'}$ are each independently hydrogen, cyano, hydroxy, amino, H$_2$NC(O)—, or a chemical moiety selected from the group consisting of ($C_1$-$C_6$)alkyl, ($C_1$-$C_6$)alkoxy, acyloxy, acyl, ($C_1$-$C_3$)alkyl-O—C(O)—, ($C_1$-$C_4$)alkyl-NH—C(O)—, (($C_1$-$C_4$)alkyl)$_2$N—C(O)—, ($C_1$-$C_6$)alkylamino-, di($C_1$-$C_4$)alkylamino-, ($C_3$-$C_6$)cycloalkylamino-, acylamino-, aryl($C_1$-$C_4$)alkylamino-, heteroaryl($C_1$-$C_4$)alkylamino-, aryl, heteroaryl, a 3-6 membered partially or fully saturated heterocycle, and a 3-6 membered partially or fully saturated carbocyclic ring, where said moiety is optionally substituted with one or more substituents, or either $R^{4f}$ or $R^{4f'}$ taken together with $R^{4b}$, $R^{4b'}$, $R^{4c}$, or $R^{4c'}$ forms a bond, a methylene bridge or an ethylene bridge;

(ii) a group having Formula (IC)

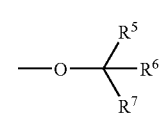

IC where $R^5$ and $R^6$ are each independently hydrogen, aryl, or ($C_1$-$C_4$)alkyl, and $R^7$ is an optionally substituted ($C_1$-$C_4$)alkyl-, or an optionally substituted 4-6 membered partially or fully saturated heterocylic ring containing 1 to 2 heteroatoms independently selected from oxygen, sulfur or nitrogen, or $R^5$ and $R^6$ or $R^5$ and $R^7$ taken together form a 5-6 membered lactone, 4-6 membered lactam, or a 4-6 membered partially or fully saturated heterocycle containing 1 to 2 heteroatoms independently selected from oxygen, sulfur or nitrogen, where said lactone, said lactam and said heterocycle are optionally substituted with one or more substituents;

(iii) an amino group having attached thereto at least one chemical moiety selected from the group consisting of ($C_1$-$C_8$)alkyl, aryl, aryl($C_1$-$C_4$)alkyl, a 3-8 membered partially or fully saturated carbocyclic ring, hydroxy($C_1$-$C_6$)alkyl, ($C_1$-$C_3$)alkoxy($C_1$-$C_6$)alkyl, heteroaryl($C_1$-$C_3$)alkyl, and a fully or partially saturated heterocycle, where said chemical moiety is optionally substituted with one or more substituents; or (iv) an ($C_1$-$C_6$)alkyl group having attached thereto at least one chemical moiety selected from the group consisting of hydroxy, ($C_1$-$C_6$)alkoxy, amino, ($C_1$-$C_6$)alkylamino, di(($C_1$-$C_6$)alkyl)amino ($C_1$-$C_3$)alkylsulfonyl, ($C_1$-$C_3$)alkylsulfamyl, di(($C_1$-$C_3$)alkyl)sulfamyl, acyloxy, a fully or partially saturated heterocycle, and a fully or partially saturated carbocyclic ring, where said chemical moiety is optionally substituted with one or more substituents;

a pharmaceutically acceptable salt thereof, a prodrug of said compound or said salt.

2. The compound of claim 1 wherein $R^4$ is a group having Formula (IA)

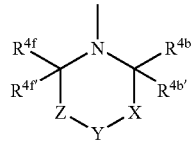

IA where, $R^{4b}$ and $R^{4b'}$ are each independently hydrogen, $H_2NC(O)-$, or a chemical moiety selected from the group consisting of $(C_1-C_6)$alkyl, acyl, $(C_1-C_3)$alkyl-O-C(O)-, $(C_1-C_4)$alkyl-NH-C(O)-, $(C_1-C_4)$alkyl)$_2$N-C(O)-, aryl, heteroaryl, a 3-6 membered partially or fully saturated heterocycle, and a partially or fully saturated carbocyclic ring, where said moiety is optionally substituted with one or more substituents, or $R^{4b}$ or $R^{4b'}$ taken together with $R^{4e}$, $R^{4e'}$, $R^{4f}$, or $R^{4f'}$ forms a bond, a methylene bridge, or an ethylene bridge;

X is a bond, $-CH_2CH_2-$ or $-C(R^{4c})(R^{4c'})-$, where $R^{4c}$ is hydrogen, cyano, hydroxy, amino, $H_2NC(O)-$, or a chemical moiety selected from the group consisting of $(C_1-C_6)$alkyl, $(C_1-C_6)$alkoxy, acyloxy, acyl, $(C_1-C_3)$alkyl-O-C(O)-, $(C_1-C_4)$alkyl-NH-C(O)-, $(C_1-C_4)$alkyl)$_2$N-C(O)-, $(C_1-C_6)$alkylamino-, $((C_1-C_4)$alkyl)$_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a 3-6 membered partially or fully saturated heterocycle, and a partially or fully saturated carbocyclic ring, where said moiety is optionally substituted with one or more substituents, or $R^{4c}$ taken together with $R^{4e}$, $R^{4e'}$, $R^{4f}$, or $R^{4f'}$ forms a bond, a methylene bridge, or an ethylene bridge, and $R^{4c'}$ is hydrogen, $H_2NC(O)-$, or a chemical moiety selected from the group consisting of $(C_1-C_6)$alkyl, acyl, $(C_1-C_3)$alkyl-O-C(O)-, $(C_1-C_4)$alkyl-NH-C(O)-, $(C_1-C_4)$alkyl)$_2$N-C(O)-, aryl, heteroaryl, a 3-6 membered partially or fully saturated heterocycle, and a partially or fully saturated carbocyclic ring, where said moiety is optionally substituted with one or more substituents, or $R^{4c'}$ taken together with $R^{4e}$, $R^{4e'}$, $R^{4f}$, or $R^{4f'}$ forms a bond, a methylene bridge, or an ethylene bridge;

Y is oxygen, sulfur, $-C(O)-$, or $-C(R^{4d})(R^{4d'})-$, where $R^{4d}$ is hydrogen, cyano, hydroxy, amino, $H_2NC(O)-$, or a chemical moiety selected from the group consisting of $(C_1-C_6)$alkyl, $(C_1-C_6)$alkoxy, acyloxy, acyl, $(C_1-C_3)$alkyl-O-C(O)-, $(C_1-C_4)$alkyl-NH-C(O)-, $(C_1-C_4)$alkyl)$_2$N-C(O)-, $(C_1-C_6)$alkylamino-, $((C_1-C_4)$alkyl)$_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a 3-6 membered partially or fully saturated heterocycle, and a partially or fully saturated carbocyclic ring, where said moiety is optionally substituted with one or more substituents, and $R^{4d'}$ is hydrogen, $H_2NC(O)-$, or a chemical moiety selected from the group consisting of $(C_1-C_6)$alkyl, acyl, $(C_1-C_3)$alkyl-O-C(O)-, $(C_1-C_4)$alkyl-NH-C(O)-, $(C_1-C_4)$alkyl)$_2$N-C(O)-, aryl, heteroaryl, a 3-6 membered partially or fully saturated heterocycle, and a partially or fully saturated carbocyclic ring, where said moiety is optionally substituted with one or more substituents, or $R^{4d}$ and $R^{4d'}$ taken together form a 3-6 membered partially or fully saturated carbocyclic ring, a 3-6 membered partially or fully saturated heterocyclic ring, a 5-6 membered lactone ring, or a 4-6 membered lactam ring, where said carbocyclic ring, said heterocyclic ring, said lactone ring and said lactam ring are optionally substituted with one or more substituents and said lactone ring and said lactam ring optionally contain an additional heteroatom selected from oxygen, nitrogen or sulfur, or Y is $-NR^{4d''}-$, where $R^{4d''}$ is a hydrogen or a chemical moiety selected from the group consisting of $(C_1-C_6)$alkyl, $(C_3-C_6)$cycloalkyl, $(C_1-C_3)$alkylsulfonyl-, $(C_1-C_3)$alkylaminosulfonyl-, di$(C_1-C_3)$alkylaminosulfonyl-, acyl. $(C_1-C_6)$alkyl-O-C(O)-, aryl, and heteroaryl, where said moiety is optionally substituted with one or more substituents;

Z is a bond, $-CH_2CH_2-$, or $-C(R^{4e})(R^{4e'})-$, where $R^{4e}$ is hydrogen, cyano, hydroxy, amino, $H_2NC(O)-$, or a chemical moiety selected from the group consisting of $(C_1-C_6)$alkyl, $(C_1-C_6)$alkoxy, acyloxy, acyl, $(C_1-C_3)$alkyl-O-C(O)-, $(C_1-C_4)$alkyl-NH-C(O)-, $(C_1-C_4)$alkyl)$_2$N-C(O)-, $(C_1-C_6)$alkylamino-, $((C_1-C_4)$alkyl)$_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a 3-6 membered partially or fully saturated heterocycle, and a partially or fully saturated carbocyclic ring, where said moiety is optionally substituted with one or more substituents, or $R^{4e}$ taken together with $R^{4b}$, $R^{4b'}$, $R^{4c}$, or $R^{4c'}$ forms a bond, a methylene bridge, or an ethylene bridge, and $R^{4e'}$ is hydrogen, $H_2NC(O)-$, or a chemical moiety selected from the group consisting of $(C_1-C_6)$alkyl, acyl, $(C_1-C_3)$alkyl-O-C(O)-, $(C_1-C_4)$alkyl-NH-C(O)-, $(C_1-C_4)$alkyl)$_2$N-C(O)-, aryl, heteroaryl, a 3-6 membered partially or fully saturated heterocycle, and a partially or fully saturated carbocyclic ring, where said moiety is optionally substituted with one or more substituents, or $R^{4e'}$ taken together with $R^{4b}$, $R^{4b'}$, $R^{4c}$, or $R^{4c'}$ forms a bond, a methylene bridge, or an ethylene bridge; and $R^{4f}$ and $R^{4f'}$ are each independently hydrogen, $H_2NC(O)-$, or a chemical moiety selected from the group consisting of $(C_1-C_6)$alkyl, acyl, $(C_1-C_3)$alkyl-O-C(O)-, $(C_1-C_4)$alkyl-NH-C(O)-, $(C_1-C_4)$alkyl)$_2$N-C(O)-, aryl, heteroaryl, a 3-6 membered partially or fully saturated heterocycle, and a partially or fully saturated carbocyclic ring, where said moiety is optionally substituted with one or more substituents, or $R^{4f}$ or $R^{4f'}$ taken together with $R^{4b}$, $R^{4b'}$, $R^{4c}$, or $R^{4c'}$ forms a bond, a methylene bridge, or an ethylene bridge;

a pharmaceutically acceptable salt thereof.

3. The compound of claim of 2 wherein $R^0$ and $R^1$ are each independently a substituted phenyl;

$R^{4b}$ is hydrogen, an optionally substituted $(C_1-C_3)$alkyl, or taken together with $R^{4e}$, $R^{4e'}$, $R^{4f}$, or $R^{4f'}$ forms a bond, a methylene bridge, or an ethylene bridge;

$R^{4b'}$ is hydrogen, an optionally substituted $(C_1-C_3)$alkyl, or taken together with $R^{4e}$, $R^{4e'}$, $R^{4f}$, or $R^{4f'}$ forms a bond, a methylene bridge, or an ethylene bridge;

$R^{4f}$ is hydrogen, an optionally substituted $(C_1-C_3)$alkyl, or taken together with $R^{4b}$, $R^{4b'}$, $R^{4c}$, or $R^{4c'}$ forms a bond, a methylene bridge, or an ethylene bridge; and $R^{4f'}$ is hydrogen, an optionally substituted $(C_1\text{-}C_3)$alkyl, or taken together with $R^{4b}$, $R^{4b'}$, $R^{4c}$, or $R^{4c'}$ forms a bond, a methylene bridge, or an ethylene bridge;

a pharmaceutically acceptable salt thereof, or a solvate or hydrate of said compound or said salt.

4. The compound of claim 3 wherein

X is —C($R^{4c}$)($R^{4c'}$)—, where $R^{4c}$ and $R^{4c'}$ are each independently hydrogen, $H_2NC(O)$—, or a chemical moiety selected from $(C_1\text{-}C_6)$alkyl, $(C_1\text{-}C_4)$alkyl-NH—C(O)—, or $((C_1\text{-}C_4)\text{alkyl})_2$N—C(O)—, where said moiety is optionally substituted with one or more substituents, or either $R^{4c}$ or $R^{4c'}$ taken together with $R^{4e}$, $R^{4e'}$, $R^{4f}$, or $R^{4f'}$ forms a bond, a methylene bridge or an ethylene bridge;

Y is —NR$^{4d''}$—, where $R^{4d''}$ is a hydrogen or a chemical moiety selected from the group consisting of $(C_1\text{-}C_6)$alkyl, $(C_3\text{-}C_6)$cycloalkyl, $(C_1\text{-}C_3)$alkylsulfonyl, $(C_1\text{-}C_3)$alkylaminosulfonyl, di$(C_1\text{-}C_3)$alkylaminosulfonyl, acyl, $(C_1\text{-}C_6)$alkyl-O—C(O)—, aryl, and heteroaryl, where said moiety is optionally substituted with one or more substituents;

Z is —C($R^{4e}$)($R^{4e'}$)—, where $R^{4e}$ and $R^{4e'}$ are each independently hydrogen, $H_2NC(O)$—, or a chemical moiety selected from $(C_1\text{-}C_6)$alkyl, $(C_1\text{-}C_4)$alkyl-NH—C(O)—, or $((C_1\text{-}C_4)\text{alkyl})_2$N—C(O)—, where said moiety is optionally substituted with one or more substituents, or either $R^{4e}$ or $R^{4e'}$ taken together with $R^{4b}$, $R^{4b'}$, $R^{4c}$, or $R^{4c'}$ forms a bond, a methylene bridge or an ethylene bridge;

a pharmaceutically acceptable salt thereof.

5. The compound of claim 4 wherein $R^{4d''}$ is a hydrogen or a chemical moiety selected from the group consisting of $(C_1\text{-}C_6)$alkyl, $(C_1\text{-}C_3)$alkylsulfonyl, $(C_1\text{-}C_3)$alkylaminosulfonyl, di$(C_1\text{-}C_3)$alkylaminosulfonyl, acyl, $(C_1\text{-}C_6)$alkyl-O—C(O)—, and heteroaryl, where said moiety is optionally substituted with one or more substituents;

a pharmaceutically acceptable salt thereof.

6. The compound of claim 5 wherein $R^{4d''}$ is a hydrogen or a chemical moiety selected from the group consisting of $(C_1\text{-}C_6)$alkyl, $(C_1\text{-}C_3)$alkylsulfonyl, $(C_1\text{-}C_3)$alkylaminosulfonyl, di$(C_1\text{-}C_3)$alkylaminosulfonyl, acyl, and $(C_1\text{-}C_6)$alkyl-O—C(O)—, where said moiety is optionally substituted with 1-3 fluorines, or $R^{4d''}$ is a heteroaryl, where said heteroaryl is optionally substituted with 1 to 2 substituents independently selected from the group consisting of chloro, fluoro, $(C_1\text{-}C_3)$alkoxy, $(C_1\text{-}C_3)$alkyl, and fluoro-substituted $(C_1\text{-}C_3)$alkyl;

a pharmaceutically acceptable salt thereof.

7. The compound of claim 4, 5 or 6 wherein $R^0$ and $R^1$ are each independently a phenyl substituted with 1 to 3 substituents independently selected from the group consisting of halo, $(C_1\text{-}C_4)$alkoxy, $(C_1\text{-}C_4)$alkyl, halo-substituted $(C_1\text{-}C_4)$alkyl, and cyano;

a pharmaceutically acceptable salt thereof.

8. The compound of claim 7 wherein $R^0$ and $R^1$ are each independently a phenyl substituted with 1 to 2 substituents independently selected from the group consisting of chloro, fluoro, $(C_1\text{-}C_4)$alkoxy, $(C_1\text{-}C_4)$alkyl, fluoro-substituted $(C_1\text{-}C_4)$alkyl), and cyano;

a pharmaceutically acceptable salt thereof.

9. The compound of claim 8 wherein $R^0$ is 2-chlorophenyl, 2-fluorophenyl, 2,4-dichlorophenyl, 2-fluoro-4-chlorophenyl, 2-chloro-4-fluorophenyl, or 2,4-difluorophenyl; and $R^1$ is 4-chlorophenyl or 4-fluorophenyl;

a pharmaceutically acceptable salt thereof.

10. The compound of claim 9 selected from the group consisting of 3-(4-chlorophenyl)-2-(2,4-dichlorophenyl)-7-(4-methylpiperazin-1-yl)-2H-pyrazolo[4,3-d]pyrimidine;

3-(4-chlorophenyl)-2-(2-chlorophenyl)-7-(5-cyclopentyl-2,5-diaza-bicyclo[2.2.1]hept-2-yl)-2H-pyrazolo[4,3-d]pyrimidine;

5-[3-(4-chlorophenyl)-2-(2-chlorophenyl)-2H-pyrazolo[4,3-d]pyrimidin-7-yl]-2,5-diazabicyclo[2.2.1]heptane-2-carboxylic acid tert-butyl ester;

5-[3-(4-chlorophenyl)-2-(2,4-dichlorophenyl)-2H-pyrazolo[4,3-d]pyrimidin-7-yl]-2,5-diazabicyclo[2.2.1]heptane-2-carboxylic acid tert-butyl ester;

3-(4-chlorophenyl)-2-(2-chlorophenyl)-7-(5-methanesulfonyl-2,5-diazabicyclo[2.2.1]hept-2-yl)-2H-pyrazolo[4,3-d]pyrimidine;

3-(4-chlorophenyl)-2-(2-chlorophenyl)-7-[5-(propane-2-sulfonyl)-2,5-diazabicyclo[2.2.1]hept-2-yl]-2H-pyrazolo[4,3-d]pyrimidine;

3-(4-chlorophenyl)-2-(2-chlorophenyl)-7-[5-(2,2,2-trifluoroethanesulfonyl)-2,5-diazabicyclo[2.2.1]hept-2-yl]-2H-pyrazolo[4,3-d]pyrimidine;

5-[3-(4-chlorophenyl)-2-(2-chlorophenyl)-2H-pyrazolo[4,3-d]pyrimidin-7-yl]-2,5-diazabicyclo[2.2.1]heptane-2-sulfonic acid dimethylamide;

4-[3-(4-chlorophenyl)-2-(2-chlorophenyl)-2H-pyrazolo[4,3-d]pyrimidin-7-yl]-piperazine-1-sulfonic acid dimethylamide;

3-(4-chlorophenyl)-2-(2-chlorophenyl)-7-(4-ethanesulfonylpiperazin-1-yl)-2H-pyrazolo[4,3-d]pyrimidine;

3-(4-chlorophenyl)-2-(2-chlorophenyl)-7-(4-(2,2,2-trifluoroethane)sulfonylpiperazin-1-yl)-2H-pyrazolo[4,3-d]pyrimidine;

3-(4-chlorophenyl)-2-(2-chlorophenyl)-7-(4-methanesulfonylpiperazin-1-yl)-2H-pyrazolo[4,3-d]pyrimidine;

3-(4-chlorophenyl)-2-(2-chlorophenyl)-7-(4-(propane-2-sulfonyl)piperazin-1-yl)-2H-pyrazolo[4,3-d]pyrimidine;

a pharmaceutically acceptable salt thereof.

11. The compound of claim 3 wherein Y is —C($R^{4d}$)($R^{4d'}$)—, where $R^{4d}$ is hydrogen, cyano, hydroxy, amino, $H_2NC(O)$—, or a chemical moiety selected from the group consisting of $(C_1\text{-}C_6)$alkyl, $(C_1\text{-}C_6)$alkoxy, acyloxy, acyl, $(C_1\text{-}C_3)$alkyl-O—C(O)—, $(C_1\text{-}C_4)$alkyl-NH—C(O)—, $(C_1\text{-}C_4)\text{alkyl})_2$N—C(O)—, $(C_1\text{-}C_6)$alkylamino-, $((C_1\text{-}C_4)\text{alkyl})_2$amino-, $(C_3\text{-}C_6)$cycloalkylamino-, acylamino-, aryl$(C_1\text{-}C_4)$alkylamino-, heteroaryl$(C_1\text{-}C_4)$alkylamino-, aryl, heteroaryl, a 3-6 membered partially or fully saturated heterocycle, and a partially or fully saturated carbocyclic ring, where said moiety is optionally substituted with one or more substituents, $R^{4d'}$ is hydrogen, $H_2NC(O)$—, or a chemical moiety selected from the group consisting of $(C_1\text{-}C_6)$alkyl, acyl, $(C_1\text{-}C_3)$alkyl-O—C(O)—, $(C_1\text{-}C_4)$alkyl-NH—C(O)—, $(C_1\text{-}C_4)\text{alkyl})_2$N—C(O)—, aryl, heteroaryl, a 3-6 membered partially or fully saturated heterocycle, and a partially or fully saturated carbocyclic ring, where said moiety is optionally substituted with one or more substituents, or $R^{4d}$ and $R^{4d'}$ taken together form a 3-6 membered partially or fully saturated carbocyclic ring, a 3-6 membered partially or fully saturated heterocyclic ring, a 5-6 membered lactone ring, or a 4-6 membered lactam ring, where said carbocyclic ring, said heterocyclic ring, said lactone ring and said lactam ring are optionally substituted with one or more substituents and said lactone ring and said lactam ring optionally contain an additional heteroatom selected from oxygen, nitrogen or sulfur;
a pharmaceutically acceptable salt thereof.

12. The compound of claim 11 wherein
$R^{4d}$ is amino, $(C_1-C_6)$alkylamino, di$(C_1-C_4)$alkylamino, azetidinyl, piperidinyl, pyrrolidinyl, morpholinyl, $(C_3-C_6)$cycloalkylamino, acylamino, aryl$(C_1-C_4)$alkylamino-, heteroaryl$(C_1-C_4)$alkylamino-, piperidinyl, pyrrolidinyl, or morpholinyl; and
$R^{4d'}$ is $(C_1-C_6)$alkyl, $H_2NC(O)$—, $(C_1-C_4)$alkyl-NH—C(O)—, $((C_1-C_4)$alkyl$)_2N$—C(O)—, or aryl;
a pharmaceutically acceptable salt thereof.

13. The compound of claim 12 wherein $R^{4d}$ is amino, $(C_1-C_6)$alkylamino, di$(C_1-C_4)$alkylamino, or $(C_3-C_6)$cycloalkylamino; and
$R^{4d'}$ is $H_2NC(O)$—, $(C_1-C_4)$alkyl-NH—C(O)—, or $((C_1-C_4)$alkyl$)_2N$—C(O)—;
a pharmaceutically acceptable salt thereof.

14. The compound of claim 11, 12, or 13 wherein $R^0$ and $R^1$ are each independently a phenyl substituted with 1 to 3 substituents independently selected from the group consisting of halo, $(C_1-C_4)$alkoxy, $(C_1-C_4)$alkyl, halo-substituted $(C_1-C_4)$alkyl, and cyano;
a pharmaceutically acceptable salt thereof.

15. The compound of claim 14 wherein $R^0$ and $R^1$ are each independently a phenyl substituted with 1 to 2 substituents independently selected from the group consisting of chloro, fluoro, $(C_1-C_4)$alkoxy, $(C_1-C_4)$alkyl, fluoro-substituted $(C_1-C_4)$alkyl), and cyano;
a pharmaceutically acceptable salt thereof.

16. The compound of claim 15 wherein $R^0$ is 2-chlorophenyl, 2-fluorophenyl, 2,4-dichlorophenyl, 2-fluoro-4-chlorophenyl, 2-chloro-4-fluorophenyl, or 2,4-difluorophenyl; and $R^1$ is 4-chlorophenyl or 4-fluorophenyl;
a pharmaceutically acceptable salt thereof.

17. The compound of claim 16 selected from the group consisting of
1-[3-(4-chlorophenyl)-2-(2-chlorophenyl)-2H-pyrazolo[4,3-d]pyrimidin-7-yl]-3-ethylaminoazetidine-3-carboxylic acid amide;
1-[3-(4-chlorophenyl)-2-(2-chlorophenyl)-2H-pyrazolo[4,3-d]pyrimidin-7-yl]-3-methylaminoazetidine-3-carboxylic acid amide;
1-[3-(4-chlorophenyl)-2-(2-chlorophenyl)-2H-pyrazolo[4,3-d]pyrimidin-7-yl]-3-(2-propylamino)azetidine-3-carboxylic acid amide;
1-[3-(4-chlorophenyl)-2-(2-chlorophenyl)-2H-pyrazolo[4,3-d]pyrimidin-7-yl]4-isopropylaminopiperidine-4-carboxylic acid amide;
1-[3-(4-chlorophenyl)-2-(2-chlorophenyl)-2H-pyrazolo[4,3-d]pyrimidin-7-yl]4-ethylaminopiperidine-4-carboxylic acid amide;
1'-[3-(4-chlorophenyl)-2-(2-chlorophenyl)-2H-pyrazolo[4,3-d]pyrimidin-7-yl]-[1,4']bipiperidinyl-4'-carboxylic acid amide;
8-[3-(4-chlorophenyl)-2-(2-chlorophenyl)-2H-pyrazolo[4,3-d]pyrimidin-7-yl]-3-pyrrolidin-1-yl-8-aza-bicyclo[3.2.1]octane-3-carboxylic acid amide;
1'-[3-(4-chlorophenyl)-2-(2-chlorophenyl)-2H-pyrazolo[4,3-d]pyrimidin-7-yl]-[1,3']bipyrrolidinyl-3'-carboxylic acid amide;
1-[3-(4-chlorophenyl)-2-(2-chlorophenyl)-2H-pyrazolo[4,3-d]pyrimidin-7-yl]-3-morpholin-4-yl-pyrrolidine-3-carboxylic acid amide;
1-[3-(4-chlorophenyl)-2-(2-chlorophenyl)-2H-pyrazolo[4,3-d]pyrimidin-7-yl]-3-isopropylaminopyrrolidine-3-carboxylic acid amide;
a pharmaceutically acceptable salt thereof.

18. The compound of claim 17 selected from the group consisting of
1-[3-(4-chlorophenyl)-2-(2-chlorophenyl)-2H-pyrazolo[4,3-d]pyrimidin-7-yl]-4-isopropylaminopiperidine-4-carboxylic acid amide;
1-[3-(4-chlorophenyl)-2-(2-chlorophenyl)-2H-pyrazolo[4,3-d]pyrimidin-7-yl]-4-ethylaminopiperidine-4-carboxylic acid amide;
1-[3-(4-chlorophenyl)-2-(2-chlorophenyl)-2H-pyrazolo[4,3-d]pyrimidin-7-yl]-3-isopropylaminopyrrolidine-3-carboxylic acid amide; and
1'-[3-(4-chlorophenyl)-2-(2-chlorophenyl)-2H-pyrazolo[4,3-d]pyrimidin-7-yl]-[1,4']bipiperidinyl-4'-carboxylic acid amide;
a pharmaceutically acceptable salt thereof.

19. The compound of claim 11 wherein
$R^{4d}$ is hydrogen, hydroxy, amino, cyano or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_6)$alkylamino-, and di$(C_1-C_4)$alkylamino-, $(C_1-C_4)$alkyl-NH—C(O)—, $(C_1-C_4)$alkyl$)_2$N—C(O)—, where said moiety is optionally substituted with one or more substituents; and
$R^{4d'}$ is hydrogen, or a chemical moiety selected from the group consisting of $(C_1-C_6)$alkyl, aryl and heteroaryl, where said moiety is optionally substituted with one or more substituents;
a pharmaceutically acceptable salt thereof.

20. The compound of claim 19 wherein
X is a bond or —C$(R^{4c})(R^{4c'})$—, where $R^{4c}$ and $R^{4c'}$ are each independently hydrogen or an optionally substituted $(C_1-C_6)$alkyl, or either $R^{4c}$ or $R^{4c'}$ taken together with $R^{4e}$ or $R^{4e'}$ forms a bond, a methylene bridge or an ethylene bridge; and
Z is a bond or —C$(R^{4e})(R^{4e'})$—, where $R^{4e}$ and $R^{4e'}$ are each independently hydrogen or an optionally substituted $(C_1-C_6)$alkyl, or either $R^{4e}$ or $R^{4e'}$ taken together with $R^{4c}$ or $R^{4c'}$ forms a bond, a methylene bridge or an ethylene bridge;
a pharmaceutically acceptable salt thereof.

21. The compound of claim 20 wherein
$R^{4c}$ and $R^{4c'}$ are each hydrogen or either $R^{4c}$ or $R^{4c'}$ taken together with $R^{4e}$ or $R^{4e'}$ forms a bond;
$R^{4d}$ is hydrogen, hydroxy, amino, cyano, or a chemical moiety selected from the group consisting of $(C_1-C_6)$alkoxy, acyl, $(C_1-C_6)$alkylamino-, $(C_1-C_4)$alkyl-NH—C(O)—, $(C_1-C_4)$alkyl$)_2$N—C(O)—, and di$(C_1-C_4)$alkylamino-;
$R^{4d'}$ is hydrogen, or a chemical moiety selected from the group consisting of $(C_1-C_6)$alkyl and aryl, where said moiety is optionally substituted with one or more substituents; and
$R^{4e}$ and $R^{4e'}$ are hydrogen or either $R^{4e}$ or $R^{4e'}$ taken together with $R^{4c}$ or $R^{4c'}$ forms a bond;
a pharmaceutically acceptable salt thereof.

22. The compound of claim 19, 20, or 21 wherein $R^0$ and $R^1$ are each independently a phenyl substituted with 1 to 3 substituents independently selected from the group consisting of halo, $(C_1-C_4)$alkoxy, $(C_1-C_4)$alkyl, halo-substituted $(C_1-C_4)$alkyl, and cyano;
a pharmaceutically acceptable salt thereof.

23. The compound of claim 22 wherein $R^0$ and $R^1$ are each independently a phenyl substituted with 1 to 2 substituents independently selected from the group consisting of chloro, fluoro, ($C_1$-$C_4$)alkoxy, ($C_1$-$C_4$)alkyl, fluoro-substituted ($C_1$-$C_4$)alkyl), and cyano;

a pharmaceutically acceptable salt thereof.

24. The compound of claim 23 wherein $R^0$ is 2-chlorophenyl, 2-fluorophenyl, 2,4-dichlorophenyl, 2-fluoro-4-chlorophenyl, 2-chloro-4-fluorophenyl, or 2,4-difluorophenyl; and $R^1$ is 4-chlorophenyl or 4-fluorophenyl;

a pharmaceutically acceptable salt thereof.

25. The compound of claim 24 selected from the group consisting of

1-[3-(4-chlorophenyl)-2-(2-chlorophenyl)-2H-pyrazolo[4,3-d]pyrimidin-7-yl]4-phenylpiperidin-4-ol;

1-[3-(4-chlorophenyl)-2-(2-chlorophenyl)-2H-pyrazolo[4,3-d]pyrimidin-7-yl]-4-ethylpiperidin-4-ol;

1-[3-(4-chlorophenyl)-2-(2-chlorophenyl)-2H-pyrazolo[4,3-d]pyrimidin-7-yl]-4-isopropylpiperidin-4-ol;

1-[3-(4-chlorophenyl)-2-(2-chlorophenyl)-2H-pyrazolo[4,3-d]pyrimidin-7-yl]-4-sec-butylpiperidin-4-ol;

1-[3-(4-chlorophenyl)-2-(2-chlorophenyl)-2H-pyrazolo[4,3-d]pyrimidin-7-yl]-4-methylpiperidin-4-ol;

8-[3-(4-chlorophenyl)-2-(2-chlorophenyl)-2H-pyrazolo[4,3-d]pyrimidin-7-yl]-3-ethyl-8-azabicyclo[3.2.1]octan-3-ol;

8-[3-(4-chlorophenyl)-2-(2-chlorophenyl)-2H-pyrazolo[4,3-d]pyrimidin-7-yl]-3-sec-butyl-8-azabicyclo[3.2.1]octan-3-ol;

8-[3-(4-chlorophenyl)-2-(2-chlorophenyl)-2H-pyrazolo[4,3-d]pyrimidin-7-yl]-3-isopropyl-8-azabicyclo[3.2.1]octan-3-ol;

1-[3-(4-chlorophenyl)-2-(2-chlorophenyl)-2H-pyrazolo[4,3-d]pyrimidin-7-yl]-3-isobutyl-pyrrolidin-3-ol;

1-[3-(4-chlorophenyl)-2-(2-chlorophenyl)-2H-pyrazolo[4,3-d]pyrimidin-7-yl]-3-isopropyl-pyrrolidin-3-ol;

{8-[3-(4-chlorophenyl)-2-(2-chlorophenyl)-2H-pyrazolo[4,3-d]pyrimidin-7-yl]-8-aza-bicyclo[3.2.1]oct-3-yl}-ethyl-amine;

3-(4-chlorophenyl)-2-(2-chlorophenyl)-7-(3-pyrrolidin-1-yl-8-aza-bicyclo[3.2.1]oct-8-yl)-2H-pyrazolo[4,3-d]pyrimidine;

7-(3-bromo-8-azabicyclo[3.2.1]oct-8-yl)-3-(4-chlorophenyl)-2-(2-chlorophenyl)-2H-pyrazolo[4,3-d]pyrimidine;

7-(3-bromo-8-azabicyclo[3.2.1]oct-8-yl)-3-(4-chlorophenyl)-2-(2,4-dichlorophenyl)-2H-pyrazolo[4,3-d]pyrimidine;

3-(4-chlorophenyl)-2-(2-chlorophenyl)-7-(4-methylpiperidin-1-yl)-2H-pyrazolo[4,3-d]pyrimidine;

3-(4-chlorophenyl)-2-(2-chlorophenyl)-7-(3-hydroxypiperidin-1-yl)-2H-pyrazolo[4,3-d]pyrimidine;

1-[3-(4-chlorophenyl)-2-(2-chlorophenyl)-2H-pyrazolo[4,3-d]pyrimidin-7-yl]-4-(3-methoxyphenyl)-piperidine-4-carbonitrile;

1-[3-(4-chlorophenyl)-2-(2-chlorophenyl)-2H-pyrazolo[4,3-d]pyrimidin-7-yl]-4-phenylpiperidine-4-carbonitrile;

1-{1-[3-(4-chlorophenyl)-2-(2-chlorophenyl)-2H-pyrazolo[4,3-d]pyrimidin-7-yl]-4-phenylpiperidin-4-yl}-propan-1-one;

1'-[3-(4-chlorophenyl)-2-(2-chlorophenyl)-2H-pyrazolo[4,3-d]pyrimidin-7-yl]-2',3',5',6'-tetrahydro-1'H-[3,4']bipyridinyl-4'-carbonitrile;

1-[3-(4-chlorophenyl)-2-(2-chlorophenyl)-2H-pyrazolo[4,3-d]pyrimidin-7-yl]-2,3,5,6-tetrahydro-1H-[4,4']bipyridinyl-4-carbonitrile;

1-[3-(4-chlorophenyl)-2-(2-chlorophenyl)-2H-pyrazolo[4,3-d]pyrimidin-7-yl]-2,3,5,6-tetrahydro-1H-[2,4']bipyridinyl-4-carbonitrile;

{1-[3-(4-chlorophenyl)-2-(2-chlorophenyl)-2H-pyrazolo[4,3-d]pyrimidin-7-yl]-4-phenylpiperidin-4-yl}-morpholin-4-yl-methanone;

benzyl-{8-[3-(4-chlorophenyl)-2-(2-chlorophenyl)-2H-pyrazolo[4,3-d]pyrimidin-7-yl]-8-aza-bicyclo[3.2.1]oct-3-yl}-amine;

{1-[3-(4-chlorophenyl)-2-(2-chlorophenyl)-2H-pyrazolo[4,3-d]pyrimidin-7-yl]-pyrrolidin-3-yl}-methylcarbamic acid tert-butyl ester;

{1-[3-(4-chlorophenyl)-2-(2-chlorophenyl)-2H-pyrazolo[4,3-d]pyrimidin-7-yl]-pyrrolidin-3-yl}-carbamic acid tert-butyl ester;

N-{1-[3-(4-chlorophenyl)-2-(2-chlorophenyl)-2H-pyrazolo[4,3-d]pyrimidin-7-yl]-pyrrolidin-3-yl}-N-methylacetamide; and {1-[3-(4-chlorophenyl)-2-(2-chlorophenyl)-2H-pyrazolo[4,3-d]pyrimidin-7-yl]-pyrrolidin-3-yl}-dimethylamine;

a pharmaceutically acceptable salt thereof.

26. The compound of claim 11 wherein $R^{4b}$, $R^{4b'}$, $R^{4f}$, and $R^{4f'}$ are all hydrogen; and $R^{4d}$ and $R^{4d'}$ taken together form a 3-6 membered partially or fully saturated carbocyclic ring, a 3-6 membered partially or fully saturated heterocyclic ring, a 5-6 membered lactone ring, or a 4-6 membered lactam ring, where said carbocyclic ring, said heterocyclic ring, said lactone ring and said lactam ring are optionally substituted with one or more substituents and said lactone ring or said lactam ring optionally contains an additional heteroatom selected from oxygen, nitrogen or sulfur;

a pharmaceutically acceptable salt thereof.

27. The compound of claim 26 wherein

X is a bond, —$CH_2CH_2$— or —$C(R^{4c})(R^{4c'})$—, where $R^{4c}$ and $R^{4c'}$ are each independently hydrogen or an optionally substituted ($C_1$-$C_6$)alkyl, or either $R^{4c}$ or $R^{4c'}$ taken together with $R^{4e}$ or $R^{4e'}$ forms a bond, a methylene bridge or an ethylene bridge; and Z is a bond, —$CH_2CH_2$— or —$C(R^{4e})(R^{4e'})$—, where $R^{4e}$ and $R^{4e'}$ are each independently hydrogen or an optionally substituted ($C_1$-$C_6$)alkyl, or either $R^{4e}$ or $R^{4e'}$ taken together with $R^{4c}$ or $R^{4c'}$ forms a bond, a methylene bridge or an ethylene bridge;

a pharmaceutically acceptable salt thereof. compound or said salt.

28. The compound of claim 27 wherein $R^{4d}$ and $R^{4d'}$ taken together form a 3-6 membered partially or fully saturated carbocyclic ring, a 3-6 membered partially or fully saturated heterocyclic ring, or a 5-6 membered lactam ring, where said lactam ring is optionally substituted with one or more substituents and optionally contains an additional heteroatom selected from nitrogen or oxygen;

a pharmaceutically acceptable salt thereof.

29. The compound of claim 28 wherein

X is a bond or —$C(R^{4c})(R^{4c'})$—, where $R^{4c}$ and $R^{4c'}$ are each hydrogen; and Z is a bond or $C(R^{4e})(R^{4e'})$—, where $R^{4e}$ and $R^{4e'}$ are each hydrogen;

a pharmaceutically acceptable salt thereof.

30. The compound of claim 26, 27, 28 or 29 wherein $R^0$ and $R^1$ are each independently a phenyl substituted with 1 to 3 substituents independently selected from the group consisting of halo, $(C_1-C_4)$alkoxy, $(C_1-C_4)$alkyl, halo-substituted $(C_1-C_4)$alkyl, and cyano;

a pharmaceutically acceptable salt thereof.

31. The compound of claim 30 wherein $R^0$ and $R^1$ are each independently a phenyl substituted with 1 to 2 substituents independently selected from the group consisting of chloro, fluoro, $(C_1-C_4)$alkoxy, $(C_1-C_4)$alkyl, fluoro-substituted $(C_1-C_4)$alkyl), and cyano;

a pharmaceutically acceptable salt thereof.

32. The compound of claim 31 wherein $R^0$ is 2-chlorophenyl, 2-fluorophenyl, 2,4-dichlorophenyl, 2-fluoro-4-chlorophenyl, 2-chloro-4-fluorophenyl, or 2,4-difluorophenyl; and $R^1$ is 4-chlorophenyl or 4-fluorophenyl;

a pharmaceutically acceptable salt thereof.

33. The compound of claim 32 selected from the group consisting of

2-[3-(4-chlorophenyl)-2-(2-chlorophenyl)-2H-pyrazolo[4,3-d]pyrimidin-7-yl]-5-methyl-2,5,7-triaza-spiro[3.4]octan-8-one;

8-[3-(4-chloro-phenyl)-2-(2-chlorophenyl)-2H-pyrazolo[4,3-d]pyrimidin-7-yl]-1-isopropyl-1,3,8-triaza-spiro[4.5]decan-4-one;

3-(4-chlorophenyl)-2-(2-chlorophenyl)-7-(1,4-dioxa-8-aza-spiro[4.5]dec-8-yl)-2H-pyrazolo[4,3-d]pyrimidine;

3-[3-(4-chlorophenyl)-2-(2-chlorophenyl)-2H-pyrazolo[4,3-d]pyrimidin-7-yl]-1-spiro[(5-methoxy)tetrahydronaphthalene-1,4'-piperidine];

3-[3-(4-chlorophenyl)-2-(2-chlorophenyl)-2H-pyrazolo[4,3-d]pyrimidin-7-yl]-1-spiro[(6-methoxy)tetrahydronaphthalene-1,4'-piperidine]; and 3-[3-(4-chlorophenyl)-2-(2-chlorophenyl)-2H-pyrazolo[4,3-d]pyrimidin-7-yl]-1-spiro[indane-1,4'-piperidine];

a pharmaceutically acceptable salt thereof.

34. The compound of claim 1 wherein $R^4$ is a group of Formula (IB)

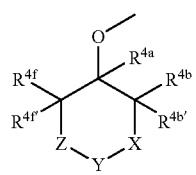

IB where $R^{4a}$ is as defined in claim 1;

$R^{4b}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)$alkyl)$_2$N—C(O)—, $(C_1-C_6)$alkylamino-, $((C_1-C_4)$alkyl)$_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a 3-6 membered partially or fully saturated heterocycle, and a partially or fully saturated carbocyclic ring, where said moiety is optionally substituted with one or more substituents, $R^{4b'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)$alkyl)$_2$N—C(O)—, aryl, heteroaryl, a 3-6 membered partially or fully saturated heterocycle, and a partially or fully saturated carbocyclic ring, where said moiety is optionally substituted with one or more substituents, or $R^{4b}$ or $R^{4b'}$ taken together with $R^{4e}$, $R^{4e'}$, $R^{4f}$, or $R^{4f'}$ forms a bond, a methylene bridge, or an ethylene bridge;

X is a bond, —CH$_2$CH$_2$— or —C($R^{4c}$)($R^{4c'}$)—, where $R^{4c}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)$alkyl)$_2$N—C(O)—, $(C_1-C_6)$alkylamino-, $((C_1-C_4)$alkyl)$_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a 3-6 membered partially or fully saturated heterocycle, and a partially or fully saturated carbocyclic ring, where said moiety is optionally substituted with one or more substituents, or $R^{4c}$ taken together with $R^{4e}$, $R^{4e'}$, $R^{4f}$, or $R^{4f'}$ forms a bond, a methylene bridge, or an ethylene bridge, and $R^{4c'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)$alkyl)$_2$N—C(O)—, aryl, heteroaryl, a 3-6 membered partially or fully saturated heterocycle, and a partially or fully saturated carbocyclic ring, where said moiety is optionally substituted with one or more substituents, or $R^{4c'}$ taken together with $R^{4e}$, $R^{4e'}$, $R^{4f}$, or $R^{4f'}$ forms a bond, a methylene bridge, or an ethylene bridge;

Y is oxygen, sulfur, —C(O)—, or —C($R^{4d}$)($R^{4d'}$)—, where $R^{4d}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)$alkyl)$_2$N—C(O)—, $(C_1-C_6)$alkylamino-, $((C_1-C_4)$alkyl)$_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a 3-6 membered partially or fully saturated heterocycle, and a partially or fully saturated carbocyclic ring, where said moiety is optionally substituted with one or more substituents, and $R^{4d'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)$alkyl)$_2$N—C(O)—, aryl, heteroaryl, a 3-6 membered partially or fully saturated heterocycle, and a partially or fully saturated carbocyclic ring, where said moiety is optionally substituted with one or more substituents, or $R^{4d}$ and $R^{4d'}$ taken together form a 3-6 membered partially or fully saturated carbocyclic ring, a 3-6 membered partially or fully saturated heterocyclic ring, a 5-6 membered lactone ring, or a 4-6 membered lactam ring, where said carbocyclic ring, said heterocyclic ring, said lactone ring and said lactam ring are optionally substituted with one or more substituents and said lactone ring and said lactam ring optionally contain an additional heteroatom selected from oxygen, nitrogen or sulfur;

Y is —NR$^{4d''}$—, where $R^{4d''}$ is a hydrogen or a chemical moiety selected from the group consisting of $(C_1-C_6)$alkyl, $(C_3-C_6)$cycloalkyl, $(C_1-C_3)$alkylsulfonyl-, $(C_1-C_3)$alkylaminosulfonyl-, di$(C_1-C_3)$alkylaminosulfonyl-, acyl, $(C_1-C_6)$alkyl-O—C(O)—, aryl, and heteroaryl, where said moiety is optionally substituted with one or more substituents;

Z is a bond, —CH$_2$CH$_2$—, or —C(R$^{4e}$)(R$^{4e'}$)—, where R$^{4e}$ is hydrogen, cyano, hydroxy, amino, H$_2$NC(O)—, or a chemical moiety selected from the group consisting of (C$_1$-C$_6$)alkyl, (C$_1$-C$_6$)alkoxy, acyloxy, acyl, (C$_1$-C$_3$)alkyl-O—C(O)—, (C$_1$-C$_4$)alkyl-NH—C(O)—, (C$_1$-C$_4$)alkyl)$_2$N—C(O)—, (C$_1$-C$_6$)alkylamino-, ((C$_1$-C$_4$)alkyl)$_2$amino-, (C$_3$-C$_6$)cycloalkylamino-, acylamino-, aryl(C$_1$-C$_4$)alkylamino-, heteroaryl(C$_1$-C$_4$)alkylamino-aryl, heteroaryl, a 3-6 membered partially or fully saturated heterocyclic ring, and a partially or fully saturated carbocyclic ring, where said moiety is optionally substituted with one or more substituents, or R$^{4e}$ taken together with R$^{4b}$, R$^{4b'}$, R$^{4c}$, or R$^{4c'}$ forms a bond, a methylene bridge, or an ethylene bridge, and R$^{4e'}$ is hydrogen, H$_2$NC(O)—, or a chemical moiety selected from the group consisting of (C$_1$-C$_6$)alkyl, acyl, (C$_1$-C$_3$)alkyl-O—C(O)—, (C$_1$-C$_4$)alkyl-NH—C(O)—, (C$_1$-C$_4$)alkyl)$_2$N—C(O)—, aryl, heteroaryl, a 3-6 membered partially or fully saturated heterocycle, and a partially or fully saturated carbocyclic ring, where said moiety is optionally substituted with one or more substituents, or R$^{4e'}$ taken together with R$^{4b}$, R$^{4b'}$, R$^{4c}$, or R$^{4c'}$ forms a bond, a methylene bridge, or an ethylene bridge;

R$^{4f}$ is hydrogen, cyano, hydroxy, amino, H$_2$NC(O)—, or a chemical moiety selected from the group consisting of (C$_1$-C$_6$)alkyl, (C$_1$-C$_6$)alkoxy, acyloxy, acyl, (C$_1$-C$_3$)alkyl-O—C(O)—, (C$_1$-C$_4$)alkyl-NH—C(O)—, (C$_1$-C$_4$)alkyl)$_2$N—C(O)—, (C$_1$-C$_6$)alkylamino-, ((C$_1$-C$_4$)alkyl)$_2$amino-, (C$_3$-C$_6$)cycloalkylamino-, acylamino-, aryl(C$_1$-C$_4$)alkylamino-, heteroaryl(C$_1$-C$_4$)alkylamino-, aryl, heteroaryl, a 3-6 membered partially or fully saturated heterocycle, and a partially or fully saturated carbocyclic ring, where said moiety is optionally substituted with one or more substituents; and R$^{4f'}$ is hydrogen, H$_2$NC(O)—, or a chemical moiety selected from the group consisting of (C$_1$-C$_6$)alkyl, acyl, (C$_1$-C$_3$)alkyl-O—C(O)—, (C$_1$-C$_4$)alkyl-NH—C(O)—, (C$_1$-C$_4$)alkyl)$_2$N—C(O)—, aryl, heteroaryl, a 3-6 membered partially or fully saturated heterocycle, and a partially or fully saturated carbocyclic ring, where said moiety is optionally substituted with one or more substituents, or R$^{4f}$ or R$^{4f'}$ taken together with R$^{4b}$, R$^{4b'}$, R$^{4c}$, or R$^{4c'}$ forms a bond, a methylene bridge, or an ethylene bridge;

a pharmaceutically acceptable salt thereof.

35. The compound of claim 34 wherein

R$^0$ and R$^1$ are each independently a substituted phenyl;

R$^{4a}$, R$^{4b}$, R$^{4b'}$, R$^{4f}$ and R$^{4f'}$ are each hydrogen;

a pharmaceutically acceptable salt thereof.

36. The compound of claim 35 wherein

X is a bond, —CH$_2$CH$_2$— or —C(R$^{4c}$)(R$^{4c'}$)—, where R$^{4c}$ and R$^{4c'}$ are each independently hydrogen or (C$_1$-C$_6$)alkyl;

Y is —NR$^{4d''}$—, where R$^{4d''}$ is hydrogen or a chemical moiety selected from the group consisting of (C$_1$-C$_6$)alkyl, (C$_3$-C$_6$)cycloalkyl, (C$_1$-C$_3$)alkylsulfonyl-, (C$_1$-C$_3$)alkylaminosulfonyl-, di(C$_1$-C$_3$)alkylaminosulfonyl-, acyl, (C$_1$-C$_6$)alkyl-O—C(O)—, aryl, and heteroaryl, where said moiety is optionally substituted with one or more substituents;

Z is a bond, —CH$_2$CH$_2$— or —C(R$^{4c}$)(R$^{4c'}$)—, where R$^{4c}$ and R$^{4c'}$ are each independently hydrogen or (C$_1$-C$_6$)alkyl;

a pharmaceutically acceptable salt thereof.

37. The compound of claim 35 or 36 wherein R$^0$ and R$^1$ are each independently a phenyl substituted with 1 to 3 substituents independently selected from the group consisting of halo, (C$_1$-C$_4$)alkoxy, (C$_1$-C$_4$)alkyl, halo-substituted (C$_1$-C$_4$)alkyl, and cyano;

a pharmaceutically acceptable salt thereof.

38. The compound of claim 37 wherein R$^0$ and R$^1$ are each independently a phenyl substituted with 1 to 2 substituents independently selected from the group consisting of chloro, fluoro, (C$_1$-C$_4$)alkoxy, (C$_1$-C$_4$)alkyl, fluoro-substituted (C$_1$-C$_4$)alkyl), and cyano;

a pharmaceutically acceptable salt thereof.

39. The compound of claim 38 wherein R$^0$ is 2-chlorophenyl, 2-fluorophenyl, 2,4-dichlorophenyl, 2-fluoro-4-chlorophenyl, 2-chloro-4-fluorophenyl, or 2,4-difluorophenyl; and R$^1$ is 4-chlorophenyl or 4-fluorophenyl;

a pharmaceutically acceptable salt thereof.

40. The compound of claim 39 selected from the group consisting of 7-(1-benzhydrylazetidin-3-yloxy)-3-(4-chlorophenyl)-2-(2-chlorophenyl)-2H-pyrazolo[4,3-d]pyrimidine; and 7-(1-benzylpyrrolidin-3-yloxy)-3-(4-chlorophenyl)-2-(2-chlorophenyl)-2H-pyrazolo[4,3-d]pyrimidine;

a pharmaceutically acceptable salt thereof.

41. The compound of claim 1 wherein R$^4$ is a group of Formula (IC)

$$-\text{O}-\underset{R^7}{\overset{R^5}{\text{C}}}-R^6 \qquad \text{IC}$$

where R$^5$ and R$^6$ are each independently hydrogen, aryl, or (C$_1$-C$_4$)alkyl, and R$^7$ is an optionally substituted (C$_1$-C$_4$)alkyl-, or an optionally substituted 4-6 membered partially or fully saturated heterocyclic ring containing 1 to 2 heteroatoms independently selected from oxygen, sulfur or nitrogen, or R$^5$ and R$^6$ or R$^5$ and R$^7$ taken together form a 5-6 membered lactone, 4-6 membered lactam, or a 4-6 membered partially or fully saturated heterocycle containing 1 to 2 heteroatoms independently selected from oxygen, sulfur or nitrogen, where said lactone, said lactam and said heterocycle are optionally substituted with one or more substituents;

a pharmaceutically acceptable salt thereof.

42. The compound of claim 41 wherein

R$^0$ and R$^1$ are each independently a substituted phenyl;

a pharmaceutically acceptable salt thereof.

43. The compound of claim 41 or 42 wherein R$^0$ and R$^1$ are each independently a phenyl substituted with 1 to 3 substituents independently selected from the group consisting of halo, (C$_1$-C$_4$)alkoxy, (C$_1$-C$_4$)alkyl, halo-substituted (C$_1$-C$_4$)alkyl, and cyano;

a pharmaceutically acceptable salt thereof.

44. The compound of claim 43 wherein R$^0$ and R$^1$ are each independently a phenyl substituted with 1 to 2 substituents independently selected from the group consisting of bromo, chloro, fluoro, (C$_1$-C$_4$)alkoxy, (C$_1$-C$_4$)alkyl, fluoro-substituted (C$_1$-C$_4$)alkyl), and cyano;

a pharmaceutically acceptable salt thereof.

45. The compound of claim 44 selected from the group consisting of
2-(2-chlorophenyl)-7-isopropoxy-3-(4-trifluoromethylphenyl)-2H-pyrazolo[4,3-d]pyrimidine;
2-(2-chloro-4-methylphenyl)-5-methyl-7-(2,2,2-trifluoroethoxy)-3-(4-trifluoromethylphenyl)-2H-pyrazolo[4,3-d]pyrimidine;
2-(2-chlorophenyl)-3-(4-methoxyphenyl)-5-methyl-7-(2,2,2-trifluoroethoxy)-2H-pyrazolo[4,3-d]pyrimidine;
2-(2-bromophenyl)-3-(4-chlorophenyl)-7-(2,2-difluoropropoxy)-5-methyl-2H-pyrazolo[4,3-d]pyrimidine;
2-(2-bromophenyl)-3-(4-methoxyphenyl)-5-methyl-7-(2,2,2-trifluoroethoxy)-2H-pyrazolo[4,3-d]pyrimidine;
2-[3-(4-chlorophenyl)-7-(2,2-difluoropropoxy)-5-methylpyrazolo[4,3-d]pyrimidin-2-yl]-benzonitrile;
2-(2-bromophenyl)-7-(2,2-difluoropropoxy)-3-(4-methoxyphenyl)-5-methyl-2H-pyrazolo[4,3-d]pyrimidine;
3-(4-bromophenyl)-2-(2-chlorophenyl)-7-(2,2-difluoropropoxy)-5-methyl-2H-pyrazolo[4,3-d]pyrimidine; and
2-(2-chlorophenyl)-7-(2,2-difluoropropoxy)-3-(4-methoxyphenyl)-5-methyl-2H-pyrazolo[4,3-d]pyrimidine;
a pharmaceutically acceptable salt thereof.

46. The compound of claim 44 wherein $R^0$ is 2-chlorophenyl, 2-fluorophenyl, 2,4-dichlorophenyl, 2-fluoro-4-chlorophenyl, 2-chloro-4-fluorophenyl, or 2,4-difluorophenyl; and $R^1$ is 4-chlorophenyl or 4-fluorophenyl;
a pharmaceutically acceptable salt thereof.

47. The compound of claim 46 selected from the group consisting of
3-(4-chlorophenyl)-2-(2-chlorophenyl)-7-isopropoxy-2H-pyrazolo[4,3-d]pyrimidine;
3-(4-chlorophenyl)-2-(2-chlorophenyl)-7-(2,2,2-trifluoroethoxy)-2H-pyrazolo[4,3-d]pyrimidine;
3-(4-chlorophenyl)-2-(2-chlorophenyl)-7-methoxy-2H-pyrazolo[4,3-d]pyrimidine;
3-(4-chlorophenyl)-2-(2-chlorophenyl)-7-ethoxy-2H-pyrazolo[4,3-d]pyrimidine;
3-(4-chlorophenyl)-2-(2-chlorophenyl)-7-propoxy-2H-pyrazolo[4,3-d]pyrimidine;
7-butoxy-3-(4-chlorophenyl)-2-(2-chlorophenyl)-2H-pyrazolo[4,3-d]pyrimidine;
3-(4-chlorophenyl)-2-(2-chlorophenyl)-5-ethyl-7-(2,2,2-trifluoroethoxy)-2H-pyrazolo[4,3-d]pyrimidine;
3-(4-chlorophenyl)-2-(2-chlorophenyl)-5-isopropyl-7-(2,2,2-trifluoroethoxy)-2H-pyrazolo[4,3-d]pyrimidine;
3-(4-chlorophenyl)-2-(2-chlorophenyl)-7-ethoxy-5-trifluoromethyl-2H-pyrazolo[4,3-d]pyrimidine;
3-(4-chlorophenyl)-2-(2-chlorophenyl)-7-(2,2,2-trifluoroethoxy)-5-trifluoromethyl-2H-pyrazolo[4,3-d]pyrimidine; and
3-(4-chlorophenyl)-2-(2-chlorophenyl)-7-(2,2-difluorobutoxy)-5-methyl-2H-pyrazolo[4,3-d]pyrimidine;
a pharmaceutically acceptable salt thereof.

48. The compound of claim 1 wherein $R^4$ is an amino group having attached thereto at least one chemical moiety selected from the group consisting of $(C_1-C_8)$alkyl, aryl, aryl$(C_1-C_4)$alkyl, a 3-8 membered partially or fully saturated carbocyclic ring, hydroxy$(C_1-C_6)$alkyl, $(C_1-C_3)$alkoxy$(C_1-C_6)$alkyl, heteroaryl$(C_1-C_3)$alkyl, and a fully or partially saturated heterocycle, where said chemical moiety is optionally substituted with one or more substituents;
a pharmaceutically acceptable salt thereof.

49. The compound of claim 48 wherein
$R^0$ and $R^1$ are each independently a substituted phenyl;
a pharmaceutically acceptable salt thereof.

50. The compound of claim 48 or 49 wherein $R^0$ and $R^1$ are each independently a phenyl substituted with 1 to 3 substituents independently selected from the group consisting of halo, $(C_1-C_4)$alkoxy, $(C_1-C_4)$alkyl, halo-substituted $(C_1-C_4)$alkyl, and cyano;
a pharmaceutically acceptable salt thereof.

51. The compound of claim 50 wherein $R^0$ and $R^1$ are each independently a phenyl substituted with 1 to 2 substituents independently selected from the group consisting of chloro, fluoro, $(C_1-C_4)$alkoxy, $(C_1-C_4)$alkyl, fluoro-substituted $(C_1-C_4)$alkyl, and cyano;
a pharmaceutically acceptable salt thereof.

52. The compound of claim 51 wherein $R^0$ is 2-chlorophenyl, 2-fluorophenyl, 2,4-dichlorophenyl, 2-fluoro-4-chlorophenyl, 2-chloro-4-fluorophenyl, or 2,4-difluorophenyl; and $R^1$ is 4-chlorophenyl or 4-fluorophenyl;
a pharmaceutically acceptable salt thereof.

53. The compound of claim 52 selected from the group consisting of
N-4-[3-(4-chlorophenyl)-2-(2-chlorophenyl)-2H-pyrazolo[4,3-d]pyrimidin-7-yl]-N,N-diethylpentane-1,4-diamine;
[3-(4-chlorophenyl)-2-(2-chlorophenyl)-2H-pyrazolo[4,3-d]pyrimidin-7-yl]-(1-methyl-2-morpholin-4-yl-ethyl)-amine;
[3-(4-chlorophenyl)-2-(2-chlorophenyl)-2H-pyrazolo[4,3-d]pyrimidin-7-yl]-pyridin-2-yl-amine;
[3-(4-chlorophenyl)-2-(2-chlorophenyl)-2H-pyrazolo[4,3-d]pyrimidin-7-yl]-(5-methylpyridin-2-yl)-amine;
[3-(4-chlorophenyl)-2-(2-chlorophenyl)-2H-pyrazolo[4,3-d]pyrimidin-7-yl]-(5-methoxypyridin-2-yl)-amine;
[3-(4-chlorophenyl)-2-(2-chlorophenyl)-2H-pyrazolo[4,3-d]pyrimidin-7-yl]-(3,4,5,6-tetrahydro-2H-[1,2']bipyridinyl-5'-yl)-amine;
(6-azetidin-1-yl-pyridin-3-yl)-[3-(4-chlorophenyl)-2-(2-chlorophenyl)-2H-pyrazolo[4,3-d]pyrimidin-7-yl]-amine;
[3-(4-chlorophenyl)-2-(2-chlorophenyl)-2H-pyrazolo[4,3-d]pyrimidin-7-yl]-pyridin-2-ylmethylamine;
[3-(4-chlorophenyl)-2-(2-chlorophenyl)-2H-pyrazolo[4,3-d]pyrimidin-7-yl]-(5-methyl-pyridin-2-ylmethyl)-amine;
[3-(4-chlorophenyl)-2-(2-chlorophenyl)-2H-pyrazolo[4,3-d]pyrimidin-7-yl]-pyridin-3-ylmethylamine;
[3-(4-chlorophenyl)-2-(2,4-dichlorophenyl)-2H-pyrazolo[4,3-d]pyrimidin-7-yl]-diethylamine;
bicyclo[2.2.1]hept-2-yl-[3-(4-chlorophenyl)-2-(2,4-dichlorophenyl)-2H-pyrazolo[4,3-d]pyrimidin-7-yl]-amine;
[3-(4-chlorophenyl)-2-(2-chlorophenyl)-2H-pyrazolo[4,3-d]pyrimidin-7-yl]-cyclohexylamine;
[3-(4-chlorophenyl)-2-(2-chlorophenyl)-2H-pyrazolo[4,3-d]pyrimidin-7-yl]-diethylamine;
bicyclo[2.2.1]hept-2-yl-[3-(4-chlorophenyl)-2-(2-chlorophenyl)-2H-pyrazolo[4,3-d]pyrimidin-7-yl]-amine;
[3-(4-chlorophenyl)-2-(2-chlorophenyl)-2H-pyrazolo[4,3-d]pyrimidin-7-yl]-(4-methyl-cyclohexyl)amine;
adamantan-2-yl-[3-(4-chlorophenyl)-2-(2-chlorophenyl)-2H-pyrazolo[4,3-d]pyrimidin-7-yl]-amine;
[3-(4-chlorophenyl)-2-(2-chlorophenyl)-2H-pyrazolo[4,3-d]pyrimidin-7-yl]-(1,7,7-trimethylbicyclo[2.2.1]hept-2-yl)-amine;
[3-(4-chlorophenyl)-2-(2-chlorophenyl)-2H-pyrazolo[4,3-d]pyrimidin-7-yl]-(3-methylcyclohexyl)amine;

2-[3-(4-chlorophenyl)-2-(2-chlorophenyl)-2H-pyrazolo
[4,3-d]pyrimidin-7-ylamino]cyclopentanecarboxylic
acid ethyl ester;
2-[3-(4-chlorophenyl)-2-(2-chlorophenyl)-2H-pyrazolo
[4,3-d]pyrimidin-7-ylamino]cyclopentanol;
2-[3-(4-chlorophenyl)-2-(2-chlorophenyl)-2H-pyrazolo
[4,3-d]pyrimidin-7-ylamino]cyclohexanol;
[3-(4-chlorophenyl)-2-(2-chlorophenyl)-2H-pyrazolo[4,
3-d]pyrimidin-7-yl]-(2,6-dimethylcyclohexyl)amine;
[3-(4-chlorophenyl)-2-(2-chlorophenyl)-2H-pyrazolo[4,
3-d]pyrimidin-7-yl]cycloheptylamine;
[3-(4-chlorophenyl)-2-(2-chlorophenyl)-2H-pyrazolo[4,
3-d]pyrimidin-7-yl]cyclobutylamine;
2-[3-(4-chlorophenyl)-2-(2-chlorophenyl)-2H-pyrazolo
[4,3-d]pyrimidin-7-ylamino]-2-methylpropane-1,3-
diol;
[3-(4-chlorophenyl)-2-(2-chlorophenyl)-2H-pyrazolo[4,
3-d]pyrimidin-7-yl]-(1-methyl-1-phenylethyl)amine;
{1-[3-(4-chlorophenyl)-2-(2-chlorophenyl)-2H-pyrazolo
[4,3-d]pyrimidin-7-ylamino]cyclopentyl}methanol;
2-[3-(4-chlorophenyl)-2-(2-chlorophenyl)-2H-pyrazolo
[4,3-d]pyrimidin-7-ylamino]-2-methylpropan-1-ol;
[3-(4-chlorophenyl)-2-(2-chlorophenyl)-2H-pyrazolo[4,
3-d]pyrimidin-7-yl]-(1,1-dimethylpropyl)amine;
2-[3-(4-chlorophenyl)-2-(2-chlorophenyl)-2H-pyrazolo
[4,3-d]pyrimidin-7-ylamino]-3-phenylpropan-1-ol;
[3-(4-chlorophenyl)-2-(2-chlorophenyl)-2H-pyrazolo[4,
3-d]pyrimidin-7-yl]-indan-2-ylamine;
[3-(4-chlorophenyl)-2-(2-chlorophenyl)-2H-pyrazolo[4,
3-d]pyrimidin-7-yl]-(1,2,3,4-tetrahydronaphthalen-1-
yl)amine;
2-[3-(4-chlorophenyl)-2-(2-chlorophenyl)-2H-pyrazolo
[4,3-d]pyrimidin-7-ylamino]-1-pyrrolidin-1-ylpropan-
1-one;
4-{2-[3-(4-chlorophenyl)-2-(2-chlorophenyl)-2H-pyra-
zolo[4,3-d]pyrimidin-7-ylamino]propyl}phenol;
[3-(4-chlorophenyl)-2-(2-chlorophenyl)-2H-pyrazolo[4,
3-d]pyrimidin-7-yl]-(1-cyclohexylethyl)amine;
[3-(4-chlorophenyl)-2-(2-chlorophenyl)-2H-pyrazolo[4,
3-d]pyrimidin-7-yl]-(1-p-tolylethyl)amine;
[3-(4-chlorophenyl)-2-(2-chlorophenyl)-2H-pyrazolo[4,
3-d]pyrimidin-7-yl]-(2-phenylcyclopropyl)amine;
2-[3-(4-chlorophenyl)-2-(2-chlorophenyl)-2H-pyrazolo
[4,3-d]pyrimidin-7-ylamino]indan-1-ol;
[3-(4-chlorophenyl)-2-(2-chlorophenyl)-2H-pyrazolo[4,
3-d]pyrimidin-7-yl]-(2-morpholin-4-yl-ethyl)amine;
(1H-Benzoimidazol-2-ylmethyl)-[3-(4-chlorophenyl)-2-
(2-chlorophenyl)-2H-pyrazolo[4,3-d]pyrimidin-7-yl]-
amine;
1-[3-(4-chlorophenyl)-2-(2-chlorophenyl)-2H-pyrazolo
[4,3-d]pyrimidin-7-ylamino]propan-2-ol;
[3-(4-chlorophenyl)-2-(2-chlorophenyl)-2H-pyrazolo[4,
3-d]pyrimidin-7-yl]-(2,2,2-trifluoroethyl)amine;
[3-(4-chlorophenyl)-2-(2-chlorophenyl)-2H-pyrazolo[4,
3-d]pyrimidin-7-yl]-cyclopropylmethylamine;
[3-(4-chlorophenyl)-2-(2-chlorophenyl)-2H-pyrazolo[4,
3-d]pyrimidin-7-yl]-(1-cyclohexylethyl)amine;
a pharmaceutically acceptable salt thereof.

54. The compound of claim 53 selected from the group consisting of [3-(4-chlorophenyl)-2-(2,4-dichlorophenyl)-2H-pyrazolo[4,3-d]pyrimidin-7-yl]-diethylamine;
bicyclo[2.2.1]hept-2-yl-[3-(4-chlorophenyl)-2-(2,4-
dichlorophenyl)-2H-pyrazolo[4,3-d]pyrimidin-7-yl]-
amine;
[3-(4-chlorophenyl)-2-(2-chlorophenyl)-2H-pyrazolo[4,
3-d]pyrimidin-7-yl]-diethylamine;
bicyclo[2.2.1]hept-2-yl-[3-(4-chlorophenyl)-2-(2-chlo-
rophenyl)-2H-pyrazolo[4,3-d]pyrimidin-7-yl]-amine;
[3-(4-chlorophenyl)-2-(2-chlorophenyl)-2H-pyrazolo[4,
3-d]pyrimidin-7-yl]-cyclohexylamine;
adamantan-2-yl-[3-(4-chlorophenyl)-2-(2-chlorophenyl)-
2H-pyrazolo[4,3-d]pyrimidin-7-yl]-amine;
2-[3-(4-chlorophenyl)-2-(2-chlorophenyl)-2H-pyrazolo
[4,3-d]pyrimidin-7-ylamino]cyclohexanol;
[3-(4-chlorophenyl)-2-(2-chlorophenyl)-2H-pyrazolo[4,
3-d]pyrimidin-7-yl]cyclobutylamine;
[3-(4-chlorophenyl)-2-(2-chlorophenyl)-2H-pyrazolo[4,
3-d]pyrimidin-7-yl]-(1-methyl-1-phenylethyl)amine;
{1-[3-(4-chlorophenyl)-2-(2-chlorophenyl)-2H-pyrazolo
[4,3-d]pyrimidin-7-ylamino]cyclopentyl methanol;
2-[3-(4-chlorophenyl)-2-(2-chlorophenyl)-2H-pyrazolo
[4,3-d]pyrimidin-7-ylamino]-3-phenylpropan-1-ol;
[3-(4-chlorophenyl)-2-(2-chlorophenyl)-2H-pyrazolo[4,
3-d]pyrimidin-7-yl]-indan-2-ylamine;
[3-(4-chlorophenyl)-2-(2-chlorophenyl)-2H-pyrazolo[4,
3-d]pyrimidin-7-yl]-(1-cyclohexylethyl)amine; and
2-[3-(4-chlorophenyl)-2-(2-chlorophenyl)-2H-pyrazolo
[4,3-d]pyrimidin-7-ylamino]indan-1-ol;
a pharmaceutically acceptable salt thereof.

55. A compound of Formula (II)

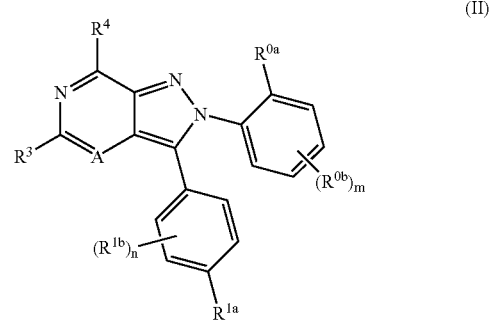

(II)

wherein
A is N;
$R^{0a}$, $R^{0b}$, $R^{1a}$, and $R^{1b}$ are each independently halo, $(C_1$-$C_4)$alkoxy, $(C_1$-$C_4)$alkyl, halo-substituted $(C_1$-$C_4)$alkyl, or cyano;
n and m are each independently 0, 1 or 2;
$R^3$ is hydrogen, $(C_1$-$C_4)$alkyl, halo-substituted $(C_1$-$C_4)$alkyl, or $(C_1$-$C_4)$alkoxy;
$R^4$ is
(i) a group having Formula (IA) or Formula (IB)

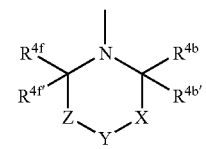

IA

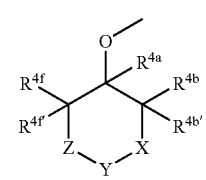

IB where $R^{4a}$ is hydrogen or $(C_1$-$C_3)$alkyl;

$R^{4b}$ and $R^{4b'}$ are each independently hydrogen, cyano, hydroxy, amino, $H_2NC(O)—$, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl$)_2$N—C(O)—, $(C_1-C_6)$alkylamino-, $((C_1-C_4)$alkyl$)_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a 3-6 membered partially or fully saturated heterocycle, and a partially or fully saturated carbocyclic ring, where the moiety is optionally substituted with one or more substituents, or either $R^{4b}$ or $R^{4b'}$ taken together with $R^{4e}$, $R^{4e'}$, $R^{4f}$, or $R^{4f'}$ forms a bond, a methylene bridge, or an ethylene bridge;

X is a bond, —CH$_2$CH$_2$— or —C$(R^{4c})(R^{4c'})$—, where $R^{4c}$ and $R^{4c'}$ are each independently hydrogen, cyano, hydroxy, amino, $H_2NC(O)—$, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl$)_2$N—C(O)—, $(C_1-C_6)$alkylamino-, di$(C_1-C_4)$alkylamino-, $(C_3-C_6)$cycloalkylamino-, acylamino-, aryl$(C_1-C_4)$alkylamino-, heteroaryl$(C_1-C_4)$alkylamino-, aryl, heteroaryl, a 3-6 membered partially or fully saturated heterocycle, and a 3-6 membered partially or fully saturated carbocyclic ring, where the moiety is optionally substituted with one or more substituents, or either $R^{4c}$ or $R^{4c'}$ taken together with $R^{4e}$, $R^{4e'}$, $R^{4f}$, or $R^{4f'}$ forms a bond, a methylene bridge or an ethylene bridge;

Y is oxygen, sulfur, —C(O)—, or —C$(R^{4d})(R^{4d'})$—, where $R^{4d}$ and $R^{4d'}$ are each independently hydrogen, cyano, hydroxy, amino, $H_2NC(O)—$, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl$)_2$N—C(O)—, $(C_1-C_6)$alkylamino-, di$(C_1-C_4)$alkylamino-, $(C_3-C_6)$cycloalkylamino-, acylamino-, aryl$(C_1-C_4)$alkylamino-, heteroaryl$(C_1-C_4)$alkylamino-, aryl, heteroaryl, a 3-6 membered partially or fully saturated heterocycle, and a 3-6 membered partially or fully saturated carbocyclic ring, where the moiety is optionally substituted with one or more substituents, or $R^{4d}$ and $R^{4d'}$ taken together form a 3-6 membered partially or fully saturated carbocyclic ring, a 3-6 membered partially or fully saturated heterocyclic ring, a 5-6 membered lactone ring, or a 4-6 membered lactam ring, where said carbocyclic ring, said heterocyclic ring, said lactone ring and said lactam ring are optionally substituted with one or more substituents and said lactone ring and said lactam ring optionally contain an additional heteroatom selected from oxygen, nitrogen or sulfur, or Y is —NR$^{4d''}$—, where $R^{4d''}$ is a hydrogen or a chemical moiety selected from the group consisting of $(C_1-C_6)$alkyl, $(C_3-C_6)$cycloalkyl, $(C_1-C_3)$alkylsulfonyl-, $(C_1-C_3)$alkylaminosulfonyl-, di$(C_1-C_3)$alkylaminosulfonyl-, acyl, $(C_1-C_6)$alkyl-O—C(O)—, aryl, and heteroaryl, where the moiety is optionally substituted with one or more substituents;

Z is a bond, —CH$_2$CH$_2$—, or —C$(R^{4e})(R^{4e'})$—, where $R^{4e}$ and $R^{4e'}$ are each independently hydrogen, cyano, hydroxy, amino, $H_2NC(O)—$, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl$)_2$N—C(O)—, $(C_1-C_6)$alkylamino-, di$(C_1-C_4)$alkylamino-, $(C_3-C_6)$cycloalkylamino-, acylamino-, aryl$(C_1-C_4)$alkylamino-, heteroaryl$(C_1-C_4)$alkylamino-, aryl, heteroaryl, a 3-6 membered partially or fully saturated heterocyclic ring, and a 3-6 membered partially or fully saturated carbocyclic ring, where the moiety is optionally substituted with one or more substituents, or either $R^{4e}$ or $R^{4e'}$ taken together with $R^{4b}$, $R^{4b'}$, $R^{4c}$, or $R^{4c'}$ forms a bond, a methylene bridge or an ethylene bridge; and $R^{4f}$ and $R^{4f'}$ are each independently hydrogen, cyano, hydroxy, amino, $H_2NC(O)—$, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl$)_2$N—C(O)—, $(C_1-C_6)$alkylamino-, di$(C_1-C_4)$alkylamino-, $(C_3-C_6)$cycloalkylamino-, acylamino-, aryl$(C_1-C_4)$alkylamino-, heteroaryl$(C_1-C_4)$alkylamino-, aryl, heteroaryl, a 3-6 membered partially or fully saturated heterocycle, and a 3-6 membered partially or fully saturated carbocyclic ring, where the moiety is optionally substituted with one or more substituents, or either $R^{4f}$ or $R^{4f'}$ taken together with $R^{4b}$, $R^{4b'}$, $R^{4c}$, or $R^{4c'}$ forms a bond, a methylene bridge or an ethylene bridge;

(ii) a group having Formula (IC)

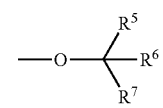

where $R^5$ and $R^6$ are each independently hydrogen, aryl, or $(C_1-C_4)$alkyl, and $R^7$ is an optionally substituted $(C_1-C_4)$alkyl-, or an optionally substituted 4-6 membered partially or fully saturated heterocylic ring containing 1 to 2 heteroatoms independently selected from oxygen, sulfur or nitrogen, or $R^5$ and $R^6$ or $R^5$ and $R^7$ taken together form a 5-6 membered lactone, 4-6 membered lactam, or a 4-6 membered partially or fully saturated heterocycle containing 1 to 2 heteroatoms independently selected from oxygen, sulfur or nitrogen, where said lactone, said lactam and said heterocycle are optionally substituted with one or more substituents;

(iii) an amino group having attached thereto at least one chemical moiety selected from the group consisting of $(C_1-C_8)$alkyl, aryl, aryl$(C_1-C_4)$alkyl, a 3-8 membered partially or fully saturated carbocyclic ring, hydroxy $(C_1-C_6)$alkyl, $(C_1-C_3)$alkoxy$(C_1-C_6)$alkyl, heteroaryl $(C_1-C_3)$alkyl, and a fully or partially saturated heterocycle, where said chemical moiety is optionally substituted with one or more substituents; or (iv) an $(C_1-C_6)$alkyl group having attached thereto at least one chemical moiety selected from the group consisting of hydroxy, $(C_1-C_6)$alkoxy, amino, $(C_1-C_6)$alkylamino, di$((C_1-C_6)$alkyl$)$amino $(C_1-C_3)$alkylsulfonyl, $(C_1-C_3)$alkylsulfamyl, di$((C_1-C_3)$alkyl$)$sulfamyl, acyloxy, a fully or partially saturated heterocycle, and a fully or partially saturated carbocyclic ring, where said chemical moiety is optionally substituted with one or more substituents;

a pharmaceutically acceptable salt thereof, a prodrug of said compound or said salt.

56. The compound of claim 55 wherein $R^4$ is a group of Formula (IA);

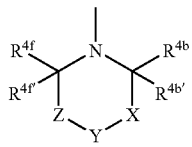

IA where, $R^{4b}$ and $R^{4b'}$ are each independently hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $((C_1-C_4)$alkyl$)_2$N—C(O)—, aryl, heteroaryl, a partially or fully saturated heterocycle, and a 3-6 membered partially or fully saturated carbocyclic ring, where said moiety is optionally substituted with one or more substituents, or $R^{4b}$ or $R^{4b'}$ taken together with $R^{4e}$, $R^{4e'}$, $R^{4f}$, or $R^{4f'}$ forms a bond, a methylene bridge, or an ethylene bridge;

X is a bond, —CH$_2$CH$_2$— or —C($R^{4c}$)($R^{4c'}$)—, where $R^{4c}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl$)_2$N—C(O)—, $(C_1-C_6)$alkylamino-, $((C_1-C_4)$alkyl$)_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a 3-6 membered partially or fully saturated heterocycle, and a partially or fully saturated carbocyclic ring, where said moiety is optionally substituted with one or more substituents, or $R^{4c}$ taken together with $R^{4e}$, $R^{4e'}$, $R^{4f}$, or $R^{4f'}$ forms a bond, a methylene bridge, or an ethylene bridge, and $R^{4c'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $((C_1-C_4)$alkyl$)_2$N—C(O)—, aryl, heteroaryl, a 3-6 membered partially or fully saturated heterocycle, and a partially or fully saturated carbocyclic ring, where said moiety is optionally substituted with one or more substituents, or $R^{4c'}$ taken together with $R^{4e}$, $R^{4e'}$, $R^{4f}$, or $R^{4f'}$ forms a bond, a methylene bridge, or an ethylene bridge;

Y is oxygen, sulfur, —C(O)—, or —C($R^{4d}$)($R^{4d'}$)—, where $R^{4d}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl$)_2$N—C(O)—, $(C_1-C_6)$alkylamino-, $((C_1-C_4)$alkyl$)_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a 3-6 membered partially or fully saturated heterocycle, and a partially or fully saturated carbocyclic ring, where said moiety is optionally substituted with one or more substituents, and $R^{4d'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $((C_1-C_4)$alkyl$)_2$N—C(O)—, aryl, heteroaryl, a 3-6 membered partially or fully saturated heterocycle, and a partially or fully saturated carbocyclic ring, where said moiety is optionally substituted with one or more substituents, or $R^{4d}$ and $R^{4d'}$ taken together form a 3-6 membered partially or fully saturated carbocyclic ring, a 3-6 membered partially or fully saturated heterocyclic ring, a 5-6 membered lactone ring, or a 4-6 membered lactam ring, where said carbocyclic ring, said heterocyclic ring, said lactone ring and said lactam ring are optionally substituted with one or more substituents and said lactone ring and said lactam ring optionally contain an additional heteroatom selected from oxygen, nitrogen or sulfur, or Y is —NR$^{4d''}$—, where R$^{4d''}$ is a hydrogen or a chemical moiety selected from the group consisting of $(C_1-C_6)$alkyl, $(C_3-C_6)$cycloalkyl, $(C_1-C_3)$alkylsulfonyl-, $(C_1-C_3)$alkylaminosulfonyl-, di$(C_1-C_3)$alkylaminosulfonyl-, acyl, $(C_1-C_6)$alkyl-O—C(O)—, aryl, and heteroaryl, where said moiety is optionally substituted with one or more substituents;

Z is a bond, —CH$_2$CH$_2$—, or —C($R^{4e}$)($R^{4e'}$)—, where $R^{4e}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl$)_2$N—C(O)—, $(C_1-C_6)$alkylamino-, $((C_1-C_4)$alkyl$)_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a 3-6 membered partially or fully saturated heterocycle, and a partially or fully saturated carbocyclic ring, where said moiety is optionally substituted with one or more substituents, or $R^{4e}$ taken together with $R^{4b}$, $R^{4b'}$, $R^{4c}$, or $R^{4c'}$ forms a bond, a methylene bridge, or an ethylene bridge, and $R^{4e'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $((C_1-C_4)$alkyl$)_2$N—C(O)—, aryl, heteroaryl, a 3-6 membered partially or fully saturated heterocycle, and a partially or fully saturated carbocyclic ring, where said moiety is optionally substituted with one or more substituents, or $R^{4e'}$ taken together with $R^{4b}$, $R^{4b'}$, $R^{4c}$, or $R^{4c'}$ forms a bond, a methylene bridge, or an ethylene bridge; and $R^{4f}$ and $R^{4f'}$ are each independently hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $((C_1-C_4)$alkyl$)_2$N—C(O)—, aryl, heteroaryl, a 3-6 membered partially or fully saturated heterocycle, and a partially or fully saturated carbocyclic ring, where said moiety is optionally substituted with one or more substituents, or $R^{4f}$ or $R^{4f'}$ taken together with $R^{4b}$, $R^{4b'}$, $R^{4c}$, or $R^{4c'}$ forms a bond, a methylene bridge, or an ethylene bridge;

a pharmaceutically acceptable salt thereof.

57. The compound of claim of 56 wherein
$R^{4b}$ is hydrogen, an optionally substituted $(C_1-C_3)$alkyl, or taken together with $R^{4e}$, $R^{4e'}$, $R^{4f}$, or $R^{4f'}$ forms a bond, a methylene bridge, or an ethylene bridge;
$R^{4b'}$ is hydrogen, an optionally substituted $(C_1-C_3)$alkyl, or taken together with $R^{4e}$, $R^{4e'}$, $R^{4f}$, or $R^{4f'}$ forms a bond, a methylene bridge, or an ethylene bridge;
$R^{4f}$ is hydrogen, an optionally substituted $(C_1-C_3)$alkyl, or taken together with $R^{4b}$, $R^{4b'}$, $R^{4c}$, or $R^{4c'}$ forms a bond, a methylene bridge, or an ethylene bridge; and
$R^{4f'}$ is hydrogen, an optionally substituted $(C_1-C_3)$alkyl, or taken together with $R^{4b}$, $R^{4b'}$, $R^{4c}$, or $R^{4c'}$ forms a bond, a methylene bridge, or an ethylene bridge;
a pharmaceutically acceptable salt thereof.

58. The compound of claim 57 wherein
X is —C($R^{4c}$)($R^{4c'}$)—, where $R^{4c}$ and $R^{4c'}$ are each independently hydrogen, $H_2NC(O)$—, or a chemical moiety selected from $(C_1-C_6)$alkyl, $(C_1-C_4)$alkyl-NH—C(O)—, or (($C_1-C_4$)alkyl)$_2$N—C(O)—, where said moiety is optionally substituted with one or more substituents,
or either $R^{4c}$ or $R^{4c'}$ taken together with $R^{4e}$, $R^{4e'}$, $R^{4f}$, or $R^{4f'}$ forms a bond, a methylene bridge or an ethylene bridge;
Y is —$NR^{4d''}$—, where $R^{4d''}$ is a hydrogen or a chemical moiety selected from the group consisting of $(C_1-C_6)$alkyl, $(C_3-C_6)$cycloalkyl, $(C_1-C_3)$alkylsulfonyl, $(C_1-C_3)$alkylaminosulfonyl, di($C_1-C_3$)alkylaminosulfonyl, acyl, $(C_1-C_6)$alkyl-O—C(O)—, aryl, and heteroaryl, where said moiety is optionally substituted with one or more substituents;
Z is —C($R^{4e}$)($R^{4e'}$)—, where $R^{4e}$ and $R^{4e'}$ are each independently hydrogen, $H_2NC(O)$—, or a chemical moiety selected from $(C_1-C_6)$alkyl, $(C_1-C_4)$alkyl-NH—C(O)—, or (($C_1-C_4$)alkyl)$_2$N—C(O)—, where said moiety is optionally substituted with one or more substituents,
or either $R^{4e}$ or $R^{4e'}$ taken together with $R^{4b}$, $R^{4b'}$, $R^{4c}$, or $R^{4c'}$ forms a bond, a methylene bridge or an ethylene bridge;
a pharmaceutically acceptable salt thereof.

59. The compound of claim 58 wherein $R^{4d''}$ is a hydrogen or a chemical moiety selected from the group consisting of $(C_1-C_3)$alkylsulfonyl, $(C_1-C_3)$alkylaminosulfonyl, di($C_1-C_3$)alkylaminosulfonyl, acyl, $(C_1-C_6)$alkyl-O—C(O)—, and heteroaryl, where said moiety is optionally substituted with one or more substituents;
a pharmaceutically acceptable salt thereof.

60. The compound of claim 59 wherein $R^{4d''}$ is a hydrogen or a chemical moiety selected from the group consisting of $(C_1-C_3)$alkylsulfonyl, $(C_1-C_3)$alkylaminosulfonyl, di($C_1-C_3$)alkylaminosulfonyl, acyl, and $(C_1-C_6)$alkyl-O—C(O)—, where said moiety is optionally substituted with 1-3 fluorines,
or $R^{d''}$ is a heteroaryl, where said heteroaryl is optionally substituted with 1 to 2 substituents independently selected from the group consisting of chloro, fluoro, $(C_1-C_3)$alkoxy, $(C_1-C_3)$alkyl, and fluoro-substituted $(C_1-C_3)$alkyl;
a pharmaceutically acceptable salt thereof.

61. The compound of claim 58, 59, or 60 wherein $R^{0a}$, $R^{0a}$, $R^{1a}$ and $R^{1b}$ are each independently selected from the group consisting of halo, $(C_1-C_4)$alkoxy, $(C_1-C_4)$alkyl, halo-substituted $(C_1-C_4)$alkyl, and cyano;
a pharmaceutically acceptable salt thereof.

62. The compound of claim 61 wherein $R^{0a}$, $R^{0a}$, $R^{1a}$ and $R^{1b}$ are each independently selected from the group consisting of chloro, fluoro, $(C_1-C_4)$alkoxy, $(C_1-C_4)$alkyl, fluoro-substituted $(C_1-C_4)$alkyl), and cyano; and
n and m are each independently 0 or 1;
a pharmaceutically acceptable salt thereof, a prodrug of said compound or said salt.

63. The compound of claim 57 wherein Y is —C($R^{4d}$)($R^{4d'}$)—, where $R^{4d}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, ($C_1-C_4$)alkyl)$_2$N—C(O)—, $(C_1-C_6)$alkylamino-, (($C_1-C_4$)alkyl)$_2$amino-, $(C_3-C_6)$cycloalkylamino-, acylamino-, aryl($C_1-C_4$)alkylamino-, heteroaryl($C_1-C_4$)alkylamino-, aryl, heteroaryl, a 3-6 membered partially or fully saturated heterocycle, and a partially or fully saturated carbocyclic ring, where said moiety is optionally substituted with one or more substituents,
$R^{4d'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, (($C_1-C_4$)alkyl)$_2$N—C(O)—, aryl, heteroaryl, a 3-6 membered partially or fully saturated heterocycle, and a partially or fully saturated carbocyclic ring, where said moiety is optionally substituted with one or more substituents,
or $R^{4d}$ and $R^{4d'}$ taken together form a 3-6 membered partially or fully saturated carbocyclic ring, a 3-6 membered partially or fully saturated heterocyclic ring, a 5-6 membered lactone ring, or a 4-6 membered lactam ring, where said carbocyclic ring, said heterocyclic ring, said lactone ring and said lactam ring are optionally substituted with one or more substituents and said lactone ring and said lactam ring optionally contain an additional heteroatom selected from oxygen, nitrogen or sulfur;
a pharmaceutically acceptable salt thereof.

64. The compound of claim 63 wherein
$R^{4b}$, $R^{4b'}$, $R^{4f}$, and $R^{4f'}$ are all hydrogen;
$R^{4d}$ is amino, $(C_1-C_6)$alkylamino, di($C_1-C_4$)alkylamino, $(C_3-C_6)$cycloalkylamino, acylamino, aryl($C_1-C_4$)alkylamino-, heteroaryl($C_1-C_4$)alkylamino-; and
$R^{4d'}$ is $(C_1-C_6)$alkyl, $H_2NC(O)$—, $(C_1-C_4)$alkyl-NH—C(O)—, or (($C_1-C_4$)alkyl)$_2$N—C(O)—, or aryl;
a pharmaceutically acceptable salt thereof.

65. The compound of claim 64 wherein
X is a bond or —C($R^4$)($R^{4c'}$)—, where $R^{4c}$ and $R^{4c'}$ are each hydrogen; and
Z is a bond or C($R^{4e}$)($R^{4e'}$)—, where $R^{4e}$ and $R^{4e'}$ are each hydrogen;
a pharmaceutically acceptable salt thereof.

66. The compound of claim 65 wherein $R^{4d}$ is amino, $(C_1-C_6)$alkylamino, di($C_1-C_4$)alkylamino, $(C_3-C_6)$cycloalkylamino; and
$R^{4d'}$ is $H_2NC(O)$—, $(C_1-C_4)$alkyl-NH—C(O)—, or (($C_1-C_4$)alkyl)$_2$N—C(O)—;
a pharmaceutically acceptable salt thereof.

67. The compound of claim 63, 64, 65 or 66 wherein $R^{0a}$, $R^{0b}$, $R^{1a}$, and $R^{1b}$ are each independently selected from the group consisting of halo, $(C_1-C_4)$alkoxy, $(C_1-C_4)$alkyl, halo-substituted $(C_1-C_4)$alkyl, and cyano;
a pharmaceutically acceptable salt thereof.

68. The compound of claim 67 wherein $R^{0a}$, $R^{0b}$, $R^{1a}$, and $R^{1b}$ are each independently selected from the group consisting of chloro, fluoro, $(C_1-C_4)$alkoxy, $(C_1-C_4)$alkyl, fluoro-substituted $(C_1-C_4)$alkyl), and cyano; and
n and m are each independently selected from 0 or 1;
a pharmaceutically acceptable salt thereof.

69. The compound of claim 63 wherein
$R^{4b}$, $R^{4b'}$, $R^{4f}$, and $R^{4f'}$ are all hydrogen;
$R^{4d}$ is hydrogen, hydroxy, amino, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_6)$alkylamino-, and di$(C_1-C_4)$alkylamino-, where said moiety is optionally substituted with one or more substituents; and
$R^{4d'}$ is hydrogen, or a chemical moiety selected from the group consisting of $(C_1-C_6)$alkyl, aryl and heteroaryl, where said moiety is optionally substituted with one or more substituents;
a pharmaceutically acceptable salt thereof.

70. The compound of claim 69 wherein
X is a bond or —C($R^{4c}$)($R^{4c'}$)—, where $R^{4c}$ and $R^{4c'}$ are each independently hydrogen or an optionally substituted $(C_1-C_6)$alkyl, or either $R^{4c}$ or $R^{4c'}$ taken together with $R^{4e}$ or $R^{4e'}$ forms a bond, a methylene bridge or an ethylene bridge; and
Z is a bond or —C($R^{4e}$)($R^{4e'}$)—, where $R^{4e}$ and $R^{4e'}$ are each independently hydrogen or an optionally substituted $(C_1-C_6)$alkyl, or either $R^{4e}$ or $R^{4e'}$ taken together with $R^{4c}$ or $R^{4c'}$ forms a bond, a methylene bridge or an ethylene bridge;
a pharmaceutically acceptable salt thereof.

71. The compound of claim 70 wherein
$R^{4c}$ and $R^{4c'}$ are each hydrogen or either $R^{4c}$ or $R^{4c'}$ taken together with $R^{4e}$ or $R^{4e'}$ forms a bond;
$R^{4d}$ is hydrogen, hydroxy, amino, or a chemical moiety selected from the group consisting of $(C_1-C_6)$alkoxy, acyl, $(C_1-C_6)$alkylamino-, and di$(C_1-C_4)$alkylamino-;
$R^{4d'}$ is hydrogen, or a chemical moiety selected from the group consisting of $(C_1-C_6)$alkyl and aryl, where said moiety is optionally substituted with one or more substituents; and
$R^{4e}$ and $R^{4e'}$ are hydrogen or either $R^{4e}$ or $R^{4e'}$ taken together with $R^{4c}$ or $R^{4c'}$ forms a bond;
a pharmaceutically acceptable salt thereof.

72. The compound of claim 69, 70, or 71 wherein $R^{0a}$, $R^{0b}$, $R^{1a}$, and $R^{1b}$ are each independently selected from the group consisting of halo, $(C_1-C_4)$alkoxy, $(C_1-C_4)$alkyl, halo-substituted $(C_1-C_4)$alkyl, and cyano;
a pharmaceutically acceptable salt thereof.

73. The compound of claim 72 wherein $R^{0a}$, $R^{0b}$, $R^{1a}$, and $R^{1b}$ are each independently selected from the group consisting of chloro, fluoro, $(C_1-C_4)$alkoxy, $(C_1-C_4)$alkyl, fluoro-substituted $(C_1-C_4)$alkyl), and cyano; and
n and m are each independently 0 or 1;
a pharmaceutically acceptable salt thereof.

74. The compound of claim 63 wherein
$R^{4b}$, $R^{4b'}$, $R^{4f}$, and $R^{4f'}$ are all hydrogen; and
$R^{4d}$ and $R^{4d'}$ taken together form a 3-6 membered partially or fully saturated carbocyclic ring, a 3-6 membered partially or fully saturated heterocyclic ring, a 5-6 membered lactone ring, or a 4-6 membered lactam ring, where said carbocyclic ring, said heterocyclic ring, said lactone ring and said lactam ring are optionally substituted with one or more substituents and said lactone ring or said lactam ring optionally contains an additional heteroatom selected from oxygen, nitrogen or sulfur;
a pharmaceutically acceptable salt thereof.

75. The compound of claim 74 wherein
X is a bond, —CH$_2$CH$_2$— or —C($R^{4c}$)($R^{4c'}$)—, where $R^{4c}$ and $R^{4c'}$ are each independently hydrogen or an optionally substituted $(C_1-C_6)$alkyl, or either $R^{4c}$ or $R^{4c'}$ taken together with $R^{4e}$ or $R^{4e'}$ forms a bond, a methylene bridge or an ethylene bridge; and
Z is a bond, —CH$_2$CH$_2$— or —C($R^{4e}$)($R^{4e'}$)—, where $R^{4e}$ and $R^{4e'}$ are each independently hydrogen or an optionally substituted $(C_1-C_6)$alkyl, or either $R^{4e}$ or $R^{4e'}$ taken together with $R^{4c}$ or $R^{4c'}$ forms a bond, a methylene bridge or an ethylene bridge;
a pharmaceutically acceptable salt thereof.

76. The compound of claim 75 wherein $R^{4d}$ and $R^{4d'}$ taken together form a 5-6 membered lactam ring, where said lactam ring is optionally substituted with one or more substituents and optionally contains an additional heteroatom selected from nitrogen or oxygen;
a pharmaceutically acceptable salt thereof.

77. The compound of claim 76 wherein
X is a bond or C($R^{4c}$)($R^{4c'}$)—, where $R^{4c}$ and $R^{4c'}$ are each hydrogen; and
Z is a bond or —C($R^{4e}$)($R^{4e'}$)—, where $R^{4e}$ and $R^{4e'}$ are each hydrogen;
a pharmaceutically acceptable salt thereof.

78. The compound of claim 74, 75, 76 or 77 wherein $R^{0a}$, $R^{0b}$, $R^{1a}$, and $R^{1b}$ are each independently selected from the group consisting of halo, $(C_1-C_4)$alkoxy, $(C_1-C_4)$alkyl, halo-substituted $(C_1-C_4)$alkyl, and cyano;
a pharmaceutically acceptable salt thereof.

79. The compound of claim 78 wherein $R^{0a}$, $R^{0b}$, $R^{1a}$, and $R^{1b}$ are each independently selected from the group consisting of chloro, fluoro, $(C_1-C_4)$alkoxy, $(C_1-C_4)$alkyl, fluoro-substituted $(C_1-C_4)$alkyl), and cyano;
n and m are each independently 0 or 1;
a pharmaceutically acceptable salt thereof.

80. The compound of claim 55 wherein $R^4$ is a group of Formula (IB);

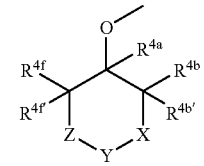

IB where $R^{4a}$ is as defined in claim 43;
$R^{4b}$ is hydrogen, cyano, hydroxy, amino, H$_2$NC(O)—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)$alkyl)$_2$N—C(O)—, $(C_1-C_6)$alkylamino-, (($C_1-C_4$)alkyl)$_2$amino-, $(C_3-C_6)$cycloalkylamino-, acylamino-, aryl($C_1-C_4$)alkylamino-, heteroaryl($C_1-C_4$)alkylamino-, aryl, heteroaryl, a 3-6 membered partially or fully saturated heterocycle, and a partially or fully saturated carbocyclic ring, where said moiety is optionally substituted with one or more substituents,
$R^{4b'}$ is hydrogen, H$_2$NC(O)—, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)$alkyl)$_2$N—C(O)—, aryl, heteroaryl, a 3-6 membered partially or fully saturated heterocycle, and a partially or fully saturated carbocyclic ring, where said moiety is optionally substituted with one or more substituents,
or $R^{4b}$ or $R^{4b'}$ taken together with $R^{4e}$, $R^{4e'}$, $R^{4f}$, or $R^{4f'}$ forms a bond, a methylene bridge, or an ethylene bridge;

X is a bond, —CH$_2$CH$_2$— or —C(R$^{4c}$)(R$^{4c'}$)—, where R$^{4c}$ is hydrogen, cyano, hydroxy, amino, H$_2$NC(O)—, or a chemical moiety selected from the group consisting of (C$_1$-C$_6$)alkyl, (C$_1$-C$_6$)alkoxy, acyloxy, acyl, (C$_1$-C$_3$)alkyl-O—C(O)—, (C$_1$-C$_4$)alkyl-NH—C(O)—, (C$_1$-C$_4$)alkyl)$_2$N—C(O)—, (C$_1$-C$_6$)alkylamino-, ((C$_1$-C$_4$)alkyl)$_2$amino-, (C$_3$-C$_6$)cycloalkylamino-, acylamino-, aryl(C$_1$-C$_4$)alkylamino-, heteroaryl(C$_1$-C$_4$)alkylamino-, aryl, heteroaryl, a 3-6 membered partially or fully saturated heterocycle, and a partially or fully saturated carbocyclic ring, where said moiety is optionally substituted with one or more substituents, or R$^{4c}$ taken together with R$^{4e}$, R$^{4e'}$, R$^{4f}$, or R$^{4f'}$ forms a bond, a methylene bridge, or an ethylene bridge, and R$^{4c'}$ is hydrogen, H$_2$NC(O)—, or a chemical moiety selected from the group consisting of (C$_1$-C$_6$)alkyl, acyl, (C$_1$-C$_3$)alkyl-O—C(O)—, (C$_1$-C$_4$)alkyl-NH—C(O)—, (C$_1$-C$_4$)alkyl)$_2$N—C(O)—, aryl, heteroaryl, a 3-6 membered partially or fully saturated heterocycle, and a partially or fully saturated carbocyclic ring, where said moiety is optionally substituted with one or more substituents, or R$^{4c'}$ taken together with R$^{4e}$, R$^{4e'}$, R$^{4f}$, or R$^{4f'}$ forms a bond, a methylene bridge, or an ethylene bridge;

Y is oxygen, sulfur, —C(O)—, or —C(R$^{4d}$)(R$^{4d'}$)—, where R$^{4d}$ is hydrogen, cyano, hydroxy, amino, H$_2$NC(O)—, or a chemical moiety selected from the group consisting of (C$_1$-C$_6$)alkyl, (C$_1$-C$_6$)alkoxy, acyloxy, acyl, (C$_1$-C$_3$)alkyl-O—C(O)—, (C$_1$-C$_4$)alkyl-NH—C(O)—, (C$_1$-C$_4$)alkyl)$_2$N—C(O)—, (C$_1$-C$_6$)alkylamino-, ((C$_1$-C$_4$)alkyl)$_2$amino-, (C$_3$-C$_6$)cycloalkylamino-, acylamino-, aryl(C$_1$-C$_4$)alkylamino-, heteroaryl(C$_1$-C$_4$)alkylamino-, aryl, heteroaryl, a 3-6 membered partially or fully saturated heterocycle, and a partially or fully saturated carbocyclic ring, where said moiety is optionally substituted with one or more substituents, and R$^{4d'}$ is hydrogen, H$_2$NC(O)—, or a chemical moiety selected from the group consisting of (C$_1$-C$_6$)alkyl, acyl, (C$_1$-C$_3$)alkyl-O—C(O)—, (C$_1$-C$_4$)alkyl-NH—C(O)—, (C, —C$_4$)alkyl)$_2$N—C(O)—, aryl, heteroaryl, a 3-6 membered partially or fully saturated heterocycle, and a partially or fully saturated carbocyclic ring, where said moiety is optionally substituted with one or more substituents, or R$^{4d}$ and R$^{4d'}$ taken together form a 3-6 membered partially or fully saturated carbocyclic ring, a 3-6 membered partially or fully saturated heterocyclic ring, a 5-6 membered lactone ring, or a 4-6 membered lactam ring, where said carbocyclic ring, said heterocyclic ring, said lactone ring and said lactam ring are optionally substituted with one or more substituents and said lactone ring and said lactam ring optionally contain an additional heteroatom selected from oxygen, nitrogen or sulfur;

Y is —NR$^{4d''}$—, where R$^{4d''}$ is a hydrogen or a chemical moiety selected from the group consisting of (C$_1$-C$_6$)alkyl, (C$_3$-C$_6$)cycloalkyl, (C$_1$-C$_3$)alkylsulfonyl-, (C$_1$-C$_3$)alkylaminosulfonyl-, di(C$_1$-C$_3$)alkylaminosulfonyl-, acyl, (C$_1$-C$_6$)alkyl-O—C(O)—, aryl, and heteroaryl, where said moiety is optionally substituted with one or more substituents;

Z is a bond, —CH$_2$CH$_2$—, or C(R$^{4e}$)(R$^{4e'}$)—, where R$^{4e}$ is hydrogen, cyano, hydroxy, amino, H$_2$NC(O)—, or a chemical moiety selected from the group consisting of (C$_1$-C$_6$)alkyl, (C$_1$-C$_6$)alkoxy, acyloxy, acyl, (C$_1$-C$_3$)alkyl-O—C(O)—, (C$_1$-C$_4$)alkyl-NH—C(O)—, (C$_1$-C$_4$)alkyl)$_2$N—C(O)—, (C$_1$-C$_6$)alkylamino-, ((C$_1$-C$_4$)alkyl)$_2$amino-, (C$_3$-C$_6$)cycloalkylamino-, acylamino-, aryl(C$_1$-C$_4$)alkylamino-, heteroaryl(C$_1$-C$_4$)alkylamino-, aryl, heteroaryl, a 3-6 membered partially or fully saturated heterocycle, and a partially or fully saturated carbocyclic ring, where said moiety is optionally substituted with one or more substituents, or R$^{4e}$ taken together with R$^{4b}$, R$^{4b'}$, R$^{4c}$, or R$^{4c'}$ forms a bond, a methylene bridge, or an ethylene bridge, and R$^{4e'}$ is hydrogen, H$_2$NC(O)—, or a chemical moiety selected from the group consisting of (C$_1$-C$_6$)alkyl, acyl, (C$_1$-C$_3$)alkyl-O—C(O)—, (C$_1$-C$_4$)alkyl-NH—C(O)—, (C$_1$-C$_4$)alkyl)$_2$N—C(O)—, aryl, heteroaryl, a 3-6 membered partially or fully saturated heterocycle, and a partially or fully saturated carbocyclic ring, where said moiety is optionally substituted with one or more substituents, or R$^{4e'}$ taken together with R$^{4b}$, R$^{4b'}$, R$^{4c}$, or R$^{4c'}$ forms a bond, a methylene bridge, or an ethylene bridge;

R$^{4f}$ is hydrogen, cyano, hydroxy, amino, H$_2$NC(O)—, or a chemical moiety selected from the group consisting of (C$_1$-C$_6$)alkyl, (C$_1$-C$_6$)alkoxy, acyloxy, acyl, (C$_1$-C$_3$)alkyl-O—C(O)—, (C$_1$-C$_4$)alkyl-NH—C(O)—, (C$_1$-C$_4$)alkyl)$_2$N—C(O)—, (C$_1$-C$_6$)alkylamino-, ((C$_1$-C$_4$)alkyl)$_2$amino-, (C$_3$-C$_6$)cycloalkylamino-, acylamino-, aryl(C$_1$-C$_4$)alkylamino-, heteroaryl(C$_1$-C$_4$)alkylamino-, aryl, heteroaryl, a 3-6 membered partially or fully saturated heterocycle, and a partially or fully saturated carbocyclic ring, where said moiety is optionally substituted with one or more substituents; and R$^{4f'}$ is hydrogen, H$_2$NC(O)—, or a chemical moiety selected from the group consisting of (C$_1$-C$_6$)alkyl, acyl, (C$_1$-C$_3$)alkyl-O—C(O)—, (C$_1$-C$_4$)alkyl-NH—C(O)—, (C$_1$-C$_4$)alkyl)$_2$N—C(O)—, aryl, heteroaryl, a 3-6 membered partially or fully saturated heterocycle, and a partially or fully saturated carbocyclic ring, where said moiety is optionally substituted with one or more substituents, or R$^{4f}$ or R$^{4f'}$ taken together with R$^{4b}$, R$^{4b'}$, R$^{4c}$, or R$^{4c'}$ forms a bond, a methylene bridge, or an ethylene bridge;

a pharmaceutically acceptable salt thereof.

81. The compound of claim 80 wherein

R$^{4a}$, R$^{4b}$, R$^{4b'}$, R$^{4f}$ and R$^{4f'}$ are each hydrogen;

a pharmaceutically acceptable salt thereof.

82. The compound of claim 81 wherein

X is a bond, —CH$_2$CH$_2$— or —C(R$^{4c}$)(R$^{4c'}$)—, where R$^{4c}$ and R$^{4c'}$ are each independently hydrogen or (C$_1$-C$_6$)alkyl;

Y is —NR$^{4d''}$—, where R$^{4d''}$ is hydrogen or a chemical moiety selected from the group consisting of (C$_1$-C$_6$)alkyl, (C$_3$-C$_6$)cycloalkyl, (C$_1$-C$_3$)alkylsulfonyl-, (C$_1$-C$_3$)alkylaminosulfonyl-, di(C$_1$-C$_3$)alkylaminosulfonyl-, acyl, (C$_1$-C$_6$)alkyl-O—C(O)—, aryl, and heteroaryl, where said moiety is optionally substituted with one or more substituents;

Z is a bond, —CH$_2$CH$_2$— or —C(R$^{4c}$)(R$^{4c'}$)—, where R$^{4c}$ and R$^{4c'}$ are each independently hydrogen or (C$_1$-C$_6$)alkyl;

a pharmaceutically acceptable salt thereof.

83. The compound of claim 81 or 82 wherein R$^{0a}$, R$^{0b}$, R$^{1a}$ and R$^{1b}$ are each independently selected from the group consisting of halo, (C$_1$-C$_4$)alkoxy, (C$_1$-C$_4$)alkyl, halo-substituted (C$_1$-C$_4$)alkyl, and cyano;

a pharmaceutically acceptable salt thereof.

84. The compound of claim 83 wherein $R^{0a}$, $R^{0b}$, $R^{1a}$ and $R^{1b}$ are each independently selected from the group consisting of chloro, fluoro, $(C_1-C_4)$alkoxy, $(C_1-C_4)$alkyl, fluoro-substituted $(C_1-C_4)$alkyl), and cyano; and
n and m are each independently 0 or 1;
a pharmaceutically acceptable salt thereof.

85. The compound of claim 55 wherein $R^4$ is a group having Formula (IC)

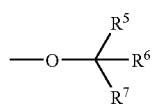

where $R^5$ and $R^6$ are each independently hydrogen, aryl or $(C_1-C_4)$alkyl, and $R^7$ is $(C_1-C_4)$alkyl-, halo-substituted $(C_1-C_4)$alkyl-, $(C_1-C_4)$alkoxy$(C_1-C_4)$alkyl-, $(C_1-C_4)$alkylamino$(C_1-C_4)$alkyl-, di$(C_1-C_4)$alkylamino$(C_1-C_4)$alkyl-, or a 4-6 membered partially or fully saturated heterocylic ring containing 1 to 2 heteroatoms independently selected from oxygen, sulfur or nitrogen, or
$R^5$ and $R^6$, or $R^5$ and $R^7$ taken together form a 5-6 membered lactone, 4-6 membered lactam, or a 4-6 membered partially or fully saturated heterocycle containing 1 to 2 heteroatoms independently selected from oxygen, sulfur or nitrogen, where said lactone, said lactam and said heterocycle are optionally substituted with one or more substituents;
a pharmaceutically acceptable salt thereof.

86. The compound of claim 85 wherein n and m are each independently 1 or 0;
a pharmaceutically acceptable salt thereof.

87. The compound of claim 86 wherein $R^5$ and $R^6$ are each independently hydrogen or $(C_1-C_4)$alkyl, and $R^7$ is $(C_1-C_4)$alkyl;
a pharmaceutically acceptable salt thereof.

88. The compound of claim 86 or 87 wherein $R^{0a}$, $R^{0b}$, $R^{1a}$, and $R^{1b}$ are each independently chloro, fluoro or trifluoromethyl;
a pharmaceutically acceptable salt thereof.

89. The compound of claim 55 wherein $R^4$ is an amino group having attached thereto at least one chemical moiety selected from the group consisting of $(C_1-C_8)$alkyl, aryl, aryl$(C_1-C_4)$alkyl, a 3-8 membered partially or fully saturated carbocyclic ring, hydroxy$(C_1-C_6)$alkyl, $(C_1-C_3)$alkoxy$(C_1-C_6)$alkyl, heteroaryl$(C_1-C_3)$alkyl, and a partially or fully saturated heterocycle, where said chemical moiety is optionally substituted with one or more substituents;
a pharmaceutically acceptable salt thereof.

90. The compound of claim 89 wherein n and m are each independently 1 or 0;
a pharmaceutically acceptable salt thereof.

91. The compound of claim 89 or 90 wherein $R^{0a}$, $R^{0b}$, $R^{1a}$, and $R^{1b}$ are each independently chloro, fluoro or trifluoromethyl;
a pharmaceutically acceptable salt thereof.

92. The compound of claim 55 wherein $R^4$ is an $(C_1-C_6)$ alkyl group having attached thereto at least one chemical moiety selected from the group consisting of hydroxy, $(C_1-C_6)$alkoxy, amino, $(C_1-C_6)$alkylamino, di$((C_1-C_6)$alkyl)amino$(C_1-C_3)$alkylsulfonyl, $(C_1-C_3)$alkylsulfamyl, di$((C_1-C_3)$alkyl)sulfamyl, acyloxy, a partially or fully saturated heterocycle, and a partially or fully saturated carbocyclic ring, where said chemical moiety is optionally substituted with one or more substituents;
a pharmaceutically acceptable salt thereof.

93. The compound of claim 92 wherein n and m are each independently 1 or 0;
a pharmaceutically acceptable salt thereof.

94. The compound of claim 92 or 93 wherein $R^{0a}$, $R^{0b}$, $R^{1a}$, and $R^{1b}$ are each independently chloro, fluoro or trifluoromethyl;
a pharmaceutically acceptable salt thereof.

95. A pharmaceutical composition comprising (1) a compound of claim 1 and (2) a pharmaceutically acceptable excipient, diluent, or carrier.

96. The composition of claim 95 further comprising at least one additional pharmaceutical agent.

97. The composition of claim 96 wherein said additional pharmaceutical agent is a nicotine receptor partial agonist, an opioid antagonist, a dopaminergic agent, an attention deficit disorder agent, or an anti-obesity agent.

98. The composition of claim 97 wherein said anti-obesity agent is selected from the group consisting of an apo-B/MTP inhibitor, a 11β-hydroxy steroid dehydrogenase-1 inhibitor, peptide $YY_{3-36}$, a MCR-4 agonist, a CCK-A agonist, a monoamine reuptake inhibitor, a sympathomimetic agent, a $β_3$ adrenergic receptor agonist, a dopamine agonist, a melanocyte-stimulating hormone receptor, a 5-HT2c receptor agonist, a melanin concentrating hormone antagonist, leptin, a leptin receptor agonist, a galanin antagonist, a lipase inhibitor, a bombesin agonist, a neuropeptide-Y receptor antagonist, a thyromimetic agent, dehydroepiandrosterone, a glucocorticoid receptor antagonist, an orexin receptor antagonist, a glucagon-like peptide-1 receptor agonist, a ciliary neurotrophic factor, a human agouti-related protein antagonist, a ghrelin receptor antagonist, a histamine 3 receptor antagonist or inverse agonist, and a neuromedin U receptor agonist.

99. A method for treating obesity, bulimia, or tobacco abuse, in animals comprising the step of administering to an animal in need of such treatment a therapeutically effective amount of a compound of claim 1;
a pharmaceutically acceptable salt thereof.

100. The method of claim 99 wherein said compound is a compound of claim 2, a pharmaceutically acceptable salt thereof.

101. The method of claim 99 wherein said compound is administered in combination with a nicotine receptor partial agonist, an opioid antagonist, a dopaminergic agent, an attention deficit disorder agent, or an anti-obesity agent.

102. The method of claim 100 wherein said compound is administered in combination with a nicotine receptor partial agonist, an opioid antagonist, a dopaminergic agent, an attention deficit disorder agent, or an anti-obesity agent.

103. The method of claim 101 or 102 wherein said anti-obesity agent is selected from the group consisting of an apo-B/MTP inhibitor, a 11β-hydroxy steroid dehydrogenase-1 inhibitor, peptide $YY_{3-36}$, a MCR-4 agonist, a CCK-A agonist, a monoamine reuptake inhibitor, a sympathomimetic agent, a $β_3$ adrenergic receptor agonist, a dopamine agonist, a melanocyte-stimulating hormone receptor, a 5-HT2c receptor agonist, a melanin concentrating hormone antagonist, leptin, a leptin receptor agonist, a galanin antagonist, a lipase inhibitor, a bombesin agonist, a neuropeptide-Y receptor antagonist, a thyromimetic agent, dehydroepiandrosterone, a glucocorticoid receptor antagonist, an orexin receptor antagonist, a glucagon-like peptide-1 receptor agonist, a ciliary neurotrophic factor, a human agouti-related protein antagonist, a ghrelin receptor antagonist, a histamine 3 receptor antagonist or inverse agonist, and a neuromedin U receptor agonist.

104. A method for treating obesity, bulimia, or tobacco abuse, comprising the step of administering a pharmaceutical composition of claim 95.

105. The method of claim 104 wherein said pharmaceutical composition further comprises an additional pharmaceutical agent selected from the group consisting of a nicotine partial agonist, an opioid antagonist, a dopaminergic agent, an attention deficit disorder agent, and an anti-obesity agent.

106. The method of claim 105 wherein said anti-obesity agent is selected from the group consisting of an apo-B/MTP inhibitor, a 11β-hydroxy steroid dehydrogenase-1 inhibitor, peptide $YY_{3-36}$, a MCR-4 agonist, a CCK-A agonist, a monoamine reuptake inhibitor, a sympathomimetic agent, a $β_3$ adrenergic receptor agonist, a dopamine agonist, a melanocyte-stimulating hormone receptor, a 5-HT2c receptor agonist, a melanin concentrating hormone antagonist, leptin, a leptin receptor agonist, a galanin antagonist, a lipase inhibitor, a bombesin agonist, a neuropeptide-Y receptor antagonist, a thyromimetic agent, dehydroepiandrosterone, a glucocorticoid receptor antagonist, an orexin receptor antagonist, a glucagon-like peptide-1 receptor agonist, a ciliary neurotrophic factor, a human agouti-related protein antagonist, a ghrelin receptor antagonist, a histamine 3 receptor antagonist or inverse agonist, and a neuromedin U receptor agonist.

107. A method for treating obesity, bulimia, or tobacco abuse, in animals comprising the step of administering to an animal in need of such treatment a therapeutically effective amount of a compound of claim 55; or a pharmaceutically acceptable salt thereof.

108. The method of claim 107 wherein said compound is a compound of claim 56, a pharmaceutically acceptable salt thereof.

109. The method of claim 107 wherein said compound is administered in combination with a nicotine partial agonist, an opioid antagonist, a dopaminergic agent, an attention deficit disorder agent, or an anti-obesity agent.

110. The method of claim 108 wherein said compound is administered in combination with a nicotine partial agonist, an opioid antagonist, a dopaminergic agent, an attention deficit disorder agent, or an anti-obesity agent.

111. The method of claim 109 or 110 wherein said anti-obesity agent is selected from the group consisting of an apo-B/MTP inhibitor, a 11β-hydroxy steroid dehydrogenase-1 inhibitor, peptide $YY_{3-36}$, a MCR-4 agonist, a CCK-A agonist, a monoamine reuptake inhibitor, a sympathomimetic agent, a $β_3$ adrenergic receptor agonist, a dopamine agonist, a melanocyte-stimulating hormone receptor, a 5-HT2c receptor agonist, a melanin concentrating hormone antagonist, leptin, a leptin receptor agonist, a galanin antagonist, a lipase inhibitor, a bombesin agonist, a neuropeptide-Y receptor antagonist, a thyromimetic agent, dehydroepiandrosterone, a glucocorticoid receptor antagonist, an orexin receptor antagonist, a glucagon-like peptide-1 receptor agonist, a ciliary neurotrophic factor, a human agouti-related protein antagonist, a ghrelin receptor antagonist, a histamine 3 receptor antagonist or inverse agonist, and a neuromedin U receptor agonist.

112. A method for treating obesity, bulimia, or tobacco abuse in animals comprising the step of administering to an animal in need of such treatment two separate pharmaceutical compositions comprising (i) a first composition comprising a compound of claim 1 or claim 55, or a pharmaceutically acceptable salt thereof, and a pharmaceutically acceptable excipient, diluent, or carrier, and (ii) a second composition comprising at least one additional pharmaceutical agent selected from the group consisting of a nicotine partial agonist, an opioid antagonist, a dopaminergic agent, an attention deficit disorder agent, or an anti-obesity agent and a pharmaceutically acceptable excipient, diluent, or carrier.

113. The method of claim 112 wherein said anti-obesity agent is selected from the group consisting of an apo-B/MTP inhibitor, a 11β-hydroxy steroid dehydrogenase-1 inhibitor, peptide $YY_{3-36}$, a MCR-4 agonist, a CCK-A agonist, a monoamine reuptake inhibitor, a sympathomimetic agent, a $β_3$ adrenergic receptor agonist, a dopamine agonist, a melanocyte-stimulating hormone receptor, a 5-HT2c receptor agonist, a melanin concentrating hormone antagonist, leptin, a leptin receptor agonist, a galanin antagonist, a lipase inhibitor, a bombesin agonist, a neuropeptide-Y receptor antagonist, a thyromimetic agent, dehydroepiandrosterone, a glucocorticoid receptor antagonist, an orexin receptor antagonist, a glucagon-like peptide-1 receptor agonist, a ciliary neurotrophic factor, a human agouti-related protein antagonist, a ghrelin receptor antagonist, a histamine 3 receptor antagonist or inverse agonist, and a neuromedin U receptor agonist.

114. The method of claim 112 wherein said first composition and said second composition are administered simultaneously.

115. The method of claim 112 wherein said first composition and said second composition are administered sequentially and in any order.

\* \* \* \* \*